US010446261B1

(12) United States Patent
Zhuo

(10) Patent No.: US 10,446,261 B1
(45) Date of Patent: Oct. 15, 2019

(54) SYSTEM AND METHOD FOR ANALYZING SPLICING CODES OF SPLICEOSOMAL INTRONS

(75) Inventor: Degen Zhuo, Miami, FL (US)

(73) Assignee: BIOTAILOR, INC., Miami, FL (US)

( * ) Notice: Subject to any disclaimer, the term of this patent is extended or adjusted under 35 U.S.C. 154(b) by 466 days.

(21) Appl. No.: 13/372,180

(22) Filed: Feb. 13, 2012

Related U.S. Application Data

(63) Continuation-in-part of application No. 12/006,898, filed on Jan. 6, 2008, now Pat. No. 8,185,323.

(51) Int. Cl.
*G16B 30/00* (2019.01)
*C12Q 1/6813* (2018.01)
*C12Q 1/6869* (2018.01)
*C12Q 1/6876* (2018.01)
*C12Q 1/6806* (2018.01)
*G16B 25/20* (2019.01)

(52) U.S. Cl.
CPC ........... *G16B 30/00* (2019.02); *C12Q 1/6806* (2013.01); *C12Q 1/6813* (2013.01); *C12Q 1/6869* (2013.01); *C12Q 1/6876* (2013.01); *G16B 25/20* (2019.02); *C12Q 2600/156* (2013.01)

(58) Field of Classification Search
CPC .............. C12N 2840/445; C12N 15/09; C12N 2320/10; G06F 19/22; G06F 19/18; G06F 19/24; G06F 19/12; C12Q 2539/105; C12Q 1/6869; C12Q 2600/156; C12Q 1/68
See application file for complete search history.

(56) References Cited

PUBLICATIONS

Denley et al. The Insulin Receptor Isoform Exon 11-(IR-A) in Cancer and Other Diseases: A Review Hormone and Metabolism Research vol. 35, pp. 778-785 (2003).*

Marguerat et al. RNA-seq: from technology to biology Cellular and Molecular Life Sciences vol. 67, pp. 569-579 (Year: 2010).*

Roy, Scott William and Walter Gilbert, The evolution of spliceosomal introns: patterns, puzzles and progress, Nature Reviews | Genetics, vol. 7, Mar. 2006, p. 211, Nature Publishing Group 2006.

Rodriguez-Trelles, Francisco, Rosa Tarrio and Francisco J. Ayala, Origins and Evolution of Spliceosomal Introns, Annu. Rev. Genet. 2006.40:47-76.

Pan, Qun, Ofer Shai, Leo J. Lee, Brendan J. Frey and Benjamin J. Blencowe, Deep surveying of alternative splicing complexity in the human transcriptome by high-throughput sequencing, Nature Genetics vol. 40, No. 12, Dec. 2008, p. 1413, Nature Publishing Group 2008.

Nilsen, Timothy W. and Brenton R. Graveley, Expansion of the eukaryotic proteomeby alternative splicing, Nature,vol. 463, No. 28, Jan. 2010, Macmillan Publishers Limited, 2010.

Baralle, Diana, Anneke Lucassen and Emanuele Buratti, Missed threads; The impact of pre-mRNA splicing defects on clinical practice, EMBO Reports, vol. 10, No. 8, 2009, European Molecular Biology Organization 2009.

Cooper, Thomas A., Lili Wan and Gideon Dreyfuss, RNA and Disease, Cell. Feb. 20, 2009; 136(4): 777-793. doi:10.1016/j.cell.2009.02.011.

Belfiore, Antonino, Francesco Frasca, Giuseppe Pandini, Laura Sciacca and Riccardo Vigneri, Insulin Receptor Isoforms and Insulin Receptor/Insulin-Like Growth Factor Receptor Hybrids in Physiology and Disease, Endocrine Reviews, Oct. 2009, 30(6):586-623.

Sanford, Jeremy R., Nicola K. Gray, Karsten Beckmann and Javier F. Caceres, A novel role for shuttling SR proteins in mRNA translation, Genes & Development 18:755-768 © 2004 by Cold Spring Harbor Laboratory Press ISSN 0890-9369/04.

Moore, Melissa J., From Birth to Death: The Complex Lives of Eukaryotic mRNAs, Science 309, 1514 (2005); DOI: 10.1126/science.1111443.

Pyle et. al., Folding of group II introns: a model system for large, multidomain RNAs?, Trends Biochem. Sci. 32 (2007) pp. 138-145.

Valadkhan, Saba, The spliceosome: a ribozyme at heart?, Biol. Chem., vol. 388, pp. 693-697, Jul. 2007, Copyright (c) by Walter de Gruyter • Berlin • New York. DOI 10.1515/BC.2007.080.

Sultan, Marc, Marcel H. Schulz,Hugues Richard, Alon Magen, Andreas Klingenhoff, Matthias Scherf, Martin Seifert, Tatjana Borodina, Aleksey Soldatov, Dmitri Parkhomchuk, Dominic Schmidt, Sean O'Keeffe, Stefan Haas, Martin Vingron, Hans Lehrach, and Marie-Laure Yaspo, A Global View of Gene Activity and Alternative Splicing by Deep Sequencing of the Human Transcriptome, Science, Aug. 15, 2008, vol. 321, p. 956.

Mangone, Marco, Arun Prasad Manoharan, Danielle Thierry-Mieg, Jean Thierry-Mieg, Ting Han, Sebastian D. Mackowiak, Emily Mis, Charles Zegar, Michelle R. Gutwein, Vishal Khivansara, Oliver Attie, Kevin Chen, Kourosh Salehi-Ashtiani, Marc Vidal, Timothy T. Harkins, Pascal Bouffard, Yutaka Suzuki, Sumio Sugano, Yuji Kohara, Nikolaus Rajewsky, Fabio Piano, Kristin C. Gunsalus and John K. Kim, The Landscape of C. elegans 3'UTRs, Science, Jul. 23, 2010.

(Continued)

*Primary Examiner* — John S Brusca
(74) *Attorney, Agent, or Firm* — Saliwanchik, Lloyd & Eisenschenk

(57) ABSTRACT

A system and method for analyzing splicing codes of spliceosomal introns is disclosed. One embodiment comprises methods of identifying introns and exons in genomic DNA or pre-mRNA sequences by locating characteristic markers in splicing junctions by computation and/or manually. Exon sequences predicted by computation can be verified and characterized by employing standard amplification methods, such as comparative genomic, RNA-seq, next-generation sequencing, RT-PCR. DNA/RNA/oligo, electrophoretic or protein chip technologies. If a given sample is verified, its polypeptide can be translated based on genetic codons. Its functions can be deduced based on its characteristics, computation predictions and related knowledge databases. These data can be used to compare databases which correlate the characterized intron or exon or gene to characterized diseases or genetic mutations. Isoforms can be detected and analyzed at mRNA and protein levels alone and with other isoforms predicted by computation, characterized by experiments and stored in existing databases.

21 Claims, 18 Drawing Sheets

Specification includes a Sequence Listing.

(56) References Cited

PUBLICATIONS

Fu, Xiang-Dong, Towards a Splicing Code, Cell, vol. 119, Issue 6, 736-738, Dec. 17, 2004.
Matlin, Arianne J., Francis Clark and Christopher W.J. Smith, Understanding Alternative Splicing: Towards a Cellular Code, Nature Reviews | Molecular Cell Biology, vol. 6, May 2005, p. 387.
Wang, Guey-Shin and Thomas A. Cooper, Splicing in disease: disruption of the splicing code and the decoding machinery, Nature Reviews | Genetics, vol. 8, Oct. 2007, p. 749, Nature Publishing Group 2007.
Barash, Yoseph, John A. Calarco, Weijun Gao, Qun Pan, Xinchen Wang, Ofer Shai, Benjamin J. Blencowe and Brendan J. Frey, Deciphering the splicing code, Nature, vol. 465, No. 6, p. 53, May 2010, doi:10.1038/nature09000, Macmillan Publishers Limited.
Soller, M., Pre-messenger RNA processing and its regulation: a genomic perspective, Cell. Mol. Life Sci. 63 (2006) 796-819, 1420-682X/06/080796-24, DOI 10.1007/s00018-005-5391-x, Birkhäuser Verlag, Basel, 2006.
Chen, Leslie Y., Kuo-Chen Wei, Abner C.-Y. Huang, Kai Wang, Chiung-Yin Huang, Danielle Yi, Chuan Yi Tang, David J. Galas and Leroy E. Hood, RNASEQR—a streamlined and accurate RNA-seq sequence analysis program, Nucleic Acids Research, 2012, vol. 40, No. 6, p. e42.
Zhuo, Degen, Richard Madden, Sherif About Elela and Benoit Chabot, Modern origin of numerous alternatively splicedhuman introns from tandem arrays, PNAS, Jan. 16, 2007, vol. 104, No. 3, p. 882-886.
Den Hollander, Petra, Suresh K. Rayala, Dawn Coverley and Rakesh Kumar, Ciz1, a Novel DNA-Binding Coactivator of the Estrogen Receptor α, Confers Hypersensitivity to Estrogen Action, Cancer Res 2006; 66:(22). Nov. 15, 2006, p. 11021-11029.
Coghlan, Avril and Kenneth H. Wolfe, Origins of recently gained introns in Caenorhabditis, PNAS, Aug. 3, 2004, vol. 101, No. 31, pp. 11362-11367.
Blumenthal, Thomas and Kathy Seggerson Gleason, Caenorhabditis Elegans Operons: Form and Function, Nature Reviews | Genetics, vol. 4, Feb. 2003, pp. 110-118, Nature Publishing Group 2003.
Banyai, Laszlo and Laszlo Patthy, Evidence that human genes of modular proteins have retained significantly more ancestral introns than their fly or worm orthologues, FEBS Letters 565 (2004) 127-132, 2004 Federation of European Biochemical Societies. Published by Elsevier B.V.
Carmel, Ido, Saar Tal, Ida Vig, and Gil Ast, Comparative analysis detects dependencies among the 5' splice-site positions, RNA (2004), 10:828-840. Published by Cold Spring Harbor Laboratory Press.
Wu, Thomas D. and Serban Nacu, Fast and SNP-tolerant detection of complex variants and splicing in short reads, Bioinformatics, vol. 26 No. 7 2010, pp. 873-881, doi:10.1093/bioinformatics/btq057. Published by Oxford University Press.
Murray, Vincent and Robin Holliday, Mechanism for RNA Splicing of Gene Transcripts, FEBS Letters, vol. 106, No. 1, Oct. 1979, pp. 5-7, Elsevier North-Hold Biomedical Press.
Jacquier, Alain and Francois Michel, Multiple Exon-Binding Sites in Class II Self-Splicing Introns, Cell, vol. 50, 17-29, Jul. 3, 1987, Copyright 1987 by Cell Press.
Roy, Scott William and Manuel Irimia, When good transcripts go bad: artifactual RT-PCR ‘splicing’ and genome analysis, BioEssays 30:601-605, (c) 2008 Wiley Periodicals, Inc.
Roy, Scott William and Manuel Irimia, Intron mis-splicing: no alternative?, Genome Biology 2008, 9:208 (doi:10.1186/gb-2008-9-2-208).
Wood, V., R. Gwilliam, M.-A. Rajandream, M. Lyne, R. Lyne, A. Stewart, J. Sgouros, N. Peat, J. Hayles, S. Baker, D. Basham, S. Bowman, K. Brooks, D. Brown, S. Brown, T. Chillingworth, C. Churcher, M. Collins, R. Connor, A. Cronin, P. Davis, T. Feltwell, A. Fraser, S. Gentles, A. Goble, N. Hamlin, D. Harris, J. Hidalgo, G. Hodgson, S. Holroyd, T. Hornsby, S. Howarth, E. J. Huckle S. Hunt, K. Jagels K. James, L. Jones, M. Jones, S. Leather, S. McDonald, J. McLean, P. Nature vol. 415 pp. 871-880 (2002).
Davis, C.A., L. Grate, M. Spingola and Manuel Ares Jr., Test of intron predictions reveals novel splice sites, alternatively spliced mRNAs and new introns in meiotically regulated genes of yeast. Nucleic Acids Res. 2000:28 (8):1700-6.
Kuhn, Andreas N. and Norbert F. Kaufer, Pre-mRNA splicing in Schizosaccharomyces pombe; Regulatory role of a kinase conserved from fission yeast to mammals, Curr Genet (2003) 42: 241-251. DOI 10.1007/s00294-002-0355-2.
Pyle, Anna Marie, The tertiary structure of group II introns: implications for biological function and evolution, Critical Reviews in Biochemistry and Molecular Biology, 2010; 45(3): 215-232••I,SSN 1040-9238 print/ISSN 1549-7798 online © 2010 Informa UK Ltd., DOI: 10.3109/10409231003796523.
Mattick, John S. and Igor V. Makunin, Non-coding RNA, Human Molecular Genetics, 2006, vol. 15, Review Issue 1 R17-R29, doi:10.1093/hmg/ddl046.
Philipp Kapranov, Jill Cheng, Sujit Dike, David A. Nix, Radharani Duttagupta, Aarron T. Willingham, Peter F. Stadler, Jana Hertel, Jörg Hackermüller, Ivo L. Hofacker, Ian Bell, Evelyn Cheung, Jorg Drenkow, Erica Dumais, Sandeep Patel, Gregg Helt, Madhavan Ganesh, Srinka Ghosh, Antonio Piccolboni, Victor Sementchenko, Hari Tammana and Thomas R. Gingeras, RNA Maps Reveal New RNA Classes and a Possible Function for Pervasive Transcription, Science, vol. 316, pp. 1484-1487 (2007).
The ENCODE Project Consortium, Identification and analysis of functional elements in 1% of the human genome by the ENCODE pilot project, Nature, vol. 447, No. 14, Jun. 2007, doi:10.1038/nature05874, pp. 799-816. Nature Publishing Group.
Toor, Navtej, Aaron R. Robart, Joshua Christianson and Steven Zimmerly, Self-splicing of a group IIC intron: 5' exon recognition and alternative 5' splicing events implicate the stem-loop motif of a transcriptional terminator, Nucleic Acids Research, 2006, vol. 34, No. 22 6461-6471, doi:10.1093/nar/gkl820.
McClellan, Jon and Mary-Claire King, Genetic Heterogeneity in Human Disease, Cell 141, pp. 210-217, Apr. 16, 2010 © 2010 Elsevier Inc.
Mosthaf, Mosthaf, Luitgard, Kathleen Grako, Thomas J. Dull, Lisa Coussens, Axel Ullrich and Donald A. McClain, Functionally distinct insulin receptors generated by tissue-specific alternative splicing, The EMBO Journal vol. 9 No. 8 pp. 2409-2413, 1990.
Black, Douglas L., Mechanisms of Alternative Pre-Messenger RNA Splicing, Annu. Rev. Biochem. 2003. 72:291-336, doi: 10.1146/annurev.biochem.72.121801.161720.
Hartmann, Linda, Stephan Theiss, Dieter Niederacher and Heiner Schaal, Diagnostics of pathogenic splicing mutations: does bioinformatics cover all bases?, Frontiers in Bioscience 13, 3252-3272, May 1, 2008.
Holliday, Robin and Vincent Murray, Specificity in splicing, BioEssays, vol. 16, No. 10, Oct. 1994, pp. 771-774.
Steitz, Joan Argetsinger, Splicing Takes a Holliday, Science, vol. 257, Aug. 14, 1992, pp. 888-889.

* cited by examiner

FIG. 2A
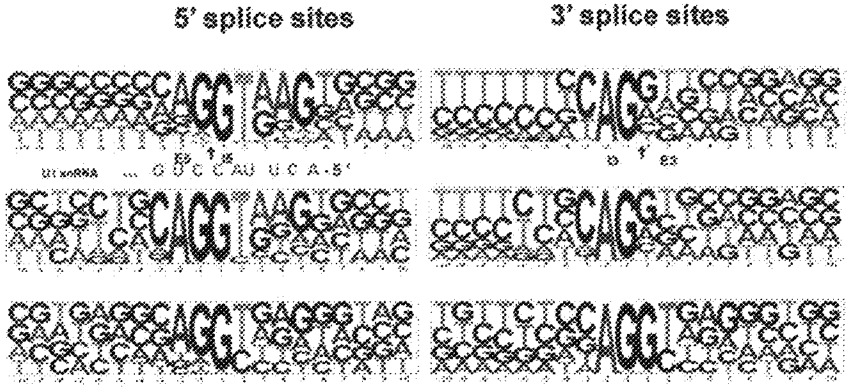
FIG. 2B
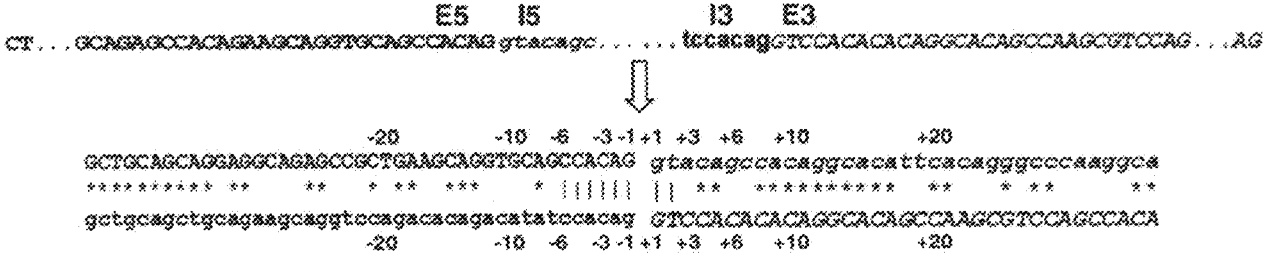
FIG. 2C
| | Datasets (# of introns) | E5-I3 with LIN ≥6 (%) | I5-E3 with LIN ≥6 (%) | E5-I3 / I5-E3 (ratio) |
|---|---|---|---|---|
| Human | 234643 | 0.544 | 0.176 | 3.08 |
| Mouse | 250095 | 0.527 | 0.220 | 2.39 |
| Zebrafish | 219720 | 0.432 | 0.130 | 3.32 |
| Chicken | 165347 | 0.345 | 0.065 | 5.34 |
| *C. elegans* | 88832 | 0.401 | 0.028 | 14.24 |
| *D. melanogaster* | 47174 | 0.231 | 0.051 | 4.54 |

E5 (total)

E3 (total)

I3 (total)

I5 (total)

E5 (E5-I3 LIN≥3)

E3 (E5-I3 LIN ≥3)

I3 (E5-I3 LIN≥3)

I5 (E5-I3 LIN≥3)

E5 (LIN≥3 for I5-E3)

E3 (LIN ≥3 for I5-E3)

I3 (LIN≥3 for I5-E3)

I5 (LIN ≥3 for I5-E3)

FIG. 10A

>isf1F1R3|insr|mm
CAGGGATCCTTTGGTATGGTGTATGAAGGCAATGCCAAGGATATCATCAAGGGTGAGGCAGAGACCCGTG
TTGCGGTTAAGACTGTCAATGAGTCAGCCAGTCTTCGAGAACGGATCGAGTTCCTCAATGAGGCATCAGT
CATGAAGGGATTCACCTGCCATCATGTGGTCCGCCTTCTTGGGGTGGTATCCAAAGGACAGCCAACGCTG
GTAGTGATGGAATTGATGGCTCATGGAGACCTGAAAAGTCACCTCCGTTCTCTGAGGCCAGATGCTGAGA
ATAACCCAGGCCGCCCTCCCCCTGCCTTGCAAGAAATGATTCAGATGACAGCAGAAATTGCTGATGGCAT
GGCATACTTGAACGCCAAGAAGTTTGTGCACCGGGACCTGGCAGCTCGAAACTGCATGGTTGCCCATGAT
TTTACTGTCAAAATTGGAGGTTGGAGGA >isf2F1R12|insr|mm
AAGAGCAGCTTGCTTCTTGCTGACACTTCCAAACAGTGGGCAAGCAAGCCTTTCTGCCTCTACATCTCTC
TCTGATTCATCTCACTTCTCATTGCCCTTCAGTAGTCTAGGCCCCCCTCCATATCCCCCCAGTACATCCT
CCAACCTGACAACATCCTACTACACAAGGGCGGTGATGTGAATAGAAGCATGTTCCTTCCAGTTCTCAAT
GCTTTTGTTTCTTTCTTTCTTGAGACGAGCTCTCGCAGATTTTAGGGTAACTTTGGACTTGCTACATAGC
TGAGGATGACAATAAGTTTTTGATCTTCCTGCCTCTACTTCTCCAAGTGTCCAGATACATGCACCACCAC
ACCTGGGTTTTGTATGGATTTTCTTGTTGCTCATGTAGAAAGTCTTTAGGATAATAAATATTGAATCATG
TCCCATCTCCCTTCATATAGATTGATGTCTTTGAGCATATTCCTATATGACTCCCATTGTTACGTAGAAA
TATAATATATAATATATCTCCTAGAATCATACATAGGTTCATCTCCCTATGTGCTTCCATAACTAATGTG
GGGGGGGGGAGATATGTTTTCAGATCTTTATGGGATCTTGCCTGTTCCTGATTCTCACTGATTTTGTAGA
GGAGAGGCAAATAAATCCTATAGCTTACAAAGCCCTTACATACCTGCTTCTTGGCTTTCAATGTAACCTC
ACAGCACACTGTCCTTGGGTTCCTCTATATCCATCCTATCCACACATATCCTATCCACCAGCATTCTAGG
CACTTAACATCTGCTTCTGTTGTCTCTTTCTTCTGCATTCTCTGACTTAAGCCTTTAGTCTTGTCAGAAC
CTATACTAAGTTTTATAGTAAGTTTTAACTGTCATCTGAGCACAGGCTAGAGTCTCCAGACAGAAAATCC
TCCACTGAAGAATTNCCTATATCAGATTGACCTATG > isf3FR2|insr|mm
TTATAGTCCCTGTCGGGTTTCGCCCACCTCTGACTTGAGCGTCGATTTTTGTGATGCTCGTCAGGGGGG
GCGGAGCCTATGGAAAAACGCCAGCAACGCGGCCTTTTTACGGTTCCTGGCCTTTTGCTGGCCTTTTGCT
CACATGTTCTTTCCTGCGTTATCCCCTGATTCTGTGGATAACCGTATTACCGCCTTTGAGTGAGCTGATA
CCGCTCGCCGCAGCCGAACGACCGAGCGCAGCGAGTCAGTGAGCGAGGAAGCGGAAGAGCGCCCAATACG
CAAACCGCCTCTCCCCGCGCGTTGGCCGATTCATTAATGCAGCTGGCACGACAGGTTTCCCGACTGGAAA
GCGGGCAGTGAGCGCAACGCAATTAATGTGAGTTAGCTCACTCATTAGGCACCCCAGGCTTTACACTTTA
TGCTTCCGGCTCGTATGTTGTGTGGAATTGTGAGCGGATAACAATTTCACACAGGAAACAGCTATGACCA
TGATTACGCCAAGCTTGGTACCGAGCTCGGATCCACTAGTAACGGCCGCCAGTGTGCTGGAATTCGCCCT
TGCAAGAAATGATTCAGATGACAGCAGAAATTGCTGATGGCATGGCATACTTGAACGCCAAGAAGTTTGT
GCACCGGGACCTGGCAGCTCGAAACTGCATGGTTGCCCATGATTTTACTGTCAAAATTGGAGACTTTGGA
ATGACAAGGGACATCTACGAGACAGATTACTATCGGAAAGGGGGCAAGGGACTGCTTCCTGTGAGGTGGA
TGTCACCTGAGTCCCTGAAGGATGGAGTCTTTACTGCTTCTTCTGATATGTGGTGAGTTATACATACATG
GGTGGATATTAGTGCTGGGCTTGAACTCCTGAAGGTGTCCCACTAATGTGCTCATCAGGAGTAAATTTG > isf4F3|insr|mm
GAGTGAGCTGATACCGCTCGCCGCAGCCGAACGACCGAGCGCAGCGAGTCAGTGAGCGAGGAAGCGGAAG
AGCGCCCAATACGCAAACCGCCTCTCCCCGCGCGTTGGCCGATTCATTAATGCAGCTGGCACGACAGGTT
TCCCGACTGGAAAGCGGGCAGTGAGCGCAACGCAATTAATGTGAGTTAGCTCACTCATTAGGCACCCCAG
GCTTTACACTTTATGCTTCCGGCTCGTATGTTGTGTGGAATTGTGAGCGGATAACAATTTCACACAGGAA
ACAGCTATGACCATGATTACGCCAAGCTTGGTACCGAGCTCGGATCCACTAGTAACGGCCGCCAGTGTGC
TGGAATTCGCCCTTGCAAGAAATGATTCAGATGACAGCAGAAATTGCTGATGGCATGGCATACTTGAACG
CCAAGAAGTTTGTGCACCGGGACCTGGCAGCTCGAAACTGCATGGTTGCCCATGATTTTACTGTCAAAAT
TGGAGACTTTGGAATGACAAGGGACATCTACGAGACAGATTACTATCGGAAAGGGGGCAAGGGACTGCTT

FIG. 10B

CCTGTGAGGTGGATGTCACCTGAGTCCCTGAAGGATGGAGTCTTTACTGCTTCTTCTGATATGTGGTGAG
TTATACATACATGGGTGGATATTAGTGCTGGGCTTGAACTCCTGAAGGTGTCCCACTAATGTGCTCATCA
GGAGATGTGTGT

>isf9FR2¦insr¦mm
ATTGCTGATGGCATGGCATACTTGAACGCCAAGAAGTTTGTGCACCGGGACCTGGCAGCTCGAAACTGCA
TGGTTGCCCATGATTTTACTGTCAAAATTGGAGACTTTGGAATGACAAGGGACATCTACGAGACAGATTA
CTATCGGAAAGGGGGCAAGGGACTGCTTCCTGTGAGGTGGATGTCACCTGAGTCCCTGAAGGATGGAGTC
TTTACTGCTTCTTCTGATATGTGGTCCTTTGGGGTGGTCCTTTGGGAAATCACTAGCCTGGCTGAGCAAC
CTTATCAAGGCCTGTCTAATGAACAGGTGCTTATGTTTGAGTCTC >isf10FR3¦insr¦mm
GTCTGTATATTTTAGTCACATCAGAAGTCTTGCTCAGGTGTCTTCTTCCCCTTCCCTTTGATGATGTTTT
CCGAAAACAGAGGGAGAATTATTTGGTCTGGATTCTTTGAGGATCTTTGGAAGACCAAACAAAGCAAAGG
GGACACACACACACACACACACACACACACACACACACTAGAAGGAAGTAAGGCAACAATTTTGAGAATA
TATTTGTAACATATTTAAAGCTTATGGAATCTCTGGTATGAGCCTAATAAGTTAGTATTTCTTTGGGAGC
AGTGGTG > isf11FR1¦insr¦mm
ATTTTAGCTGCTCTTGGCGTCCAGGGACCTCAGCTTGGGCCAGATATAGTGCCTGAGTTTATTTCTCAGG
TGCTTATGTTTGAGTCTCTAGAGACTAAAGTCTGGAGGAGAAAACATCAGAGACTTTCTTCTCACCACCA
AGAACTCGTGAAAGGACGTGAACTCACAACTTCTCTTTGCATAAAACCACAGCTGCTCAAGTAAAAGAAA
CAACTATGGTGAACTCAAAATCCTCCCAGAGGTTCTTTCCTGCGTGCATTTCCCACAAATATTTGATGCC
TTTCTTCTCCCTTAGGAGATATGAGATAAAGACACACTGGCCACCCTGATTAAGAACACAAGGAAACATA
AATCCTGGTTGTCAATTGCTGTGGAATTTATATTATAAAAATTGCAGCATGTAAAAATGTTGCCAGGGAA
CTCAATGATTGGCATAAGCATCAAGAGTTACAGTTACTTTTACCCAAAACACTTTGTAAATAGAAGGTCT
GTGCATCAATGGAAGACACCGTAGGTATGGATATTTTTTGTTTATTCTTCCTTTTCACAGTAAATTTGTA
GTGATGCTATACTAGCAGAAATTTTCACACCTTTCTACTTCAAAAGGTTTTCTTATAGTACCGGGGAAAG
TATTTATTTTAATATATAAGATCACTCTTGAAAATCACTTTTGTAAAAAAATGTTATGAATGTAAATTTT
TTTTTTATCAAGGAGAAATAAAAACAGGTGAGTGTGGGTCATTTTTTTTCCCTCTTCTCAGTACAGTCTA
CCTCAGTGTCTTATTAGGATGTGGTTCAGTAACAGATGTTGAGGCTTCAAGATTCTGGCTGAATCATTCT
CTGAGTTGGGGGAGCTGTGTACCATTTTGATTTTTTAAATGCCAGGGNCTAGGGGAGAANTTTGAAGGG
AGAGAGTTTAGATTAAAAAGTTAGAGCCCTTCCTGTGAACCNNAAGTCTTCNTNGNNGGNGATATTCNTT
CAGAGTATATTCTCCATACAA

SEQUENCE LISTING

```
<160> NUMBER OF SEQ ID NOS: 35

<210> SEQ ID NO 1
<211> LENGTH: 128254
```

-continued

<212> TYPE: DNA
<213> ORGANISM: Mus musculus

<400> SEQUENCE: 1

```
gccggcgtgg cgtgctctga tcgccggggt cccagcactc ctactgctat gggcttcggg     60

agaggatgtg agacgacggc tgtgccattg ctggtggccg tggccgcgtt gctggtgggc    120

acagccggcc acctgtaccc tggagagggt aagtctggga caagaggcga tcacagtatg    180

tcggggacac ttctcccacc gccccagcca atctagaacc ctcaccctaa ggagtgaggg    240

tcggggacac ccctctccac cgccacagcc aacctagaga attctccctt tgggctgagt    300

aatggggaca acccttccca ttgctccata caacttagag ccccccaggc cccaccaagg    360

agtcagggtt acagacaccc atttcaccac tccagcaata tagtcctttc acgagagttg    420

tggacatttc tcgttcttct tccatcaacc tagagccccc tctccacgga ctgaaggttg    480

aagactcccg tagcgtcctt gtgtctatga agagtcccct ccctatagtg atcatcttta    540

cactggggaa ggggaagagt gggtttggtg gccctggccc tgcgtgaaac cccggctgac    600

cttggccttt gctcactggg cttgtggctc tgtaccccgc gtgtgtccat ctcgggtctg    660

aggaaccttg ccccagtgcc cgcccaggct tcgggtgtct gtccccagtg cacctctcaa    720

ctgtgtctgt tcttttctct aaccccaaat ctgtcctctg aggctctttg aggttgcttt    780

aagtaagtat ggttactggg ttgcaacaga ttcagacatc tgagcagttt aaacccaaag    840

ccaggggtat cctcttcgac ggaggacact tgttggagaa tcgacccctt gtggctgcta    900

tgtttataat tctctacttc cagatgtcta gaggcaaagt ctgcatacct ttggccccac    960

agcaatcata gtaacagtag gggtagtttt caggatggtt ataattagaa tgattatgag   1020

tctccaggct ggttagcgct agaacctccc agtgttccct ggaggccaac atagttacat   1080

acccatttca gagagggcta aaatgaggtt cagttagccc atttgttcag aggctggtct   1140

tatagttctg tgcttggtta tggccaaggc aggaggatag cgagttgttt gaagcaagcc   1200

cagctattga gtgagttttg aggctagtta gacactgttt caaaaaacat gcaatgacaa   1260

atgtcttttg agttactggt tcagctttct ctgaaaatgg aaattaatta caatagggaa   1320

ggggtcaagg agagaaggaa ctgccacgct tttgtgaatg agggagatgt gtgtgttggg   1380

aggagggtgc aggattatgg aacaggttgg gttgatcttg tggagtgggt ctgctaaact   1440

ggtaatgtct ctgaggcccc caggatccga tatacagaag gtactcaatg aggaatggcc   1500

attggtttgg tttgtgcccg agtgcacgtg ttcgtgcgtg tgcatgtgtg ttcgcgtgtg   1560

cactcctgtg cctgtgtgtt tgtagaggac ctaggttgac atccagtgtt tgtctctgtc   1620

actttcagcc ttgtgttttg agtcagggtc tctcaatgaa ccttgagttt gctgatttgg   1680

ccgcactgcc tagcctgtga gtgccagttc cccctctccc ttcacctctt tttatcacta   1740

gagttataga tagatgtatg ctgaagtgct ggcttttagg tgggtgtgga gagatctgaa   1800

ctcaggtttt catgctcggg cagcaagtgc tttgacttac tgagccatcc atctcagtaa   1860

gtaaaaacgg agccagtcca tggtttgggt tcttattaga aaaatccaag attgttaaca   1920

tctacattgc tctctgaggc cttaaggaag tagggttatg ttgtatatgc acctgtgcac   1980

ttgggcgcat agtgttgtac cttgagctct gcttttacat tttttggtaa ttgattgttt   2040

gtccatgtct ggacttcctg agcccaggag acagagcttc tgggggcttt taaatataca   2100

tgcagtgttc acaaggatag ggcctggtgt ttgttcctca ccgatgttag aacctgagca   2160

gtgctggaca catagtaggt gcatataaac attgttccct aatggcacac agaaagccaa   2220
```

-continued

```
gacattgggg tttgtgcagt aaatatactg ggtgtgtggc cagagtgtag ccctccctgt   2280
gcacacacaa aatccctggg tttcatccct agacttacat aaaccatgtg tggcgttgta   2340
tgcctgtcag caagcactct gaaggtatag gcaggtctat caggagttca aggtcatcct   2400
gggccaagtt agtgattttg aggccagcct gagctacggg tgaccctgcc tcaaacaaca   2460
acaagaataa caaaagtctt aattttctag aaaatcccca tactttgtaa atatgatctc   2520
atgagtcctt cccacacctc ttcaaagcct ctggcttttg catgggatga aaggacagga   2580
ccatgaaggc agctggctgg ccacatggct agttccctgc tgcctactgg ctttctctgt   2640
ttccttagtt ttgaatttaa ttaattaatt cgttaatcta gctgagacca ggtcctgtgt   2700
gtagcctagg ctggcctatg tagaccaggt tgtcctctta actcacagag acctgcctgc   2760
ttctgcccca gaagtcctgg gattaaagtc attatgccca gctttactta ttataaattg   2820
agtgtacgtg gggccgcacg catgagtcac ggtgtgggga tcagaggaca gctttcagga   2880
gtcagttctc ttctactatg ggttctggag attggactca ggtcatgagg cttggcagca   2940
agcgctgtta cccatctccc ttgaccttgt actggatttc ttaatagaca cttgctcttt   3000
tggattggaa cctcccggac cctgctttgg ggtaatcgtt aacaaaatac tatcaaatga   3060
atgagtcgtg gtgcctctga gaggcttggt gtagggcaag gaactttcta gaacatgagt   3120
atgtaacatc caccaacagg gtatgtttgc ttgggagggg aggttgtggt ggtggtgagg   3180
atctgtgtga tgctaagaaa ggaatgggtg ttttttgaga gatgcatccc taagggcagg   3240
ttacccagtt gtctttcggt ggagtcttgg tagctgggct gggctaaatg gataactcct   3300
ccgttcctct cttgatcagc ctggctctgg gctgagataa ccctctgagc attgtgaagt   3360
gagaggacaa ggcagtgtgt agtgctgaga attagaaccc tctgagtgtt ggggcatctt   3420
cagtcaggtt gacttttaga ggtacgagtg gtcaccttcc atggctcatg tgtgtgtgag   3480
tgtagtggat atatgtgctc atgtgggtgt gttcacgtgt gtgaggtcag agctcaatac   3540
tagatgcctt cctaagttgc tttcaacctt ttctttttat aaaattactt cctaattaaa   3600
aaaaaaattt aattttgcag atgtatgcat gttttgggca catgtgtgta tgtgtgtgct   3660
catatgtgtc agggcgtgtg tgcagaggtc agaggtcaac cttatggagc cagttctcct   3720
catctatctt taagtgtgtc ccaggggtca gactcaggtc ctcaggctcg tgtggcaagc   3780
tctttcacct actgagccat cttgccagat cccaagcttg tcttcttaac ttcactgctt   3840
ggggtcggct cactctgggt tgtagcggct gttttagctc cactaaggtg tttagtgggc   3900
acccttggtc tctgctagct tgttgccagt agcatctgga tgcgtttaag ttgcaacaat   3960
gaaaaaaagc ttcaatcatt acagacactg tctcagacac ttgcctgcag atgccttgct   4020
tccccctctc ctccttctgg aatcttccat ctccttgcag ctcttctctc tttaaatacc   4080
tcatataccc taaattccat tagtcacttc tgacctctga ttctcctgtg ttctttcagg   4140
gacatactct cacactcttg ctgtcttgtc tgttggctgc tatacggtgc ctctcttatg   4200
cctgaataca accccttgcc tcccagtccc atctcctgcc agtctggcct cagggaccac   4260
cttgggtttg ctttcctggg ttcttcagta ggggtaccct tgttcttttc atgtgtgtgg   4320
tgtgtaggct gcccttcacc cctctcctga cccactgtgg cagttctagc tagtcacaag   4380
tctgcaaaag aggtcagtaa actggggaac ctgtgctaaa ttcactgtaa aattttattg   4440
gcacagggcc acacaccttt gcatactctt ttctgactac tttcatgccc tgatcttagg   4500
gagttaagca acaacaacaa cgacaacaat gacaacgaag acaacagtga caacatgtac   4560
acgtcagcct ttcaccaaga cttttctgga ttatggcttt tttttggag ggggggggtgt   4620
```

-continued

```
ttgtcttcag acctaggaac ttgaatatgg cagacaagtg ctgagccact gagcaccctt   4680
cttcctccat ctccttcctt ctttctcccc tcatctcctc tttttcccc cttcttcctt   4740
ctctttcttc ctttttattt ctaacttcct ttccacccct cccaaccacc ttcttcttct   4800
cctcccctct cccctcttcc tctaacatat ttccttattt tctttttcat tttggagaca   4860
ggctcataca tagcctaggt tagcctcaaa tttcttacgt aactgagaag aatgttgaac   4920
tctcaggccc ttgcttctgt gtgctgtgat gacaggggtg agcccggtat acgtcatctg   4980
gtggatgcag aactgggcat ggaaccctgg gctttgcttt tctgggcaag ctctagaaaa   5040
actgagccac atctccagct ttctatgtaa taaacataac tagcctttat ctgtccttca   5100
tctgtctatt cataactcaa agagaactca aagtcctgta gtcatttaaa ataatattgc   5160
tttggagact gggaatgtgg ctcagttggt aaggtacgtg cctaatgtgc agaaagcctt   5220
ggattctgtc catcgtgctg cttaaatgag gtgtgggggt gtcccccgct aacaacactt   5280
ggtaggtata gactgaaaga tcaggaattg aagcttatcc tcagctacat aggaagtcaa   5340
ggccagcctg ggctttggga gggagaacct gtctcaaaac aaagggtctg gagacattaa   5400
ctccagtccc accttaagag cactggttgc tcttctagag gccctcagtt tgatttccag   5460
cacccaagtc aggaggctcc taactgtctg taactccagc tccaggagtc cctgaaggaa   5520
tgcacacata cccagacaga cagacagaca gacagacagc agacacactt aaaacaactg   5580
ggtgtcatat tgcatgcctt taaccccagc actcaggagg cagaggcaga tctctgtgag   5640
tttaaggata gcctggtgaa gatagtgagt tccaggtcag ccagagctta tatagtgaaa   5700
cctagtctaa caacacacaa gcaagcaacc tagatctaaa acacccaact ctctcaaaac   5760
aacaaacaaa aaaacccaac ctcaacaaaa caagacttaa aaataaataa ataggggctg   5820
gtgagatggc tcagtgggta agagcacccg actgctcttc caaaggtcca gagttcaaat   5880
cccagcaacc acatggtggc tcacaaccat ccgtaacaag atctgactcc ctcttctggt   5940
gtgtctgaag acagctacaa tgtacttaca tataataata aataaatctt taaaaaaaaa   6000
ataaataaat aaatattatt ttaagaaaat taccgttgcc tattgaagat tttatgtgag   6060
ctgaagtgct gtctcctgag cctcacctct tcctctggat agagcccatt catgcacagc   6120
tgtacacttc tccaaacatc tgcctgttcc ctctcaatcc ttggatcccc taattccaac   6180
ctggctaagg gaagggtaga aggaaaatga cttttctttc tctacaagat tttctgtttc   6240
tctcctcccc ttctgcctag ttagttcatg ctgactgcaa gacttgcttt ctatatgtat   6300
ttacctattc ttttggtttt tattatctat ctatctatct atctatctac ctatctatca   6360
tctgtctgtc tgtctgttgt ctacatattt tttttgaaac agtgtttcgc tgtgtagtgc   6420
tggctatcct ggaactcacc ttgttgacca aagatctcaa actcagagat ctggctgcct   6480
ctgcctcccc agtgctggaa ttaaagccac cacactcagc ttattctttt atttttttaaa   6540
gattttgttt ttaattattt gtctgtgtca gtgtgggttt gtgcatgtga gtgcagtgtc   6600
tgtggagacc agatgagtgt gtatgatcca cctggagctg gagttccaaa gcattgtgag   6660
ttgcccagca tgggtctgga actgaaccct ggttgtctgc aagagcaata tgaactgctg   6720
ggcagtggta gtgcatgcct taggaggcag aggcagacaa atttctgagt tcgaggccag   6780
cctggtctac atagtgagtt ccaggacagc cagggctaca cagagaaacc ctgtctcaaa   6840
aaagccaaac aaacaaacaa acaaaaacca atatgaacta ttaaccactg aaccatccag   6900
tcccattttt gattttaagc catctgtata gatgtgtgta ttctaacact cagactcaga   6960
```

-continued

```
acagtttcat caatggctat actctctctt accacctctt tactattttt ttaaattttt   7020
aattaactca ttaattaaaa aatttcttag ggcaggattt tactgtgtag ctgaggctgg   7080
cctggaactg ctaatgtgta gcccaggttg gcctggatct tgtggtgatc atcctgcctc   7140
tgcctccaga gtgccaggat tacacgtctg tgccccccatc ccagcttcca cctctctgat   7200
gccataactc catccctata atctataacc tatagattat atactataat ataatctctg   7260
tttccagagt gaaagaaaaa gtcctgttat tagatgaata aattcttaag actgaaagtt   7320
ttggtccttt tatccccagg ccctagtatt tataaagttg cttgtttgct gaaatttatt   7380
tggaacccct agattaattc ctgtaataca cttatggtta tttgaggaca ttcaaaacta   7440
aaaaaactgg agctttgaat ttgcaggcca gccaggtaac actctacgtt ctgcaacaca   7500
aagctagccc atgaatgcca tgttcatgac tggggatcag tgcatgcgga tattttgtta   7560
ttgtattatc tttttgtttg tttcttgttt tccctttgag gcagtaactc agtagttcag   7620
gttgatctca gattcgctgt gcagctaaga atggtcttga tctcctgatc cccctgcctc   7680
caccttctga gtgctaggat tatagacacg cactcccaca cctggtttat gctggggatg   7740
gaatccgggc tttgtgcatg catggtaggc cagtccttta tccactgagc tacagctgga   7800
gcccacaact gtctaggctt cctgtctgct catttttgtg tcttttgttg gggatctggc   7860
tattaaaatg acccccctgaa gccacacagg ctgtacctca gagagtctgt gtactcagag   7920
atactcggcg gtcatttgtg ttcactgttg caatgtgcag gatagccaag ctctaggaac   7980
agcctagatg ttcattggca gatgaataga caaagaaaac atagtttata aaatggaatt   8040
ttatgcagcc attaagaaaa atgtaattat ggcattttaa agaaaatgaa tgaaactaga   8100
gatcattatg ttaagggaaa taatccagat ccagaaagac aaaaaaccac ctacgccatg   8160
ttctctttca tgtatgggat ataggttaaa aagtatatgt ggtatgtgtc tggtgtgtgt   8220
gtgtgtgtgt gtgtctgtgt atggtgtctg tgtatctgtg tgtctgtgta tggtgtctgt   8280
gtgtctgtgt atggttgtgt gtgtctatgt atgctgtgtg tgggtgtatg gtgtggtatg   8340
tgtgtcaatg tgtgtggtat gtatgtttat ataggagatt gtgagagggg aggaagagat   8400
cttaagggag gtgggaaatc agttgatgga atgcctgtga taacagagtc agaggtgagc   8460
tggggctgtg ctcagtgggt agagtgcttg cctagtaagt gtgaaagttt ccatccccag   8520
caccacataa acaagaccca tagctgttgt cctatcactc aggggatgaa ggcaggagga   8580
tcagaagggt ctgttgtcct tggctacgta gtgagtttta ggccagtttg ggctacatga   8640
gaccttatct caaaagtaaa taaatacgtg attgtgagca gacactcctg aggcacccgg   8700
cccattacca ggtaatttag ggtgttccat ggacagaact aatataaaca attggttgta   8760
ggtgttcctc atgattgggg tgtgatagtt ttgagtttca atttcccgtc tagagtactt   8820
tggaatgcaa acgattgttt ttgctaatat tttcatcctt ggttatactt tctgggaagt   8880
tcaatgtgac ttgggacacc ccgggcttga gtgccagtga acaggttgga atctgttgcg   8940
ggaaatatta aaaaatgaac ctgccagctc tccacagtat taggccaccc ttctgtgccc   9000
tgccatcccg ccaactctct ggtcacgctg gaccacaggg ctcccgctgg gccatgtctc   9060
cggcacgggg tggtggtggt gataatggtg gaggtggcag gggccctgga gtttctctcg   9120
ctaccaagca ccccactgtc aaccatcaca tcacaatacc cagtaccctg gtagaatcag   9180
gactcttaat gcttaattaa ccaatcagat ttatgtatca ataacatcac aattcacaag   9240
atgccaatac aataatttca attgataatg ataaaagctt tatcccaata tttctaacct   9300
tgtgaaatca tagctacttg tggctggaaa acgccaagca ggtacatgtc tgcagccatg   9360
```

-continued

```
tcctcctcct cctctgagag gctttctgtc tctgccactc ttagctccgc ctccctttcc   9420
cctgtttaat cacaggcctc ccaatgccct aatgtagttg gacaaggaaa atcctggagc   9480
aggaacctgg gagtacttca ctctctggag tttaacaaac taattaattt tttttttttt   9540
tttttttttt tttttttttt ttagaaaaaa cacttattta ttttgcgtgt atgggtgctt   9600
gtggaaatca gaagacaacc tgcagttggc tcttttcttc caccatggcg cctaggtggc   9660
tagcatccgt gcatattccc tgagccacct cgccagtcca cctttttaac agtttagaaa   9720
cctgttctgt ttcttccgtg gggcagggag ggggattttt ctggtctgcc tgctgaaggg   9780
cacaggttgt ttctttgcag tatgtagtat gtgtgtgtgt gctcagtaag gagcacaaag   9840
tgacgtggtc aaatgctgaa ctcacatagt tcagaaccca aatccacaaa tacagagagt   9900
tttggttgca agcttttcca agttggggag atggttgtga gtaagataat taaccttgca   9960
atcctgagga ccagagttta gattctcaac atccatgtaa aacaaaacaa aaggaaaaac  10020
caaacagaag tggctctgtg cacctgcatc cccaggactg gaggatggag gctgcaggat  10080
tgactggttt cctagggata ctctgagtat atgtaagctg cacatctctt tacttaccac  10140
acacacaagt gatgctggca tacatagcct gctcatctca ctgataacat cttaggatcc  10200
ttctgtgtca tcgaggtgag ccccctggca tctttttata ctattctatc acatctgggg  10260
ctcacagaga gatcttttct tggtgtgtca ttcccctcac cacatgttct gaaaggtgtg  10320
gaggaccatc tacaagtggt tgaacacaac ctcaaacttc tctttcataa cccgtgaaac  10380
atgtagtttg aaaggcaata tctatttctc tttaaatttt taaaattaca ttcatttatg  10440
cagtatgcat ttgtgctcag taaggtacag aggtggaggt cagaggacaa cttgtgtgtg  10500
tggggggggtt ggttctctcc ttccacgatc ctgggtgttg actttaggat gtcaggcacg  10560
atgagccatt gagctatttc gttgtcttag gagaaagcag cttcaatgat aaaaagaact  10620
tggaaaccag gatcctggaa taggggacca gggatggttt taaagacatc tgtgactaag  10680
gaacaggcat tgctgatggt tgaaacagag acactcaaat tctgaccata agaaaacatt  10740
tttcagaacc tgctggacct tgtcttcctt gctctatcta gcacgtctcc tcttctgtgg  10800
tcatagtgga gagaaagcca cagaagaaga aatttccaag agggctctgg tagcagtttt  10860
tcctcctttt agaattccca ggctcctaga aaccaggaat cagtcctttc caatgagaca  10920
ctctgctttg agggctgggt tgatggtgga tgagtgctcg ctgtgaaacc aggagagtct  10980
caattcaacc tccagcatct gtgggcatga cagagcctaa tgggccctac gagctcatga  11040
tgaagctagt gagcctcaga ttaatcggag accctgtctc aaggcaatat ggcgcagagt  11100
gatggaggaa ggcacctgac gtcccactca cacattttct tgtttggctt cgtccagcat  11160
ggcagccccg atccacaatt ctgaggttat tgaaactggc caggggaaga gtttttagat  11220
tacattttgt aattactttc aacaattatt tacttttgta tggatgcata tgggctcgtg  11280
tagaagccaa aggacggctt ggaggcatca actcttcttt caccatgtgg gctctgggaa  11340
tggaattctg gttgtcagac atggcagcaa ttgcctgtac ccactgagcc atcgttttgg  11400
ctcttaaata aaaagactca ctaaggaaaa aaaaatttat aggtcaggtt caaaggaaac  11460
ttcatctccc caaattctgg ttggttagac aaaagtcagc attcctcagg aacgtcagaa  11520
gctaagctcc cctctactaa aagaagccat ttccctttat caccggaaga agggacagat  11580
gacttatctg tggtgcctat cagcatgtca gaagtacatg gtggcctcca ggctcccaca  11640
gtgccaatgt acattggtct tctcacttcc ttccccaccc tgaatttctc ctgtacacga  11700
```

-continued

```
gctttcttcc tccagctatt ccttacaacc tatgttctct cttggtcttc tcctgtgccc  11760
acattctctg tcttcttctc acactcttct ctgtgcctcc tctctctgct ttgcttctgc  11820
ttccctcagg gccagggcca gggccagggc cagggccagg gccagggcta gggccagtgt  11880
gttggccatg ttcagtcaac tgctttctct ttggattctt ccagataccc ctggctattc  11940
tctcttatct acaataaaaa ccttcctctg aaacatgttg gggctgtctg tctacacagt  12000
gtgtttgtgt gtgggtatgt gactgagtgc cggtgccctt ggaggccaga ggtgttaggt  12060
tccccactgg agttaagttg tagatggttc tgggctagtg ctgggtacag aagaccagta  12120
caagttctta accaccaagc catctcttca ggtttttcttt ttttctttca gtgtgtcgtg  12180
tgtagtctat gtatgtgtaa gtacgtggag agcatgtggg tgggtatgtg tggaggtcag  12240
aggttgacat caggatattc cccctctaaa accagtctcc gtcttatttg ttgggatgag  12300
gttaaagctt tgttgattag gtttgacagc ccagtgaacc ctgtgacctg cctgtctctt  12360
tcttcccagt gctgggccac aggcatgtgc tgccgtgcct ggctttttct gtatggggta  12420
ctccttcctg tgctgtgaac aagttaccca cggagccatt tcactagtcc ctaggtgtgt  12480
gtttatttgc ttatttattt ttgtcactgg ttcgcatgta gctcattctt gtctagatct  12540
ctctatgtag taggaacctc tgggcgcttg aacccctgcc cctcctgccc ccacttcctg  12600
agtgttggga tgagctgctt gtatcacgat acctagttgg tgtggtgcag aggatgccac  12660
acaagacatc tctgtatgct agaatcagga gtttaaggtc atctttgact ttgtagaatg  12720
tttgaggcca gcctgggttt catgagacta tcttggtagc attatctatc gacaacagaa  12780
acagaaaaaa gaaagaaaga aagaaagaga gagagagaga gagagagaga gagagagaga  12840
gagagagaga acaaaagaaa gagagaaaag aacaaaagaa agaaagaaaa ggacaaaaga  12900
aagaaagaga aaagaacaaa agaaagaaag agaaggaaag agagagaaag aaaacttcat  12960
cagggtgtga cagcataact gtgatcctag ctctgagaag gctgagctag gaggatatgg  13020
gttcaaggct agcctggact acagaacaag atctagtctc aaaggattga aacacaaagg  13080
aaaacaacat caacaaaaca accaaggggt agagaggtgg gcatgagcaa gtgatgggcc  13140
aaaggctggg gggattttag ctgctgagag gacctttcca cttgctgctt tgggcacctc  13200
cttgtaaatt agatactcct tgcttagatt tgatttattt tgttttatgt atatgagtat  13260
tttgcctgca tgtatgtctg tacatcaggt gtgtgcctag tgcctgtgga ggtcagaaga  13320
cgatgttgga tcttctgggg ctggagatac aagtgtttgt gaggtgccat gtgagtgcag  13380
agattcaaac caagaacagc cagtgctctc aactgctgag ccatctctgc aagtccctta  13440
tttaaacctt gaagtatccc tcattcctgc ccacaggggt ggggctggag caaagctgct  13500
ggaggtccta tgagaatttc tggtgccagt tccatcttct gggtattttt tcccctgttc  13560
cagcagtaaa ttgttctatt gttttcaact agcaggagac atcaggcttt aatgagttaa  13620
gagttagatt cactgggaga ttagaaaagc aaagtgcttc tttattgccc ctgcaattag  13680
atccttttaa tctttattta tagtagctta agtgagagag tttacatgct atatggatct  13740
tccagcgcaa gcacataatt cagtcgtttg gagtgtattt gtgggattgg gcaacagtca  13800
ctacagtcag ggttagaaca tttttcttat ccttcaaaga agcactggcc ccttcagccc  13860
ccctccttgg cttccagcaa ccactagtgt acgtcctgat tctctgggat ttgcctcttc  13920
tggacacttt aaatagcact ttcccacaca ctttgtggga agaatgtatt atatttttca  13980
aggttcatct gcatggtagt gcccatcaga actttactta ggccacagac atgagttcct  14040
tgatggcatt tgagtggtat ccagtctttg gctagcaaga aaaattgtca tggacgattg  14100
```

```
catgcaagtt ctttgtgtac ttgcatgcat gcacgtggac cttaaaggtc acttttttcct  14160
ttctaaatac ttttttttta tccattatat tttgattatg atttttcctt tctcccaatt  14220
cctaccagat cttttatacc tccgatgtac ccaactttct ctgtctctct gtctctctct  14280
ctctgtgtct ctcaaaacaa acaaacaaat aaacaaacaa acaaacaata gaccaaacca  14340
aaccagaaat caacgccctc aaaatctaca aaaacacaaa aaatgaaaat caaaataaaa  14400
aaactaaaga ccagtaagac aagaaaaaaa aaagtctaca aaatatcatt gagctcattt  14460
tatgttggcc aactcctgct cttgggcatg gggtctaccc tgaagtgtaa tatacccagt  14520
gagaatccac tgaagatact tttccctttg ccattgggta tcagttgctg atagcttcct  14580
ggttagaggt gggagcccgt gtgcattgcc ctctcttagt ggtgggaccc agcctgagtt  14640
gaccctgtgt aggccctgag catacctta cagtctctgt gagttgacct gtgcatcaat  14700
cctgttatgt ctggaagaca ttgttttctt ggagtcatcc atctgctctg gctcctatgg  14760
tctttttgct ctctcttctg cttagttcct tgatccccca aggggaagta ttcaacattt  14820
catttaggac agcgtgttga agttctctta tcctttgtac actgtctagc tgctggtctc  14880
tgttagttcc catctactgc agaaggaagc gtctctgagg atggccgagt gatacacaga  14940
actgtggtat agcagtatgt tattagaatt aattgttatg ttcttttagc agagttattg  15000
cattagtttt cctatagact cataacctat ctgtctcagg ttcttgaccg ttttagcctc  15060
ttcaggtata gattccattt tatggaggag gcctgaattg tgctcagaaa atggttactc  15120
ccatggcatt tgtgccgcta ttacaccaat atactaggtg ctgtccaccc agagctcagt  15180
gtttagggta ggttggcttg tctgtggacc ttcaggattt ttctgtttct gcatctccag  15240
cacttgaatt gtaagtgtat gcatctgttt ctgccttttc ttttttcttt tcttttcttt  15300
tttttaaatg tgggttttaa ggatggaaca caggatcttc atgtttgtgc agcaaggact  15360
ttaccaactg agctcttcct tccttccttc cttccttcct tccttccttc cttcctttcc  15420
ttgtttcttt gtttggttct ttctttctat ttcgcatcag tggtggattg atatgtgtat  15480
gcatggtagc atgtgcatga gtgcatgtgt ctgtgcttgt atgtggaggc cagaggttga  15540
ctgatgttgg atgtcttcct tgaggcaagt gaggcagggt ctatcatctg aaaccagagc  15600
tctcttattc agctactcat caagtccatt tgttttgggc atccttattg ttgtctccca  15660
agtgctgggt ttacggagag actgcccatc tacctgccat ttatgtgggt cctgggaatt  15720
gaactcagga cctctggaag agcagtcagt gctcttaacc actgagccat ctctcagccc  15780
cccaactaag tcctttttaa attacccatt ctctcctttt tattcagccc aggaccccag  15840
tccatgggat aggattaccc acattcaggg tagatcttcc catctcagtt aacccagtgt  15900
agaaacttcc tcacagatat accgggaagc ttgccttctg agtacatcta gatcctgtcc  15960
acatcaagat taaccttgcc acaatatatc tatctatgag tctctgactg tcactatgtc  16020
catgtatgga agccattgag gtgtctctgg ctaggaattt cagacctgct tggtgtgaat  16080
acaccgggtt tgacctggtg tcctgatctc ttcaaagctg tctcccagcc aaggctgtag  16140
gtaccattgc agggggcctc ctgctctgtt cagaggcagg ttggcaagta tcttgggcag  16200
ggtggtggtt ttattgttgc ttggggctgg ggcctctaac ttcctcatga cttttatgtt  16260
aattgagttt aatatgctct gtgtgggttg taaggcaaga gcaccaaacg caggagcttc  16320
tggaatcact tttgcaacgt tttcctaact tgtgcttctt ctgtggttca ttcccagcaa  16380
agatttacat gcattgtgtg tgtgtgtgtt catgtatata tgcatgtata tgtgtgtgtg  16440
```

-continued

```
tctctctgtg tgttcatgtg tatgtgcata cctgtatatg atgtgtatgt gtgtgcattt  16500
acacatgtgc acatccatgt ggaggtcaga cagcaacctt gggtgctgtc cctcagacac  16560
cctgttgttt tagacagggt cctcactggt ctggaccatg gtagtctgtc tggctagcca  16620
ttgatcccca gggaggctcc tatctccacc ttccttgtgc ggaaattata agtgctcact  16680
accaaggcat ggagttcatt cagccttcag gcttgcaagg cagcacttca tccactgagc  16740
cagctctcca gcttctttta tttggagata gggtttcatt attttgccag gctcaaacta  16800
tctgtttctt ctaccttagc ctcctaagaa gctgtgtctc tgtggtgtgt gtgtgtgtgt  16860
gtgtgtgtgt gtagttcaga ggatgttatt ttctttgtac tatttgagtc ccaggaattg  16920
aacttcaacc taactttgtt aggtttgggg aaggactttt acctgttgaa ctatctcagt  16980
gaattccaga gtagatttta aagaggatgt ttaaaaaagt ctatttgcct caaagatatt  17040
gggtgttttg gaataaagta aataggggtt gtatgggtgc agagggggta ctggttggta  17100
agaaaaatac tatctaagga gtgtgatttt gacaagttct aactcatgtg taaaggaaca  17160
cagagaaggg acagaatgtc tctaagggac catgacccgg agctgagcag agtgtgctgt  17220
acacacatgt gattccagtg ctttgcagaa gccagaacga tctagggaga tagctcatct  17280
tgtaaactgt ttgcctttgc tgtggaagca tggggacaga ggaggaagag gaaggagagg  17340
agaagaaaga gaaggaggag gaggaggagg agggaaggag gagaaggagg aggagggaga  17400
ggagaagaag gaggaggagg gagaggagaa ggaggaggag ggagaggagg agaaggagga  17460
ggagggagag gaggaggaag aggaggaggg agaggaggag aaggaggagg agggagagga  17520
ggaggaggat gacaagaaaa agaagctgag gaagatggct ccgtcaataa aggattgccc  17580
ttgcaagcat ggggaaccta accatccaac agctcatgct tgtaatccta gctggagcag  17640
tagagaaaga ggggatccct ggggcccact gacctggcgg ttagcctact cagtgggctc  17700
caagccagag agaaactttc tcaaaaaggt agtaagaggc atctgaggaa gaatgacact  17760
gtcgtcctgt gctggaggtg tggatgggag ttgcaagggc acaagatggg ctcgcccata  17820
tatgtgtgtt ccatatttgg ggtgtggtaa acatcgacac aggtatacct gtatactatt  17880
caaagcctgg gctcttatct tgaattcctc tttttttttt attgctcctg acaggtcatg  17940
tgacattggg gacaaggagt tttataattg tttgaaagag taactgttta gcatggtgtt  18000
tgcttcctgg gaaggagagg gtatgtttca tcttacaggt tatagtatgt tgtgaaggga  18060
agtcagagcg ggaacttcaa ggctgaagca gagacgatgg aggaactctt ctcacaggct  18120
tgcttctcct ggcttgctta gcttgctttc taagacaatc caggaccacc tgcctggggt  18180
ggcaacaccc acagtgggct gggcacttcc acatcaatca tcagtcaaga aaatatccca  18240
cagacttggc ctacaggcga gtcagatgaa ggtagtttct aaatcgaggt tccctcttgc  18300
cagatcactc aagtttgtgt caagttgaca aaactaatca gcatacatgg cttatgggac  18360
agaggttttt aggaatattg aggactgtga ttatggagtg tgcaggacta tgggaagccc  18420
tggtgcattg tgttggaatt ggcaggcaca ccatgcttag gagatcagca cttccgttgt  18480
gtttgggcaa agcgatggag actggatttc ctgggaagcg cttaccacac ccaggtaaaa  18540
gggaattaga ctttaattgg tagcccggag gacaggccaa ggaagtggag tcagccaggg  18600
aggtgggtaa acacaaaacc aatacattca ttctgatgtg actttttttt cccctgtcag  18660
tcacttcctg aagaacttcc gtgctgaggc tcaggggcac tgagctgggg tctgctgctc  18720
tttcctctgc acttgacatc ttactcaacc ctcagtaatc ccgctgagcc gattgcctca  18780
tagatagggt gacgattatg ttcaggcttt gaatcaggcc tgccaaagga attatgttat  18840
```

```
ttgctttttg aaaggaatta tttaggcatg gttgctttac agggagagcc attcatcggg  18900
gctggcttaa gagtttgaaa tgcagagccc acaatgggtg accacaaagc tggcactgtc  18960
cctaattgta gctttcccca tcttggattg ggcagagggc tgtctgcata gtaggcaggg  19020
gcctctacct ctgaaccatt gccccatctc ctccctcact ggggaattct atgaagggct  19080
atgtaccctc actgggagat ctaggcaggg gttctacagc tgaacagtgt cctcctgtga  19140
cacaggttat ctttaaactc ataatcctcc tgcctcagcc tctttatcaa tggagtttaa  19200
gtggtcacca tgcctagcac atcatatatc attatctgtc atccacagtt agggcaatgg  19260
ctggtatcat aaagacaaga agtaacaaat actagtgaga atattaagga aggggagcgt  19320
ttacatactg ttaacaacca ggaagattga aaaggagtcc tagttctttt tcttcctcaa  19380
gtcttttggt tgacttatag acgaatgggt ttcacgcgat gtcatcttat gtgcatcgat  19440
cgtaccttgt ttatcacctc tgctgcattt tctgcactca gctctctgct cacccattag  19500
tatctttctt tactcaactg gtctctcttc tgttcctgcc gtgcacatat acagtgcata  19560
tatatctaat tatttcattc tttctggcta ctaccccatt gtttctatat cccacatttt  19620
tgatcttatc tcttattatt attactttct tgagacaggg tctcaaatag cctaggcagg  19680
catagtctag ctcccaccca ttgaccgctt atttcataac ttggttattg tgaagatgcc  19740
tctatatgat atgtgccaca ttttcttcat ctgtttttct gttggcagac atttcctcag  19800
ctgtggtgaa cagagcaaca gtgagagtag atgtgcagtg gagtgtctgt gatatgctga  19860
cctagagtgc tctgggacat acacccctgg tttttttttt tttttttgt gtgtgtgtga  19920
gaagccaaga ccaatttcaa gggttagttg ttcctcaggt gccctccatc ttgtctcttg  19980
agacagggtc tcttactggc ctggagttca ctaatagaag tagcccagtg agccctgggg  20040
atccatctat ctctaaatgc cccctgccct cacagacata ttatgttaca caagcttatt  20100
acatgggtcc tgggcataga tgctaggccc tcatccctgt acaacacttt gttgtctccc  20160
cagttctagg ttctagttcc gttagccgtt ctagagtccc tggctcacct actttgcttt  20220
gcctttatta tctgccttct agtgtgccct ggtatggaca tccggaacaa cctgaccagg  20280
ctacatgagc tggagaactg ctcagtcatt gagggccatc tgcagatcct cctgatgttc  20340
aagaccagac ccgaagattt ccgagacctc agtttcccca aactcatcat gatcacagat  20400
tacctgcttc tcttccgtgt ctatggtctg gaaagtctga aagacctctt cccaaatctc  20460
acagtcatcc gaggctcccg tctcttcttc aactatgccc tggttatctt cgagatggtc  20520
cacctgaagg agctggggct ttataacctc atgaacatca cccggggctc tgtccgcatc  20580
gagaagaata atgagctctg ctacctggcc actatcgact ggtcccgtat cctggattct  20640
gtggaggaca actacattgt actgaacaaa gatgacaacg aggaatgtgg ggatgtctgt  20700
ccaggcaccg ccaagggcaa gaccaactgt cctgccactg tcatcaatgg gcagtttgtg  20760
gaacggtgct ggacacacag tcattgtcag aaaggtatgc tgaaggcagt gccttttaaa  20820
gatttctccg tggttagtat gcccaggaga agtagactcc tgtaaaagtt taggtgatgg  20880
aggttgtagg gtacaaaccc tagaatctcc ataaaaaata cattcgtccc cttatctgcg  20940
aggcatacct atttgatgtt gtacacttaa ctgtgggtta ctgagactgt aggaagcaga  21000
atttctgatg gggagagatg aatgcgtgta ctgatacttg gccattgcag taggaaggta  21060
gccacagtta ggtatcaaga tatggtgttt ttttttaat gtggcttata tgtaaaaaaa  21120
tttttatatg caaaaaataa ataggggggcc agatttcttt tgggggagag ctgtttgcca  21180
```

-continued

```
ccctctgtgc tggatagtga ctgtttctgt ggtcctctgc tttgttgggg agtagactat  21240
gcaagagtat gggtttggct tagtgttttt cttatctgat catagaagtc aatttgttag  21300
agatactcag aaaaagaaat gtaaaaattc agctttgacc gggtgtggtg gcgcacgcct  21360
ttaatcccag cactcgggag gcagaggcag gtagatttct gagttctagg ccagcctgtt  21420
ctacagagtg agtttcagga cagccagggc tatatagtga aaccctgtct caaaaaacca  21480
aaaaaccaaa acaaacaaac aaaaaaaccc cagctttgat gagggtagct catagttttt  21540
tcttttcttc ttcttcttct tttttacatt ttcatctatc atctaccttt atctatctat  21600
ctatctatct atctatctat ctatctatct atctatctat ctatctatca tttatctatc  21660
atctatctat catttatcta tcatctatct atcatttatc tatcatctat ctattatcta  21720
tctatcatct atcaatctat ctatctatca tctatctatc tttctatcag tcatcatcat  21780
tcatctctat gtgtgtgtgt gtatgcacat gtacacacct atgtgtgtgt ctatgtgtta  21840
taaatgtgaa tgtgtgtatg ccatgaccaa catggaggtt agagaacagc tctccttcca  21900
cacatgtggg catagaggat caaactgagg caatctggct ggtggcaatc atcttgaccc  21960
actgagccat ctctctgctc cctttgtgga tctattgcct tcatatcttt agccttctga  22020
gttataaggc atttaattgg aatatttcag gtgtttttgt tgtttgtttt tttaaagatt  22080
ttggttgttt tgagatttaa gctttattta tttatttata ataattttaa tttttggtgt  22140
atgagtgttc tgtctgcatg aatgtctgtg aactacatgt gtgcccttca atgccaggaa  22200
agggtgttgg atcccctgga attgtagcta ctgatgtttc tgaagtgcct tgtgggtttt  22260
ggaaattgaa cctggatctt ctgcaagaag ggcaagtact cttagcagct gtgacttagc  22320
cctagctcca tgtgtgtttc ttttaggctt gttttccaga aatgaaattt ctgggtcaga  22380
ggctcctgat taggattgcc aaatggcttt ccagaagtgt tggacctgtg gactggactc  22440
ctagccttga gtggcgagag ctggactttc acaaagtccg gggtgggtga gaaacccata  22500
gttttatctt tgtgtgtgtt tgagttcagg gtagagcctt tgaaaacatg tttactgatc  22560
attcagggtt cctctgcttc ctaccttcct tgtctgagga cctctgtggg ctttggagaa  22620
tctaatctgt gattttcttc tttgaagctt gcttaatcct ttgtcagttt catttgtgag  22680
ccttcttgtt cagcggagaa aatatctctg aatgttcaga ggtactagag agtgatggca  22740
gtgttgatgg cagttggtgt caatctgttg ttggcagatt gaccctgaag ccttgtgcac  22800
ttgagggctc tgctgtgctg ttgtgcagtg ctcccggcct ctcactggat gaccttgaag  22860
ccttgtgcac tctgccaggg ctatgccagt gctgccatgc agtgctcccc gcccctcact  22920
gggggattct aggcaggggg ctctgagctg atttccacat tcctttttta gaaaaatctc  22980
tacacataag atgatgtccc atttaatatt aactattacc atgtagaaag tcttccactc  23040
tccactcagg ggagctctcc atgtatgtga tttagtgaag tatccgtgtg cttcctagag  23100
acccactggg gagtcttgat gctgtttgtg gcataaacca attagcctca cctgctattc  23160
cagtcctgag aggatggagg caggagggtg gcaaatgaga agccacctta aattagagag  23220
tgaaaccctg gaacccagaa acaagaaaga agggatgaaa gagagaaggc aggagaaaga  23280
gacagaaaga agaaagggag acattctatt ctaaagaagg aagaaaagga gggaaaggag  23340
aaagggaaga gggaaggaag ggcgggggga agggagaagg aagggaggga ggagggaagg  23400
aagaaggaag ggaaggagga gggaaggaaa aaggaaggga aggagaaaag gaaaagagga  23460
ggggaggaag ggagggagga gggaaggaag gaagggagga cgggagggag ggggaagaag  23520
aaactctctt ccttttcctg tggttgttcc tgcctccctt ccctgtacct gggcatttgt  23580
```

```
gttctgagtg ccaactttta ttgtgttttg atgcccaaga gaacagttca ttaactgttt  23640
atggcttcag tgacctcatt cacttgttgt aaaactccct gggaaggact agtgaatggg  23700
agagaaaagt gggtggctta gggattagtt cacagaatgt aggggaggga ggggaggaaa  23760
tattatttct ttttgcctcc acctgagcct aaagaaccaa tgggtgttga atctttggag  23820
ttgtgggtta ggaggagtct tggatagtag gagttagggt atgtcttagc cttcagttcc  23880
tgtgataaac gctctgacca aaagtgacct ggagaggaaa aggtttattt tattttatag  23940
tttatactcc gttatctagg tagatcaagg caggaacaca gggcagaaat ctggaggcag  24000
agatcatgga agaaccactg cttactggct ttcttcccgt ggctttctca gtctgctttc  24060
ttacagaacc gaaggccacc agtctaggga ttggcaccac ctatagtgag ctgggctctt  24120
ccatatccat cattagtcaa ggctatccca aagaactgcc tatagcctaa tcctgtggag  24180
atattttctt aaataggatt ttgtcttccc agttatatct gggtttgtgt caagttgaca  24240
aatcacagcc gggatgagga gactgtggga aagacagatg gttgagggga tgaagatatt  24300
aaccttggaa aggttttgag aatattggaa ttcgggcaca aagagttgcg aagctgtgac  24360
ccagaggaag gtgtatggtg ggagcaaagt tttggaagaa accaagacca ctttggggcc  24420
tggaattttt ctagagcctg tgaattctgg cctgggattg ggtatggtct aaatgcaagt  24480
agggatggga ggtaagtctg tactcagttt cagggagaga agttttcccc aggggcaaat  24540
aagagtcctc atgtacgtgc tgaagtgtcc aaattttcct ttgtattttg agtgcagtga  24600
attagatcag agacatctgg tgagaagcag aaacagagac aacttatgaa gatggggaga  24660
gcattctaga caacggatgt ggattagtga gccaagggaa aacctaaaaa gctctggacc  24720
aggagtcaca ttacttttta gaggacattt atccaacatc cacttcactc aagattgtgt  24780
atcacagact tttcgttcct catgcaagta cacgcatgta taccaccgta cagacaaacg  24840
cacacgataa tgattggaga atcgccaaac ccctagaatt cacattttca atgtaccatc  24900
ttagatagat tgatggaact gtgcactgtt ccttctgcag tatgatggtg actttgtcca  24960
gtgtttccat aggtagatgc catgttcctg ttagtcatct gatggccatc ttggctactt  25020
aggctactgc tgttttactg cgctcatgtt caagcaatag tcatcttacc taatatcagc  25080
tcagaggttt atacaggcat gtcaataatt ctcatatgcc agggagaagc tgcaaagggt  25140
taagttgggt ttaaggctgc ggcccttgaa tacatttcct catgttgttg tgactcacaa  25200
ccataaggtt attttattgc tacttgataa ctgtaatgtt gctaaagtta tgaattgtaa  25260
tgtaaatatc taatacacag gatatcagct ttgtggccca caggttgaga acctccttta  25320
agtgaggagc tgaaggctta aaaagtattt ggaaagagac aaggaaagga ggagggggag  25380
cgacagaaca ccttaacata atgtttacta cagtatattg ttatgtttta ttattagttg  25440
ttaatcccta acttatttaa ttacaaattc agtcatctgt ctgtctgtct atcttatcta  25500
tctatctatc tatctatcta tctatctatc tatctatcta tgatttatct attatgagtg  25560
ggtctattta tgtatcatat ctatctattg tgtgtttgtg tttgtgtatg tgtgtgtgtg  25620
tgtgtgtgtg tgtgtgtgag agagagagag agagagagag agagagagaa tgatagagag  25680
aatgtgggag tgggagtaca cgtgtacctc agtgtgcttg cagagctcag aagacagctt  25740
aggggagttg attctcttcc ttccaccacg tgtgccctca gttaccaaaa ctagatgatt  25800
agatgttctc ggtggtaaat gcctttccct gctgattcat cttgctggct cacccatgtt  25860
attttttgag acaggctctc ttactgaacg tggagcttat caagtaagca ctactggctg  25920
```

-continued gccagcaagc cccagagatc ctcctgcctc tactttccag gttctcaagc ttgcaggcaa 25980
gcactttacc cactgcacca tctcccctgt ccctaatgtt caaatcatac cagcatgcag 26040
atgaacgcac acatgataag aattggagag taatgatgac tatgaagact tgtctgacaa 26100
gtgctcagtt tccgggaaga ttcttagggg tatcgatgga aagcttcatt ttcctgcttt 26160
gctcatgaga ggattattgt cccaatcatt catggaagac gctggataga gggcagtgca 26220
tgcttatgaa gaggtggttc tggctggctt gcccggtgac ttggtaactg gtctaactgg 26280
tttttctttg gtgtgatgaa attcattgac cagttatttt ctatcctgcc accagatcct 26340
tgtgggaatt gaaatctgtt ctttgtcaca gaacacctga catacccccg gggaggtgcc 26400
cgggacatag attcagctgt ggtgtgctct gtgtgtctct ctctgtgctg gctagaactt 26460
tcatttcatg gaggggatat ggatattgga ttcttttttt tttttttttt gagataaagt 26520
cccactatgt agtcctaggt tggctccaac tcttggcaat cctcctgcct tggttttctg 26580
agtgttggga gtctagcatt cctggctaaa acactgtgtt ctgattgtgg taaaatatat 26640
ctcatatgta cattggaaat attgtgttac tgttcccatg ctctggttct ggaacattct 26700
tatcctcccc accccccacc cctcgccccc cagtaagaag tcctgtaccc actattgctt 26760
acttcccaat cttgattccc acagctccta gcaaggagca agccttccag ttgtgtagat 26820
tcacttgctc tggatatttc ctatccacag gatcagataa taagtagctt gttatgtgtt 26880
cttgctttcc tttgtctgag gagggctctg aaaattcact cacatagcaa tctcattagg 26940
tcttgatttt gtgtgtgtgt gtgtgtgtgt gtagctgagt aatagtttat catatggatc 27000
cttccagttt taccacctga ccaacatgtg tggtgttccc ccccttccgt tatttgaaat 27060
ggggcttctg taaacacttg cgttccggag cttatttgtg ccattccttt gcctttaagt 27120
aataagtaac taacttttgt agggctgaag ttcaatccca gggtcttatg catgctaggc 27180
taatattcca ctgagctata ccccagctat accccagttt tgcatcaccc caaccccag 27240 catctggctt acaggccacg ggtcaccaca cctggccttt gtgtgggttc tggggattga 27300
actcagctca tcagaaatac ttcgcccact gattcatctc cctggccctg atggctcctc 27360
tttagagcat gtaaaaatat ttatcagttt tcattctgtt cagttggaat tcccgccttg 27420
tggtggttca cattgtcaac cagacaggat ccagaaacac ctaggacatc aatctctggg 27480
tgtgtttatg gtgacatccc cagattgtgt caactgaggt gggaagagag acgtaattgt 27540
ttcctgtctt tgggttctgg acagtatagc gggaaggaaa gttggggata gctttcatca 27600
gtcactcacc tcatgatcct ctgtcatggc ttccctgttg tgatgggctg taccctgtaa 27660
cggtgagcca gaataagtcc ttccttctct gtgttgctct tgtcagaatt tccctctctt 27720
tcatgagtag aataaataat acatactccc taatgttgaa gtacaacact ggttattctg 27780
tgtctgggcc cctgacagtc ccagaaaaga ggaagcagtg gattgagaac attaagctca 27840
acaaagacac tcttctagtg agaggaggaa ccaggaaggg gtagcaactg gccagggctc 27900
agtgtgtccc tctatggttg accaagaacc aagaattggt tttagttcct tcctggcttc 27960
ttcctctgag gaaaagcatc agcatagcag aatgggtgtg gacaaggcgt agggtgcaga 28020
tggtgaggcg ctgatggaga gaagccgcag cctgagctga cttttcatag ccattcacag 28080
aaattgtttt ggggcctggg gagtagctca gtgaagagga tccgagtttg atcccggaat 28140
acatgtatct tgttatgttt cctcattgct gagatcaaat aacactgatg aaaatcaact 28200
taagggagaa agggttaact tggcacatag ttcagacaac atgaacctct cagtcactga 28260
gaagtcacag cagcaggaac ttagaatcag tcacatccca tccacagtcc ggagcagaga 28320
acaatgaatt aatacatata tgcttgtgct tattagctca gtttctccag tgttgtacag 28380
tccatgatct gagcctacag gatgatgcct cccacagtgg tagagtcttc ccacataatg 28440
tataatcaga acaaatatcc tacatagacg ctaaaaggcc aactagacag tctttcactg 28500
agactccttt cctaggcgat tctagaccag tggttctcaa cctgtgggtt gcaacccctt 28560
tctcagtggt ctcctcagac catcagaaaa cacagatatt tacactagat ccatatcagt 28620
agcagaatta aggttatgaa gtagcaatga aaataacttt atggcttgca gggggtcacc 28680
acaacctgaa gaactatatt aaatggtcac agcactaggg aggttgagaa ccactcttct 28740
acaactgtgt caggctgata accaacacta accatcaggt agtgtgagaa aggctggccg 28800
tggtggtatg tgcttaacag tctaagctct ggagagacag ggccaggggg atctctgggc 28860
tttcttgcca gccagcctag cctacttggc aagctccagg ctggaaacag aatcaagaac 28920
ttcaagactc gttaagtctt taacaatggc atctatcacc tgacagccat gtttaagggg 28980
ttttatggtc caggccatcc ttgctatgct gtgagtgtga cttgcttgct gaacttttct 29040
tttggcatgg tggtgacttt gattggcaag gcttgctttg ttttgtgtct tgggattttg 29100
ccatttctgt tcatgagtga aattgggctg tgtttgtggt tcctgtcatt ttgcaatctc 29160
ttcgttaagt tttgttatcc aatcttctag tcacttaaag tgaattaggc acttttccac 29220
tttaaaggtt ttcaaacaat tttagcatta gaattagtct ctccctgaac aactaacttc 29280
ttgggaaatc tttgtgggaa gaaatttttg aaaaaaaaat atatatatat atacacaaac 29340
atataaataa ataaaaggtg tttggtgagt ttaggctaaa gtctttttgt tgctgttttg 29400
ccttttaaaa cccttttaac atcatttgat caacttttgt gattcatagt ttcttagaat 29460
tagtgagttt tctgaactga gagtgtgcta ttcagattac aataagtgtg tgcagtctcc 29520
ttatttaact gagagctgga agtcttgaag atcttggact tattcatcac tttttttttt 29580
tttaataatc caatagtttt tgctttggat gtaattcttt tcactttgag atttgttcta 29640
acctacgctc ttagttttgt tctttttaaa tccccccttga tgtgaatttt tttctagaag 29700
gaattacaca tgtaaatatt tttggagtaa attccaaatt gtgaagtgaa caaataaaat 29760
aatcttattt catttaaaca tttgatagtc aaagactcca ctcctgagtc atgctcccag 29820
tatttcactg agaaattcta ggcagggctc ttcccctgag ccacgcccct agcccctcac 29880
tgaaggatac taggcagggg ctctaaccat gtgaagaact acacctccag gcctaatttc 29940
attcttttaa tgcaattaaa gcttttaaag ccacatgttc acttttgatt tggcttttgc 30000
cattctcatt ggtcctggat atataccttg ttttctaaag aatccttgat ggtattttaa 30060
tatactattt ttgtttccca ttgaaataag agcagctctt tcagtttatg ctatataaat 30120
gctcttgttt tgtcccccca ggtaccccac cgtctttatt tcagaggctc ttttataaca 30180
agtgaaatag gttcagtgga tgttaactga cttgtggatc tctacgtggg aggagctgcg 30240
gcgagggttg ggcagctcct tgttttgact gcaggtctct tcctccgttc tctggttgag 30300
tgagtttgag tcactgattt ttttaggttg aaaaaaaaaa gagttttcac tgtttcttag 30360
tttcattttt gttgctacaa taaattatga tgacaaaaat caactaggga gaaaggggct 30420
cacctcagct tatgtgctgg gtgacagttc aatactgagg gggaagtcaa ggcacgaact 30480
tcaaacagtc acatcggcag ggaagaacag agagaatgct tgtttactct gcaccatact 30540
ctgacctcct gcttagggaa cgatggtgcc caccatgggt gagatctttc cacatcagtt 30600
aaattaagat acgcaccccc agcacacaca catacacaga cagacacaga cacacagaca 30660

```
cacacagaca cacacacaca atgtagacag tccctcattg agacatcctt cctcagtgac  30720
tctagattgt gtcaaattgt tgcttaaaac acccttggtg ggtggagaga tggcttagta  30780
gttaagagca aaggctgttt ttttttcag gagtcctgag ttcaattccc agcatccaca  30840
tggtagctcg tgaccatcta taaaggaatc taactccctc ttctgtcatt caggtgtaca  30900
tgcagcagaa cacacataca taaaatacaa gaaaaaaaaa aaaaaagaaa gagacagtcc  30960
ataaaatatt gaaacaaaac aaaacaatct aatcctaaat tagtgtgatg gattatcaag  31020
gtttctagtt gatagtgctt tacaaagttt tttatatttt taatttgaca cagagtccca  31080
agctgttatt gaactttcta tgtatcctag gttggccttg aactcctgat tctcctcttc  31140
cacttccccg gcacaggaat gacaggtgtg caccacacac ccacaattat gttgtactgg  31200
ggatgggact caggtctcct gcctgcttag tgtttggatt tttcagactt tctctattag  31260
ctcaggctgg cccaggactg ggtatagctg aggatgacct tgaactattc ttcctgcttc  31320
tacctcctga gtactgagat gatacctatg tactgagagg cccaatttga tattatgctg  31380
gaggtggaac ccaggtcctc attcatggaa ggcaagtgcc tactgagcca catcctcggt  31440
gtagcccttc ccgcatacaa ttttaaagtc cttttatggg agagaaggcg ctggccccag  31500
tatgtgagct agagattctg tgttaaagaa ttgcaggcag cttttgggta actgactatt  31560
cagttgattt caggagatct atttcacagc agcaggagcc ataggcgatg tctgaatgga  31620
aattcatagt atgcagccat ccaagggaaa acactaattt tctccagtaa acagagtaag  31680
aattctccac ccagatgcct ggctttgtgg ggctgccagg gtatgtgttt acaaaaccac  31740
tttctctttc tcttgtcttg tgtttgtggt tttatgatct ggttttggga gcgctcaccc  31800
agggctgagt gtgacctgtc aggccacctg cccccatggc cttcctgtct atttctggcc  31860
ttcagtgtga gcttgctgaa aagctagcat gacttgaggt gatgtcagac ttttctttag  31920
aagggcacag tgattcatct ttgtatttaa tgggcctgtg tcatgttaga agtatgactg  31980
tagtagtttt tgtttgaaat ctaataagga attttgcacc tgccatctgg aggccatgtt  32040
ccttctgttc tttttattgt ttttgactaa gagtagcatt gaggggcagg aaataggttt  32100
tgcaatattg ccgacatctg ccctgagggt ctgtcatctt tcctcaactt cattttttt  32160
ttcttctgtg agccagagat agatatgagg cagctatact tggcgggtcc agttttgtat  32220
tcgttttcat gtgtaattgt gtgtatatgt tatagtctca tgtggccttg agttcactgc  32280
acagttgagc ctggctttga atacctgacc atccagtctt tacctcctga tttcatcctt  32340
aggatcacag gtgtgtggca tgatgtatgg ctacatacat atggatatgc ataagtaggt  32400
atgtgtatat acattggtgt catgattggt acccccttct tccatcacct aaaaaattat  32460
gagttgtggg gactgaactt gaggtcttca tgacttggtg acacatccta taatcactga  32520
gcttggtcct tggacttttc taggccacat ttttaaatgt cagaaagcat ctaagagaca  32580
tggcacacac gtttctttgg ttgtataagt ttatactgta gccttttctt ttagagaagg  32640
gagaatcagg tttaaaacat tttaatatta atttactttt tatttttgga gcatgacatc  32700
tgtcagtttt cattgctaac tctaaacaat ctagaatcat ttgggaagag agtctcactg  32760
aggggttgtc tacattgggt tgacctgtgg gggtttgtct taatcgcatg agttcttacc  32820
gccgtgggca gcatcatttc tggggccgta taagaatgga aaaggtaact gagcacagct  32880
tgtatgtgtt ggtccctaga ttggattgtg gttgcttcag aatcctgtca cattgatttc  32940
cccaggaatt gggagccaaa taaagttgct cctgttgtgg tcttaatccc agcaacagaa  33000
atgaaaccag gagggtgcgt gtttggtttc ttttctggtc ttgaactcgt ggactcaggc  33060
```

caccctgcca attctgtctc cagagtatcc taatgcctga gtcaaactat tttcaaacta 33120
ctgtggtttg aatatgcacc atccctgata ggttcacata tcacacttgg ggtgttcaag 33180
cagatgggat cttgttttgg gaagtatgtg gaacctttag gaagcgaggc ctcgctggag 33240
caagtgggtt attggagatg gtcctggccc cacttcctgt cctctctgtt ctgttcctag 33300
ctgcacactc gcacagtctg cagttaccag ctgctgtgct ctattcccca tggtggcttg 33360
cgtcccttca agctgtgagt gcaaatgaac cctcctccct tcagttgctt cttgtcaaag 33420
aattgctcat aacaatggga aaagtagcaa aattaccaag agtacatttg ggatttcttt 33480
ttctttttaa aattttgtgt atgagtgctc tatctgtatg tacatctgaa tgccagaaga 33540
gggcatcaga tcacattata gatggttgtg agccaccatg tggttgttag gaattgaact 33600
cagaacttct ggaagagtag ccaatattct taaccactga accatctctc caggccccct 33660
ttttagaact ttttactggc tattttactt aactaaaaga catgcctcac tggtaaagtc 33720
tatccatgta atatgatcga ccagccccat tagtttaaaa aaagtcctaa aacacagtgt 33780
ttggagtggt gattcagtgg ctaagagcac tggctgagca cacttaagga ccagagttca 33840
aatccctagc acctacataa aaagccaggt gtggccatgt aactccatcc ctgtcgtgga 33900
gcagaagcag gggaatgacc acagcttgct ggctgccagc ttagccctgg gttcagtgag 33960
agattaccca tggctgctac atacataaat ggttgcatgc aacatacaca ctacattcca 34020
ctagttgccc cattccacaa catttattat atctttaaaa atgtatactc tctgtttctt 34080
gcccataatt tactttttta ctttacgtcc tgtcttagtc agggtttctg ttcctgcaca 34140
aacatcatga ccaagaagca cttggggagg aaagggttta ttcagcttac tcttccacat 34200
tgctgttcat caccaaagaa agtcaggact ggaactcaaa caggtcagaa agcaggagct 34260
gatgcagagg ccatggaggg gtgttcttta ctggcttgct tcccctggct tgctcagcct 34320
gctctcttat agaacccaag actgccagcc cagggatggt cccacccaca aggggccttt 34380
ccccccttgat cactaattga gaaaataccc cacagctgga tctcatggag gtacttcccc 34440
aactgaagtt cctttctctg tgataaccac agccgtgtca agttgacaca aaactagcca 34500
gtacacattc caataacaac cccctctttc ctgttttcct agtccagtcc ttacaaatcc 34560
tccaaaccat taccctcctc cccttctcct cagagaacgg gaagcccccc ttgggtatca 34620
cctcaccctg gaacatctag ttccagcagg gctaagcgtg tcttcgcact gaggcctaac 34680
taggtagtcc agtaacggga aggggatcca atggcaggca acagagtcaa agacagccct 34740
cagtccaatt gttaggggac ccacaggatg acaaagctgc acattgctac aaatatgtag 34800
agggtctagg tccagcccct gcatcctttt ggttggtggc tccaggttag ttgactctgt 34860
aggtcttctt gtggttatct gtatattctt tgttttataa cttgtccttt atttcagaat 34920
tatagatgaa attataatat caccaactgt ttgtattgct tacgactatc tttctagata 34980
gtcaagatat ctcctgctca ggcaggagga tcactttttg tagaccttct ttggctgcat 35040
aatgaacctg ggtgacttgg tatagttgtg gagtacttgt ttatcatcat gagtaacatt 35100
caatcagtaa cagcaacagc aacaataata ataaataaac atttacgcag ccttcctaga 35160
cctatgcttg tttgtttgtt tgtttgtttt ggggacaggg cctcatgcag ccctggctgg 35220
cctcaaactt ggctgactat ctagctgagg ctcactttga actcatgatc atctggcttc 35280
cacctcctga gtgccaccat gcccactttt atgtggtgac agcatatacc ttagggccct 35340
ctgtatgcca ggcaagcact gtatccagtg agtcacatct ccagaccaag cttcaccttg 35400

-continued

```
agtcagtgtt tgttagtgtg tgcagcaaac acatgtgtac attcagctgg actccaagtt  35460
acctgaggct ggggtagcaa catgtctgtg ttgcttagat tggtttggac tcttcccatt  35520
tatatgagat gtgaattgca tgtttaattc ctgtatgaat ggctgttcaa agatgtgact  35580
aatatgtcat tggcctgaaa aacaaaaaca aaacaaaaca caacaaaaaa agcttgatac  35640
aaacttaact gtttatcttc attgactttg cagactgatc cccagtgatc tttctttagc  35700
cttctggaga taattgtgca aacaagaaat gaactttgtc attcatggtt ccaagtgcct  35760
tggcaaaggg catgcctgag tcgctactgc cttggcgagg caggaacgct ctttggtttt  35820
aaagctttct tgttattcat gcatattaat gatacataat gtttttcaca tggcattctc  35880
gcacatgatt ataatgcttg tgcatcctag tcctcccaat tgccttcttc tctcttctgt  35940
tgttgttcac atttcgcttt gcaaatagtc ctacttttat gcctgggccc agtgagattc  36000
actgttactg ctttcttgag tgtggccatc cataccactg aagaaaccat ctcttcctgt  36060
ttctcctagc aactccagct ttccatcaga gaggggcggg gtctcgtgag accttcctcc  36120
tattaattgt tatctgccta gcaatcctct gggatgggta ggaccttgtg tctcccctct  36180
ccttgtgtct ttaactgctt aaaggggtga gactcatgag ctctctctcc ttcagcaact  36240
gttagctgtc tatccttagg gagaggtaga ctcataagcc tctctagtaa ccactaaagg  36300
tttataatgc atccacaggg aagggagggt tctcctgagt ccccaccctt agcaattatg  36360
aactatcttc agagagagag gtggaacatc atgagtccct ctcccgatga ccattaaagg  36420
cctataatag attttcaggg aggtacaagg ccatgctaac ccctgcttct tcatgatgga  36480
atgtcgatgg ggtcaatcac atgcagatct tgttcatcac atgaagcttg ttcagtaggg  36540
ctgccacatg tcatgcctgg gagacagggg agccaagaca catgacccct tgggcggtta  36600
cacccatacc atatgtaacc ctatcacaga ccaaggcttg agcttctgaa ttggccacac  36660
aatacggggt gcgctcacta tgtggttctc aagtgatcga cattcttata aacgggttcc  36720
tcccttcata tcatcaaggt gcacctctga ctcatgtcat tgtgggagtg gtctcatcaa  36780
ctttgtgtaa ggcacccacc agagctcccc tcttctttac tttgtatttg ttgggtgact  36840
cctcggtaag atggaggtgt atttcagttt ttatacttgt tgctgtaaga aaatacattg  36900
gcagaagcaa cttaagggag aagagttcaa gggtatcaca caggaactta aagcagtgaa  36960
tcacatcaca tccacgatca ggaggtagag agtggtggat gcatgctagt acccagttcc  37020
ttttctgtac tgtatatatt ctaggactca gggactgtgt tctttcccac atcaattaca  37080
gtaattaaga gaatccccta caggcctgtc cagagtcctg tctcccagat gatgatttag  37140
attctatgaa gttgataatt aaagctatct gttataaggt gggagaatat gaaagtggat  37200
atctcagcca gagtgatggc tcagtggtta agagccctgg ctgctcttcc acaggatcca  37260
ggtttgattc tcagcaccca taatgtgcct cacatccatc tgcaactcca gcctcagagg  37320
atccaacatc ctcctctagc ctgaaagcac taggcataga catgcatgta tgcaaaatac  37380
ccaggcacct aaaaataagt aagtataaaa taaataaaaa ggaaagcaga tatcatggtc  37440
ttaaagaatg tagtgtgtgt gtgtgtgtgt gtgttggtgc tgaacttctc aggaaaatat  37500
gtgaacaaat gtctattaat cctataacac tctcaaagta attctaccga agttcaactt  37560
aatgtccgaa ccttaggtct taaggtttcc caggcaagtg ctgtaccagt gaggctcacc  37620
ttagcttgcc tcctttgctc tcttttgttg ttgttgctgt tttgtgtgtg tgtgtgtgtg  37680
tgtgtgtgtg tgtgtgtgtg tgcacatgca ccagcatgaa tatactaagg tgtacatgtg  37740
gagattagaa tagaagacga cttttggtaa ttgttttttt gccattcacc ttgtttccat  37800
```

-continued

```
gtgcagtccc ttttactgtt ttgcacacca ggctagtttg tgtgtgggat tcaaggtgat  37860
tctgactttt atacaggttc tggaaatttg aactcaggca accagtcttg tgtggcaaaa  37920
acctctccct gatgagccat ctcttcctat cttattgaca atttgacaca ggatctcact  37980
acattgctca ggcaggctct gggcttatgg tcttttggtt ttaatttccc tagtagctgg  38040
gattacaagt ctgcaccacc agacctggca ctgtctgtct gtctgtctgt ctgtctgtct  38100
atctatctat ctatctatct attcattctg gtgagtgtga aaagacagat aaaccacaat  38160
ttatcatctt agcttttttt ttttttaaga gcatagttaa gcaacatgaa acacattcac  38220
atagttgtgc aattattgac accccttttcc agaactttct catttcccaa actgaagcgc  38280
cgtctccatt tctcaatatg tctcctgagc tctctcagcc tctcgtctac cactttcctt  38340
ctttctttat gggtctgaca ttttagggac ctcctaaaag taaaatcctt ttatgatggg  38400
cttagtttac tgagcaccat gacctcaaga tccatccatg tagtagcatg aactagaatt  38460
ttgttccttt tcaaagctga ataatattcc agtgtgtgga tattcattcc actttggttg  38520
gtgtatttat ctgttggtaa acatttgcct ctttccatct ttaagagctt ctgtgtacac  38580
acatagacaa atatctgtct tggctatcta gattgttagg gttcattttc gtttcttttc  38640
tgtattttgt ttttaaaaga cttatttatt ttatgtatgt gagtacactg ttgttctctt  38700
cagacacacc agaagagggc attagatccc attagagatg gttttgaacc acccatgcgg  38760
ttgctggaaa ttgaactcag gacctctgga agagcagtca gtgctcttaa ctgctgagct  38820
atctctccag cccctcattt cacttctcaa tttgatgaaa cctagttcag gttagttaaa  38880
cctagaatag ggttaactga ggtagtaaga ccattccctg gggggggggg tatcctaaac  38940
cttataaaac aagtcagcag agcacaagta tccatatttc tgctacttct tgactgtgat  39000
gtaacacttt tactgcctca acctcctgac accatgactt ctcacccagg tggactgtac  39060
cctcaaactg tcggccaaaa cagtttctct cttaaattgc ttttgttgta tgttatcaca  39120
gcaaaaggaa aggtaacaaa gacaggaggt cctgcagatg tttcaataca atgtgtcttc  39180
tggtaaatct gagggagaga cagagagagg gaaaaggatg ttggctgctt tctcccattc  39240
ttgttgtgcg aggcttttct tgttgggatg agaagcctct tggctgggat cattttctct  39300
tctgaatttc tgttgcctcc actcaaagtc cattccatgt ctggcctgga agtggacatt  39360
tccagtgtgg atgtggaatg tggtgtttgg caggaaattg ctgctttatt cttcgctact  39420
gttccatttg ttcggtagtg ttgagagatg gggaaacctc tttcatttgg gagggaatct  39480
gagatggatt taatttgcca ttggaggctc aagcctcagt cttttcacat gcttccaggg  39540
cttgcttggt ggggtcaagt ttgcgccaag attccctttc caaatgtctt atataaaatc  39600
aaatccaaga acaaagaaga ccttttcttc tctttcatgt tttctttcct gttttttttt  39660
cctacacaac tgcatatttt tctattttaa atcttcagtt aaatcactaa aggtttcttt  39720
tagatgtgta tgtgtgttct tgtgcgttct gtatgcgttt tgtgttcatt tgtgttatat  39780
gtccttgcag atatgcatgt atatgcttgt gcttgtttca cggtggcagg gtgttttctt  39840
caacctttct ctaccctttt aaaactatat ttgtttatct atttattgaa tgtttttctt  39900
tttgtgtgtt ccttcacatg cagtaatcag atgacaactt agggaagtca gttcttgcct  39960
tcatttctgt gagtcttggg gatcaactca ggtggagagg tttggcaaca agcccctgta  40020
ctcgctgagc tgcctcactg gccttccacc ttatgtcttg agacagggtc tctcactgaa  40080
ccaaatgact gggttggtga gccagtgagt tccaggaatc tgcttctcat gacctcttcc  40140
```

tcaacaatgg gagtaaatag atagagtcat gctcagctat ttccatgggt gttggagatc 40200
aaactcaggg acacatgctg gcgtggcagc acattactga ctgagccaaa tccccagccc 40260
tctttctggt tttgtttgta cttagaacaa gtttttgctt tttgttttgg gtgtgtctgc 40320
atgagatgct ggggatcaga cccattgtag ccttgagcat gctggacaag ctctctccct 40380
ccgagttaca cctctaactt ctactcgtgt tttgtttttg agacaaggtt ttgatatgta 40440
gtacagtttg gccttaaact cacaatcttt tcgcctcttc tttccaagta taggaactgt 40500
ggatgtgtac caccaagcca cacatctaaa aagtttctta aaaagattta tctttatttt 40560
taattgtgca tgtgtgcaca cacacatgca cacacgcaca cacgcacatg cacagtactc 40620
atggagatca gaagggagtg gtggatctcc tggatcagga gttataggtg attgtgagct 40680
gactgacatt ggtgctgaga actagatctc agtcctctgg aagagctgta aatactctta 40740
accatgaagc cactactcca gctcttaacc actccagctc actactagct atttgaaaat 40800
acataattaa ttattgatta taactaaaag cttcctgatg tgaagataga gacttaagca 40860
attggactaa attcgtttaa tcaggtctaa ggtttaggtt atttgtattg gcttgtcatt 40920
tgttgagata aggttgcatg tagcccagga tggtcctaaa cttgttacat ttggcagaac 40980
atagtgcctg tacttctgtt ccttttttgcc tccacctctt cagtgatggg actgttccat 41040
catgctggca ttatgtagag ctggggattg aacccaggct tcctacaggc taggcaagta 41100
ctctagcgtc tgagcccctg ctgacatagg gactgtgggt atggctcagg atggagctcc 41160
taggagtccc cctgggaagg atgaggggtg ttggctcagc cttagagtgc ctgactagtc 41220
tgtatgaggc catgggctcc attacctgca tcaccaaatg ggtaatgcta tgacaggttg 41280
tctttgagat ttttgtatta caagcatttg tattgagccc ttcactgtca ggaatgtgga 41340
agaggggcag ggtgactgct gggtgttggg tggtagaaat acatagcttt tgaattctag 41400
cttttgaaca aacgcttctt ttcctttctg aagcagcttc ccgtaagttt ttcctttttta 41460 tggtgcttct acagtgttcc agggtgatct cctcggttct caatggcttg agccttacca 41520
agttagtgag ttattctgag ttctggaatc cagcatctgg tgcagcttgt ggctcttggc 41580
tttgacctag gaggttgtgc cagccaaagg aggtggcttc cccgtgcctc ggggccagcc 41640
tgggaggctg caagctttta aaggccatgg cttgtgctgg agacatgtgt tcctctggca 41700
ctggctttgt tgaaaacaca ttccctagat agtttctttt ctacacagac gtttggagat 41760
tcttgggtgt gctagaggca tcctctctct ccgtctctct ctctgtctct gtctctctgt 41820
ctctgtctgt ctctctgtct ctctgcctct gtctctctgt ctctctgtct ctctgtctct 41880
ctctctctct ctctctctct ctctctctct ctctctctct gtgtcttctc tgtacagtgc 41940
agtgatttgc tgttttctag gtttggaaag tggtgtgcag gaaagtggga ctttgcatgc 42000
tgatctcagc cagccccacc tgacttcact aagtcaaggc tggtagaatc cctcagttta 42060
tggacaagaa atggaggctg gcagaaaagc caaggggaag cagcagctgc tgtgatgggc 42120
tgcagggttt gctctgagct cacagcctga cctgggttca gggccagtag ccatcttctc 42180
tcctaattcc tgtgcccagc tggccacagg agccctcttg acatttctgt tttttatttt 42240
ctgggctgtg agtaggacct agcagccgtg tgcgttctgg gcaaatattt gccactgatc 42300
tgtatctcag gctcttactt taacttattt actaaggatc tcacgtagcc caggctggcc 42360
ttaccttgaa ctcactatgt aactgaaatt ccttcaaatt tatttatttt taaatgtaat 42420
ttattttttt cacctacaaa caaaaacaaa aacaaaaaac atcaagagca gctgctttct 42480
agacaaggga acagggatgt ctcacctcct cattgctgcc ttgttaactg cctgctggat 42540

-continued

```
ctaagcaccc tgtggttggt tcctttccat tttccagctc tgtcatcagg cacctgtaga  42600
gcaggaggac ttgcctgact cttgccaaca gttatgtcca tgattgtatc ccagaaggaa  42660
gtttgcaggc agtgttaagg gactgagcca gaatgtggtc agagctggct cccatcagat  42720
ttgagtggaa cgcctcaatt gtcccactgc agaggataat tatcttaatt gttaatactc  42780
ttgactttcc tgtttggggc catgcttagc aaatggggtg tgagcgtgaa ctcttgactg  42840
tctcccgagg ccaacagaca caaataatat tatgcagttg caaagacagg ccatttatga  42900
agctgttagc tgtggcggca gccttcgctc ctttactcat ttccccaacc cttgaagcac  42960
tggcttatct ttacctactg aggcttaatt gattccacgt tagtccttta aagattattt  43020
ttgtgtgcat tgcatagcac acacgtgcac acatacacac atgcatgtgc acctgcaagt  43080
gggtatcatc tcccatgcat aggagtgtga tggccagagg ttgatgtaag aatatccttg  43140
gttggtttcc cactttattt tatttcgtgt gtaagggtat gtatgtgtga gtgtgggcat  43200
atgcgtgcca cgttgcactt gtagaggtca gaggactgtt aggagtcact actctctacc  43260
ttgttttgaa acaggtttct tatttctggc actgtataat gtattccatg ctggtggtct  43320
ctagctcatc aagccagttt ttctgcctct gcctctcttg ctgtacgagt gctgggttta  43380
cagatacttg ctaccacatc tttacatggg tcccagggtt cacactcagg ttatcaggct  43440
tgggctacag tttctttgcc caccaaacct tctctccagc cccaggttta tcttctatac  43500
agaggtctgg tatttttctag ggatgggacc tctctctggg ccttacacct tcatctcttg  43560
gtgaccagag caaatccact tacaggcgca gcacccgtgg cactgccctt ggactcaggc  43620
tttgtgcctc agaaaggacc agagtttgtg acagtctgag cacttggcag tttcgactta  43680
ggctatgacc attgatacct tagggaaatt gacattgcaa atgtcaatag aacaggtata  43740
ttaaaagtta tttttctcta cattcatgtt ctctacaatt ccatatgtgt atataatgaa  43800
ctttgaccat aatcgtcttt attatcctct cttatcccct tcaccaccca ctgagccccc  43860
tcttcccgac aaatacctgt cctgctttat tagtttttgt gtgtgattca tttcatatac  43920
ttagggggtc cttggatgag catggatgtg tgggggtatt ggctatacca tggagtactg  43980
tgaccctcct tcctgctgag ttacagggtt tttttttttt ttttaatgta gtacatttat  44040
ttaattttac tcttgtgtgt tacttttatt tttaaattga tttttttctt tataaattcc  44100
cttattacat tttatctagt gtgtgtgtaa gtatgtgcag cacaccatgg ttgggaacag  44160
atataatagc ttgcaggggt tggttctctc tttttaccat ctgagttcag ggaattgaat  44220
tcagatcgtc aggtttgtca acaagcatct ttacccactg agctattttg ccagccagtt  44280
agttacagtt tttgttgctg tcacaaagta cccgtgatgt gagacaaaac ttttcctggg  44340
gagatgcaac acacacatct actcacccca ggtagcaaac tcatgacgga tcaaagtaca  44400
attcctatca aagtccaact tggtgagttt aatttgtgtt ccttacaggt gtatgggtga  44460
gggattactt acaggagcag aaatgactca aagacagttg catcactgag gctcatccca  44520
gcatgggtga cagctcataa aaattgggaa ccaggagccc actgtacagc ctgcaggcag  44580
cccaacagtg tggagagtgt cctgtccagg tggctcagtt gatcaaaacc tcttcgaggc  44640
agctgctctg gtctcagtct ttttctttgc agtgcgactt gtctcagagt catcttgcag  44700
tttggctttg ctcttctgag aagggccctc agcttttatt gctcacccgg gcagggagag  44760
gtatagtgag tctcttcaga gcctagtgaa tctcctcagt tttggagaca ccctgaagcc  44820
attctgagtg gtttgccttc ctgcatcctg tagggtgaga tgtttcattg cacagcgctc  44880
```

-continued

```
gacagcaaca atgggaggta gtgaggttca gcatggtact cagtttcacc aaggtggagg  44940
aggaggcttg acagaggctg tggcttggca agagcttgtg ctggaggcac ttcatctgtt  45000
agtaggtcat cttctccagc catcttcttc cctacaccat gaatgcattc ttagggttct  45060
acagctcagc cagacaccac caccagcttg gctgaagggt tcaaacacac gagcctgtgg  45120
gaacatttca ctttaaaaca tcaaaggaag aaaatgagca ggggctagac aaatggaatg  45180
gcttggtggt taaatgagct tgtggccaag cctggcaacc tgagctccat ccctgggacc  45240
cacatggtag aagcagagag gggactctta aaagttgttt tctgaccttt acacatgtgc  45300
acacctgttg tccaagcact taggaagtag aggcaagagg ggagagctct agctgtccag  45360
aatcaggctg gagggtgagg gtgtgagtgc atgtgtgcat ggatctgtgt gtgtatcagc  45420
ttaaaaggtt tctttgagca tttttttttt tttggtggaa gtgtcttatg tagccaaggt  45480
tggcctcaaa ttcactgtgt atccaggaat gagcctgagc tgtcctctgc tcttttgtgt  45540
gaatttcagg ctgacctgaa ctgttcaagc aagactgtct caaaagaaaa aagaagcaac  45600
cacaaaataa acacctttca gaatacagtg ttaatcatgg ataataccta aaaaatgacc  45660
tgagttagat tctgagacct gaatggtaga aggagaagac tggcttgggc aaaatacctt  45720
ctgacctatg tatacacaca cttgtacact ctctctctct ctctctctct ctctctctct  45780
ctctctctca cacacacaca cacacactta cttgtacgca cacacactca cacacacacc  45840
gagagtaaat acatttaaaa aatgtcagaa caggtcatgc cactgctatc agttttagtc  45900
tggggtaggc tgctccttca gtcctcaacc ccaagtagct aggtccaatc agatgtacag  45960
tatctgtcag tacttggtgg aaggagagac cagctcctgg agctgtcctg gttgggctgg  46020
gcttgatata aaactaatat gctatttgaa aaacaagtgt gtgtgtgtgt gtttaaattt  46080
atttttattt attaccctgc ctcgcctacc tccctgtgct gtgggggtga gccctgcatt  46140
tctccatgct aggcaagcgc tttccaccaa atctataaaa aagagaggaa gaaaaaaaaa  46200
cgcattctgg aaagcagcct gtgttctgga aagcagcatt ctagaaccac ccatactgac  46260
caaccacctc tgcagcagat gcactgagcc accagcactc agagggagac cgctctggaa  46320
ggccttgtgt ctagtgttgc tgatttccaa agaccaactc tgaactgctt actgaaggaa  46380
gttactgaat gtgatctctc ctcttgcatc actgatacat tgctcaagtt gtccagaatc  46440
aggctggagg gtaaaggtgt gtgagcatgt gtgcttgtgt ttgtatgttt gcacacacac  46500
acatgcacac atgcatgtgc atggatttgt gcattagctt aaaggatttt tgtatcagta  46560
tttttttttt tgaggtagag tcttatgtag ccaagttggc ttcaaattca ttgtgtatct  46620
atgagtgaac ttgagctgat cttccagcct ccacccctag tgttggaatg acaggcatgt  46680
gccactacat ctacacatac tcacaagtgc acacatgcac acatagatac acactttgga  46740
catgtctcag ttgctctctg cctccttttt tttttttttt tttttttttt ttttgtgggt  46800
gctgaggttg agttctcatg ctcacagtgt tagcacaaac aatgaaccac ctcccagacc  46860
attcccaatg catgcctggt ctttcactga aatagagctt ggttcagaag gctagactag  46920
ccagagggcc ccatgggtcc ccctatcttc acctctccca tactagggtt atagtattat  46980
gaattcatgg cgcagtacct gttttttttt ttttttaaa ccacgggttc tagatatcaa  47040
atttttgtgc ttatgcagta tcctagtttc ttttttgttg ttttgataaa tactttgtcc  47100
agaagcaact tagggaagga agttggctta tacaggtcac aatccatcac agagggaaga  47160
caggacagga ccttgacgaa gaactgaagc agaaactatg cttggctagt tttcttagcc  47220
caggcttcct gcttagggaa tggtgccact catggtggac taagtcctct tgcattgatt  47280
```

aacactaaga caattcctca cagaacaacc tgattcaggt ggctctggga catgcaaaat 47340
gaactttatg aactgagctt gtcttcccac aaatttctgg tttgtttctt aactgaatca 47400
ctccatcata cttcccttgt ttccccctct actcctcgtc ataaagggag agcacattgt 47460
tcaagctgcc agtcttactt ctttttgaga cagggtttca tgtagccaag ctggtctcaa 47520
cctcactagg cagccataga tgaccttgag ctgatgatct tcttgcctat atctcctgag 47580
tgagggattt ttccatcaca tccactttcc accaagcttg agaaggaacc agagtttcat 47640
gtatgctaag caagtactct accatctgag ccccaggccc tgcccagctt caactggcag 47700
tttaaaaagc catttatgat tgagctgatt catagaatgt ctggccaggc tgaaaatagc 47760
caaaagcctg tgtttaggaa attcaactgt tccttttcta tttattagcc attattatta 47820
taatcacggt caggaccttg ttatttcaaa gagctggggc tggaaaccag gacctcttcc 47880
acacggagga ggctttgcca gtagagagct taaccctctt ctcttaactg caggctgaca 47940
ttgccaggtt aacaatgttt cagtgtttca aatccttact ctaggctgtc attgccttgt 48000
taatgtttcg aatccttact gtttcttcta cagccaccct ggcagctctc ctatgttctg 48060
ctaaatatac ccacaattct tagcttccaa tttttttctt ttttaaaaaa ggttttatta 48120
cattttattt attgtgagtg tgtatgtaca catgggtgtt tgtgtacacg tgccatagta 48180
catatgtgag gatctgagaa caacttttgg gagttggttc attccttcta ccatgtggga 48240
tctagaggtt aaactcaggt catcagagtt gatggcaagt gccatttccc actgagctgt 48300
cttatcagcc tgctattttt atttttgcag ataatgtatg tgcgtatgca cgtgctaagt 48360
ctgggggtca ctttctggtg tttactgcct tccaccttgt ttttgagagt gtttctcact 48420
gaactcggag cgtattgatt agtcaggttg gctggcagag atccgcccgc cacattccca 48480
gccctccctt cccatgtact gggtaggtta cacacttgtc ttttttctgt ggatgcagag 48540
gtcatgaact cggctcctca ctgtttcccc agccttggga ttttttcatt tctttttaaa 48600
aatttttggt atgcatatca aagcaacatt cattgttatc aaggagtttt taaaagttat 48660
atgtgtttat ttttgggggg tgatgcatga gtgtggaggt cagagaagga cttgtacggg 48720
agttagtttt gtccttccac catttgaact caggttgtca ggctgggctg agaagacatt 48780
cacccactga gctgtcctac tgaaccttgc agagcaattt tatctttggc tagtcagtag 48840
tcctgctctt caaagaaact gataagacct aacagatgtg tttagcagga agacacagag 48900
ccacttagga gaatgtcttg cctgaggctg gttgccacag ttctttgttt ttctgagtca 48960
tttgtttttg tctttttaaa aatcccttta tgtatatgaa tgttttgccc acatatatgt 49020
ttatatacca tgtatatgtc gtgtctgtga agggtggaaa aggtgtccca tctcctggaa 49080
ctggagttac agatggttgt gagctagtac ataggtgctg agaactgaac caaggtcttc 49140
ttcttatttt ttaaatatat gttttaatta actctgagat aattttgtac aatatatttt 49200
ggtcacattt acacttagaa ctccctcaac ttctcccagc tctaccccac ctccctgccc 49260
ctttcaactt cttgtctttt tctttaataa acctctgagt ttaatttgtg ctccttatag 49320
gctcctgggt atgggctgtc tctggagtat ggtgaccaat cagtggccaa acttttaaag 49380
acaactgagt ttctgtttcc cagaagccat cgactgtcag tagttcttca ggtagtgtgg 49440
gactcatatt ggggtgttga tcagcttgat tttttacagg cttggtgcag gcaaccatgg 49500
ctgctattgt tcatgagtac agcgggcctg ttatatccag aagacactgg tttgctctgc 49560
ccctctttac aaggctcata actagtgtta tgagccttat ctaggctgaa gttgaaaaat 49620

-continued tgtaagtttg cctgagttac aaatgaaaat gttgtttcat acaaaccggc aatcaatatg 49680
caagaaagta tgtaatgttg aatttaccat tcggactgta tttaagccac cgttcaacag 49740
agatcagtat actcacatgt cttcatggca atcccaacca tccatttcca gaactttctc 49800
ctgtacccaa actgaagttc tgttcttatt aaacactagc tccccttcct tgtgtggtgc 49860
tgggtacctg ccattctgtc tctggatttg atgactctcg gaaacagcag catatccctg 49920
taggatcacc tcctacgttc aaagcatgat gccttcaggt ttcgtcccta tcataacaga 49980
tgtgaggact tttctttttc ccttgcctct ctctaacccc taccctgatg gactctctct 50040
tttctccttt ctccctctcc tcccctgtcc tccctttatc ctttttcctt tgtatcattg 50100
cttaagaatg caactgacct tttttcttta agactcattt ttatttgtgg gtgtatgtct 50160
ggttgccata tgcatgtatg tgcgtgtata tgtgtttggt tgcttcagag gccagagaga 50220
gcattgtatt tacttacagg tggttgggaa caatctgaca tgggtactgg taatcaaact 50280
gggtctctaa aagaacatgc ttaactactt agctatctct ccatcttctt tgagatgagg 50340
tctctcactg gtttggactc ccaggaatta gcagtgtttg ccaccttact tggtgtatgt 50400
ggtactgagg ataaaacctc tgttgtgatt tgaatgagga atgtcctcta caggctcctg 50460
tagctgaaca cttagtttcc agatggtggc actgtttggg gagctgtagc cttgctgtaa 50520
gaagtatgcc attgaggggc aggccccact tcttgtcccc ccttgcttcc tgtatggata 50580
gaaatatgac tcatagctgg gcatggtggt gcataccttt aatcccagca cttgggaggc 50640
agaggcagag gcagaggcag gtaaatttct gagttcgagg ccagcctggt ctacagagtg 50700
agttctagga cagccagggc tacacagaaa aaccaaaaaa agaaaaaaaa aaaagaaaaa 50760
aaaagaaata aaagaaatat gactcactag cttcctgctc ccactaccat gtcttccatg 50820
ccttttgcca tgccttcccc tctatggtgg gctctagctt tttagaacca taaactgaaa 50880
taaacatttc ttctctaggt tgcttttttc agggtatatc tatcacagta gcagagagtc 50940
actaaaacac aaggtaggcc ctctccagat gactccaccc cgctgcagct ctgcccttcc 51000
cactccccac tttcccgttg ttccccaggt tcttgctgag gtgactctgt gtgtgtctgg 51060
gggttgtcac agttgggtgg ttctactggc atagggtagt taggtaagga cagggtaggt 51120
aggagagaca tcctacaaag gctggcccct accacagaga acaggcaagc tcaaaatgtc 51180
tatcacctga gttgataagc ccacctctta gacagcaggg ctgctggaag tatctggctt 51240
gagtctgtga catgggactt cccagcactg gtattagcaa ggctacactg aagggtgaag 51300
gggggctgga ttttcttcct gtcctgtttc taaagttctc ttagaaagga gtgtctgttg 51360
cttctttgtc agaacatggc atttgtgagt tgcttcggaa cagttctgta ctttccgtga 51420
ggctggttcc agggctttcc atccgtggga cagaaagcac ctgcttgctc ctccctgacc 51480
ctgtgcaaat gtagctgccc atgttctggt tcacaagggg tcagcagatc aggcccttgc 51540
ttttgtcgac agttgattta atttgttact cataataaaa ctggaactca cctggctcag 51600
agccctgggc cgttaagaat gcttgctaga atacactatg tagactaggt tcattggaaa 51660
agctgagaat agcagctaac ttaccatgag cagaagggct gacaagaggg acagtctccc 51720
aaacagaatt tacctattgc ttaataagtc aacagattta tcagagggga tacccccacc 51780
ccaattgttc agtaactttt ctttcctgta agacaggtct catgtagctc aggctggcct 51840
ccaattcact atgtagctga ggatatgctt aaagtcttct gatcctcctg cctctacctt 51900
cccagtgctg ggatgacgga acatcatcat ctgccaacag gcctggttta ggcagtgctg 51960
gggatggaac ccagaatttt gtgcatacta tatgagctct ctacccactg agccacatcc 52020

-continued

```
ccaggctaag gctccagacc ataagagcag aagttgattg gtaggtcatt ggtgtacaaa  52080
atttaagaaa gctgatcacc actattatta cctcaaaacc caattgtctt catctggagt  52140
tttccataga aacaggatta taaaatttgg ttttaggtcc cttacattgg tgtgcatagc  52200
tgtgaagagg tgtgctgtgt tgttgagctg atgagtgtct ctaggattaa aagtcattat  52260
tgtgtatctc agtggttaga gcaattgcct agcatatata aaaccccggg tttcagcccc  52320
agcactgtat aagccaggtg tggtggtgca gacctgttgt ctctgcactc aggaagtaga  52380
tgcaggacgc tcacttgaca catgagagat cttgtgtcaa ggtacaacaa acccccacaa  52440
ttccttggtg aacacctagc atagtagtac cttgctcaaa ggaaagtgct gacattctgg  52500
tgcagaatag aagaagagaa ttgtagcccc atgaattcat ggcatctttg aaatggcaag  52560
tttaaagaac ttgtctagtt taaagaactg tttcctcctt gcatcagctc cacaaggtag  52620
gtctaatgat acaccatttt tgaaaaggct cagagaagtt aagacacttg gctaaaatat  52680
cccatcatcc atcagggaat ggcagattca cgctcaggtc tttatacctt tctggcttcc  52740
accactactt cttcctcttc cgattcttct tcttcctctt cttcctcctt ctccttttct  52800
tcctcctcct cttctttctc ttcttcctct tcctcctcct tttcttcctc ctcctcttct  52860
ttctcttctt cctcttcctc cttttcttct tcctcctcct cttctttctc ttcttcctct  52920
tcctcctcct tttcttcttc ctcctcttct tcattttctt ccttttcctc ctcttcccct  52980
tcctcccccc tccttctctt cttcaagatt tatttattta ttttatgtat atgtggcttt  53040
catttctaat catagacata ccaatcaatg tagctctgcc tgatgtgtct ctgccctgcc  53100
tttctaatgt tccaccaatt ggtgttttaa aattcaagct actgcagtga gctcacccgt  53160
tctctgacat cagagtgtta gaagaccatc tcacaagtgc tcaaggaccc agcataactg  53220
ggtggagcct tctgccccac atttccttgg aaccagtatc aggaggcagg gcctttcttg  53280
gctcctccca tctgtttcca tggagcccct gctgttggtt tctcataccc ttgagaattg  53340
ttttctgaag ctagtcaatc tcatgatgct gtgtgtgtgc acaagtgtat atgtgtgtat  53400
tagacctcac ttttctaaag caaaggttct gattgggtat tcactgttta attttcaaac  53460
attttctccc ccttttattt cattattaag gtatgttcaa atttgtcttt gtatcttgtg  53520
gaactgcaaa ggccaatgac tgccaaggaa acagatagga aggggatttg ggtcggatt  53580
ttgagtgtga gaacccaggt ggacctttga tcatgggact tcaaagggag agttgaagca  53640
taagtggaat ccggagtcta gaagggaagg tggagttggc tacggaaggg gtcatgtctc  53700
atggaacagg gtagtgattg tatctgcctt aaacgggttt caaggagcta acatctgagg  53760
gtgccgaggt gaaagaggct ttccgggagc tgtggagtag gaaggggtgc gggaacttca  53820
ttgtaaatcc ttttccacat tcaaggccaa gtttcctgca attctccttt ctcagggcag  53880
ggtaggaaga cgtaactggg tggacatgtg ttttacttga gagtagaact tcgtttgcct  53940
tagtgagaat ttcttgattt ccaacttcct tataacctca gcaactgctc ctcccctcaa  54000
cttctgtctg tatgagctga cttagctgcc tcctaccccc ttttaagaaa actcatttta  54060
gtcgtgagcc cagatttcac tctaggctca tgttcccaat tcccctggta tcccacaatc  54120
ataggcctca tggaggaatg tgctcaagag ccctcaaatt atggttttct aaatcttgat  54180
ttctgagagg aacattgggc attccacgtt tcccctcttc aatcctgagt gttctgctac  54240
tgtgtgggag gccttgcaga catttccagg caccgacaaa ggtacctatg tgaaatacag  54300
tcattttact acctgctatt gggatttaaa aaaaattgtt ttaggttgcc tgacaaatct  54360
```

-continued

```
tttgggatgg acctggatcc tttggcggac tggtgggata tgggtagggt aaaagggaag  54420
atggagaaat tatattatga attcagaagt tcatggacag acggaggggt ctgtctggcc  54480
tttctgaaga gtagggtggg gacaacaggt ttcactgact ttccctttga ctgtctctgt  54540
gtgcttgcct gtatgtgctt gcttttgtgt gctcacctcc agtgcatgtg gaggcaggaa  54600
ggcatgtctc aggtgccctt tttgatggct ccccactgta tcattatatt ttgagacctg  54660
gattcccgag attcagcttg gctagttgac cagtatgctt caggaattct cccatctctg  54720
tctacccaga acagtggtaa cagacatgta ttgctgcacc tggcttttaa tgtggatgtg  54780
ggagacccat gatcactcct cagacttgtg cattaaccag ttcagtgcct aagcctaacc  54840
aacattcacc tttggactct atacccatac atgtacacct cctatagtac atacgtgatg  54900
aaacagtaag gagaaaaaat aatggctaca gatctctgag gaatctattt tctggtcatg  54960
tctatttcac atacaataca catgtgtgca catatatatg cacaaatata gataacacat  55020
ataacacatg tgcacacata caaaacacat atacacacat ggcgcacatt gcacacgtaa  55080
tacatatgcg tataaacaca tgcacaaata catagcatac acacttaggc ttcctaccgt  55140
tgggaatgaa ccaatcagga aataaactga aacttatgcc atctttgtca ctatgaggtc  55200
tggtggccaa tttcactttg ttagtggcag ttcaggacac tgtttagcag ctaggaaagt  55260
gtctttgtat cttgcttcct gtccctaacc tcagctggct tgtgcccgca gagaggcttc  55320
tgtaaaaaga catctgtgga cttgtctata atgccaatat tgtaggtgga gacagacgaa  55380
ttctcagagc ccccagccat ccatctagcc tatagcgtcc ctttcagtga gaccctatct  55440
taaagctaca agatttagag tctatgaaga ttcctgacat ccttctctgg cttgtacata  55500
tgtgtacagg gacatgggca ctcaaatact cacatgtaaa acacacacac acacacacac  55560
acacacacac acacagggta aatgttacag ggtaaatgtt aggcagcaag gagttaggta  55620
gcatggtgat atagaagctg aaactaaaca gtactcattt tcaagtacag agggaatatt  55680
ttaaaaagtt aatcatctgt taagagaacc agtgcattcc caaagtacag acattgctct  55740
ggactgtatc tacaattgac aatgttctta tttggaaatg aggttttaaa aagctcaaac  55800
aaacacgaaa gacaattttt tgctacttga tcatttaaat aataacttag ggctgtcagg  55860
agggctcagc aggtaaaggt gcttgccacc atgcctgatg acgtgcgttt atttctcagc  55920
acccacatag tgggaggagg gaactgattc cccagagttg ccctctgaac ttcatacttg  55980
tatggggcta cacacacctg tatacaaatc ttactttgat tgttagctgc ctaaagtgtg  56040
taccctagac atatacaagg aaaagattaa aaaaaaagta gacgaaacat aggtcaatgc  56100
ccctttgcaa gagatttctc agaacagccc aaggctactt aagaagcctg attttcaggt  56160
tcaatttttt tttttaatta tgtttatttt ttaaacaggg tctcatctag tccaggttgg  56220
tctcaaactt ccttgtatag caagagggta accttgaact cctgatcctc ctgcttctgc  56280
ctcagtactg gaattaaaat gcccagttta cctggtgtta gggatggaac ccagggttcc  56340
tatctgctag gcaaacacca actgagctgc atctccaacc tcctaaggtg gaaactggca  56400
ctgcctaact actaagtcat ggcaactcta cccctgctgg attcatcatc agaatcttcc  56460
ttcctgttca ctctttccct tggcttcctc agaaccctcc tctcccctcc cctcccctcc  56520
cctcccctcc cctcccctcc cttcccctcc cctcccctcc cctcccatcc cctcccctcc  56580
tctcccctca gtggatcaag atttgtcctc ctcaagttta actttggact ttgcctttca  56640
tcagctctga actgttcgag ggttctggtg attcatgcat tggcatatct tgtattattc  56700
ttcccttctg ggaaacactt gagcataatc cattggaaat aactcagtga taacaaccac  56760
```

cagttagtcc cttcaggggg cctgagtttg agttctgggt gagccgactt taatgaatta 56820
gctattgttt tattttctca catctaaagg ggagagatat tttaatattt agtgagtaag 56880
atcatatcaa ctatgtacag taaatggaat atatgtggga catacacata cacacacacg 56940
cacacactgc atacacagtg tgttttgtgt gccccacttg tgtataggcc agagttcaat 57000
gtcctttgcc ttcctccttc atgtgtctct tactgaaccc gaagctcacc cttttggcaa 57060
gactacgcag ccaacacttt ctagggatcc actgatctca acctccgccc tgagattaca 57120
aactagtact gttggctttt gttggtccat tttagagctc taaagccagg tcttcatgct 57180
tgcatggcaa gcaagcactt gatctattga gccatttaca cacacacaca cacacacaca 57240
cacacacaca cacacaaact gaaggatctg ctaattgcac aacttccctt cactcttctt 57300
tagtgtactg gagtcaagaa aacaagaagc gtggactgag ctagtgtgca gtattcaaat 57360
caaagaacct tgatgcaaag acagcctcta gtgctggcat tagaattcag aacttcctga 57420
gtaaccgctg agctctacct ccagcctcag tcagtctatt taaagaatgc acctatgcct 57480
gcgcttgttg gttttctggg tgttgagcag atgaagacac tagcttcttg ctcccttgcc 57540
atccagttcc acaaagggga tcctactgtg tgatccggct gagccgctgc ccttctctgg 57600
catctctcca gttgaggtct ggggccaggg tgtcccgggc gtcccgggct tcccgggctt 57660
tgccacgcgg tgaccagatc tcttcctgga cacatgccca gcgccccgca ccacccgatg 57720
gatacatttt gcactctgca ttcttagcgt cgcctttttg caaaacttaa gtttgcaaga 57780
ttgtgtgcct tccagggcga tcccgtaagg cctgaaccta ggagaggctc tcgggggtgg 57840
gtgggacaga cactggtggc tgtcccagct gaagaatagg gagcccagag ccccgcgcac 57900
tacgggtggc ggagccagta caccgcagca cgcccgccca ttggctgagc cggagggcgg 57960
cgctgcggcc gctaccaccg gacctggaat ccagaggagc ggagtgaggc acgcttttgt 58020
gttgctcagt cgccttggtt cacggtggga ggggcttcga gcggccaagc cgcacccttc 58080
atttgcatac tccgtcttcg ggcacgttgt ttgtaggaac agaacttcga ccccggctgc 58140
acgcacccac acaaaacaca tcctctctcc cacccctacc cctgcgcgcc tctctctctc 58200
tctctctctc tctctctctc tctctctctc tctctctctc tctctctctc tcttccttcc 58260
tcccctgctt cctttcttcc ccccccccct ttcatctcct ctcactcttc catattcctg 58320
tcttctaccc tgcagtctgc taagacctgc atcgagaacc aaagctgact ccaacgcgcg 58380
tgcgcctatc atgctcctat tgttttggaa taggaaaggg tcgtcttcta gttctaggat 58440
ggatacaagt tcataagggc ttgctgctga ccccaaactg tcaaaattca gggctattaa 58500
atcagttact agattccaaa ggggagggat ttggctttgg gggactcgaa catcagaggt 58560
caggggccca gtgagggaga gaaaggcttg gaatggaaac caaatacatg attttaaggc 58620
gtttctaaat ctcaccttca gggcggcaga gttgagaggc tctcagccaa aagacacaac 58680
tgttcctatt tggaaatttc tgaaaagcag tgatgatgtt tgggagcata aatctttctc 58740
tctctctctc tctctcaaca tcaggctttg gaaagaaatg tcataaagta tgtgtagtgg 58800
tgtggagaca ttaaaatttt gtttttgttt tttgtttcac atctgtagtt tgtcgaggaa 58860
agcacaaggt ttaacacctg aagcaaagca acgtggggag gggcgggtgt cgaaatgcat 58920
ttctgtggac tggttatttg tttacagtgc aaagctggtc tgtgtcttct gctactgtag 58980
tatttagcct ttgctctagg caaggggttg ctctttttga tgcagttaaa acacatttat 59040
cgcgcgcgtg cgtgcgtgca tgtgtgtgtt tcagatgaaa acttgcagaa gttggtttgg 59100
caggcgtgcc atgtagtttt ggacttaaag aaaagtagga attggatgac tgggagtgag 59160
ttgctgacat ttttactcta cttgtttttt aatttctgca ctctattcct atgcaagcat 59220
tagttttttt ctgtgttgct ggcgtctgtg acaataaccg tgtcccttac ttcttgagtg 59280
tgtttcctaa caagaaaact ctttatacaa ggatggcaca acaatcagaa ctaggaaatt 59340
aacacgaata gaatatgtta atccacttgc aaaaatctcc tcgtttggag ctgttgaggt 59400
agctcagcag ttaaggttgc tggtcataca tgtctgagaa cctaatccat gtgacaggag 59460
agcaggttga ctccatagag ctgctctgtc tctgcctcct tgacaatgca aattaagaaa 59520
ttgaaattct actgcctatc actacagtgg tctttcttca cgtgtttttc ctcctgatcc 59580
agttacactt tatatctgta caactcttta tcttttttta aaatcacatt tatttatttg 59640
tgttgggagg gcatgcatgt gccagagaga gcttttggag gccagaggac aacttttgag 59700
agtcaggctc agttcagttc ctccaccttg tgggtttcag ggattgtcac gcttggcagc 59760
aagcccctca ctggctgagt catctcagtg ctcactttcc ttccttcctt ccttccttcc 59820
ttccttcctt ccttccttcc ttccttcttt ctttctttct ttctttcttt cttctttcct 59880
tcttcctttt cttattacaa cagtgacgtt ttaatgtctc taaagtgaat tgttattgtt 59940
ggggaagaaa atatgtaaat accttgcctt tcccaacaca tcctacctgg aagccagtgt 60000
tgggttatcc aggtattact ggtaagacta tttgaaaaaa aatttttttt ttgaggggag 60060
aagtatttct caagataggg tttctctgtg tagccttggc tgtcctggaa ctctgtagac 60120
catggtcgca tcaaactcac agagatctgc atacctctgc gattaaaggc gtgcaccacc 60180
actgcctggc tatttgaaac atttctgact ggattcgtta agaggatgtt gcagtcacaa 60240
ggcacacaca gggaaaagaa ttcgtgcaag aagatttact ctttttatta gtttggttta 60300
tgttgctgtg ataaacacca tgatcaaaag caacttgggg aggaaagggc ttatttcacc 60360
ttttacttcc aagttaaggc aggaacctga agcaagacct gaagcagaga ccatggagga 60420
gtgctgatta atgacttgtt caacttgctt tcttataccc aggactacct gctcagggat 60480
aacagtgcct atggtgactg ggaatctctc atatcaatcc ttatttaaga aataaacctc 60540
ataggcttgc ctacaggcca atcagatgga aacacttttc ttagctgagg ttccttcttc 60600
ccagatgatc ttagcttgtg ttgagttgac agaaacaaac actctggcta cttgcttgca 60660
ctttacttct ccttcttatc ccctttttctt ttcttcatcc tctattcttt cttcctctct 60720
ccttttcatt tgcttctttc ctcttgttgc tttctagtct tctcctcctc ctcttcctcc 60780
tcctctctcc tcttcctctg gttatgttcc tgttctgtgt tttatgatac catctcatga 60840
agtccacact ttgacttcca aattactttg tagccacacc gaccttgata ttcttgcttc 60900
agcccccaga gtgctgagat tgtaccacca cggaacccag ggctccgtat gctgtctgcc 60960
agttgaacca cagttcctgc cccaagagat tctcaacctc cccacctcaa gcctgtgtcc 61020
cacagaagtg agtgtaggcc aatgggagaa cagaactaga ccttggttct agaggtcatg 61080
ggtggcagtg ctgtactacc tatggtctgt cctttattgg tctgtgtatg acaacaccca 61140
gcatgctatg tgcttgattc acatttgtca aatgacatga gaacaattta ttaaatggtg 61200
catggaagaa gacagccatt actgaagtgc actctgtggc tctttgctga gcttctaggg 61260
ctaacagtag tgatcacaaa agaacctcat aatttttttt tttgagacag gttcttacgt 61320
gtagctgagg caggccttcc ttatcttacc agtgctagaa tagcaagcag tccctcctat 61380
gacccatctg atgttctgat gtctgcatac actgttcagt gtttggatgc gaatgacaca 61440
cttagctcct tgggctaaaa cagtagctta gtaggtacgg agccctggca cccatcttca 61500

-continued

```
gcatcattgc aaagaaagta gaacaaaatc cagaagaaca aaccgaactg tatctcaact  61560
atttctcctt tataattctt tttaattata aattctcttt aattatatat tacaatttaa  61620
atatttttga aaatttcatc tgtcatgaag tatatttcag tcatattcac ccacaactct  61680
tctctgcatc tcccttcaaa cttcatattc tctgttttaa atccacagag tccagcaagt  61740
gctttcagga tgtgtatggg tgtgaggcct gtctactaga acctgaaaac aaagtaaaac  61800
aaatggaaac aaaataacca aactcccaac tttcctcgca ccagcagtca tcaactgcgc  61860
atagcatctc tgcctgggta ggggtgggct tattagtccc caatccattt ctccccttta  61920
tagctttctc aaatggacag cctctagtgt tatctgtatt cacccccctct ctgcacctcc  61980
ccccttccc catatgattt gcaactttat aactgttact cagtactttt ctgccaactt  62040
ctcaagagta tctcacctgt cctcaccctg ttggttccag gtatcctgtt cccaccagcc  62100
ttggcacaag gctgtggtgt agttcctaac acagaaagaa agagacaaga taaagaggga  62160
aggctggaga gatggctcag tgggtaaaag cccaagcctg agatctcagt ttgaatccct  62220
agcacttagt aaaaaggatt gagtggccat atgccagcct gtaaccttgg tgccgtgggt  62280
ctggacatag gagtatccct gcagtttgtt ggcttccagc ctggctccag gctcagtgag  62340
agaccttgtt tcaaagaaat aaggcctcta aggggaatag gaaccccccac aggaagacca  62400
acagtgtcaa ataacctgga cccctgggag ctctcagaga ctcagtcacc aaccaaagat  62460
catgcataca tgggctgctg gtccgaggcc ccaggacaca tatatagcag aggagtgtct  62520
tgtctggcct ctgtggagag gatgtgccct aatcctatag agacataatg caccaggatg  62580
ggaaatatca gggggcgggg tgaacccaca gtctaagatt caaaggggag gcgcttggga  62640
gaggggaccc tgtgagggga gactgggagg gggcagcgtt ttgggtgtaa ataagtaaaa  62700
aaggataaga tacttagata aaaagtaaaa gtttcaaaga acatttgtga taattgttta  62760
agtactcttg aattttgcaa tttcactggg cctactccag ggtaaagatt tgtagtaaag  62820
atttttgaga acttcatatg gaaaaaaaaa agaagtaagg cctttaaaag gttaaaaagt  62880
aaatcataaa tttaagatag aagatgtgaa gttgtgaggg agagatgtat atgatgtggg  62940
aggaatctaa aaggggactt ggtggagcta ctggaggata agtatgatca agatgcagtg  63000
tataccatta tgaaattttc aacaaataaa tattaaaaga agaaaagaaa tcttccggac  63060
ctctccctct ggtctctgca actgtatcat acacccctat atatatgaat aaataaaatt  63120
taaaagtcac acccctccct taaccccccca gttgcttggt gcctttgcag cctgctcata  63180
ccaaattcca gatgtagtgg ccagagggct atgtctgcct tgtcaggttg tttgcttttc  63240
ttcttcctgg atgtcctata aatggaattc tacagtgcaa agtgcaagat cacactgcct  63300
agtctggctg tctgcccctg gctctgtttg cagcattggg cccttttagc atttcatggg  63360
ctgcagagct tatgtgtttg ggaagtgttt attggagctt tgatgaagct tcttgtgaat  63420
gaaaaacact gacccttagc tgcagtccca gcccaggaaa tgagctcctt cctgtccttc  63480
tgtgtgttgt acaggggagc ctgtgtcttt gtgagccata gataactggc tgctttcatt  63540
attgcttcct ccaatttagt ttcagccctc agatctccct agacagagca gtgctaatga  63600
tgataacatt gtttggcata gctttgcctt ctgtatccct ggactcataa ttgcaggaaa  63660
ggggatcgag ggcaggggga ggcgaggtgt tgcaggatgc tatcctctga gcataaaggc  63720
caacctcatc agagcagatg caactacctg ccattcagtg ttcccctcac caccactagc  63780
ctcagtaagg ctcgctgact gttgatgtcc cttcatagaa gaaaaggtat agtggattac  63840
```

tgaataacac ctaaccctca ctttctagct gctcctccct ccatggcctc atggtcttta 63900
tgctagggta tagagagggt tgaagttaat gaagggagtc ccccatctgt gcagctcttt 63960
agagaagtgg taatctatgc tgggatgagg ctttcctatg atctggctgc tttgagtcac 64020
cctaactcct gtctgtatcc cacacttgtg ctttgtatgt aagtccagta gatcccttgg 64080
ttggacagtg gcagaattgt accttggttt gttgttggta cctataagga aaagcggaga 64140
gactgcaata ggatggggct tcgtgggtag agacctgcat ccatggaacc ttgggttcca 64200
agattggcag tgtgcttgta gtctcagcac tggggcaggg gagagagggt ctgtggggct 64260
gcaggatcct caaggacatt tcttcagccc ctaagaagtc tctgtggtga tttgaatatg 64320
cttggcccag ggagtggcac tatttggagg tgtggtcttg tcaaagtagg tgtgaccttg 64380
ttagagaagt gtgtcactgg gcgtgggctt taagagtctt gtcctagctg cctggaaacc 64440
agtcctctcc tgtttgccat gagttggact gaaccataaa cacttggctc ctcaggagcc 64500
atcatagtct ttatgaatgg ttgttgggaa tataaagtaa tttagtggct atagaaaaca 64560
gtatggtggc tcattggaaa ggttaagaga attaacgtag ttggggtttg gaagttggct 64620
gggtaagagt tgttaatgtg caagcatgaa gaactgagtt cagatcctca gcatctatgt 64680
aaaaagcagg gtatagtcat gagcatgcct gtaacatcag agaggttggg gggagagaca 64740
ggaggatctt tagggcttac tggctgccag tctagctcta ggttcagtga gagatcctgt 64800
ctgtccaggc tcatgcccag ggcatgtact taatattcaa taatcccact actgaataga 64860
tacatggaag aatgaaaatg gggctcagac atttgcatag ccatgtccat agaagcatgt 64920
ttataatatc ctaatgataa aggctgttta agtgccacat ttgaatgagt gggtcagtga 64980
agatgattca ctcctgaata ttattcagcc ctaagaataa acagaaggaa cctttgatat 65040
atgctaccat ggataaattt ggaggacctg ataaaggatt ccactcatcc aaagttccga 65100
gaaacaagag agagcagaaa ggtgggttgt gggccgatgg acgggccgtg agagtcctga 65160
acagagagtt tccatttggg aaaattatga gattctgtgg atggttgatg agggtggcta 65220
cacagccaga caaatgtggt tattcattaa ttaattcatt aaaaattaca tacgtatgtg 65280
tgtggtaaac atgcatctct ctctctctct ctctctctct ctctctctct ctctctctct 65340
ctctgtagag gaggtctaag gttgatatca ggtgtcttct atttttctcc accttaaata 65400
ttgaactcct ggttttcctg tctctacctc ttgaattctt ggatgacaga agtgcaccat 65460
cgcacctgtt tttggtgatg cttcaaaccc agtatcttgt tcatgctcgg ggcaccctac 65520
ccttcccagc cacatctgca gccagagatg gaagctctta gggtattttt ttttttttaac 65580
catagtttaa attattttat tttattttat ttttttgctt tgtgtgttca gtaactacac 65640
aggggagaaa ggactacaca ttggacagct catatttctg tcatagtaga gggttgacat 65700
gaacagtgtt gctgacagta tggagaactg aagctgaagg cctatgctgc cacaaggagt 65760
gcctgggcaa ctgttcggaa ggctagtaga ctgggaccca cttgatactg ggagagctac 65820
acttgagaat ttgggagaca tctggttcct ggctattcag tcctgctcca gagtatacaa 65880
gtaaaaagag agagacatac cttagaggga agattaggca cacagcagag gaatacgtag 65940
agtcgtaaaa gccacagata ctcacaagca tcctaggaag caaagggctg aaaagaagag 66000
atgattagga aggggctggg gagatgattc acagtgccaa gctattgcta cacaagtgtg 66060
acaacatgag tccagatctc cagaacccat acaaagctga gctctgtggc acaagtatat 66120
aatctcacag tagcaaacaa cagagacctt gtctcagaca agatagaagg tgaggactga 66180
tagaggttgt gctctgacaa tggtgacacc cctccacaca tatgcctgtg tctcctgggg 66240

-continued

```
ggaaagtgtt gaacaatgag gtaatgggat agaagggttc gagaccagcc tcccatggac  66300
aaattcagtg acgtcaaaca agaaagcctc tctagccaaa agttgaggct caagctgtgc  66360
ctccacctgg cgggcctcct ccttcttcag gaacaggatc cctcactcat gtttcaacag  66420
agcatggtgt gcgtacaggt cctgaggcac gggggtggca agtgcaaggc taacacgcat  66480
ttcagagtga gctcaaagag agccttcata gcttaatgac aacttgtctg caaataaata  66540
catataaggg cagagggtgt atctcagtag tagagctctt gcctagaatc tcccagtgga  66600
gtattgggag tatgggtcag ttgtagaggg cctacctaga gtccaccatt gaggactggg  66660
gtatagctca gtggttaaaa accaggtcta acatttgcaa gttctgggtt ccatccccaa  66720
caatgcagta gtacgcacac acacacacac acacacacac acacacataa gtaattaagg  66780
caataaataa aataaaatta tataaaccta taattaaaac aaatcacatt taaaataaat  66840
aataaccacc ttttagctgt ggtatggcat ttagaaaata tttacttatt tgtgtgcata  66900
tgaaacatga acaggtacct gcgaagccca gaagagggca ttggatcccc tggagctgga  66960
gttaaaagtg aaccacctgc ttgttctggg tgctgggaac tgaactcaag tcctctgcaa  67020
gacaagaagt gctggctact attaagccat ccctccagcc atcaggcata gcatgaaaaa  67080
agtctgtgtg cccttgaagt tattgcgact gtatctatct tagacataga ctgtatggac  67140
tataggaaac actatttagt agtgtgttac attgtgtctc ctgccaagga cttggtttct  67200
tggcttcctg ttagcagcct gaagttgatg gtagtaactg gtgaatgcag tgagtcaggt  67260
ctcttgcctt ctcttcctca ggtgtttggt taatttttgc caagtgtgga gctgctttgc  67320
gggggctact gccctttctg ttcacagacc agtcagacac gtgtcaagca ctgtttaagc  67380
gtggctttta ttgttattat tttgtttggc cgtttgtgca gacaaaattg gacagagtcc  67440
ttgaccagct gtttcgtttt tccttcttgt ctccagtttg cccaaccatc tgtaagtcac  67500
atggctgcac agctgaaggc ctgtgctgcc acaaagagtg cctgggcaac tgttcggaac  67560
ctgatgaccc caccaagtgt gtggcctgtc gcaacttcta tctggatggt cagtgtgtgg  67620
agacctgccc gccaccctac tatcacttcc aggactggcg ctgtgtgaac ttcagcttct  67680
gccaagacct tcacttcaaa tgcaggaact ctcggaagcc tggctgccac caatacgtca  67740
ttcacaacaa taagtgcatc cccgagtgcc cgtctggcta taccatgaat tccagcaagt  67800
aagtcctgga tgagggtctg gggaaggaat tggaagctgg tgctatgctc aaagatgctg  67860
ttaaagaggc tgaagatgta gctcttttgc tagaatgcat tccccagcat caaacagtgg  67920
tctctcacta gatccaggac tggtggcaca tgccagtgat cctagcattt ggaaggtaga  67980
ggcatgagga tcagaaggtt tgagtcatcc ttggctacat agagagttca aagccagcct  68040
gagctgcatg agattctgtc tcaaaaaaac caaaccaaac aaaaaaatca gaaagaaata  68100
accctcctca tccctcctac tctgcacagg aaaaaaaccc tgtgccaaac cagaatgtgc  68160
tgggcaagaa tgggcttgct gttgataact accacttata ttttaaaaat tctgtatgtg  68220
ttcatgtgtg tgtgtgtgcc atatgtatat gcagatgggt acatacacac gtgcacacat  68280
gtaatgcaca aagtgggtat gtgtgcgggc atctgtgtcc aggtggatgc gtgcacacat  68340
gcttgtatgt gtttatgcat tatgtgtgtg catgggtgta tgaaggtggg tgtgggtatg  68400
tatatgtgtt catgtatgtg aaggtgggca tgtgtctgta tgtgtttatg tgttcacttt  68460
tatggagaca tgtgtatgca aatgagcaca tgtgtatagt tgagctcttg tgtgtgcata  68520
tttgtgtgtt tgggcacatg ttgcaggtga gtacaggtgt gtgtatgtgt tcacctgtgt  68580
```

agacgtgtgt gtgtgtgtgt gtgtgtgtgt gtgtgtgtat gtgtagacca gtggttgatg 68640
ctggatgctt tcctcaatca ctctccatgt tatttagttt taaaaatact ttattcttat 68700
ttatgtgcat gtatatatat acagtgtttt gtgtgcatgg aggtgtctgg ggaggccagt 68760
gagtgcatca gatccatccc cttgagcaga agttacaggt gaatgtaagc ctccacatgg 68820
gcacaaggaa tgggactcag gttctctgga agagcagcaa gctctccaga ccactgggcc 68880
atgtccccaa ccctcacttt tgtttctgag aaaagtttcc tctccagatc cagagcttgg 68940
gctccttccg tgtctgcctc cccagtgctg ggattgcagg tatgactttc gtcctggttt 69000
ttttatgtgg tgctggggaa gcaagccaag gccctcatga gtacagcaaa tattttgcca 69060
actgagggat ctacacactc tcagtagcat ttttttgttg ttgttttata ctctttgtgt 69120
cctgggcttt gatgatggac ttgatcagaa gtgacttggt tctttgcctg aacatctcat 69180
ttctgagtgc tgcgcagagt gagctgaaga tggaattttt ttgtttcacc tgcctcctcc 69240
tccttggctc agtgactcac tgtaatacta ggaagatggc tgtgcagttc atagcctacc 69300
ccacctgact ccgacacaag ttggggcata ctgtcttaag gaggggaggg cttacaccta 69360
cactgtttcc agggcttcgc tgttcttcca agataagcac catcaagcca tttcctacca 69420
cttgggtgag aaacagggtt ttctttctct ttggtggttt aagtcaggct tcacacacac 69480
acacacacac acacacacac acacacacac acacacacac acaccaggtc atttgttcag 69540
gaccttaact tcttggatga gatattttgg tgtctgggac cttcaccgag ttgttgattt 69600
ttaaatttct tggtttttgt tttaggattt gagaaaaggg aggggttggg gggaggatgt 69660
ccagcaaaga acagaaaacc aaatcagaaa cagacgcaca ttgcaaggcc ttgagctgac 69720
ctgctgacgt caaaattctt cctctcagac ttgggcacta gccaagtaag tgagcaaaaa 69780
agagtgtttt gattttggtg ggaaatttta tttccctgag tagaaagggc aagaaggaaa 69840
acaatcttta ttttagctcc tgtgaacttt ttttttaag tgtttatgaa acctgaaagt 69900
acaatatgtt ttgttttgct cattattaaa aaaaaaaaaa accaaagaaa caaaacagca 69960
agaattgttg gcccaaatag acagacctct ataaatcagt ctgcatgttg aatgggactt 70020
ttacattttt tattacttca agggcagaag gaggtttatc aggaagattg gagaagcaaa 70080
catcattcta tttatctatt tcagttttta agaaagatca gggactgatg tcaagacctt 70140
tgtttaaaag acattgcctt tagggctgga aagatgaccc accagagaaa gcaggaattc 70200
agatccttag aatccactcc aggctgcatg ttggcccact tgttatctca gccttagaag 70260
gtggagacag gttggctatc tacattagct aattgatgag ctctgagttc agaagaggga 70320
atcctacctc agtctatatg gagggctggt gagatggctc aacagataaa ggtgcttgcc 70380
accaagcctg acattctgag cttgaaacct taagacccat agaaggagaa agctgacttc 70440
caaagttttt ccctctgacc tgcatactgc aggcatacta caggctgtga tgtgtacatg 70500
actctctctc tctctctctc tctctctcta tatatatata tatatatata tatatatata 70560
tatacacaca cacatataca tatatacaca tatacacaca cacatacaca cacatatata 70620
tacacacaca gtcacacaca cacagtcaca tacacataaa tacacacaca gtctcacaca 70680
cacagtcacc cccgacaaat ctaacctatc tatctatcta tctatctatc tatctatcta 70740
tctatctatg tatgtatcat ctatctatgt atgtatcatc tatatgtata tacatacata 70800
cacatatata atagagagca atccaggagg atatccaaaa tcatctgtgg aactccacat 70860
gggcacacat gcttacataa tacattctaa agaagaaaaa gatgttggct ttaaataata 70920
ggcatttttt ttaatgctca ccaaaaccac aatgatgact ctctgcacat tgtctaggtg 70980

```
tgagtgtctg tatttttccc agctcctata ggaggacact tctctgatga tgaccgagag  71040
agactgatct acaagtataa aagaatgtcc ctaagagtca tgttattgct atattccttt  71100
agcagaacaa tagtattggt ttttccatgg gtccataacc tatctattct tagattcttg  71160
gccaccttag cagtatcagg catgggttct agttcatcga atagactaga tagtggttgg  71220
ttgctctgca agttttatgc cactattgca tcaaggtatc atgcagggaa gttactgtag  71280
atcgaagggt ttgttgcttg gttggtgttt atctttgtcc tctggtagca tgcagagtac  71340
cttccagtac caggagcaat tgtgagcaag agtaaggctc taagaaagaa cgagcttgac  71400
tttcccatgt ccaaagagat acagtgctgc tgtctttaac aatagggctt taccattagt  71460
ttgtggagaa caaccaattg tcttattggt aatatcctga gttgtttggg agtttctttg  71520
agggcccctt tctttgtcta acaacacaat tggaagtaac tgattcttgt ccctggaggt  71580
ttttacttgg tggctataaa tgtgtaggtg ggtcttcatc tccttgttgt ttggtgattc  71640
caaataacaa gatctaaaga tttaaaataa taaaaccaaa agatttattt atatatgcat  71700
ttgaaagagt gtccattgta gtaggtttcc atatgacacc tccaattctc ttagtgttag  71760
cagttcctcg ctgtattctc tctcttgccc tcctcttccc ttccccccctg aatcttttg  71820
tcccagtttc ttttcccctc tctccccaat ccataattat atatcccatt ttcccttcct  71880
ttagagatcc tcccctaccc cctacttctc tatacctctg tggttatact tttttgtcca  71940
tctaagggtt aacagttaaa ctcaaacttg caatgtccgc aatgttgtct gtttggatcc  72000
ttcaagtgct gaatttttac atattttatt tatgcacata ctgatttatg ggagaggaaa  72060
ccaaagcaaa catgtagagc tctgaggata actttggatg gatgagctct ttactttcac  72120
catgtgggtc ctggggattg aattcagctt cgaggtaagc acctttacct aatgagccat  72180
ctcatcacta gaacattgta actatatgtg catattcacc acacccacgt ggggccaact  72240
atgtaacctg atggttgaga ctttttatat tctatgtcct ctaggaagag cagaggcagg  72300
taaggagtca ggcttccaag gctggggaac tggagaatta gctccattag caggcaaata  72360
cagagacctg agttcagaaa tgtacacact ttcctttttgg aaacctgggc atggtggcat  72420
gcacttatga ccccagtgct gggtaggaaa caggatggtc cgtggagctc cctggccagc  72480
cagccacaca gcaagttcca ggttcaatgg aagattctat ctcaaaaaca agctaaaagg  72540
ctcctgaaga atgacaccca aagttgacct ctgatctcca taaaggtgtg tatgtacccc  72600
caacacacac acacacacac acacacacac acacacacgc ctacacatca catgcatatg  72660
aacataaagt tctatcatgt gatcaatgat tctatcaacc gtgcctagag actccaagac  72720
aaactttata ggactagtga ggtgacaggg ttggtaaaat gtggacttca gtttgatctc  72780
tagcaccctt gggaaaggtg gacatggtgg tctgtgcttg ttataccagc actggagagg  72840
tgtggtgctg tcagatctgc cctgtgcagg gaatgaagga agttttttat accaggaaag  72900
gaattttgtg tgtttgtgtg tatgcagcta tttgtgagtg ggtgtaggga gatcagagga  72960
caacctcaga tattattctc agaatttcac ctactttctt tgtgataggg tctcccagtg  73020
accctgagcc tgacctatta ggctaggcta cctgatcagc aaaccccagg attctctctc  73080
cttcctcagt actactctta ccaatatcta acagtgtttg atatttccaa gaaaaccttt  73140
cattgcgtat gtatttattt tttatgcgtg tgtgtgtgtg tgtgtgtgtg tgtgtgtgtg  73200
cgtgcaagcg cacgcgcgca cagggttagt atgtggtgct cagttctcag aacttgcttt  73260
ccttctttca ctttgttggg cccagggatt gaactcaggt tagcaggctt ggctgcaagc  73320
```

-continued

```
aggtaccttt accctatgag ctgtctttcc agccaatgcc tgacattttt aggtgggcta  73380
taggggttca actgaggttc tcatatttat gaggtgaata ttccatggtc tgaacactcc  73440
cttaaaccct gggcaatgaa ttttaagggg ataattggcc atttaaaaac tgtaggagaa  73500
ggttgacaat gcctgggaat aattttgatt gtggcaattt agagatgaga tggtgttggt  73560
actgagcacc agttgggaat ctggctctgc atcgtatact gcccaaggtt gcctcatgac  73620
cactgtgaag acatatttgg tgtcaaatat ttggaatact atatcagtga actttctctt  73680
gctgtgataa aacactctga ccaaaggcag cttaggggag gacaaggttt gtttcagctt  73740
atactgcttg gttacattct gtcacagagt gaagtcaaat agaaacataa agcagaaacc  73800
acaaaacaga gtttctcaac cttcctagca cgaacctttt atacagatcc tcatgttgta  73860
atgacctata accataaaat tatttatctg ctacttcata agtgtagttt tgctactgtt  73920
atgagtcata atgttaatat ctgataggta ggatctctga tatgtgacca acagaggggt  73980
agcagtgctc aggctgaaaa ccactgccat agagcagtga tgctagttga ctctgtttct  74040
agctcatgtg cagctagctt tctcagatag accaggccca cctgccttgg aaatggccac  74100
ccacagtggg ctggaccctc ccccatcaat caacaatcga gataactccc cacagtatag  74160
tcatggacca atctgattta ggcaattcct caactgagat ccccctcatg atgactctag  74220
gctatatcct gctgacagtt aaaagttagc tagctcaact gctgagctca gcacatccac  74280
tttagagtaa cagactgagg ttgccactgg gttcctgtga agagtgctgt attccaaatg  74340
acggggtgag ggaaccctgt gcacctcatt gatctctttg cctgtgctcc actctcagct  74400
tgatgtgcac cccatgtctg ggaccctgcc ctaaggtctg ccaaatcctc gaaggtgaga  74460
agaccattga ttctgtgaca tctgcccagg agctccgagg ctgcactgtg atcaacggta  74520
gcctgatcat caacatccga gggggcagtg agtattttgg agcatccccc acttcctatg  74580
agctgtgagc agggaagtgc acagctcagg gtattccaca cattcccctc ttaactttca  74640
cggccaaatt tactttgttc ctgtggtctc agctattcag gaggctgagg caggaggatt  74700
gctttaatct agcaagttca gtctagccta gatgacataa tcttgtccaa agaaataaaa  74760
caacataaca tgcaaagtga cacatccttt agtggccccc aaatgagaga cttataccag  74820
gagttgcctt aaaatccaaa atgaaaattt tatggctcta cctctgcctg aaattcttat  74880
tttgcaatct gcagcaggaa tctctattct ttatattttt atgtgtatga gtgttttgtc  74940
tgggtatatg tatatacatg gtgtatatga ggtgtccaca aaaaaagagg gtatataata  75000
ccctggaact gcagttagag atgactgtga gttaccatgt ggatgtgggg actgaaccca  75060
ggccctctgt gatagcacct gattctcgta attaattctg ggccatctct gcagccccag  75120
gaatctcttc ttactaatat gcaccaaggc tgctggtata cacttgctag ccaagcactc  75180
aagagatgga ggtagaagtt gttcaaatgt gagtttgaag tcagcctaga ctacatgaga  75240
ccccatatca aagaggtaaa taaaggctcc aagctaaaac taacaaaaca aaacaagcaa  75300
aacaaaacaa aacaaaaact ttgctatggg tagtgtgaag gtaggtagag cccagcattc  75360
ctggattcat gggttttagt cctccgtact aagtcactat ggcatactgg tgaaataatc  75420
acagcactgg gagaattgta gagacagcaa gatcagaaat tcaaagttat ctttaggtga  75480
agagtagatt tgaagcaaac ttgggcttct tgacatgaca aacatatctt tgtttcaaaa  75540
atagaaataa ataaaataaa agcaaacgtg ccgtattgta gatttgtttt aaactcatca  75600
cttctcctac cttcacatcc tgagtgctgg gattaacagg tttgcaggag tgcgcgtgca  75660
cgtgcacaca agcccacaca tgcacacccc cgccccgcgc acacacacat acaaacacat  75720
```

acatacacac acatacaagc acacacacaa acatgcacat actcacacac atacaaacac 75780
aaatacacac aaacatgcac acacatacaa acccacatac acacacatac aaacacatac 75840
acatacaaac acacacaaac atgcacatac acatacacag gtataaacac acacaaatat 75900
acacacatac acacatataa acacacatat aaacatacac acaaatacac acacatacac 75960
acacatactt acacacacaa acacacgtac acacatttat aaacacacat acaaacacac 76020
acacatacac acacacacaa cacacacaac acacacacac acacacacac acacacacac 76080
acacacacac acaagataaa actcttctgt agatactcat gggcatttcc tcctttttgc 76140
agacaacctg gcagctgagc tggaggctaa ccttggcctc attgaagaaa tttcgggatt 76200
tctaaagatc cgccgctcct atgctctggt atcactttct ttcttcagga agctacatct 76260
gattcgagga gagaccttgg aaattgggta tgtgagcctg tgtttgagac tgccaaccaa 76320
gaaactcatg agttaggaga acaacgtagg aaacgggaga tggctctctg gataaactgc 76380
ttactttgct acattaagac ctgaatttga ttacaggttt agaaaaaagg caggcctagt 76440
agtgttgggc acacagagtc tggggcttcc tggctagtca atctttacct gtttatcagg 76500
tttgaggcca gtgagagacc ttgactcaga aaaccagggt ggatcaggcc taaggagtgg 76560
cagccaggtt ttcctctgtc ctccacactt gtgaacacac tcatgcacat gctcagccat 76620
gcatgtgtga gtgtgtgcaa acatacacac acacacataa gaatttagga cttttgtttt 76680
ttataatcca actgaaccaa attgaagcat ctgttgggtg aaaatgcctg taacatttgt 76740
gaatgtccat ttaacaagaa agatctactt ttgttgttgt tgttttttgt ttttgttttt 76800
tttcgagaca gggtttttct gtatagctct ggctgtcctg gaactcactt tgtagaccag 76860
gctggcctca aactcagaaa tctgcctgcc tctgtctcca caaaatctac tttatagtct 76920
ttctagagaa gccagatggt actggctggg atttactaat aatgtgtaca cctgtcaaaa 76980
ctacactgtg ataatttcct ggccacagcc atgtttggaa actttccaat tggttctgtc 77040
aattcaaaac tatcacctta aagggataag agatagttta tcctggaacc aattatgagc 77100
agcttgaccc aggaacattg ataaacgtta tcccaaatta catattccaa tgtggtaaca 77160
gtctcaggat atttttatac taatagaaca caaagtcata aacaggtcac ctttaaaata 77220
cattggtatg aacatcaaag aggcgagtaa tagaaaacca gggaaatctc tgctataggc 77280
ctcagaggtc atcttagtgt tttggttgat ggaagctgat ggtctgctac actagtacat 77340
tccaaaaggt ttacatgcta gtcacaagga ggttaggtca gatgaagagg tgggtaagag 77400
tggctattaa gagggctaaa gtcagaccag gattaagtgt aattagactt tggacctgca 77460
acattctaac ctctccatgg tcattgagat tgtaatgaaa taatcaacct tgtagaaggt 77520
tcaacataag gtctcatgtt catggtccct tctcttccat tcccacttcc accaacaaga 77580
cattttgttc acttagcaga gaacatacct gctctttgtt gagatgctca tctttccgag 77640
tcctggaatt ccacctcttt aaggcatcct tccagccacc cccaggtggt ccttcctaat 77700
tttcctctca gtctctattt tctatttgag ttgtcaacct gggctcctag tcatggccca 77760
tgtcttggga tcttgtccta cctaagctgc agtattcagt cttgacttct ctctttatcc 77820
acaaccttaa gcctgtctct gtagattgtc tcgggtgacc actgggaacc tcagattctg 77880
atcctagtta tccttgtttc tggaattctt ctttgctctg ctctccttta ggtcccacag 77940
tccttgctta agttgctcaa acaaatagaa gtcctgaatg tggtgtttaa aaagtgggga 78000
tggactcatg agcaagaagt ctgtagaggg tcattgagaa atgagatgga gaagttagat 78060

-continued tctatttctt gtgggcacag aatgggtacc ctgtactcag tctcattgat gaaaaaccaa 78120
cagcaaacag gggaaggggc aaaaggacag tatggccaat ccatactgtc ttaaagcaaa 78180
atcatacaac taggttgcag atatgcacct ctaatcacag gacttaagag gtggaaacag 78240
gctgatctca gggccagcct ggcctggtca gtgtagtggt ttttaaggcc agccaatgga 78300
tggggtgggg ggtggaggag ggagggaggg agagagagag agagagagag agagagagag 78360
agagagagag agagagagag aatttctcaa aaccatttaa aacacaaaga aacaaacagg 78420
aatgtagcac aaacacaagc caaacatgtt tgcaaccttc catagttttt atccccaaac 78480
ttgatttctg tttctatttt atttgccaga cctgggtcac atggttgttt ctggatagct 78540
gtgagggagg tgggaagaac atatatctat cttttcaaac ctttgtgatt gagaaagggc 78600
atagaaaaga cggatggaaa ggtgtttgag aaccaagatc accatgttta aatttattcc 78660
cctaaaataa ccacctgctc atgctgtcac aaatattttc tttttttttt ttttttaatt 78720
ttagctgggg ccttttgatt ggctggactt tctggaaaca accagagctg tccagtagaa 78780
ttattatata agtcatgaat gagactttca gtgttccagg tcccaactta aaacttacct 78840
agcccattat gtctcaaatg ttcaaattta gaatcattaa tttaaacaac ccagaatttt 78900
ttcatcttcc cttttgcggt acctctttga aaatgtatct atctatctat ctttctatct 78960
atcatctatc tatcagatca agactcattt tcgtttagcc caagctagcc ttgtacttgt 79020
tctgatgacc ttgaacttct gatccttctg cttatatctc ctggagtata cagtgatggg 79080
atggaattca tggcctttga gtaccaggca agcactctac aaaccaggct atatctccaa 79140 tgccttttc tacctctttc aaggcagttt agaattacta gcctgttcat atggtacaca 79200
gggtatggct tctgtgtcat ttatggaggt ccaggttctt tccttactca tcacttgcta 79260
gtaggctgct agttgtttca aaacacaact ctaataaaac tcatcaagaa tatataaaac 79320
cttgagctct gtaatgccca tagggattgt ataacctaga gtctttcttt cttccttcct 79380
tccttccctc cctcttttct ctgccccccc tctcttcctt ccttccttcc ttccttcctt 79440
ccttccttcc ttccttcgtt ccttccttcc ttcgttcctt ccttccttcc ttccttcctt 79500
tctttctttc tttctttctt tctttctttc tttctttctt tctttctttc tttctttctt 79560
tctttctttc tttctcttcc tccttccctc cctccctccc tcccttcctc cctccctccc 79620
tctctctctc tctctctctc tctctctttc tttctttctc tctttcttct tcctcctttt 79680
cttcctcttc ctgatcttcc tcctctcttc ttcttattcc gcctctttct tctttctcct 79740
cctgcttctt tctcttcttc ctcttccttc tccttctttc ttcagctttc ttcctctttc 79800
cttctcttcc tctttcttct tcctcctctc tggtttttct ctttcttcct acccttcctc 79860 ctctttttc ttccttctct tcttcttcct tcctcttctt ctttctcttc tttctccctc 79920
ctccctcttt ctccttttc ctcctcctct tccttctacc ttcttcctct tctttcttcc 79980
ttcttctgcc tccttcttcc ttttcccccc ttcctcctct ttttcccttc tctttctttt 80040
ttgtcttctt ccttctcctc ctctttcttc ctcctcctcc tgcttctctt tctccttcct 80100
ccttcttcca gagaaggata tatattcatg atcttgattt agtatacagt agactcaagg 80160
gttcatttta ttgcaagggt gtttcctcaa aactgctagg taaatagcac tactttgctc 80220
tttccctggg tttagctcat atgcttgtgc ttgaattttc tctcctccca agcccagtct 80280
gacccccacc cctgttcccc ctctgcccct ctctctcttt ctctctcctc ctttgcttct 80340
gctttcttct ccatctcctt cttttcttct ctctcttatt ttgccatacc aagagttgta 80400
tctagtactt ggtacatgct aagtaagcac tcttaccatt gtggagtagg ggattatagg 80460
cagggtctct actactgagc tatatcccag gccctcactg gaggattctg gttacattac 80520
tcctcaccca tgccctcagt cctcaatgga agattctagg caggggctct atcccttagt 80580
cacactacca atcctttatt cggggattct aggagcatgt tatacactcc atgaaaacaa 80640
cttctttgtt ttccatattc ccaaagattt ttttgtgtct gtacatagaa tgtattttga 80700
tcataatcac ccccatgcat tcctcatatt ccacatagac ccacccccacc ccaccccacc 80760 ctacctcacc ctacctccct ctcaagttca tttcttcttt tttaaaataa aattataacc 80820
cacttagtgc actctgtggc acctgccatc ctcgaactaa gaacattggt tttgagtaac 80880
tagttgtgtg tgtccctgta gaactattct ttttatgcct tggacaacca gaacctgagg 80940
caactctggg actggagcaa acacaacctc accatcactc agggcaagct cttcttccat 81000
tacaacccga aactctgctt gtctgaaatt cacaagatgg aagaagtctc cggaactaag 81060
ggccgtcagg agaggaacga cattgccctg aagaccaatg gggaccaggc atcgtgtaag 81120
ttgcttcatt cttagatccc cagcagctgc ccccagggtc ccctctggca gccactaccc 81180
tagctgccag gaaggtgcca ttgttgtttg ttgagctaca gctttctgtg agaggagttt 81240
tgaaatacaa aaggcaggta tagatgtgtg tatgtgtgca tgtatgtgca tgtgtgtatg 81300
tgtgtttatg gatagacatc catgtgtctc tggaagccag aaagcaacct caagtataat 81360
tccctggaca ccatccacta gttttctttt gctagatttt tttttttct gcctaaagcc 81420 caacagttgg ctttataggc tgtgtaagaa cctcagggat ccatctttcc tatttttttc 81480
agtgctgagg atagaagtgc tctattgctg tgaagagaca tatgatcaat tgttataaag 81540
aaaagcattt aattggggct ggcttaattt ccttctgaag cctaggctgt catcatcatg 81600
gtgggaacca cagaggcaga gagacaggct gagagcttat attctgatcc acaggcagag 81660
gcagagaaaa gagagccact gggcccacat ggacttttaa tcctcaaatt ccacccctag 81720
tgacacactt cctccaacaa ggccacaccc ccaacaaggc cacacctcct aattcttccc 81780
aaacacacct acttgggatt aagcatttaa atttatgagc ctgtggggac cattcttatt 81840
caaactacag tgctccactc ctgggcctct atagccttat agacatatca taacacaaaa 81900
tccattcaat ccaacttcaa aatcccccat attcaataat cgcagtctca acactgttta 81960
aaaaaccagt cttttctgag attcaaggca atctctttac tgtaacccct gtaaaataca 82020
ttatacgcaa catacagtgg cacagaatat aattgccatt ccagaaggga ggagaggagg 82080
atggtgagca aatactggac caaagcaagt ctgaagccca taatggcaaa ctccaaactc 82140
tctattaggc ggctctttct tcccagcttt gctgatgcaa cacatttctc tcccttgggc 82200
agctctcctt ggtagatacc ccataactct ggcatctcca acatcttggg gtctccaatg 82260
ccatctaggt tttattttca cttcttcaaa caatgaccta tcctggcctc tttgcaggga 82320
cttcctgttt gactaacagg agactaagca ttcaaacata tgagcctctg gggtcattc 82380 tcattcaagc cagcacagcc atgatggctg gagttttctt ctctttcccc tccctccctc 82440
cctccctccc tccctccctc cctccctccc tccctccctg gccctctctc cccctcttcc 82500
ttccttcctt ccttccttcc ttccttcctt cctcccttcc ttccctcctt ccttccttcc 82560
ttccttcctt ccttccttcc ttccttcctt ccttccttcc ctccttcctt ccttccctcc 82620
ttccttcctt ccttccttct tctccccctc ttctcttcct cctccttctc cccctcctct 82680
cttcccccac ctcctcctcc taaacgtggg ttctgtggtc agaactcaga ttcccaggct 82740
tacacctgag cattcacata cttggaatat tcaccaagta aactgttttc cctctgccag 82800

-continued

```
aggcaggctt tatgtatttt atctgagcca gttccacaaa gtacaatgtt ttatgtccca  82860
taatcataaa actcatgcta agagcatcaa ggctaatgaa gtatatgcag cagtttatat  82920
catctgggaa gcaacaacaa gatgaagttt gggacttgaa aaatggttca gttctgttgc  82980
tctaatccaa tctaatctaa tctgctgact ccccaccttt caaactcagc aatttggggg  83040
agaaagcatt tatttttctt acatttccag atcacaatgc atcatttagg gggctcacag  83100
caaaaaatta aggcagaaac ctggaggcag gaactgaagc aggaaccatg gaagaatact  83160
atttatggtt agctaccgtt cttatatagc ccagggctac ctacccaggc atggcactgt  83220
ccactgtagg ctgggacctt cctatgtcaa tcagcaacca aaaaaaaaaa aatgcttcac  83280
agacatgacc acaggccgat ctgatggagg aaccttttca attaagattc tctcttccca  83340
ggtgtgtcaa gttgctgacc aagattagcc atcacacctg cacatacatg gacatgcata  83400
cacatgtata catacacaca cataaacaat tccatccctt tgttcaaaag tggctgatta  83460
gttgtccttt ttacgttggc atgggtcatc caggattcag ttgagcatta tattcagttg  83520
agtcttcaat atgtagttat ctgctgactc cccacctttc aaactcagca agagtcctct  83580
gcttatgtgg ataagagcca tgtaagcagt agccgattat tacccgcccc cccccccccg  83640
ccccccattt taattttcaa cacaatccag aatcacatgg aaagagaatc ctaattgaag  83700
agttttccag accagactgg cctgtaggca tacctgtgga gcatgttctt ggttcacaat  83760
tgattccttt gggggttcat gttggcccag agctcaccaa gtacacttgg ctggcttggc  83820
tttagttttg attgttagtt gaaatgagat gagctattcc atgatctgga tcttgaacaa  83880
catgagagtg gagaaagcta gttaagtaaa agtagcaagc aggcatcatc catgcatcat  83940
tcatgcatca tttttctctg ctgttgactg tggatgatga gaaatgacta atagtttgac  84000
ttcctgcctt aatttccctg aaatgataat ctgacctgta attgtaagcc aaacaaactc  84060
ttcctccctt acgtggcttt ttcttatgat attttatcac agtaacaaaa tgaaaatagg  84120
actcccgcca tccttcaatc ccacctctct tcccaaagag gcaggaggag gttgaatatt  84180
ttggcctgaa actaactatt cactattctg attgcctgac tttttttttt tttttttctc  84240
ttgaacattt ctaggtgaaa atgaattgct taaattttct ttcattcgga catcttttga  84300
caagatcctg ttgaggtggg aaccctactg gccccccgac ttccgagatc tcctgggatt  84360
catgttgttc tacaaagagg cgtaagtgaa aggaggtaga cttttgcttc ttgttgcaaa  84420
tacagacaaa gacagaagaa ggttaaggaa gggaagttcc atcttggctc acagcttgca  84480
tgatagggat gtcatagcat caggaagcag ctggtcacat ggcatccaca ggcaggaagc  84540
agttggtcac atggcatcca cagggaggaa gcagctggtc acatggcatc cacaggcagg  84600
aagcagttgg tcacatggca tccacaggca ggaagcagct ggtcacatgg catccacagg  84660
caggaagcag ctggtcacat ggcatccaaa ggcaggaagc agttggtcac atggcatcca  84720
caggcaggaa gcagttggtc acatggcatc cacaggcagg aagcagttgt tcacatggca  84780
tccacaggca ggaagcagct ggtcacatgg catccacagg caggaagcag ctggagacat  84840
gaatgctggt gctcagatca tgctctcctt taaaataaga aaatattttg tgtattcttt  84900
tacattttca cacatctctg tagtgtattt tgctcatatc tatccgccat gttctccctc  84960
caccatccca cagtgtgtct atcctgtttt cctctcaact tcatgtgctc tctgtgttgt  85020
tgacaagcct ttgaatctag ttagtgctgc ccatgtgtgc atgcatgggg agacatacac  85080
tcgagcttaa gcaaccaacc agtgtccatg tcccaaaagg acagtgactt cacctcttag  85140
tagctacaca ttactcctct gctagaagag gaccttggag ccaccctacc atccttgctg  85200
```

-continued

```
ggatgatagt atgagctgct gtgtgtagaa accatgccat gtctaggaat cagcactgca  85260
cagctcctcc caatcagctt tccccttttc ctgtaggcta cagatatacc tgtctccatc  85320
tcacagtgct gggattacgg atgttcacta ccacacccgg cctttccatg ggtgctaggg  85380
atcaaactct ggtcctcatg cttgtataac cagcactttg tccactaagc cgtctcccag  85440
gcccagtggt cgtatgctgt taactcatgt tgagaatatg aaattttcta tgggtacata  85500
gaaaatgttg gggtgggaag aaaaaaaaag catcaagtac acccaagcta ccacacacca  85560
tacaccctag ctgtgccaca gagtcttagt catttaccct tatggctatg tggtaggttg  85620
agctgatggc tcattagtca gcatcatgaa cgtatcacac ctcatgctgc tagctttgga  85680
gaagacccac attcagaact ggaattagga agaagttcac tttggagtgc tggagaggag  85740
actcagcagt taagtcctgt gcttccacag gacccgagtc tgatttccag catccaagtc  85800
aggcatctcc caaccaccag aaccagggga cccagtgttc tctctgaccc ttgaaagcac  85860
atacatatat taacacacac tcaggtacac attcacactt ttagaaagct acatgctgtg  85920
gaacgtacat aaaatcccag ctccaaagaa gcagaagtag acagatcttt tgtggtctct  85980
gactagccag agtagccttt gaggtgaatt tgaggcctga tcatttaccc tgtctcaaaa  86040
cacaaggcag cactcagatg tgtatgctgt tagtcccagc actgaggaga caggaggcag  86100
gtagacttct gtgagtttga ggctagtcag gactagagtc tgtttcatca acagacagaa  86160
aaaaaaacag gtacatggaa cctgatgctc ttctctaggt ccatgtacac acacacacac  86220
acacacacac acacacacac acacacacac atctgcacct aagcaccaaa tagaaaagaa  86280
gagagaactc tccaaggttc ccatcccact ttagtactga gcttgacact tacacagtgg  86340
taacccacct ctccctctta tttttctcaa aagcccttat cagaatgtga cagagtttga  86400
tgggcaggat gcttgtggct ccaacagctg gactgtggtg gatattgacc cgccccagag  86460
gtccaacgac cccaagtctc agaccccaag ccaccctggg tggctgatgc ggggcctcaa  86520
accctggacc caatacgcca tctttgtgaa gaccttggtt accttctctg atgaacggcg  86580
gacctatgga gccaaaagtg atatcatcta tgtgcaaaca gatgccacta gtaagtgtgt  86640
cctgggaaca ggggtttgct gatgaattga cactattatc tttggtaggc agcttctgtg  86700
acagggtttc tcccgtggtt ggcatctaga ggagctaagg gctgagactc atattttcat  86760
agataatgaa actataaccc atgaactact tcagagttca agagttccct tttgggcttg  86820
gaagatggct tggtgggtaa gattatgtgg tgttcccagt acccacactg aaagctaagt  86880
gtgcccatgt tcatgttcca gagtcctggt tacttgcatc tattcccaga gcactggggc  86940
tcagggacag gtgcagggta acactaggat ttgatagctg ccagcctagc tttagtttca  87000
atgaaagatt ctgtttcaaa agagtaaggt agacaatgat agaatgggat agaataggat  87060
gcctgacctc ctctgcttgg ctctgcacat gcacatgcat atgtaacaca cacatgtacg  87120
cctccccaca tataatacac acataccaca tataacatac cacacaaaac atatactaca  87180
tgtaatacac acacatatat atatatatat acacacacca catttaatac acagcatatg  87240
caacacacac tcacacacag catatgcaac acacactcac acacaaaaac acctgcccat  87300
catataatgt gcacatatag cacacataca cacattgcat gtagcacatg catgcacaaa  87360
cgtgcatata cataacacat ataacacaca tactatatat aatactcaca cagacactac  87420
atgtaacaca gtcacaacat gtagcacata tgtgtgtaca cacttaccac atatgacatg  87480
ctcacatacc acatgaaaca tatttgaaca cactaaagca cacatgcaca catgtaacaa  87540
```

tatatatgca cacatacata cattgcgcac actatatagg tgcacatata tatacacaca 87600
catgtataca catagagtgg gcacatacca cacataaaac acatacacct gtagcacaca 87660
cattcttgaa ctcagaacag ctaaaattat ccacaaatga ttgtcttcaa tctctgtctt 87720
tgagagggga gagtcttagt gtggtggtac actaattctg ccattgggag gcagaggtag 87780
atggatttct gtgagttcaa gcctagccta gtctatgtag tgactactag gtcaagcagg 87840
actacacaat gagacctgtc ttttaagaag tgaattcaat caataaataa cttagttagt 87900
taattaaaaa tgagagttag acctggttat acacatctgt agtctcatca cttgggatgc 87960
tgaggcaaga aatttgctgt gtgtttgagg ccagtctggg ttaaatatta agatcttgtt 88020
acaacctcaa aacaacaata aaataatagt gaaatgtttg ggaggtagag acaggaggat 88080
caggagttca gggtcatagc tatctacata ttaagtctga agccaacctg gactacataa 88140
gacccagtat caaaaaacaa acaaacaacc cccagaatat aacaaaaatg gaactttgct 88200
aactgtccat tatgttagtt ctattttatt attgctattg ttaatttcta ttggctataa 88260
gttaagctta attgtatgta tgtacatgta agaaatactg attgttcagt gctgtgtgtg 88320
gttcccaata tctactgcaa ttataaaatg tgccactata gataaggaag gattagtgaa 88380
tagtttttcc ttcctgttgt gacaactttt caaatataga ctgattttat gtgagcatct 88440
cccagcttcc tcatggtgtg gccttgtttt attttcacat ttgtctccct tttctcattt 88500
ttcctttctt ctttatgact atagtgtctc atggccacct agttatgtaa agactaactc 88560
cttaacttag aagttctcaa atagggataa ttctgtccct cccaatggag ggaggatgcc 88620
tggaaatgtc tagagacact tttgttggtc atagttggga gtgggatggt ggacagagtt 88680
atctgcccca aatgtcaaca tgcagagagt tagcaacatc ctcacaaagg atagaatcct 88740
aacttcatcc actgtcctgg gttcttcacc atctccactc tcatcttgta tctagaccaa 88800
gtttaatttc cacaaacttt tgcctttctg gtatttgcac actttttgct ttctgctttg 88860
agaagtcctt gtcctcccaa ctctttcagt ctccactgtt tgagtgcgtg catttgtgtg 88920
ttcctgcttg tgtgtgtgtg tgcatacatg tgtgtaggta tgtgtgtgtt tgtatgtgtg 88980
aatcatattt gaatgtgaca catgtcagag gtcgacatta gggtcctccc tagttgtttt 89040
ccacattata tattgtggcc atgtctctca atagacctgg aggttgctga tcctctgtct 89100
tttggtgctg gatttatagg taggctttac agccattgct gtctggtgtt tatgtgggta 89160
tttgggatat gacctgtcct tatgccatct ccctaggcac aggtaccact gttcttcaga 89220
ggaagatatt agggtacatt ttgaaggatg ttgcatgaca gctgaatatc atcatctggg 89280
gcttagggat gtgacttggt tggtagagtg cttacctagc atgtatgaat ccctcggcta 89340
aatcccccaa gtccctcaga accacataaa ccaactatgg tggtgcacat ctctcatcca 89400
gcactcagga ggatcacctc atccttggct atattatcaa atttgaggct agcctgggcc 89460
acatgagaat ctgtctcaaa caaacaaaca aacaaacaaa caaacaaaca aacaaaacca 89520
gtttgatggt ttcaagtact ctcagtgact gggcttgatt ttgctatacc ccaattaatt 89580
tcttccctcg attctctttt ggccccaaga acatcttctt attgccccaa acagcaagag 89640
cttggcatct ctcagaaccc aagtctatgg agtaaatgaa taagtggtgg tcacataatc 89700
actaacctgg ccatgccttc ctgggctggg caagcatttt acctgtcact actttctct 89760
gatgttatat aatgctgtat caaacaattg tggtgtcact tgggaaactc ctccctgctg 89820
agatacaccc aacaacttac atactctccc tcatggtaaa tctgtttctc ttctcctttc 89880
cagatccttc tgtccccctg gatcccatat cagtttctaa ttcctcatct cagattatct 89940
taaagtggaa gcccccctct gaccccaatg gcaacatcac acactacctg gtgtactggg 90000
agaggcaagc agaggacagc gagctgtttg agctggatta ttgtctcaaa ggtgagtgca 90060
ggccaccgga atggggttca ctgtaccttg attctcttat ggagacacag gtctcttttc 90120
ctgtttccca ggatgtatac atgcatgtgt aaatgtatgc acacacatac atatgcacac 90180
aagcacacac tccattctgt cttatgtaag acactgtgtg tgtatgtatg tgcacatgca 90240
tgcactgtgt atagatgtgt atgggtgtgt aggcttgtgt atacatgtat atgtagaggt 90300
cagagaataa cttgggtatg tccaaaaatg ttgtgtgttt tgtttttaat tttttttgct 90360
tggttttgag acagtctcgt gaagaccgag ctggacttaa actcactatg gagctgaaga 90420
agataatggg tttcttgcac ctcctgcctc tacctactaa gtgtgggatt acaggactat 90480
accataactc atagtttatg cagttctggg attcaaaccc aggactgtat gggtgttgac 90540
attctacaac agagttacac actcaaccca ttttttttta attacaagta tttttattca 90600
tttatttatt ttcctagtct ctgtgtatgg acacacatgt gccatgacat gtctatggag 90660
gtcagaagac agcttacagg agtctgtttt cttgtcagcc atgtgggtcc cagggtcagg 90720
caaggaggca agctctttta tctgctgagc catcctacta ccccctactt taaaaaaaat 90780
tcagttctgt gctttgaagc cagtgcctca tgcatactag gaaatactct acctctgagc 90840
tacagcccag ccctcatctt gtaggtttct atttttattt ttgtttgaga cagggtatct 90900
tactagacca gacttaccca gcaggccaat ttggctagtg agtgaccctt aagaatcctc 90960
ctgtctccaa ctccccattg ctgggattac aagtatatct cacataacca gcttttcaca 91020
tgggtcctgg ggatccaaaa ctcaggtcct catgcttgcc tgcactttag tgtctgagcc 91080
atctcctcgg agcacacaca tactgttaga cattgcacat ggatccatat ctaccatctc 91140
cacagtgcac atacatatct tttgacattg cacatggaac ttcactcacc atctccacag 91200
tgcacagaca cagacacaca gacacacaca cacacaattt actaaaacag aacaaaaaaa 91260
cttacaaccc accatcaaat tagagaaagt gaaaatgtgc tgttcattta gttgatggat 91320
tctggattct gtctttgatt cgtttttggt tagcaatatc cttagcctgt gaccttgtag 91380
aagcaggcca agggggctgc tggagaggtg tggctgaggt ctgtccttga atccacccct 91440
ggcctggtat ctggttttgg ctaagtcaca gcagcaagta gtctgtctcc ttttgtagag 91500
aggggcagag gacagatgac tcctgggaac agtcccaact ctaagatcat gtgctatatg 91560
tatgcctgtg acatcattcc tgccttggcc aggatcacca gctaggttta tctccttgca 91620
tactttatat agtttgggag caagtccagt cctaggctca gcactgactt gttggctctg 91680
aatttgagta taggaaacca ccagctagcc aaagctatac tttttgtttt gttttgtttt 91740
aaaaaccagc aacttaaaaa agtttgattg tgctgttgtt tgtttttaaa caaagtttca 91800
catgacccag gttggcctta aactcatgat gtaccccgag gatgaccctg atcgtcctgt 91860
ctctgccgat ggagtgttag ggtgacactc tccactatgc cagggctact gcagccaact 91920
ttcattctgt aggtggaaat tccagattgc agaagctgag gatatagctt agtccgtaga 91980
aagcttccta gtattcagga agccctgggc tccattccca gcaccatata gacccagtgc 92040
agggggttca gtcctgctac tgcagcattt ggaaggtgga agcaggaaag ttgggcattt 92100
aatgttatcc ctacctacat agcaagtttg agtcctttct aaggtatatg agaccctgtc 92160
tgaaaacaaa aacaaaatca ccttacatcc atgaataacc acaagggtat tttaaaaaat 92220
ggtgataagt gaatattaca gaatttattt gcacttgaat gagtatagat gcatacacat 92280

-continued ttctggtctg actgagacac atttaagaag gtgaatgcat atcttcttaa atgttacaca 92340
cggtcccaca ctcttctgga agcacacgaa ggactttatt tgaagttgat gacaggtgtc 92400
ttgctctgtg gatccttgtt ttctgaggta ggactttttt tttattagct ccctaatttg 92460
tctaacctgg ctggccaatg agttccaggg atcctcctgt ctctactttc ccagtcctga 92520
ggactaagat gtgtgttatt atgtttggtt ttcatgtggg ttaccagggt ttgaactcag 92580
gtcctcatgc ttgcgtgcta gtcactttac ctactggatc acttcaccag tccacagagc 92640
ttatactaag gaggcctaac aatagttgaa caattatgaa ttatgtggac aaaggcagag 92700
tgtggaggcc acctttggag gaaatggaat accagtgttg aatgaggaca gagcttcggt 92760
ttagatgaga gttctggaaa tggttagagg caatgatggt gccacactgt aagtagacac 92820
cactaactat gtacccacac atgatttcaa tggtaccatt ttatgttatg tttatttaac 92880
cataatttct ataatacata taataaatga ccagtagtac ctttctgttt atatcataat 92940
ttgagtctat ttttaattgt ggtgaatttg gagctaagga aatgatactg gataaaatgt 93000
ctgctgtaca aacagaatga cctgagtttg gatccccaac gtccatgtag agaaaagctg 93060
gttttgacag cgtgcatttg taaccatcac actggggagg cagagacagg cagatctctg 93120
gagcatgctg gccagctggc ctagcaactt gtgaggtcca agtttagtga aagactctgt 93180
ctcaatgact aagatggagg actggtaaga tatatcagtg tgtaaaggta tttgctgtca 93240
aaccttactg attaacttta atcactagaa cccacgtggt agagaaaata gattccagaa 93300
agttatcccc tgacatcaac atgtgcacta tggcttgttc ccctccctca taaaattaat 93360
ttaataataa tattaacaat aataataaac aaagaaatga ctgtaggaga cacttgatgt 93420
catgtagtca atcatacata gatacaagta acacaaacat acacacagaa tgcacacaaa 93480
cacacagagc aactttggag ctcctgtatt gtaacactgt aatttgactc tttgggaagg 93540
ggaggaagga agagagagag tccaggccag tctagggtgg ggagtgagtt cattgccaac 93600
tggataacat actgaagccc tgtctcaaaa aatggggtct ggagacatga attgtgatag 93660
agtgcttgct tagaacctcc aatgaggaga catggctgtg gcctaaggaa tgacacccaa 93720
gaatgacctc tggcctaaat atgtgtgtgt gcatacacca tacacacaca cacacacaca 93780
cacacacttg aactaggatt tgtttatctg ttccacctta ccgagaaagc actgtggtgc 93840
tgtgtgtgtg tgtatgtgtg tgtgtgtgtg tatggtgtat gtatattgga gtatacttta 93900
tgtcatgtgt atgtgtgtat gttgtgtgtg tggtgtgtat atgtgtatgt tggagtgtgc 93960
tttgtgtcat gtgtgtatgt gtgttctgtg ggagacttga gcccacattc tgcctctccc 94020
tagggctgaa gctcccttca cggacctggt ccccaccctt tgagtctgat gattctcaga 94080
agcacaatca gagtgagtat gacgactcgg ccagtgagtg ctgctcatgc cctaagactg 94140
actctcagat cctgaaggag ctggaggagt cttcattcag gaagaccttc gaggattacc 94200
tgcacaacgt ggtttttgtc cccaggtcag agctttgcac gggccagctc tctttctgtc 94260
tgttagcttg gtgccatgac ttcttaggga atgaactcag gagactgtgt aagtggggag 94320
gtggctggag cctgagctca attgtgtgct tttggttgga gggggaaaac agtcttgttt 94380
gttgttggga agagggccca cttaggaaag tatttgccct ttttaggaca aagggcacaa 94440
ggacctgagt ttggtgccca gaacccacat aaaaagccag gtgtgtgctt atattcccat 94500
tactggggag gcagacacag tattcctggg cctttctgtt atccagactg gtctaactag 94560
taatgtctgg gcgtataagg acaaggtgga cagcatctga gaaaccatag ccaactctgt 94620
cctctggctt tacatgcatg tctacctgat cacacatgtg cacttacaca catatgttca 94680

```
catgtaagta cacatgtgac ccacaggtgt atttgtgtac acacacacac acacacacac  94740
acacccacac cccccccccc cacacacaca aataatgcct gttggtcaca tgtgcacttg  94800
tacatgggta caaacacaca aaaatatgtc tatgggttac acatgcacaa acacatgtgt  94860
atacacacac agaaatactc ctatgaatat gtatacacat gtatgcacac acacaaatac  94920
accagtagat cacatgttcc tgtacatatg tgtgcacaca tatataaata tgcctgtggg  94980
ttataagttt cttcttttc ctgtgcctga tttgaactga aaacaagtag gcatgcgtgg  95040
gtctagttcc catcccatgt atgtgtctta cagaatgtca taactctggg catcagggac  95100
cctggaagcg gtctgtcttg gctctctact cttatatata ctggtttgaa caagttactg  95160
tactgctctg tgtcccagtg ttcttatctg tacaatggac atagcacagt tgacctttgg  95220
ggtctcgagt ggattggatc caggatcctg aggttacccc acagattctc aagtctctta  95280
aatagatgtc ttaatcatat tcaatcacct tcagataact tataacatct tcagacaatg  95340
acatgttata taatattttt tacaccacat tgtgtaacac aagcaacatg acaagaaaaa  95400
ccctgtacat ggttagaaaa tatgacacaa ctttctagag tcattctttg acaatttcat  95460
acacatacac aaagggtctt tagcatattg actctcagct tctcccttat actcccatca  95520
acatgtctgc ctctttcttg ttgttcttgt cctcctcttc ttccttctta tgactcattg  95580
aaccagttag ccctacctgc tggaatttca agtggttctg gcttgacctc atgtaggtct  95640
tgttcaggta gccagtgcta tattcagttc ataagtgcaa tgaccatgtc atgtcctgaa  95700
gacagcattc catagcacgc tcccattctc tggtccttac gtgcgtttgt ttcctgagcc  95760
acggtagtgg cattgataga aattttccat ttaggactgg acacccaaca gtcactcatt  95820
ctcagcactt tgatcagcta tgactctctg cccagtataa aaagaaattt ctctgaccag  95880
ggttgagaag agcagtaatc tacatgcata aacataaata cttcaagggc agtttgacaa  95940
catgtttctt tagtaaaaca actgaaggct ccccattagt gcatgtaact tcctgaactg  96000
ggcttttgaa cagggtcaca catgaattct ctcccatgga gcaggcctcc tatccctgag  96060
ggcagttgtt acctcttgta atggtcatgc tactgtttca tcagtggcct atcttgcctg  96120
acaggtctac agataatttt gatccatagt tggttgaacc caagaatgca gatctcctgg  96180
atcccacggg cttactgtgt aatcgttctt tgtgttctaa ggttgtaagc ctgaaagact  96240
tactccgggc ttctcaacag tggtgttgag tgcttggatt catgttattc ctctggggtg  96300
ggacccatcc tgggactcgt aggatgctga ccttcttggt ccccaactgc tcaattctag  96360
tagcgcctct tctcagacat gacttctaga gtatacttcc agaaactccc agatgtttcc  96420
aagaacatga gctttgaata tgcctgctgc taagggattt tatatttttt ccatcttagt  96480
ctcctttcct caagttcttc attagatttc ttgtctgccc acccacctcc taaatcagat  96540
gcaatttttc attttctgag cacatcaaaa ccctagaaag tgccaggcag tggtggtgca  96600
catctttaat cccagcactt gggaggcagg ggcaggcgga tttctgggtt cgaggtcagc  96660
ctggtctaca gagtgagttc caggacagcc agggctacac agagaaaccc tgtcttgaaa  96720
aaacaaacaa acaaaaacaa aaccaaacca aaaagaatcc tacaaagtct ctgtgctaaa  96780
caaagtttc ccgcacgcgc atacacacac acactctaaa cagtagagac ttacatgata  96840
aatggctgag tattttatga ctaggtatag tcgtatttaa catccatggc aatagcatca  96900
tgtgaagtag ttttctctca cttttccttt ccttctccgg attcccttca atttcaaaaa  96960
aggtgtagtt cttttcttct gatcaatgat gagtaagact tgtattagtc tcctttctgt  97020
```

-continued tactacaatg aattacctaa gagttgttgc attatgaaaa aaaaaagatt gatgtagctt 97080
acagttttgg atctgtgcag ctttagagat gatatatcaa gggagatgat atcaaagtag 97140
gagaggtatt atattgtgag acaggaagct gtgttgactg gggaggagcc aatagtgagc 97200
ttctgctagg ccctgcctct taaagggcct actacctttt attaccactc caaggaccaa 97260
atctccagta gatgaacctt ggggaaaaac aaagtcaacc tacatcccag acacagcagt 97320
attttttttt ttttcttttt tttttttgga gggaacatta cctcaaaggt gtcagagtca 97380
aatgggccct aagttgaaat tctgtctttc ctcaaagtga tgaattttgt tttcacagaa 97440
aaacctcttc aggcaatggt gccgaggaca gtaggtatga ctcagctatg ggacatctat 97500
gtgacccctg tggccattaa atcagtggga ggggggttgc taagtccaaa atattaggga 97560
tttatggggc tttttatttt ttttttgcat gtgataaaca gagctcttga gactggatgc 97620
ttcacaaatt ctccaattaa acaccttcac tgggaaatgg aatcagggca tgaatgtggg 97680
ggaaattttt gactaacaca ctcttcctac aatatgtgat caagggcaca cagttcctgg 97740
gtccttcctc agtgggttat ttcccctcca tgcatctgct cacgaaatat ctgtctacaa 97800
gtaactgggt gtgaacacag acccatgcct gaggcttgat gttctagctt caggggggtag 97860
gggatcctac ttgttattaa acccaatctc atcattctta atgaccattt ctctgggtct 97920
ttagacaaag caatatgaca agaaaaagtg gcagatcaaa ggaatacagt gttgccaaat 97980
ttcagcagga gactgaggga ccatatctct tcagtcttag gaaggccacc aagggagaca 98040
atgcagaagc agacagggag atgaaacact attacataat tagctcatat tggaacaaga 98100
aactagacaa aagagccagg taggggctgc tttgaaggat aatccactga tccaatcagt 98160
actacccatt tgtagccatt cattggtata tgtgcaacct atctctggtc acaacttcac 98220
aggaaagcga ctctccttcc caaccaggca ttagttgcca atagctcctc agagagggat 98280
agccctcctt ctcctatgtt ggaattttta cttggcttga ttttgtacag gtctgtttgt 98340
gagctcagta gccatgtcat atcaagagga gagtatttcc taccctttga ctctcatagg 98400
tttttcacag cagacacttg ggggtggggt tgatataata tcccatctac tgctgagcac 98460
tcccagtcac ttactctcag cagcctgaac tgcaatgagt ctctgcatcc attagtactc 98520
actgcaatga gaagcttctc tgatcaaggc tgagagcagc acagatctag ggatagaaac 98580
acaaacacat agaaggctgt ttgacaacat gactattcag aaaagcagca tcaccttgcc 98640
ctatggcttt cctagctgag gatttgacca tgttcacagt acctggcaat tcctaatgtg 98700
tccatgtctg tctgtctgtc tacctatcta tctatctatc tatctatcta tctatttatc 98760
atctattaat ctaatttata atttatctat ctatgtatcc atctattaat ctaatctatc 98820
tatcatccta tctaatctat aatctatatc tattaatgta atctatcatc tatctaatct 98880
ataatctatc tatagtaata aattaattta atctatcatc tatcgtgtct gtcctctctc 98940
tctactagtc atctatctat ctatctatct atctatctat ctatctatct atctatctat 99000
catctatatc tctacctatt accaggccta atctgacctc tagtggccaa ctgaaataaa 99060
atctgttgtc attgaaagtc tagagttttt tgaccttcat tctaagctgg atttctcatc 99120
ttatcccaag ttgatatttg gggctagatt actcaatggt gagaggaaca ttttgtgtat 99180
ggtagcatgc tgaactctgc tcactccata gcagggacat cacagccttc caaagaagtg 99240
atggaggcat actcttgtta acactactgg tttaatatga aattgttcga taatgaagtc 99300
atgtttatga agggagttca gagagtttca ttgatactct tcctcaggag tcattcatta 99360
acacagtagt ttttaaattt aatatcgtgt ttagggattt acttattttt attttaaagt 99420
gtttggattc tgtgctcata tgtatgtcta tgtaccatgt acatgtctgg tgccagcaga 99480
tgccaggaga aagcactaga ttctctggga ctggagttat gaagagttgt gatgccatgt 99540
agttgctgga aactaaacta tctctacaag agcagacagt gcttctaacc accgagccat 99600
ctctccttat attagtttga tagaacctct ttgagatgca gtcatacctt agagatctta 99660
tggctaaagc agtcaagcca atgtagtatg taagtaagtc acacaaaata ttggtttggt 99720
tatgctgggg ctggagagat gtctcagtga ctaaaagaac ttactgcctg tgtagaggat 99780
tggggttcag ttctcagtac tcatattggt tcacgaccac ccataaatta agattcaagg 99840
aatctgctgc cttcttttga gctctgtggg cactgcacac atatgtaggc cctgaagtca 99900
aaataaaata aatttttaaa aagttatatt cacattgtac tgcagttagt gtgtaattac 99960
agatatcttt taaataaatc ttaatctatt atatttattt aaaatacttt actgagctga 100020
gagttttagt gcattggtac ttgggtagca tgtgacaggc tttgagcgcc gtatcaatga 100080
agtaaaataa aaagtaaaaa ctgagttcaa tatctgatgt tgcaattaag taagtaatag 100140
attcagggcc ctccctgccc cgtagacatg aggtgaaatg agagcagaag agtggctgag 100200
cccacagctc tgcagaaaca aaacaaaaca atgagtgcaa cagagtaagc gttcggaatc 100260
tagtactgca aaattaaaat actttaaaat aagatagaac aaagactcac tgtccaacac 100320
tgcaaaagtc aagtttagtt ctcaacacta cacaaataaa ataaaaactt ttcctttttg 100380
ctagaaaatg ccaacatgca gcttgtaggc ttgcacaaag caaagttact gcggatcttc 100440
aattttaaaa atgtaaggga tcagagatag tttaagagta ctagctgcaa gtgaaaaata 100500
catataaata ataatcataa caataaacat tcaaaataaa ataaaaactt caataaaaca 100560
aagcacagtc tctgcctgtg gcatgtttga tgagtccaca tagtctttag atgctcagat 100620
atgaattctt cagtgttagt tgtgaggttt gagtatccct gttatttttg tcagatcgtt 100680
tttgactata cagaaattat ctcaatccca ctaaaatgga tccaactgag acttactaag 100740
ctgttttctt tttcagttaa gaaggccatt gtacaaaaat gagggctaaa aggataatag 100800
ccacaggctt taatttgtgg cgttatatcc aagtatctta aataagaggc tgaggtagaa 100860
ggattgctgg gagttcaagg ccagcacatt gtgaattgct gcaaaacctg ggctacagag 100920
tgagactgtt tccaaacagc aaacagagaa aaagaagcaa ccaaaaccaa atgtctgaat 100980
gactctagat ccatagtttt aatctctcag gaacaatgta aggtttgcaa ccaggaagga 101040
gactgggaag tcatgagaaa gtatgatgag gacaggaagt gatttttctg gagaattaca 101100
gaacccagca ggcaaacaga gcttcctgaa gcactgtaaa gagctacaag gtgtgcagtc 101160
tagggatact atgtttttgt ttatatattt gcatttattc tttgagaatt tcattctttt 101220
gcatgatgta ctttgattat atcacctcct acaacccttc aacacctcca gactcatccc 101280
accacatctg ctccccaaat ctcttctttt gttaacccat ttacataatc tactgagttg 101340
tccaaataga aaagtccatc tacccatgag tgtggggata tccgcagggg tgtggatgcc 101400
aggagtcaca tcctcaaaaa gaaaggtaac tcttctcccc tgttggtagc tcctcagcta 101460
agctccatgc ccttcctctg ttcacggtgt gtttgaccag cttgatcctg tacagatcag 101520
gtctaggcag cagtaggtgc tgtgagttaa tgagtgccac agccatgtca tgtctggagg 101580
ctggccattc acagcacttc tccccacctt tcaggcctta cactctccac ctcctctccc 101640
atgatgttcc ctgggccttt gcgggaagag tatgatttag ttgaccgatt gagagctgag 101700
aactccacag tctggttcca tatttttaat cttttaggtt atataatttg gaaaaaacaa 101760

-continued acaccaactt ttaaccctca gcttaggtta tgctaaggtt attccagaga ctataagtta 101820
atattatatt cagtttgtca gacataggaa gtttctgaag cttcagaatc ctttcaggtt 101880
gacaatagtt tcttccggcg aatctacttt gaaaaatagt aagacttaga ataatcaaaa 101940
ctatttgtgg tgagaaaaaa ctaggaattt tttttttcct ttttggatca aacctcaggt 102000
ctcaggcaag gtaaacatgt actgtattat tgagctgtac ccaagggata ttcttatttg 102060
aaaagtagaa aaatggttaa ctgaaaaata gatcatgctt taactgatct gagccccctg 102120
ataggtatgc agtcttaagt tgtcagccct agacatatgt acatattttt tatatatatt 102180
gtatttgtat caataataat taaggaagga aaggtattga gagggagtag gtgacaaggg 102240
aggagttggt ggaaatgata taaattacaa tactcatatg aagaaaaata agttttcatt 102300
ttcagaagca caccatttgc agtcaaaagg agaaaatcct aatgttaact gaggatacca 102360
agccaatcca atccaaacca aaccaaacca aaccaaacca agccaagcca agccaagcca 102420
agccaagcca agccaagcca agccaagcca cgccacgcca cgccacgcca cgccaagcca 102480
agccaaacca aaccaaacca aaccaaacca aaccaaacca aaccaaacca aatcaaacca 102540
aatcaaacta agccaagcca agccaaacca aaccaaacga aaccaaacca aaccaaacca 102600
aaccaaacca aaccaaacca agccaaacca aaccaagcca aaccaagcca aaccaagcca 102660
aactaagcca agccaagcca agccaagcca agccaagcca agccaagcca agccaagcca 102720
agccaaacca aaccaaacca aaccaaacca aaccaaacca agccaaacta agccaaacca 102780
aaccaagcca aaccaaacca aaccagagat cttgttcttc ttaagacttt taaaaggagt 102840
ttattttttt ctttctgcct atctgtgtga gcatatgcca tgtgtgtagg cgcctacaga 102900
agctaaaaga aggtgttgga tcctgtggag catttgtgag cagcccaata tgggtgctgg 102960
aaaactacct caggtcctct ggatgttcag gaagctctct taagtgcatg ctttaagaga 103020
agtattcagt gactgtttcc cacctaacat gtgcagcatg cagctggcta gatcatcatc 103080
acagtcccac attttataag caaaaggaat tgtgccgagg agcagtggag tggaccgtag 103140
gagttcgaag actacatttc actacatcct ttctctcttc agttctttat gtgtcatctc 103200
tctgtgttta tttgttatgt accttttagg tgcaggggcc atctgccaac tggacaggca 103260 ttttttttt cttgtgataa ctccagtggt aagattttat taccaagaat aggtgctttg 103320
tctctcaagt tccacagtgc cctctatgca cagtgcatgt ttgaatgaca atgtggggcc 103380
tgggataatg actcagttag tgaaatgtgc accctcatgc ttatgagaag ctaagtaaaa 103440
aaaaaaaaag aagcaaaact ctggagactg gagaagttgc tcagtgatta aaaatactca 103500
ctgcacttgc agaggacctt aattcaattt ccagcatcca caatctgcct gcaactctag 103560
ctccaaggga tctggtgccc tcttctggac tctgagggta tttgcacgca catgcatata 103620
cacatgcaca tatacaaatt cttaaaagta agacagatct ttttaaagaa aaggcccaac 103680
atggtgactc gtgttagtaa ttggagtgct ggggaagtga agctaggtgg ttccctgggt 103740
ctaggtgaca agtcagttgg cctattcagt gagttgtagg ccaatgagag gcactacgtt 103800
aaggaacaaa ggtggacagc ccttgaggaa caacacccca ggttgtcctt tggaatatgc 103860
acatatcaat ataaacacat gtgtacacat gcatgcatac gtgcacacac catccccaca 103920
cagattggtt atgtgtgact atggactgta cccttctgtc gagctccaaa tagctatact 103980
tttttgtgct ttccaaatct tattaactct gctcctaatc accctttctt cagaaaattg 104040
gaatccttta attaagcata ttgagaggat ttagggtagc cttgtagcca agaacaccca 104100
gagaatgggt gtgtcatcat tgtcaatatc tctgagaagg gcatctgtgt ggaaattaat 104160
ttgtgtcccc tgtacctctc ctctaccctg tctctttctt tttaattaat taagcattgc 104220
tttctccagt gttattttat ttaaagatgg tgatgttatg acccccacac atgctttctt 104280
cttacaggcc atcccgaaag cgaagatccc ttgaagaggt ggggaatgtg acagccacca 104340
cactcacact tccagatttc cccaacgtct cctctaccat tgtgcccaca agtcaggagg 104400
agcacaggcc atttgagaaa gtggtgaaca aggagtcact tgtcatctct ggcctgagac 104460
acttcactgg gtaccgcatt gagctgcagg catgcaatca agattcccca gatgagaggt 104520
gcagtgtggc tgcctacgtc agtgcccgga ccatgcctga aggtgggctt gcgctttcca 104580
aggttggaga ggcaactggc cacagactag ctgtctccct actacacagt gaagatgtgt 104640
tcttaaacat gttctcattt attgtttttg ttttaaaatg ggtatgcttt gttaccaatt 104700
ttggcattga actcctaggt ttaaggagtc ctcatgccta ctcaagtatc tcctaatgtc 104760
ttagtttctg ttcttattat tgtgataaaa atcctctaaa taatcaactt aaaggaggaa 104820
gggtttattt tagctcactg ttcaaggtac atttcactgt gactgggaag tcagtgtaga 104880
aggagcttga agtaggtgat accatcacat ctacagtcag aaggaaagaa cagcaaattc 104940
attcagcccc ctttctccat ttgtacagtg tacgatcctg tatagggaat ggtgctaccc 105000
aaagtgggcc ttcccaatcc atttagcata attaagaata ttccccacag gcaagctcag 105060
gttcccatct cacttgattc tagatcctgt ctgattagaa attaacatga accattacac 105120
accatatcct aataatttct ctgtatgtgt tcatgtgtgt gcctgtttat gttgaagcca 105180
aaaattaacg ttgggcacct ttttttgagg ttccatttac ttttgttctt ttgaggcaag 105240
atctctcaag ggctgagtac ttgattaggt ctgactagct gggcagtgag tttgagggat 105300
ctgcttgtct ccgtcttttc tacattggga ttcttagaac actatgtttc agctcttttg 105360
tgtggattct aaggattgaa ctcaggtttt actgactgag gtatcttctt actccatgag 105420
ttttacattt tctgcggaag aaaataagac atggaaaaat tacatagcca gctttaacca 105480
ggtcttttta gatgttggtg gctgcaatag aatttgattc aagagttata tttgaccctt 105540
tacttgcttt ttatagctaa ggcagatgac atcgttggcc ctgtgactca tgaaatcttt 105600
gagaacaatg ttgtacactt aatgtggcaa gagccaaagg aacctaatgg tctgattgtg 105660
ctatatgaag tgagctatcg ccgatatggt gatgaggtaa ggattccagg tcttgatgtt 105720
atatggtgcg attctggggg agatgtgaac aaatgtctac tcactccaag tagagaccaa 105780
atgacagagc aaactaagaa tattaccaaa gtctaagtgg tgatgagcca atgacttttt 105840
attggtggtt acttatgtat agacgtgggc ttacttatag gtacagagat gactcaagtg 105900
gctggtacat tgccaaaagc ctatctctca acatggatga taactcatga aagctggaac 105960
cctggagctc tctgaaggat gttgcaggca gctttcccag tcagagtctc ctcagtagtc 106020
cttctgcctg tttaatctta gggaagacaa ggccttgtga atcccagaag tttcagggac 106080
ttcctgagac ttgtgagtgg ttgacttcct gagccttaca gagcctccct ttagaacttt 106140
ctgagtctta agaaatttcc ttccagcttg gaaagcttta atttgttgaa agttggtaca 106200
caatactggg caggaacttt ccaagtttct caagttatcc aaagcttccc acatcagatg 106260
ctatgttatt agaattcaaa tctttgatgc agtcttccca gggagataaa tagtaatgcc 106320
agtttagaat cttttatttc ttttatcact tacatttttt aaaaattaaa tttatttatt 106380
gtatgtggag gggtaggggc atgtatggcc atgccagagc ctgcttgagg aaatcagagg 106440
acaaattttg agagtcagct tgctccttct actgtgggtt ctgtggactg aactcaggtc 106500

-continued attgggcttt gctgcacgtg ctttactcat ttaaacatct ttcctatgtg gtctttcatc 106560
atatctgtgg caggattttc agctgtgtcc ttcaagctgg gtggtaggct gcttgccttt 106620
ctgtcctttc tcacaggaca agacttgttc tactttagag agaaactccc ccactctggg 106680
aatgcatcac ttaaatcttt cttctgtgcc tcctttctac accagcagct gtgggggttt 106740
atgagaggtg cagatatagt aagcatccag gagaaaatct gaagttgtag ctaagctacc 106800
agagggaaca ctgtgagctg acactcagtg acattacagc ttcctctaag ctgccagaga 106860
gcctcccgag agctgaacac tcacctttca ccagggtgct acaggtctgg aacaggtact 106920
catgtttgtg cagtttacta agtcagtatg gcaacatgag ctttatgtaa acgtaattgt 106980
gagccagtaa aactttataa taacagatgg tgggctgagt ttgactatgt gacagaattt 107040
gtccttaata tagtaaaacc aacttcacaa aactttcaaa gttctataaa aatataataa 107100
atcatcaaaa gttgacagga ttcctctgag gactccttcc tttttaacag tgactcagaa 107160
catagtcagc acccatggcc tacaggacaa atcttcagtc tgtttttttt ttttccttcc 107220
ttccttcctt ccttccttcc ttccttcctt ccttccttcc acttattttt acttgtgtat 107280
agctcatgta agtagtgtgt atatgtgcca cttttgtaca ggtttctgga tctcctggat 107340
ctggacttac aggtagttgt aagcctttca gtatgggcaa tgaaaccaaa cctgggtctc 107400
tccagcttca gcttctttac ttttgaccaa gtttccctgc tcatctctct ctctctctct 107460
ctctctctct ctctctctct gtgtgtgtgt tttgtgtaag tatgtatatg atgtgtgctc 107520
attgtgtggt gtatatgtct cttgtgtgtg atatgtctat gactctgtgt gcatatttgt 107580
gcatgtggta catatctatg tttctatgtg atgtgtgtct ctgtgtgtat gtctgtacat 107640
tgtatgtcca tggaaaacag ttatgctcca gaattttctg ttgcatttct ttcttgttct 107700
acccttggag gtatctatgg taattatcta gccttagaga cagggctcca cttgagccct 107760
caacaactat cctgcttctg aagttgctta tctgtttttt tctgcctgat gactcattcc 107820
attgggaaga accttagaac tgagttagcc acccacctct tgctacctgg atcagctcat 107880
ttgtttctcc ttattaatgt cacatgatga gcacaggact tcttacattt tctttccttc 107940 catacctgc atctcttaaa tctttgccat cccagttctc tgcatgagat gcaagtgaga 108000
gaactgtttt tggaattttg ggtctagtga atacaggctt gactaagtta ttccccaggc 108060
aacatggctt tcttcctaat gatctctggc cttatctttg gctgcatgct tatcagaggt 108120
gtgttccccc atttatttat gtcctatcct aataaatctt tggaggaatg ccaacacttc 108180
tttttgtccc cctcctcctt ctttttgaga caatggctgg cctccaactt ctcaagtact 108240
caacgtaagt gaagatgacc ttgagcttct gcacttcctg actccatctt cctatgctgc 108300
ttgacacaca tgtgcatcaa tctggtttat gtggggctaa gatggatccc agggcatcat 108360
gcatactagg caagctttgt accacctgaa ccaccaatcc attattgctt tcctgctctt 108420
tttatgaagc tggcgggtag agggaagatc ttttgtgttt gttcatagac attaagtctg 108480
tggctccatt taattctgat gagcctgggt ggtctagaaa atgacttaaa ccacagaggt 108540
ccattcacta acctcttgtt tttgactgtg ctggattcct taacaaaata ccctactgtg 108600
gtgggatggg aaggaggaga aattttggaa acaaaaggtt ctgtgttcaa gggctagctc 108660
tgtgttgtgt gacacaaaca aatgtctctt ccccccagat agagcactga ggacagatta 108720
aagaaatgat cccactcagg tttagtttag tgagccagtg gatttattgg ggttgcttat 108780
agaagtatgg gttaccttag ggaagctcca tcatcaagaa accagctcca gcatgataac 108840
ccctcagaag cttcatccct caagctcctg attgactggt tggagagcct ccttccccag 108900

-continued

```
cacactcatt cccagatctc tgtttgcttt ctgttttgag acaaggtctc agtggtgggt 108960
gcttagctag aatatacata cagtaaggag ctggggtata gtctctgggg caaatcccca 109020
ggtgaggggt tgtagacttg gctgacttgc atagaactgg cctctaaatc ataagttgga 109080
caccatattg agctagatga gaccttctca agaaaacaaa agcataacct caacattccc 109140
acaaaatata aatggaaaca aacaaataaa caaattctca aagcctctga caggttagac 109200
tcttctgcct attgcttccc ctacttaaac tgagcatgat gtccccacct gagaggcatg 109260
tgcccaggta tacaaaactc aactaaccat cttctctttt cttccaggag ctgcacctct 109320
gtgtctcccg gaagcatttt gccctggagc ggggctgcag gctgcgaggg ctctccccag 109380
gaaactacag tgttcgagtc cgggctacct ctctggcagg aaatggctcc tggacagaac 109440
ccacctattt ttatgtgact gattattgta agtctccata gcaacctcaa gggattgggt 109500
tagtgcttgg tgctgtagga gtggtgggac agtttagaga atgatcctga tgaaagaatc 109560
tataggtaca ttaactttgg atcaaccaga aactgcaaaa tgacgagtcc taggtttccc 109620
aatttttttct accaacaatt cacatcctca tcacccacat aaaaatgccc atactcaatg 109680
tggaatctca atttttggaa gatggaacta ggcagttccc tggggctccc tggccagcca 109740
gtctagccaa ttggtgaaat ctgtgttcac tgaaaaatgc tacctcaaag attaataacc 109800
tgaagagcaa ggagggggat atgagagggt ttgaagctgg gtaagggaaa ttggaaatga 109860
tacaattgta ttataatctt aaaaaggaaa gggaggaaga aaggaaggaa ggaagaagga 109920
agggaggaaa gagagaaaga aagaaagaaa gaaagaaaga aagaaagaaa ggaaggaagg 109980
aggaaagaaa gaaaggaagg aaggaaggaa ggaaggaaga aagaaagaaa gaaagaaaag 110040
gaaaggaaag gaaaggaaag gaaaggaaag aaaagaaaag aaaagaaaag aaaagaaaag 110100
aaaagaaaag aaaaggaagg atccatcact caggaggcag agataggcag agttctaggc 110160
tagcctggtc tacatagtga gttctgggct agtaagggct acataatgag atcttgcctc 110220
aaaaacaaaa caaaacaaaa caaaacaaaa caaaacaaaa caaaacaaaa cagaccaaaa 110280
agacaacatg gaacataata gagaaagata catgatgtag atggcttggc ctccatagac 110340
aagtagtata tatgtgtaca tacacataca aacccacaca gacacacaga cacagacaca 110400
cagacacaca gacacacaga cacacactgc acacacacac tgcacacaca cacacacaaa 110460
cacacacaca cgcgcacaca cacagacaca cacaaacaca cacacataca cacatacaca 110520
gacagacatg cacaaacacc cactaataac agaaaagaat atatacttta aaatcataaa 110580
tcattggggt ggatatgatt aagaaacatt gtacacatgt atgaaattgt tagacaaatat 110640
attaaaaatc ttaaaagaat ttaaaattat aattttcaca attttttcag agaatccttt 110700
gtcctgatta tagcctccct tctcttaaag aacaagggag gaggtgggga cacacagggg 110760
catgtaacca gacccctgtc atttcttgga tctcattcaa ccatcagcat ttacaaatac 110820
atcctgtggg ctaggggcca gcaggtgcaa ggaaacagtc aattcacaga gaaactcaaa 110880
gtagcgtttg tcaggacaga actggtgaca gatgtcatga tgaagcaata gccaacactt 110940
gacctatggg ctgggagaag gctcagtcag tagagtgctt acattgacca gaaagcccca 111000
gggatcagcc tgtctctgcc tcaccagtac tttgaaggca agtatttaac agcatgccca 111060
ggtttttcac atggtttcta tgtaggtctc ctcatgttca caatacaggc attctattga 111120
cttagccatc tctcaccact tttcctttca acttctcatg tttttaaaca aataaacaaa 111180
caaacaaaca aataaacata taacaaatga acatgagtcc actatgtgcc attgagtttc 111240
```

-continued

```
cattatacac atcaggtgcc ggccgtctac tgggacatga ggaacttctc actggccacg 111300
tctctgaaga ctcttcctct cctagcaggc accaatcacc aatggctgcc atgtgctgtc 111360
agtttatgtc ctcaatggcc ctgtcttgct tggaaatatc ctaggatttt gctttatagc 111420
ccagggtggc cttgaactca tggtcctcct gccttcatcc tcactcctac atcaggtggt 111480
gcaataacag cttgtgttta atggtgtaat tttttttttt taccatcaat ttattttgat 111540
gctaaacatg taccttatta ttctgttgca gtagatgtcc catcaaatat tgccaaaatt 111600
atcattggac ccctcatctt tgtcttcctc ttcagtgttg tgattggaag tatttatcta 111660
tttctgagaa agaggtaagc aagggagtat gctggcaaat ggctaacaac tgactctctt 111720
gggggaaaa acaatactat aaatattgag ttagagtgag gtttcttata agttttatcc 111780
atataggatt tgctacattg caattaaggt aataagttta ttgtgtaata ctataatata 111840
ctctattata aattctcttt gagtcattga ttctccccac atgcttccac tgatttattt 111900
ttacccagct cttaatatct gcagccaact tagagttgca actgatgagc aagtataatt 111960
ctaacatgta ttactttcct gatgctgtga tagaatacct agacaacaag caactttggt 112020
gaggaaaagt tgatttcagc ttacagtgca gtccactgtc aaagggaaga cctggctaca 112080
ggagagtgag caccatcctt caaaattcat acaaacacca gcagtagaga aaaaaaaaat 112140
acaaagtggg ccttgggtgc aaaatcctca aagctgttcc tcactgacat atttcttcat 112200
ctgggctcca ctcccaagag ggcctataac cttccaaaac agcactacaa gaggcatcca 112260
agtgttcaga catatgtggt gggcatttga tgtttccacc acagtgaagc ataaacgtgg 112320
ttgtgttttg ttgttttact gctctagcta gcttacacaa tgatgggttt cattataatg 112380
ctttcataca tatatatcac tatattttct tatagatacc cttccttgct cttcctcccc 112440
ttcctcccac attctttcta gacattttct ccctttctgt tttcatatcc tatgtatata 112500
tgtatatatg ggacacacac atgtgtgtgt atatgtatgt atgtatatac atatatattc 112560
ttttatatat atataaaaga agcacaccat ttggtctttg cccccatttt gctcttgtcc 112620
tatcatctcc cttcctttga gccttttccc tttccctcct agtccccaat ctatagctat 112680
ttatagctat ctttgtcttt ctatgtctag attattttgc ttaacacagt agcttccagt 112740
tctgtctttg ctctgtttgc attttggcca tatagccaag gttgaccttg aacttgtgct 112800
catcctgctt cagcttctca aatactagga ttacaggatt gtgccaacag gtttgcatta 112860
gcatacctgg cttgatttct gttgcttttc ttcctttcat taaagagtaa gacaaaaatt 112920
aagtaagaca tacatatttg aaaactacaa gcaatgcctc tggctaatca ggtaaaattt 112980
aaatagtggc agaacaattt tttttcctct gtaatttatt ataccatcat tgcaaaaatg 113040
acattctttt acattcaatc tgctttattg ttctagtgtc ctttctgtag ctaggataaa 113100
acatttttac ccaatgaact tggggaagaa aggggttact ttagtttaca cttacaagtc 113160
ttagtcaggg cagggaatta agtaggaact tgaagcagaa accaggaagg aaggcttgct 113220
tgctgttttc tggtttgtgc tcagcttgct ttcttataca gcccaagacc acctgccaaa 113280
gaatgatgcc acctaccgtg ggctgggccc ttccgtatta ctgtttaaca aaatcacact 113340
ctcatagata tgtccacgga ctaatctgct tgaggcaatt ctccagttga ggcttctcct 113400
cttacatgac tctaggttgt gtggggttaa cattgaaggc tagacaggac actaattgaa 113460
gttttttggt ccctcacttc ctctaatttg gacaaaatgt cgaacaatcc attcctaatt 113520
tatatagcat ttgcctatgt ccagaatgcc atgggatgtt caagatgttg tgtctctctt 113580
cctccattag gcagccggat gggccaatgg gaccactgta tgcatcttca aaccctgagt 113640
```

acctcagtgc cagtgatggt gagcatcacc tccttctttg tgggaatcca gaacccagcc 113700
cttggttttc tttgctatca ctgttaagtc agatctgagg ataggctagc atcacaggga 113760
ggatggagaa gccccccttga gtggtgagct tgccaatgtg cccttgctgc agagactctg 113820
ctactatggg gtgttagggc tgttgtctag acctgtttgg gaaggttgat attgcctact 113880
tgggaccttc aggctggaat gtgagactaa aatccttttg ccatagccat aggagtgtgt 113940
gaaagatcag gaccagaaat ccaccaccaa acttgtcatt cttactaaga aggaagtact 114000
tagaagccat gacaggatac taagagaaga gaattagaga caataatgtt gaggaaatga 114060
ctcagtagac tcagtaggtg aaatgtttgc tgcccaaact tgaggactgg gtttgacttt 114120
acatagtgcc tatgtaaaaa gctgggtggt gtgatgtgta cctgtcattc cagcactgat 114180
gaagcagaga tgtagggctc aatggcaagt tagcctggct taatctgtga gctccaggtt 114240
cagtgagggt tcatgtctca gaaaaggatc aaggaagaca gctcatgtta acctctggct 114300
ttcacgtgca tgagcactta tgtgtacctg cctataaatg cacgcacaga cacaaatgtc 114360
cacacacata tacacacagg caaatgaagg gaagatagaa ttgggcagtt aggggctgga 114420
tgagtgctaa ggagacattt gctgctggtg gtagttgatt attaactgat gcttatggta 114480
ggaacttagg attgatatcc ataccacacc taactgcatg aaagggcagc gagtgtcctc 114540
tagagagaag gcatacctga ttttaaagaa ctttgttata agatattctc ttctttaaag 114600
tccctcgtgt agcatgatca cagtgtgact ttcaaggcac aaatgtattt gacctgtagg 114660
ctgttgcctt gaatagataa cgtcatttac ttgtatgttg gttgacagca tgagtggttc 114720
caagaagtag ccacagctac tggttaagtc tccccttata tgtggtttct ctcctggtgc 114780
ccttcttagc atgctctgtg ggttcctaac tgtaaaggtg gactacaaaa catcttcttg 114840
ttgagttcta tggaccaaag tgaatcagaa ggccatgaag gagtccagag gataggggca 114900
gagaatctac cactttctag gaagaactac taggcattgc agacattttt ttccctagtt 114960
tattttaacc tataccctttt cctccaccat tctattgata tttggtcaaa caactccaat 115020
gggaagtatc tagttatttt ggtaattact gtgacaaaat acttgacaaa gcaactgaag 115080
gggagaaggc tttattgtgg ctcacagttg gattgtacgg tccctcatga tggacaagtc 115140
ttggctgctg gtcgcattgc attcatagtt aggaagcaga gagtagtgaa tgttgttgct 115200
caggacactt tttgctcttt atttagtcca gaattccagc ctatgggatg ctgctgcctg 115260
catttagtgt gggtctttct acttcaatta acttaatcta aaaacttcct tcataaacat 115320
tccctaaggc ttgtttccta ggtgattcta gattctatga cattcacggt attaattctc 115380
aggaaaaggt ataatgaagt agcagggatc tagaatcaga catctttcta gaatctagaa 115440
agatggagat acagcatcat tttaatgctt cctatgtaga atcctgaccc agttgtagct 115500
catcccctag cctgtgccat ctttttgatg gcagacactt gtccttttct gggttgtata 115560
tccaatgcct taacagaagt cttaagtcac aaaatgagta aattatgtat atagatcaag 115620
aaaaatgtgg tgggaggtgt ttgggggccc ttaagaggtt ggctggcaat accgtgtaga 115680
taaatgaaaa gtagtgtttc catcttctgt gtacgtgccg gacgagtggg aggtgcctcg 115740
agagaagatc acccttcttc gagagctggg gcagggatcc tttggtatgg tgtatgaagg 115800
caatgccaag gatatcatca agggtgaggc agagacccgt gttgcggtta agactgtcaa 115860
tgagtcagcc agtcttcgag aacggatcga gttcctcaat gaggcatcag tcatgaaggg 115920
attcacctgc catcatgtgg tgagtctatc tgggatgggc taaagacttc ctttcatgct 115980
cctcgtttgt tctgcttcca ttgcctagag ccgcccagga tactgggtgt agactggtgc 116040
ccactcccca ttctattcag cctcctatcc tgaagaggag gggaggtgat aactcctttc 116100
tcaatctcct cttctcccag gttatccaga atcaaactct ataactgttc tgtcgctccc 116160
tagaatcttc ctttgtattt cagactttct cactgatttc cttcttcttc ttgactgtcc 116220
tgtaaccctt aactgcatgg aagtccacct ctttataact gcctttattc atcttgaagc 116280
caaaaaaaaa aaaaacaaaa acaaaaaccc aaaaaaacaa aaatcaaaaa acaaaaaaaa 116340
cccttccctg cctttctgtt cccagaatgg gctctttact ttttgttgag ccttatgttc 116400
ttttatcctt ttcaggcata tttagggtca ccttttgtgt gatgtctact gcagacaggt 116460
gaaaaaaatt atttacctct ggtataatat ttagacaaaa gaaaggactc cattagaact 116520
ctattggtga gccaatgagt tatttcaatt ccttgcagga gtatggattc acttacagga 116580
gtatgaacaa cgcacatagg tagctatgtc accaaaacca ctacccttgt ctgagtgata 116640
actcatgaaa tctggaatct cagtgttctc tgtacaactt ataggcagct tgagagagca 116700
tacaatctat tctatctaaa atttttacta ctaatataat cttgaaaagg gttgttgttg 116760
ttggtcttgt gaatcttatt aagttcagaa actttcttag atttatgaat tgtttactcc 116820
ttactaaagt aagttccctt tacttcctca gtctaacgga gctttcttca aggacggaaa 116880
gctttaattc agaagaaatt gctaggtatc agctcctaaa tgccttgctc ttgctgacac 116940
tgaagcagat tcttgacctc cctcttagac attctactgc agggaagaca gttcccaaac 117000
tagtagtggc atgttacgag acaaatgctt gaagaaattg aaaaagagag aggaagagga 117060
ttgtactcta cctgagcaaa gtcttaaagg gatgaaccat gtgtccatgg gagtgaggga 117120
ccagactaag gagagcagga agtgcgaagg tctggaggtg gaaatatggt ttatataccg 117180
aggaacagta ggcaagtgag atttgcttgg gatgttctat atatgagtgg gtctgtttgc 117240
tccctcattc tagggctgcc tatgctccat ccaaacacag ggtggcccgt gttttactgt 117300
taccagagag agcattgtga attgaagtaa aacctggacc ctcttctaat aacctccctg 117360
cttgttctca tgcttgttct gcaggtccgc cttcttgggg tggtatccaa aggacagcca 117420
acgctggtag tgatggaatt gatggctcat ggagacctga aaagtcacct ccgttctctg 117480
aggccagatg ctgaggtaag ctgcctctag gtaagaccca taacagggta cctgatctta 117540
cgtataccaa cctcactaaa tgcaaaccca tgttttaact tcagaaatac cctggctaca 117600
cccctgaccc acacacccta taagagatga tttagatgga atcagagtgc taattgcaac 117660
ccctgttttg actttagaat aacccaggcc gccctccccc taccttgcaa gaaatgattc 117720
agatgacagc agaaattgct gatggcatgg catacttgaa cgccaagaag tttgtgcacc 117780
gggacctggc agctcgaaac tgcatggttg cccatgattt tactgtcaaa attggaggtg 117840
tgtcttagaa tccttgagag agaaaggaag agagagagag agagagagag agagagagag 117900
agagaatatt gtgtgtgtat gtatgtatgt atgtatgtat gtatgtgtat gtgtatgtgt 117960
atgtatgaat gtgtattgtg tgagcgtgtg cgtcataggg tgtgggtggc atggcagatt 118020
cttgggtcct aaattcatct tatgctgcct gaaaaagact tttacccact ctgggcattt 118080
tcccagccca gaaagctaac atttctgttc tagtttccgt ttagtcaaaa ataagtaagt 118140
aagttattaa ttaaataaat ataacaactt ggggaggaag gaatttgttt catcttatag 118200
tctatcactg agggaagtca ggcaaagaac ttgaaatgga aaccatgaaa taatgctgct 118260
tgctgatttg ttctggctca tgcttagtag cttttatata tagcccagga gtctcttcca 118320
agggaatggt gatgcccaca gtgagcttag cccttctata tcaatgatca agacaaccct 118380

-continued cataggcatg cccataggtc aatctgatat aggtaattct tcagtggagg attttctgtc 118440
tggagactct agcctgtgct cagatgacag ttaaaactta ctataaaact tagtataggt 118500
tctgacaaga ctaaaggctt aagtcagaga atgcagaaga aagagacaac agaagcagat 118560
ggtaagtgcc tagaatgctg gtggatagga tatgtgtgga taggatggat atagaggaac 118620
ccaaggacag tgtgctgtga ggttacattg aaagccaaga agcaggtatg taagggcttt 118680
gtaagctata ggatttattt gcctctcctc tacaaaatca gtgagaatca ggaacaggca 118740
agatcccata aagatctgaa aacatatctc cccccgcccc cccccacatt agttatggaa 118800
gcacataggg agatgaacct atgtatgatt ctaggagata tattatatat tatatttcta 118860
cgtaacaatg ggagtcatat aggaatatgc tcaaagacat caatctatat gaagggagat 118920
gggacatgat tcaatattta ttatcctaaa gactttctac atgagcaaca agaaaatcca 118980
tacaaaaccc aggtgtggtg gtgcatgtat ctggacactt ggagaagtag aggcaggaag 119040
atcaaaaact cattgtcatc ctcagctatg tagcaagtcc aaagttaccc taaaatctgc 119100
gagagctcgt ctcaagaaag aaagaaacaa aagcattgag aactggaagg aacatgcttc 119160
tattcacatc accgcccttg tgtagtagga tgttgtcagg ttggaggatg tactgggggg 119220
atatggaggg gagcctagac tactgaaggg caatgagaag tgagatgaat cagagagaga 119280
tgtagaggca gaaaggcttg cttgccccact gtttggaagt gtcagcaaga agcaaggtca 119340
aaaggagacc ccaagtttag tcgagagagc aacatattat ttggataaag gaaaaggatc 119400
tgtttgggac actggggaag gagtgggtgg aaggatgaca gcccctattc tccatccaca 119460
ccctccatac acctcaagaa tcctttccct ctgagtttgc ctgctaccct cagctctagt 119520
ggtgcttcaa ggggtagagc actcaagatg gtaggaggat gacctgaaaa acctgtgcac 119580
tgtttgttgt cagactttgg aatgacaagg gacatctacg agacagatta ctatcggaaa 119640
gggggcaagg gactgcttcc tgtgaggtgg atgtcacctg agtccctgaa ggatggagtc 119700
tttactgctt cttctgatat gtggtgagtt atacatacat gggtggatat tagtgctggg 119760
cttgaactcc tgaaggtgtc ccactaatgt gctcatcagg aggtgataga ggaaagccca 119820
tctttcacat atagaaatga aggtttatct gtctgggttc tcttagatgg ctatctttat 119880
gtattgattg aggatagtct tagaacttat tcatgaatta taatataaat cactgtgggt 119940
gcatgcatgt gcatgtgtga gatgcaggtg tgaccgtgct atggcacaga tgtggaggac 120000
aaaggacgac ttgtggaaat caattctctc cacccacctc cgtatgaagc ctgaggatct 120060
aactcaggcc atcaggctgg gcaccaagtg ctgcccactg agatatcttc ctggcttgca 120120
catccaggtc tttactcagg tttttgggca ttgaactcag gtcctcatgc tttggtgcaa 120180
aggactttgc caactgagat atcaccttag tccatcactt gttctattca ttggtcaaca 120240
aagttctagt aagccaaaag gggtattgaa caaatgtatc tgagatagag actattgtac 120300
gttttgttgg cttctttgtt tactgcgttc aattgtcatt ggcaggtcct ttggggtggt 120360
cctttgggaa atcactagcc tggctgagca accttatcaa ggcctgtcta atgaacaggt 120420
gttgaagttt gtcatggatg gaggctatct ggatcccccct gataactgtc cagagagact 120480
gtaagtatag aaaatatctg gagtgtgtga gggtttgcac attacatatg ttttgtgtct 120540
gtatatttta ggtacatatg catggatttg gtttgcaggc cttatgccca catatgttta 120600
tatagcatgc ctttacatcc aggcttgtat tcgcatattg tatcttggat gcccactttc 120660
attttcacat gtgcctacat atatgtttat gcttacatat atttatgctg gtgcatgtgt 120720

-continued catgcagttg acatacatat atttgcatat caaatccatt ttaaagattt atttttatct 120780
taggtatatg agtgtttgcc tacacgtatg ttcataacat atatatactt ggtgcccaaa 120840
gacattagga gagggtgtta ggtcctctgg acctggaatt acaggtggtt gtgaaccaat 120900
acatgggtgc caggaactaa accttagtcc acttcaagag aagcaaatgc tcttaaccac 120960
tgagccatct ctttagcccc ttaaatcttt tttttttaa aaatgcactt atgtgtacct 121020
gtgtgtagta tataaatgtg tggagggcat catcctgaga agtacttact actcatctcc 121080
attgagacat ggcccttcat tggtgtggtt ctcactgatt cagctaagct ggctggccag 121140
ccattgagtc ccttggatcc tcctgcctgt atcgtcccag ccctgggatt gtaaatgtgt 121200 acattttta aaaattactt acttatttat attttatttg cattggtgtt tttcctgcat 121260
gtatgtctgt gtgagggtgt tggatccact ggaactggac ttacagacag ttgtgagctg 121320
ctgtgcaggt gctaggaatt gaacctgagt cctctggaag agcagctagc cactgagcca 121380
cctttccagc cccaaatgtg tacatttttt ttttaaatgt aggctctgag gatctaactc 121440
aggttctcag gcttgaggga tgaacacttg tagagttttc atttgtcata gtcagttgtc 121500
attgagggct tgtctagaca acgctggctg gtgggcatgt cgatggggat tgtcttgatt 121560
gtgttagttg atgtcacctc tacgaggcac cgtttcctgt gcagagggtc ctgaactctc 121620
tatataaagt ggaggaagca ggctgagcaa gcttgcccgt gtccattctc tatctgctct 121680
tgaccgagtg tgctgtgact aggtgctttg agttcctact gccctgactt ccccaccctg 121740
atggactgca gcctgaaatc atgagctgag atgagctctt tcgaccgtgt cttttattgg 121800
ggtgtgttat catcatagca actggaacag aaattaagcc ctgggacaga gattcaccac 121860
ctttccttaa aggttctgtt gtaaatagtg acaacacagt ggccctctgt ggtcgaagct 121920
tgaatatagc cataggcatt acacagatgt atcgatgaga ccatatgtat tagctatcac 121980
tgctagggaa tacctgagaa attctactta aaggaggaga gactcaactg tggctcataa 122040
tttcagaggt ctcagtctat gctcactggg cttcactgct cctggcattt ccttttgaat 122100
aagctggaaa ctcactcccg gtgtttagcc cctatagtta tacctgccaa ggttcaagga 122160
tacctccctg aagggtcttt aaacctagaa tgactactgg gtacaggtaa gcttctgcaa 122220
gagaaagaca ccaaatgcca aggcatcaga gacagcggat acatattgtg ataaatgata 122280
tacaatgtct gcccagtttc tgtcctttta agacctctgt tgccatggtg aaacctgacc 122340
aaaagtaatt taggggagga gagatttagt tggatcactg atgggcaagt caaagtagaa 122400
actcaagcac caagtcacat cacatcctct gtcaagagct gagagagaga agtgtatggg 122460
actttgcttc cttgttctta gcctgctctc aacactctca tgaagtgtag gagccacctg 122520
ctcagggtgt ggtgttatcc acaaagaact gggtcgtccc atatcaatta acaatcaaga 122580
caaatcccca gaggtatgtt cacagcccaa cctaatctaa acttttcctc agttggggct 122640
ctttcccagt tgacagcttc ttgggctcca ttatgttatt ccccccttacc catctctttc 122700 ctcttccctt tccattcctt cctttcccta tttttccttt ttctttctat ttctgcttct 122760
tcttttcctc tcctctgtcc ttcctcttcc tccactgaga attgttcctt gtttgtactt 122820
tttatttaga gacactggtc tcactaaggc acccagactg gcttgaaagt cactctaatg 122880
gacagacctt aaatttacag tcctcctacc tcagcctcca gagtagctgg gataacaggc 122940
atgtagtatc gtgtctggct ggctttcttt tcaaagctgt ctttcagtcc ccctataatt 123000
gttgatccag ccttgaatac catctgtgca tacagccaca gccaaggcaa ggctgtattc 123060
actacttgaa tgtcgtctgt agtggggcag tacaggaggg agcagcctga ctgcaccttg 123120
aaacttatct accctggttc ctgtccccac agcactgacc tgatgcgcat gtgctggcag 123180
ttcaacccca agatgaggcc aaccttcctg gaaatcgtca acctgctcaa ggatgacctc 123240
caccccagct ttccagaagt ttccttcttc tacagcgagg agaacaaggc tcctgagagt 123300
gaggagctgg agatggagtt tgaagacatg gagaatgtcc cgttggatcg ttcctctcac 123360
tgtcagagag aagaggctgg gggccgggag ggagggtcct cactgagcat caaacggacc 123420
tatgatgaac acatccccta tacccacatg aatgggggca agaagaacgg acgtgtcctt 123480
accctgccaa ggtcaaaccc ttcctaacag cgccttctcc gggaaggatt cttttctttc 123540
tttctttttt aaaactcttc tgtagtttga ctgcctccag gaaactcagg attatcagga 123600
ctctgcccag atgtgaaact gagctcagag atagttcata cacatttctg tttgtctttt 123660
gacctgaaaa cacacaagcg tgatcgccaa ccctgtaagc ctgtggaggg ctaactgtga 123720
acctagaggg gttgggctgt ccatgctccc ttccctgcct ccaccgtatc aaaccaagat 123780
tttgttgttg gtggtgttct tttccccata gattggaaga atgtacctgc ttttttacag 123840
atattttct tcttttcttt tcttttcttt tcttttcttt tcttttcttt tcttttcttt 123900
tcttttcttt tctttctttt ttttccccgt tagtgtctga gttacagtta gttgtcaaag 123960
acagactatt tatggagcac aagtcagaaa gcaaagaaga aacagacaga aaacagaaca 124020
aaacaaaaca aaaaccaaac ctgacctaca gagcctggct ctagaattat atgctctgca 124080
gggttgggct ttgagaaggt ttcattaatc taagagaagg attttatttt attttatttt 124140
acttttttc ctcattcaca aaatcagttc ctcaaattga ccaatagctg ctgctttcat 124200
attttatttt gggaaagggt gtgtattcct aagtgtgtgc tcatctgcac acctgtgtgc 124260
atttgtgtgt atgttgtgtc caggttagag atcacagggt ggggtggggt ggggtggggg 124320
tggggtgctg tgtaaaatag tctctggact gatgcttggt gaattggctc ccgaagctcc 124380
tgctgcttgg agtgggtgac ctcatattgt cctcttcctt ctcatgaact gagagtctgt 124440
gccctcgaga gagtcttctc agtcacatca gaagtcttgc tcaggtgtct tcttcccctt 124500
ccctttgatg atgttttccg aaaacagagg gaggattatt tggtctggat tctttgagga 124560
tctttggaag accaaacaaa gcaaagggga cacacacaca cacacacaca cacacacaca 124620
cacacacaca cacactagaa ggaagtaagg caacaatttt gagaatatat ttgtaacata 124680
tttaaagctt atggaatctc tggtatgagc ctaataagtt agtatttctt tgggagcagt 124740
ggtgggcaca tctgcctgtg tggggacaca ggacaatatg tgagtggcct ctgggtttgg 124800
tctttgaaac acatattttt ctgggaatta taccacatta gctgctagcc ctttaggact 124860
cggggagttc ttgtggagtc tgtgggtaac tggatattcg actgtttcag atagtaacat 124920
tgactggatg tttcttgctt ggatacactg gtggttacct ggagctgaga tggccttcca 124980
gaacacctgt gttcatctgg tttttctctg cttgtgtacc tcacttcttc aaggcctaca 125040
ctttgctcaa tcattgtata aacatactaa actcagatcc cgaagaccaa tgacacagat 125100
ggactttgag aacactaagc aatatgtaag gagatgtacc cttccgatcc ccgctggtct 125160
cctccacctt tggggcatct ggctattctc tacactaaac tcccacagct gctcttggcg 125220
tccagggacc tcagcttggg ccagatatag tgcctgagtt tatttctcag gtgcttatgt 125280
ttgagtctct agagactaaa gtctggagga gaaaacatca gagactttct tctcaccacc 125340
aagaactcgt gaaaggatgt gaactcacaa cttctctttg cataaaacca cagctgctca 125400
agtaaaagaa acaactatgg tgaactcaaa atcctcccag aggttctttc ctgcgtgcat 125460

-continued ttcccacaaa tatttgatgc ctttcttctc ccttaggaga tatgagataa agacacactg 125520
gccaccctga ttaagaacac aaggaaacat aaatcctggt tgtcaattgc tgtggaattt 125580
atattataaa aattgcagca tgtaaaaatg ttgccaggga actcaatgat tggcataagc 125640
atcaagagtt acagttactt ttacccaaaa cactttgtaa atagaaggtc tgtgcatcaa 125700
tggaagacac cgtaggtatg gatattttt gtttattttt ccttttcaca gtaaatttgt 125760
agtgatgcta tactagcaga aattttcaca cctttctact tcaaaaggtt ttcttatagt 125820
accggggaaa gtatttattt taatatataa gatcactctt gaaaatcact tttgtaaaaa 125880
aatgttatga atgtaaattt ttttttatc aaggagaaat aaaaacaggt gagtgtgggt 125940
catttttttt ttccttcttc tcagtacagt ctacctcagt gtcttattag gatgtggttc 126000
agtaacagat gttgaggctt caagattctg gctgaatcat tctctgagtt ggggagctgt 126060
gtaccatttg atttttaaat gccagggact agggagaact ttgaaggaga gagtttagat 126120
taaaaagtta gagccttcct gtgaacccaa agtcttcttg ttggtgatat tcttcagagt 126180
atattctcca tacaaaaacc catctgttga ttgcacactc ctcacacaca agccacactt 126240
caagtcatca tgatttagct ctttggaggc ccctgatctg aggtctttga aaagtgggtg 126300
ttccttttac tgatgaggct gtgagccagt accttcagaa gtcacatgaa atcccccgga 126360
catgaatgca aagggaatct gggttttctg accatgattt ctcaccctgt ttagacccat 126420
gaggctgttt gtgggcacct cttacacaaa tagctgatgc aagggtattt ggagaaatcc 126480
tgctatgaaa cctatcagtt tcctgaacat atcttaaaca ataagatagg aaccctatgc 126540
tggggttggg ttgacttcaa gctgacactg tttggccttg tgcaatcttg agaactctgg 126600
aaatcaaggc ggggccagca tggctcctag tttcaagctt tgacatatta tttcacttta 126660
gaacactgtc cttaaaattt tactcttttc catcttttct ggaaaggtgc accaacttgg 126720
gtgaccctac caaaaaggac tccactaatt ccatgttgat atctactgtt gctgggaagg 126780
aaacaagtag ctattgggtc atgagactca ttttggtttc agaagatgtt agctttgtga 126840
gatctagaaa atcatggcta tcctgggagt tcgtagtgat ggatgaaaga gagagagaaa 126900
agaaaataga aacaaaagca agttacattg atatttcttg ttgagttttg ggagatgtct 126960
catcatttta aaactacttt catgatcatg atgaaatgca gttatttctt ccaggatagc 127020
agcagacatg ttgtctggtt caatgatgtc aagcatacat caggagatgt tcatgtactt 127080
ggagcctttc taaatgtttc cctgtcattt gatgctagct tgaagggaag agccttgatg 127140
gctttctgga tttaggctga gcacagtttg ggagagtgga gattggcagg aagagctgaa 127200
ctgtattgtg tggcagctgg gtgtggtgcc accaacacaa gtaaaaacta tccttactat 127260
cttatcagga cagacgttct accatgcaca gtgattattg ggttaagggc tgtaatttta 127320
tttgaaacct accataacac tggctggtgg gcagtatcac tgtgagagtc tggttcatac 127380
tggtgatctt ggtaaatgaa tgatggttgt tctagtaatg gttctatttt atgatagatg 127440
gatgtattcc agattctagc taatgaattc ttgacaacat aggctcttca aaaattatgg 127500
ttttgtcgga catgcgaaaa gaatagtgct gattttgtgt aaatggtgca catagcatat 127560
agtcattttt agaaaaacct tccagtatgt tcctcagaat atgaacttat acaaaagatg 127620
aagttgggca atgggaataa cagaatatca cttgtttaaa cgacacaaaa taatatgatg 127680
gtcttttaag aggtaatgac tgaaggcata tgcatcctca gatagtactc aagaaatgga 127740
gatcaatgag tatttgagct aatttgatac caatcaggat acaaaaatca gtctctggtc 127800
aaatttttat ctgtatgtgg gccatttaaa aaacaaacaa aatgaaacaa aaacatgtta 127860

-continued aaaatcagat catggttctg gaacccttgt tattatttga gaagaaagga aggtccctca 127920
gatgtgtgtg tgtctgttca catgtgcagg aatggcttgt ttggtcttta tcctttgtat 127980
caaagttgct gcttctttcc cctttatgtg cctgggtggt tatatcccat gtgtcaacag 128040
tgtgggatca aatgtgccat agcactgcag aaaacgcaga aacacaaaac ccatccaaag 128100
cacagtgaca ttttcctaca agagccaagt agcatcatgt ccagaatatg cctttttttg 128160
tgtggggagg agagggactg aaattgttct gcatgtataa tacaggctaa ttacttgttt 128220
atattaaaat ttggaataaa ttatcttgag acta 128254

<210> SEQ ID NO 2
<211> LENGTH: 8914
<212> TYPE: DNA
<213> ORGANISM: Mus musculus

<400> SEQUENCE: 2
gccggcgtgg cgtgctctga tcgccggggt cccagcactc ctactgctat gggcttcggg 60
agaggatgtg agacgacggc tgtgccattg ctggtggccg tggccgcgtt gctggtgggc 120
acagccggcc acctgtaccc tggagaggtg tgccctggta tggacatccg gaacaacctg 180
accaggctac atgagctgga gaactgctca gtcattgagg gccatctgca gatcctcctg 240
atgttcaaga ccagacccga agatttccga gacctcagtt tccccaaact catcatgatc 300
acagattacc tgcttctctt ccgtgtctat ggtctggaaa gtctgaaaga cctcttccca 360
aatctcacag tcatccgagg ctcccgtctc ttcttcaact atgccctggt tatcttcgag 420
atggtccacc tgaaggagct ggggctttat aacctcatga acatcacccg gggctctgtc 480
cgcatcgaga agaataatga gctctgctac ctggccacta tcgactggtc ccgtatcctg 540
gattctgtgg aggacaacta cattgtactg aacaaagatg acaacgagga atgtggggat 600
gtctgtccag gcaccgccaa gggcaagacc aactgtcctg ccactgtcat caatgggcag 660
tttgtggaac ggtgctggac acacagtcat tgtcagaaag tttgcccaac catctgtaag 720
tcacatggct gcacagctga aggcctgtgc tgccacaaag agtgcctggg caactgttcg 780
gaacctgatg accccaccaa gtgtgtggcc tgtcgcaact tctatctgga tggtcagtgt 840
gtggagacct gcccgccacc ctactatcac ttccaggact ggcgctgtgt gaacttcagc 900
ttctgccaag accttcactt caaatgcagg aactctcgga agcctggctg ccaccaatac 960
gtcattcaca acaataagtg catccccgag tgcccgtctg gctataccat gaattccagc 1020
aacttgatgt gcaccccatg tctgggaccc tgccctaagg tctgccaaat cctcgaaggt 1080
gagaagacca ttgattctgt gacatctgcc caggagctcc gaggctgcac tgtgatcaac 1140
ggtagcctga tcatcaacat ccgagggggc aacaacctgg cagctgagct ggaggctaac 1200
cttggcctca ttgaagaaat ttcgggattt ctaaagatcc gccgctccta tgctctggta 1260
tcactttctt tcttcaggaa gctacatctg attcgaggag agaccttgga aattgggaac 1320
tattcttttt atgccttgga caaccagaac ctgaggcaac tctgggactg gagcaaacac 1380
aacctcacca tcactcaggg caagctcttc ttccattaca acccgaaact ctgcttgtct 1440
gaaattcaca agatggaaga agtctccgga actaagggcc gtcaggagag gaacgacatt 1500
gccctgaaga ccaatgggga ccaggcatcg tgtgaaaatg aattgcttaa attttctttc 1560
attcggacat cttttgacaa gatcctgttg aggtgggaac cctactggcc ccccgacttc 1620
cgagatctcc tgggattcat gttgttctac aaagaggccc cttatcagaa tgtgacagag 1680

-continued

```
tttgatgggc aggatgcttg tggctccaac agctggactg tggtggatat tgacccgccc   1740
cagaggtcca acgaccccaa gtctcagacc ccaagccacc ctgggtggct gatgcggggc   1800
ctcaaaccct ggacccaata cgccatcttt gtgaagacct tggttacctt ctctgatgaa   1860
cggcggacct atggagccaa aagtgatatc atctatgtgc aaacagatgc cactaatcct   1920
tctgtccccc tggatcccat atcagtttct aattcctcat ctcagattat cttaaagtgg   1980
aagcccccct ctgaccccaa tggcaacatc acacactacc tggtgtactg ggagaggcaa   2040
gcagaggaca gcgagctgtt tgagctggat tattgtctca aagggctgaa gctcccttca   2100
cggacctggt ccccaccctt tgagtctgat gattctcaga agcacaatca gagtgagtat   2160
gacgactcgg ccagtgagtg ctgctcatgc cctaagactg actctcagat cctgaaggag   2220
ctggaggagt cttcattcag gaagaccttc gaggattacc tgcacaacgt ggtttttgtc   2280
cccaggccat cccgaaagcg aagatccctt gaagaggtgg ggaatgtgac agccaccaca   2340
ctcacacttc cagatttccc caacgtctcc tctaccattg tgcccacaag tcaggaggag   2400
cacaggccat ttgagaaagt ggtgaacaag gagtcacttg tcatctctgg cctgagacac   2460
ttcactgggt accgcattga gctgcaggca tgcaatcaag attccccaga tgagaggtgc   2520
agtgtggctg cctacgtcag tgcccggacc atgcctgaag ctaaggcaga tgacatcgtt   2580
ggccctgtga ctcatgaaat ctttgagaac aatgttgtac acttaatgtg gcaagagcca   2640
aaggaaccta atggtctgat tgtgctatat gaagtgagct atcgccgata tggtgatgag   2700
gagctgcacc tctgtgtctc ccggaagcat tttgccctgg agcggggctg caggctgcga   2760
gggctctccc caggaaacta cagtgttcga gtccgggcta cctctctggc aggaaatggc   2820
tcctggacag aacccaccta tttttatgtg actgattatt tagatgtccc atcaaatatt   2880
gccaaaatta tcattggacc cctcatcttt gtcttcctct tcagtgttgt gattggaagt   2940
atttatctat ttctgagaaa gaggcagccg gatgggccaa tgggaccact gtatgcatct   3000
tcaaaccctg agtacctcag tgccagtgat gtgtttccat cttctgtgta cgtgccggac   3060
gagtgggagg tgcctcgaga gaagatcacc cttcttcgag agctggggca gggatccttt   3120
ggtatggtgt atgaaggcaa tgccaaggat atcatcaagg gtgaggcaga gacccgtgtt   3180
gcggttaaga ctgtcaatga gtcagccagt cttcgagaac ggatcgagtt cctcaatgag   3240
gcatcagtca tgaagggatt cacctgccat catgtggtcc gccttcttgg ggtggtatcc   3300
aaaggacagc caacgctggt agtgatggaa ttgatggctc atggagacct gaaaagtcac   3360
ctccgttctc tgaggccaga tgctgagaat aacccaggcc gccctccccc taccttgcaa   3420
gaaatgattc agatgacagc agaaattgct gatggcatgg catacttgaa cgccaagaag   3480
tttgtgcacc gggacctggc agctcgaaac tgcatggttg cccatgattt tactgtcaaa   3540
attggagact ttggaatgac aagggacatc tacgagacag attactatcg gaaagggggc   3600
aagggactgc ttcctgtgag gtggatgtca cctgagtccc tgaaggatgg agtctttact   3660
gcttcttctg atatgtggtc ctttggggtg gtcctttggg aaatcactag cctggctgag   3720
caaccttatc aaggcctgtc taatgaacag gtgttgaagt ttgtcatgga tggaggctat   3780
ctggatcccc ctgataactg tccagagaga ctcactgacc tgatgcgcat gtgctggcag   3840
ttcaacccca agatgaggcc aaccttcctg gaaatcgtca acctgctcaa ggatgacctc   3900
caccccagct ttccagaagt ttccttcttc tacagcgagg agaacaaggc tcctgagagt   3960
gaggagctgg agatggagtt tgaagacatg gagaatgtcc cgttggatcg ttcctctcac   4020
tgtcagagag aagaggctgg gggccgggag ggagggtcct cactgagcat caaacggacc   4080
```

```
tatgatgaac acatccccta tacccacatg aatgggggca agaagaacgg acgtgtcctt   4140
accctgccaa ggtcaaaccc ttcctaacag cgccttctcc gggaaggatt cttttctttc   4200
tttctttttt aaaactcttc tgtagtttga ctgcctccag gaaactcagg attatcagga   4260
ctctgcccag atgtgaaact gagctcagag atagttcata cacatttctg tttgtctttt   4320
gacctgaaaa cacacaagcg tgatcgccaa ccctgtaagc ctgtggaggg ctaactgtga   4380
acctagaggg gttgggctgt ccatgctccc ttccctgcct ccaccgtatc aaaccaagat   4440
tttgttgttg gtggtgttct tttccccata gattggaaga atgtacctgc ttttttacag   4500
atatttttct tcttttcttt tcttttcttt tcttttcttt tcttttcttt tcttttcttt   4560
tcttttcttt tctttctttt ttttccccgt tagtgtctga gttacagtta gttgtcaaag   4620
acagactatt tatggagcac aagtcagaaa gcaaagaaga aacagacaga aaacagaaca   4680
aaacaaaaca aaaaccaaac ctgacctaca gagcctggct ctagaattat atgctctgca   4740
gggttgggct ttgagaaggt ttcattaatc taagagaagg attttatttt attttatttt   4800
acttttttttc ctcattcaca aaatcagttc ctcaaattga ccaatagctg ctgctttcat   4860
attttatttt gggaaagggt gtgtattcct aagtgtgtgc tcatctgcac acctgtgtgc   4920
atttgtgtgt atgttgtgtc caggttagag atcacagggt ggggtggggt ggggtggggg   4980
tggggtgctg tgtaaaatag tctctggact gatgcttggt gaattggctc ccgaagctcc   5040
tgctgcttgg agtgggtgac ctcatattgt cctcttcctt ctcatgaact gagagtctgt   5100
gccctcgaga gagtcttctc agtcacatca gaagtcttgc tcaggtgtct tcttcccctt   5160
ccctttgatg atgttttccg aaaacagagg gaggattatt tggtctggat tctttgagga   5220
tctttggaag accaaacaaa gcaaagggga cacacacaca cacacacaca cacacacaca   5280
cacacacaca cacactagaa ggaagtaagg caacaatttt gagaatatat ttgtaacata   5340
tttaaagctt atggaatctc tggtatgagc ctaataagtt agtatttctt tgggagcagt   5400
ggtgggcaca tctgcctgtg tggggacaca ggacaatatg tgagtggcct ctgggtttgg   5460
tctttgaaac acatattttt ctgggaatta taccacatta gctgctagcc ctttaggact   5520
cggggagttc ttgtggagtc tgtgggtaac tggatattcg actgtttcag atagtaacat   5580
tgactggatg tttcttgctt ggatacactg gtggttacct ggagctgaga tggccttcca   5640
gaacacctgt gttcatctgg tttttctctg cttgtgtacc tcacttcttc aaggcctaca   5700
ctttgctcaa tcattgtata aacatactaa actcagatcc cgaagaccaa tgacacagat   5760
ggactttgag aacactaagc aatatgtaag gagatgtacc cttccgatcc ccgctggtct   5820
cctccacctt tggggcatct ggctattctc tacactaaac tcccacagct gctcttggcg   5880
tccagggacc tcagcttggg ccagatatag tgcctgagtt tatttctcag gtgcttatgt   5940
ttgagtctct agagactaaa gtctggagga gaaaacatca gagactttct tctcaccacc   6000
aagaactcgt gaaaggatgt gaactcacaa cttctctttg cataaaacca cagctgctca   6060
agtaaaagaa acaactatgg tgaactcaaa atcctcccag aggttctttc ctgcgtgcat   6120
ttcccacaaa tatttgatgc ctttcttctc ccttaggaga tatgagataa agacacactg   6180
gccaccctga ttaagaacac aaggaaacat aaatcctggt tgtcaattgc tgtggaattt   6240
atattataaa aattgcagca tgtaaaaatg ttgccaggga actcaatgat tggcataagc   6300
atcaagagtt acagttactt ttacccaaaa cactttgtaa atagaaggtc tgtgcatcaa   6360
tggaagacac cgtaggtatg gatatttttt gtttattttt ccttttcaca gtaaatttgt   6420
```

-continued

```
agtgatgcta tactagcaga aattttcaca cctttctact tcaaaaggtt ttcttatagt   6480
accggggaaa gtatttattt taatatataa gatcactctt gaaaatcact tttgtaaaaa   6540
aatgttatga atgtaaattt tttttttatc aaggagaaat aaaaacaggt gagtgtgggt   6600
catttttttt ttccttcttc tcagtacagt ctacctcagt gtcttattag gatgtggttc   6660
agtaacagat gttgaggctt caagattctg gctgaatcat tctctgagtt ggggagctgt   6720
gtaccatttg atttttaaat gccagggact agggagaact ttgaaggaga gagtttagat   6780
taaaaagtta gagccttcct gtgaacccaa agtcttcttg ttggtgatat tcttcagagt   6840
atattctcca tacaaaaacc catctgttga ttgcacactc ctcacacaca agccacactt   6900
caagtcatca tgatttagct ctttggaggc ccctgatctg aggtctttga aaagtgggtg   6960
ttccttttac tgatgaggct gtgagccagt accttcagaa gtcacatgaa atcccccgga   7020
catgaatgca aagggaatct gggttttctg accatgattt ctcaccctgt ttagacccat   7080
gaggctgttt gtgggcacct cttacacaaa tagctgatgc aagggtattt ggagaaatcc   7140
tgctatgaaa cctatcagtt tcctgaacat atcttaaaca ataagatagg aaccctatgc   7200
tggggttggg ttgacttcaa gctgacactg tttggccttg tgcaatcttg agaactctgg   7260
aaatcaaggc ggggccagca tggctcctag tttcaagctt tgacatatta tttcacttta   7320
gaacactgtc cttaaaattt tactcttttc catcttttct ggaaaggtgc accaacttgg   7380
gtgaccctac caaaaaggac tccactaatt ccatgttgat atctactgtt gctgggaagg   7440
aaacaagtag ctattgggtc atgagactca ttttggtttc agaagatgtt agctttgtga   7500
gatctagaaa atcatggcta tcctgggagt tcgtagtgat ggatgaaaga gagagagaaa   7560
agaaaataga aacaaaagca agttacattg atatttcttg ttgagttttg ggagatgtct   7620
catcatttta aaactacttt catgatcatg atgaaatgca gttatttctt ccaggatagc   7680
agcagacatg ttgtctggtt caatgatgtc aagcatacat caggagatgt tcatgtactt   7740
ggagcctttc taaatgtttc cctgtcattt gatgctagct tgaagggaag agccttgatg   7800
gctttctgga tttaggctga gcacagtttg ggagagtgga gattggcagg aagagctgaa   7860
ctgtattgtg tggcagctgg gtgtggtgcc accaacacaa gtaaaaacta tccttactat   7920
cttatcagga cagacgttct accatgcaca gtgattattg ggttaagggc tgtaatttta   7980
tttgaaacct accataacac tggctggtgg gcagtatcac tgtgagagtc tggttcatac   8040
tggtgatctt ggtaaatgaa tgatggttgt tctagtaatg gttctatttt atgatagatg   8100
gatgtattcc agattctagc taatgaattc ttgacaacat aggctcttca aaaattatgg   8160
ttttgtcgga catgcgaaaa gaatagtgct gattttgtgt aaatggtgca catagcatat   8220
agtcattttt agaaaaacct tccagtatgt tcctcagaat atgaacttat acaaaagatg   8280
aagttgggca atgggaataa cagaatatca cttgtttaaa cgacacaaaa taatatgatg   8340
gtcttttaag aggtaatgac tgaaggcata tgcatcctca gatagtactc aagaaatgga   8400
gatcaatgag tatttgagct aatttgatac caatcaggat acaaaaatca gtctctggtc   8460
aaatttttat ctgtatgtgg gccatttaaa aaacaaacaa aatgaaacaa aaacatgtta   8520
aaaatcagat catggttctg gaacccttgt tattatttga gaagaaagga aggtccctca   8580
gatgtgtgtg tgtctgttca catgtgcagg aatggcttgt ttggtcttta tcctttgtat   8640
caaagttgct gcttctttcc cctttatgtg cctgggtggt tatatcccat gtgtcaacag   8700
tgtgggatca aatgtgccat agcactgcag aaaacgcaga aacacaaaac ccatccaaag   8760
cacagtgaca ttttcctaca agagccaagt agcatcatgt ccagaatatg cctttttttg   8820
```

tgtggggagg agagggactg aaattgttct gcatgtataa tacaggctaa ttacttgttt 8880
atattaaaat ttggaataaa ttatcttgag acta 8914

<210> SEQ ID NO 3
<211> LENGTH: 707
<212> TYPE: DNA
<213> ORGANISM: Homo sapiens

<400> SEQUENCE: 3
ctcagaagag cccacagaga aggaacctcc agggcagtta caggtgaagg cccagccgca 60
ggcccggatg acagtaccga aacagacaca gacaccagac ctgctgcctg aggccctgga 120
agcccaagtg ctgccacgat tccagccacg ggtcctgcag gtccaggccc aggtgcagtc 180
acagactcag ccgcggatac catccacaga cacccaggtg cagccaaagc tgcagaagca 240
ggcgcaaaca cagacctctc cagagcactt agtgctgcaa cagaagcagg tgcagccaca 300
gctgcagcag gaggcagagc cacagaagca ggtgcagcca caggtacagc cacaggcaca 360
ttcacagggc ccaaggcagg tgcagctgca gcaggaggca gagccgctga agcaggtgca 420
gccacaggtg cagccccagg cacattcaca gcccccaagg caggtgcagc tgcagctgca 480
gaagcaggtc cagacacaga catatccaca ggtccacaca caggcacagc caagcgtcca 540
gccacaggag catcctccag cgcaggtgtc agtacagcca ccagagcaga cccatgagca 600
gcctcacacc cagccgcagg tgtcgttgct ggctccagag caaacaccag ttgtggttca 660
tgtctgcggg ctggagatgc cacctgatgc agtagaagct ggtggag 707

<210> SEQ ID NO 4
<211> LENGTH: 25
<212> TYPE: DNA
<213> ORGANISM: Mus musculus

<400> SEQUENCE: 4
gcaagaaatg attcagatga cagca 25

<210> SEQ ID NO 5
<211> LENGTH: 25
<212> TYPE: DNA
<213> ORGANISM: Mus musculus

<400> SEQUENCE: 5
ccttgcaaga aatgattcag atgac 25

<210> SEQ ID NO 6
<211> LENGTH: 25
<212> TYPE: DNA
<213> ORGANISM: Mus musculus

<400> SEQUENCE: 6
gcaagaaatg attcagatga cagca 25

<210> SEQ ID NO 7
<211> LENGTH: 21
<212> TYPE: DNA
<213> ORGANISM: Mus musculus

<400> SEQUENCE: 7
ttggtatggt gtatgaaggc a 21

<210> SEQ ID NO 8

<211> LENGTH: 21
<212> TYPE: DNA
<213> ORGANISM: Mus musculus

<400> SEQUENCE: 8
tccccctacc ttgcaagaaa t 21

<210> SEQ ID NO 9
<211> LENGTH: 22
<212> TYPE: DNA
<213> ORGANISM: Mus musculus

<400> SEQUENCE: 9
attgctgatg gcatggcata ct 22

<210> SEQ ID NO 10
<211> LENGTH: 27
<212> TYPE: DNA
<213> ORGANISM: Mus musculus

<400> SEQUENCE: 10
gtctgtatat tttagtcaca tcagaag 27

<210> SEQ ID NO 11
<211> LENGTH: 20
<212> TYPE: DNA
<213> ORGANISM: Mus musculus

<400> SEQUENCE: 11
attttagctg ctcttggcgt 20

<210> SEQ ID NO 12
<211> LENGTH: 20
<212> TYPE: DNA
<213> ORGANISM: Mus musculus

<400> SEQUENCE: 12
tttgcttcct tctgctcttg 20

<210> SEQ ID NO 13
<211> LENGTH: 24
<212> TYPE: DNA
<213> ORGANISM: Mus musculus

<400> SEQUENCE: 13
tcctccaacc tccaattttg acag 24

<210> SEQ ID NO 14
<211> LENGTH: 23
<212> TYPE: DNA
<213> ORGANISM: Mus musculus

<400> SEQUENCE: 14
aagagcagct tgcttcttgc tga 23

<210> SEQ ID NO 15
<211> LENGTH: 25
<212> TYPE: DNA
<213> ORGANISM: Mus musculus

<400> SEQUENCE: 15
caaatttact cctgatgagc acatt 25

<210> SEQ ID NO 16
<211> LENGTH: 25
<212> TYPE: DNA
<213> ORGANISM: Mus musculus

<400> SEQUENCE: 16
acacacatct cctgatgagc acatt 25

<210> SEQ ID NO 17
<211> LENGTH: 24
<212> TYPE: DNA
<213> ORGANISM: Mus musculus

<400> SEQUENCE: 17
ggacgaccca gttcttcatt tcta 24

<210> SEQ ID NO 18
<211> LENGTH: 21
<212> TYPE: DNA
<213> ORGANISM: Mus musculus

<400> SEQUENCE: 18
acgacccagt tctcctgatg a 21

<210> SEQ ID NO 19
<211> LENGTH: 22
<212> TYPE: DNA
<213> ORGANISM: Mus musculus

<400> SEQUENCE: 19
tgatgtgaag tctctctgga ca 22

<210> SEQ ID NO 20
<211> LENGTH: 30
<212> TYPE: DNA
<213> ORGANISM: Mus musculus

<400> SEQUENCE: 20
tgaggtagac tgtactaaaa tatacagaca 30

<210> SEQ ID NO 21
<211> LENGTH: 25
<212> TYPE: DNA
<213> ORGANISM: Mus musculus

<400> SEQUENCE: 21
gagactcaaa cataagcacc tgttc 25

<210> SEQ ID NO 22
<211> LENGTH: 20
<212> TYPE: DNA
<213> ORGANISM: Mus musculus

<400> SEQUENCE: 22
caccactgct cccaaagaaa 20

<210> SEQ ID NO 23
<211> LENGTH: 21
<212> TYPE: DNA
<213> ORGANISM: Mus musculus

<400> SEQUENCE: 23
cagggaaaca tttagaaagg c 21

<210> SEQ ID NO 24
<211> LENGTH: 21
<212> TYPE: DNA
<213> ORGANISM: Mus musculus

<400> SEQUENCE: 24
tgagcagctg tggttttatg c 21

<210> SEQ ID NO 25
<211> LENGTH: 20
<212> TYPE: DNA
<213> ORGANISM: Mus musculus

<400> SEQUENCE: 25
gagatggtcc acctgaagga 20

<210> SEQ ID NO 26
<211> LENGTH: 20
<212> TYPE: DNA
<213> ORGANISM: Mus musculus

<400> SEQUENCE: 26
tgtgctcctc ctgacttgtg 20

<210> SEQ ID NO 27
<211> LENGTH: 42
<212> TYPE: DNA
<213> ORGANISM: Homo sapiens

<400> SEQUENCE: 27
tttttgcctt ttgttttaac ttttccaggt gaaaatgagt ta 42

<210> SEQ ID NO 28
<211> LENGTH: 448
<212> TYPE: DNA
<213> ORGANISM: Mus musculus

<400> SEQUENCE: 28
cagggatcct ttggtatggt gtatgaaggc aatgccaagg atatcatcaa gggtgaggca 60
gagacccgtg ttgcggttaa gactgtcaat gagtcagcca gtcttcgaga acggatcgag 120
ttcctcaatg aggcatcagt catgaaggga ttcacctgcc atcatgtggt ccgccttctt 180
ggggtggtat ccaaaggaca gccaacgctg gtagtgatgg aattgatggc tcatggagac 240
ctgaaaagtc acctccgttc tctgaggcca gatgctgaga ataacccagg ccgccctccc 300
cctgccttgc aagaaatgat tcagatgaca gcagaaattg ctgatggcat ggcatacttg 360
aacgccaaga agtttgtgca ccgggacctg gcagctcgaa actgcatggt tgcccatgat 420
tttactgtca aaattggagg ttggagga 448

<210> SEQ ID NO 29
<211> LENGTH: 946
<212> TYPE: DNA
<213> ORGANISM: Mus musculus
<220> FEATURE:
<221> NAME/KEY: misc_feature
<222> LOCATION: (925)..(925)
<223> OTHER INFORMATION: n is a, c, g, t or u

<400> SEQUENCE: 29
aagagcagct tgcttcttgc tgacacttcc aaacagtggg caagcaagcc tttctgcctc 60
tacatctctc tctgattcat ctcacttctc attgcccttc agtagtctag gccccccctcc 120 atatcccccc agtacatcct ccaacctgac aacatcctac tacacaaggg cggtgatgtg 180
aatagaagca tgttccttcc agttctcaat gcttttgttt ctttctttct tgagacgagc 240
tctcgcagat tttagggtaa ctttggactt gctacatagc tgaggatgac aataagtttt 300
tgatcttcct gcctctactt ctccaagtgt ccagatacat gcaccaccac acctgggttt 360
tgtatggatt ttcttgttgc tcatgtagaa agtctttagg ataataaata ttgaatcatg 420
tcccatctcc cttcatatag attgatgtct ttgagcatat tcctatatga ctcccattgt 480
tacgtagaaa tataatatat aatatatctc ctagaatcat acataggttc atctccctat 540
gtgcttccat aactaatgtg gggggggga gatatgtttt cagatcttta tgggatcttg 600
cctgttcctg attctcactg attttgtaga ggagaggcaa ataaatccta tagcttacaa 660
agcccttaca tacctgcttc ttggctttca atgtaacctc acagcacact gtccttgggt 720
tcctctatat ccatcctatc cacacatatc ctatccacca gcattctagg cacttaacat 780
ctgcttctgt tgtctctttc ttctgcattc tctgacttaa gcctttagtc ttgtcagaac 840
ctatactaag ttttatagta agttttaact gtcatctgag cacaggctag agtctccaga 900
cagaaaatcc tccactgaag aattncctat atcagattga cctatg 946

<210> SEQ ID NO 30
<211> LENGTH: 909
<212> TYPE: DNA
<213> ORGANISM: Mus musculus

<400> SEQUENCE: 30
ttatagtccc tgtcgggttt cgcccacctc tgacttgagc gtcgattttt tgtgatgctc 60
gtcagggggg gcggagccta tggaaaaacg ccagcaacgc ggccttttta cggttcctgg 120
ccttttgctg gccttttgct cacatgttct ttcctgcgtt atcccctgat tctgtggata 180
accgtattac cgcctttgag tgagctgata ccgctcgccg cagccgaacg accgagcgca 240
gcgagtcagt gagcgaggaa gcggaagagc gcccaatacg caaaccgcct ctccccgcgc 300
gttggccgat tcattaatgc agctggcacg acaggtttcc cgactggaaa gcgggcagtg 360
agcgcaacgc aattaatgtg agttagctca ctcattaggc accccaggct ttacacttta 420
tgcttccggc tcgtatgttg tgtggaattg tgagcggata acaatttcac acaggaaaca 480
gctatgacca tgattacgcc aagcttggta ccgagctcgg atccactagt aacggccgcc 540
agtgtgctgg aattcgccct tgcaagaaat gattcagatg acagcagaaa ttgctgatgg 600
catggcatac ttgaacgcca agaagtttgt gcaccgggac ctggcagctc gaaactgcat 660
ggttgcccat gattttactg tcaaaattgg agactttgga atgacaaggg acatctacga 720
gacagattac tatcggaaag gggcaaggg actgcttcct gtgaggtgga tgtcacctga 780
gtccctgaag gatggagtct ttactgcttc ttctgatatg tggtgagtta tacatacatg 840
ggtggatatt agtgctgggc ttgaactcct gaaggtgtcc cactaatgtg ctcatcagga 900
gtaaatttg 909

<210> SEQ ID NO 31
<211> LENGTH: 712
<212> TYPE: DNA
<213> ORGANISM: Mus musculus

<400> SEQUENCE: 31
gagtgagctg ataccgctcg ccgcagccga acgaccgagc gcagcgagtc agtgagcgag 60

-continued

```
gaagcggaag agcgcccaat acgcaaaccg cctctccccg cgcgttggcc gattcattaa    120

tgcagctggc acgacaggtt tcccgactgg aaagcgggca gtgagcgcaa cgcaattaat    180

gtgagttagc tcactcatta ggcaccccag gctttacact ttatgcttcc ggctcgtatg    240

ttgtgtggaa ttgtgagcgg ataacaattt cacacaggaa acagctatga ccatgattac    300

gccaagcttg gtaccgagct cggatccact agtaacggcc gccagtgtgc tggaattcgc    360

ccttgcaaga aatgattcag atgacagcag aaattgctga tggcatggca tacttgaacg    420

ccaagaagtt tgtgcaccgg gacctggcag ctcgaaactg catggttgcc catgatttta    480

ctgtcaaaat tggagacttt ggaatgacaa gggacatcta cgagacagat tactatcgga    540

aagggggcaa gggactgctt cctgtgaggt ggatgtcacc tgagtccctg aaggatggag    600

tctttactgc ttcttctgat atgtggtgag ttatacatac atgggtggat attagtgctg    660

ggcttgaact cctgaaggtg tcccactaat gtgctcatca ggagatgtgt gt            712


<210> SEQ ID NO 32
<211> LENGTH: 325
<212> TYPE: DNA
<213> ORGANISM: Mus musculus

<400> SEQUENCE: 32

attgctgatg gcatggcata cttgaacgcc aagaagtttg tgcaccggga cctggcagct     60

cgaaactgca tggttgccca tgattttact gtcaaaattg gagactttgg aatgacaagg    120

gacatctacg agacagatta ctatcggaaa gggggcaagg gactgcttcc tgtgaggtgg    180

atgtcacctg agtccctgaa ggatggagtc tttactgctt cttctgatat gtggtccttt    240

ggggtggtcc tttgggaaat cactagcctg gctgagcaac cttatcaagg cctgtctaat    300

gaacaggtgc ttatgtttga gtctc                                          325


<210> SEQ ID NO 33
<211> LENGTH: 287
<212> TYPE: DNA
<213> ORGANISM: Mus musculus

<400> SEQUENCE: 33

gtctgtatat tttagtcaca tcagaagtct tgctcaggtg tcttcttccc cttccctttg     60

atgatgtttt ccgaaaacag agggagaatt atttggtctg gattctttga ggatctttgg    120

aagaccaaac aaagcaaagg ggacacacac acacacacac acacacacac acacacacta    180

gaaggaagta aggcaacaat tttgagaata tatttgtaac atatttaaag cttatggaat    240

ctctggtatg agcctaataa gttagtattt ctttgggagc agtggtg                  287


<210> SEQ ID NO 34
<211> LENGTH: 1001
<212> TYPE: DNA
<213> ORGANISM: Mus musculus
<220> FEATURE:
<221> NAME/KEY: misc_feature
<222> LOCATION: (888)..(888)
<223> OTHER INFORMATION: n is a, c, g, t or u
<220> FEATURE:
<221> NAME/KEY: misc_feature
<222> LOCATION: (900)..(900)
<223> OTHER INFORMATION: n is a, c, g, t or u
<220> FEATURE:
<221> NAME/KEY: misc_feature
<222> LOCATION: (952)..(953)
<223> OTHER INFORMATION: n is a, c, g, t or u
<220> FEATURE:
<221> NAME/KEY: misc_feature
```

<222> LOCATION: (962)..(962)
<223> OTHER INFORMATION: n is a, c, g, t or u
<220> FEATURE:
<221> NAME/KEY: misc_feature
<222> LOCATION: (964)..(964)
<223> OTHER INFORMATION: n is a, c, g, t or u
<220> FEATURE:
<221> NAME/KEY: misc_feature
<222> LOCATION: (966)..(967)
<223> OTHER INFORMATION: n is a, c, g, t or u
<220> FEATURE:
<221> NAME/KEY: misc_feature
<222> LOCATION: (970)..(970)
<223> OTHER INFORMATION: n is a, c, g, t or u
<220> FEATURE:
<221> NAME/KEY: misc_feature
<222> LOCATION: (978)..(978)
<223> OTHER INFORMATION: n is a, c, g, t or u

<400> SEQUENCE: 34
attttagctg ctcttggcgt ccagggacct cagcttgggc cagatatagt gcctgagttt 60
atttctcagg tgcttatgtt tgagtctcta gagactaaag tctggaggag aaaacatcag 120
agactttctt ctcaccacca agaactcgtg aaaggacgtg aactcacaac ttctctttgc 180
ataaaaccac agctgctcaa gtaaaagaaa caactatggt gaactcaaaa tcctcccaga 240
ggttctttcc tgcgtgcatt tcccacaaat atttgatgcc tttcttctcc cttaggagat 300
atgagataaa gacacactgg ccaccctgat taagaacaca aggaaacata aatcctggtt 360
gtcaattgct gtggaattta tattataaaa attgcagcat gtaaaaatgt tgccagggaa 420
ctcaatgatt ggcataagca tcaagagtta cagttacttt tacccaaaac actttgtaaa 480
tagaaggtct gtgcatcaat ggaagacacc gtaggtatgg atattttttg tttattcttc 540
cttttcacag taaatttgta gtgatgctat actagcagaa attttcacac ctttctactt 600
caaaaggttt tcttatagta ccggggaaag tatttatttt aatatataag atcactcttg 660
aaaatcactt ttgtaaaaaa atgttatgaa tgtaaatttt ttttttatca aggagaaata 720
aaaacaggtg agtgtgggtc atttttttttc cctcttctca gtacagtcta cctcagtgtc 780
ttattaggat gtggttcagt aacagatgtt gaggcttcaa gattctggct gaatcattct 840
ctgagttggg ggagctgtgt accattttga ttttttaaat gccagggnct aggggagaan 900
ttttgaaggg agagagttta gattaaaaag ttagagccct tcctgtgaac cnnaagtctt 960
cntngnnggn gatattcntt cagagtatat tctccataca a 1001

<210> SEQ ID NO 35
<211> LENGTH: 181745
<212> TYPE: DNA
<213> ORGANISM: Homo sapiens

<400> SEQUENCE: 35
gagaaggacg cgcggccccc agcgcctctt gggtggccgc ctcggagcat gaccccccgcg 60 ggccagcgcc gcgcgctctg atccgaggag accccgcgct cccgcagcca tggccaccgg 120
gggccggcgg ggggcggcgg ccgcgccgct gctggtggcg gtggccgcgc tgctactggg 180
cgccgcgggc cacctgtacc ccggagaggg tgagtctggg ggcgcgggcg tgggcgggga 240
gcgccgcgat ggggagagga ccccacccaa gccaaaatcg agcccccgct tgtggactga 300
gaaccctccc caggggcggg gggcggtggc caggacggta gctcctgcat cgcgtagggg 360
gagcgggaag cctctgacct tggcctttgc ccgcccgggc tcgcgcctcc gcgccctgcg 420
tgcccgacct gagcccgagg aaccttgccc cggtgcccgc cccgccgcgg gctcctctct 480

-continued

```
ggagcgcgcc tccgacccgt gccccggccc ctccgagccc aagtcgctcc ggagacacga    540
cacgcgtcat ctttgggtcg cggccgggaa gtggggtcac tgggtctgga cagccccgaa    600
cagccaagtc ccccgagcgc atatggtgta ggtagagcca agcgccctga gtgcctcacc    660
ggtgggtgac gctgcctggg gtcagggact gcagagcccc cctctaccca actaccttgg    720
atctaggccc gtggccaccc cggactctag gtccatgttt accctttttgg gttctgtttc   780
cagatgtccg gaggcaaatt ctaaagcctt agcaacagca gcaattgtag cagaagtagt    840
ggcggttttt taccctattt attgtaattg gtatcaccgc acgccacagc ctagtctatc    900
ttatctctct ggactgtcac agtggccccc ggaggcagat acagttatgc acccatttca    960
cagaggagta aactgaggct catgtaggac gcataactcc cttgccctaa agtcagtgcc   1020
agagccagga cttgagcctc tgtgtgtccc gttctgccca agaatctgga ctactgtccc   1080
ttgtctgctg tctccttgac ccctcctctc ccctcagccc tgcgcttcat gaaggagcct   1140
ttgaccttga gtgagccttt cgttcccccct gaccccatgg gcccctctcc cacgtgtggg  1200
cagcatcttc cttgggcttg acaataggca cctttggggt tgtaagatga agatggcgca   1260
atcatttaag gaatatagcc tgggtttccc actgtggggt ctgaggccct gctttaaaaa   1320
tatctgttgg gttactgttt cagatttctc cataaaagga aatcagtcgt gatgaggaag   1380
gggtcaggga gggaaggaat tgaagctctt aaatgtattg atggggaaac gggtgcatgt   1440
aaaatcaggt gctagagtgg accaaccggg tttgctgagt cgactctgtc aatcacataa   1500
tgtctaaaag ccccgggccc acccccccccc agccccgccc ccaggtgcct gggagacagt  1560
aggtgctcaa tgaagggtgg cggttagttg gagttcttgt taagaaaatc tggccagctg   1620
cggtggctca agcctgtaat ctcagcattt tgggaggctg aggcgggcgg atcacgaggt   1680
caggagatgg agaccatcct ggccaacatg gtgaaactcc cttctctgct caaaatacaa   1740
aaattacctg ggtttggtgg cgttcgcctg tagtcccagc tacttgggag gctgaggcgg   1800
gacaattgct tgaacccggg aggaggaggt tgctgtgagc tcagatggca ccactgcact   1860
ccagcctggc caaagagcga gactttgtct caaaaaaaata aaaaaaaagg cggggcgtgg  1920
tggctcacgc ttgtaatccc agcactttgg gaggccgagg cgggtggatc accagttcag   1980
gagatcacga ccatcctggc taacacggta aaaccctgtc tctactgaaa aatagaaaaa   2040
attagccggg cgtggtggcg ggcgcctgta gtcccagcta ttccggaggc tgaggcagga   2100
gaatggcgta aacccgggag gcggagcttg cagtgagcca agatcgtgcc actgggcgac   2160
agagcgagac tctgtctcaa aaataaataa ataaataaaa agaaaatcca agatgagtgg   2220
tttcgaacta tgccagattc tatgtgtgcg tgtgtgtggt tccctgttct tctgttcctt   2280
gtagctttgg taattaattg tggatctgtg cctgggcttt cagggtcagt aaatggattt   2340
accatttctt tgcacattta tggcttccat atgggcaggg gtttatggtt tgttgttgtt   2400
caccgttgca tttctagagc ccagaacgat gcctggcaca tagtaggtgt tcagtaaata   2460
tttgttctgc agtggggcac aagtggtgga gttcctgggt gtactgggct cctttatcat   2520
cttaaggagt tccttattct ctgcataata ccttcctaag aattagaaga gcaagctctc   2580
agcaggtgct gttctatgcg ctttgcatat ataatctcag ttaatcctca cggcaaaacc   2640
ccacgaggtg cggtttaatc ttccctttttc acaagtgaga aaacttcgct tgaggccagc  2700
aggcagcagg gctgggattg caatctagct agtgtggctg cagagcaatg gtttcttaac   2760
aaatctttgt tcttttgagt ccgagcctcc gtacccccca cgattggggt gatggtgaac   2820
aaaatcctgt caaataaatg ggctgtgatg cctcttgaag gcttggggag gggcaaagaa   2880
```

```
cttttcagat cattaatctc taatgtcaac caatatggct tttttttttt tgagacggag   2940
tcttgctctg tcacccaggc tggagtgcag tggcacgatc tcagctcact gcaacctcca   3000
cctcccaggt tcaagggatt ctcctgcctc agcctcccca gtagctggga ttacaggcgt   3060
gttccacaac accggcttat tttttgtatt tttagtagag acagggcttt gctgtgttag   3120
ccaggatggt ctcgacctcc tgatcttgtg atccacccgc ctcggcctcc caaagtgttg   3180
ggattacagg agtgagccac cgtacctggc cttttttttt ttcttttttt tttttgagac   3240
agggtgtcac tctgtcaccc gggctggagt gcagtgacac gatctttgcg acctccgcct   3300
ttcaggttca agtgcatctc ctgcctcagc ctcctgagta gctgggatta cagtcgtgta   3360
tcaccaccct tggctaattt ttgtattttt agtagagatg ggatttcgcc atattggtta   3420
ggctggtctc aaacttctga cctcaagtga tctgcctgcc tcggccttcc aaagacctgg   3480
gattataggt gtgagccatc actccgggcc caatatggca ttttgattgg gatgaagggt   3540
ggaggaaaat cagtgtgatt tttgtatcta tctctctagc tatctattat tttttgagat   3600
gaggtcttgc tctgttgctt aggctggagt gcagttgggc aatgatggct cactgcagcc   3660
tcgacctcct ggacgcaagc catcctccta ttttagcctc cgtagtagct gggaccacag   3720
gcacacgcca ccctgcctgg ctaattttta ctttaatgtg tagagctgaa gtcttgctat   3780
tttgtccagg ctggtctcaa actcctggcc tcaagcgatc tgcctgcctt ggcctcccga   3840
agtgctggga tcacaggcat gagccacggt gtctggcctc tgcagttatt cttattcttt   3900
gcttctctcc tggagacctg cttcttgccc ttccccattc atgcatagag accacagggt   3960
gtgggctgag tccccagggc tccccacctc accccactct acccttgact tccattcctc   4020
tttggtttaa gcagaactct caatcttggc actgctgaca tttggggctg gatcattcct   4080
ggtggtgggg gctgtcctgt atgtagagtg ttgagctgga accatggtct ccacccatgt   4140
ggtcctggga ggatcccctt ccccccaggc atgacaacca ctaatgtctc cagacattgc   4200
caggcacgtc tctgcaggag ttaacctttt ccctgtctga gacatttacc catctgggct   4260
cttgctcttt ctcctctctt tgttcaataa tcctcggccg ggtgcagtgg ctcacgcctg   4320
taatcccaac accttgggag gctgaggtgg gcggatcccc tgaggtcagg agtttgagac   4380
caccctggcc aacatggtga aaccccatct ctactaaaaa tgcaaaaatt agccaggtgt   4440
ggtggcgggt ccttgtaatc ctagctactt gggaggctga ggcaggagaa tcgcttgaac   4500
ctgggaggca gagcttgcag tgagccgaga tcacaccatt gcattctagc ctgggcaaca   4560
gagagagact ctgtctcaaa aaaaaaaaaa aaaaagaaaa gaaaaaagaa tcttcattta   4620
cccacgtgct tttcagcct ctaaacaccc agtacccccc aatccccatt acctaccact   4680
gacctccagc ctccaccctg tccagcttcc ccaggccagt cctccctgcc ctttccatct   4740
cactcttttc tcactgttct gcccccagca tctggcttgc atctccgctg ctttaccgat   4800
ggctctcgaa gttaatctct catctcccag ttgcgtctcc tgcagcctca cctcacttga   4860
cccctctggg tttgacattg ccagtccccc ctcctggaag gctgtgtctc ccgtctcacc   4920
tgtgcctaag ttcttctgtt ttactgttct cttctccttc tacctgggct aagatgttgg   4980
ctctctcttc ccagagggtc agtgtttcct ttaatcttct ctcagctcac tttttttttt   5040
tttttttttt cacttcttca cccgggctgg tgtgcaatgg catgatcttg gctcactaca   5100
acctccgtct cctgggttca agcaatggtc ctgcctcagc ctctccagta gctggaatta   5160
caggcatgtg ccaccccgcc tggctagttt ttgtactttt agtagagaca gagtttcacc   5220
```

-continued

```
ccattggcca ggctggtccc aaactcctga cctcaagaga tccacctacc tcagcctccc   5280
agagtgctgg gattacgggc atgagccacc gtgtccggcc cttttttttt ttttttttt    5340
ttccaatttt tatttctttt tagagacagg attttgctct gtcacccagg ctggagtgca   5400
gaggtttagt cctagcttac tgcagcctcc aagtcatggc ctggagcagt cctcccacct   5460
aggttcccca agtagctgga atcacaggca ggtgccacca tgcccagcta attgaaaaat   5520
ttgtttgtag agacagagtc tcactatgtt gcccaggctg gtcttgattt cctggcctca   5580
agtgagcctc ctgccttggc cttctgagaa actaggatca caggcaggca ccaccatgac   5640
tagctaattt ttaaaattta tttgtagaga cagagtctag ctatgttgcc catgctggtc   5700
ttgaattcct ggcctcaagc aacctgcttg cctccgcctc ctgggtacct gggctcacag   5760
acagtcacca ccatgcctgg ctaattaaaa cttttttttt tttttgtag aaacagggtc    5820
ttgctatgtt gcctaggctg gtcttgaact cctagttcaa gcagtcttcc ctcctgggcc   5880
tcccaagtgc tgggattata ggcatgagga accattgcgc ccagctaaga aatttacata   5940
gattccgact tcttcatctg aacaggggtc agcaaactat ggccctcagg ccaaatccca   6000
cggtttttgt aaatgcagtt ttattggcat gcaaccacac tcatttgtct actcatcatc   6060
tatgactgcg caaaaatgcc ccgacacggc aggttgagta gttaaaacag gaattccatg   6120
gccaaaatat ttacactttg gccctttaca gaacagcgtt tgctgacctc tgatctggaa   6180
cagacgcctt gaggtttcat tcatgatagc atgcctaata gcttgtgcag tccctggtac   6240
aactcgaatg aagtgagtga aatgaaacgc tatgtctttc tctttacacc gcaagagatg   6300
ttaaagaaac gtgtgtcatt tgctgcactg aatatacgga ttccaaggat gagaaaaatc   6360
accgtgatgt tgcctactta gccatgtgta tttatttaaa cagctatatt ggcattgaat   6420
gaggatttca tgctctcaac cctgtatcta gaacccaaaa tataactggt gtatataatg   6480
agattttttt tttttctctc aggcctctct tgtgttaatt tctgttaaga atacttctgg   6540
gccaggtgtg gtggctcacg cctgtaatcc caagcacttt gggaggccga ggtgggtgga   6600
tcacttgagg tcaggagttc gagaccagcc tgaccaacat ggtgaaaccc catctttact   6660
gaaaaaatac aaaattagcc aggcgtggtg gcgcatgcct gtaatcccag ctagttggga   6720
ggctgaggca ggagaatcgc ttgaacctgg gaggtggagg ttgcagtgag ccgagattgc   6780
gccactgcac tctagcctgg gtgacagagc gaaactccat ctcaaaaaaa aaaaaaaaaa   6840
agaatatttt tggccaggtg cagtggctca tgcctgcaat cccagcactc tgggaggctg   6900
aggtgggagg attacatgtg tccaggagtt tcagatcagc ctggacaaca cagcaagacc   6960
ctgtctccac taacaataaa acaaaaatta gctgggcatg gtggcatgtg tctgtagtcc   7020
cagctacttg ggaggctgag atgggaggac ctcttgaggc tggaagggca aggctgcagt   7080
gagctgtgat tgtaccactg cactccagcc tgggcaacag tgagatcctc tctctgtctc   7140
aaacaaaaaa agaatacttc ttggggtggc ctggttgata ttttgcagct gcatggtatt   7200
tacagttttt aattaaatag tgacgggtaa tgcattctca ttgcaaaaag aaaaattaca   7260
aaagtgtaga aaggaaaaaa aaaacacaga agtccttctg caaaatcttg tggtggggtg   7320
cagtggctca cacctgtaat ccctggactt tttaggaagc tgaggtggga ggaacacttg   7380
aagccagcag tttgagacca gcctgggcaa cataatgaga cattatctct agaaaaagtt   7440
taaaaattag ctgagcatgg tggtgtgtac cggtagtccc agctactcag gaggctgagg   7500
tgggaggatc gcttgagccc agaaggttga ggctacagta agccatattc atgccactgc   7560
actccaacct gggtgataga gcccgaccct gtctcaaaaa gaaaagaaat aataaaaaaa   7620
```

aatcttgtcc ccctgtcccc aaaagcattc cattcatgtc cagggaggta actgtgccat 7680
tggtttatgt atctttttga tgtttagtaa ttttttaggc taggtgtcat ggggccactc 7740
ctgtaatccc agcactttgg gaggccgaag caggtggatc tcttgagccc aggagttcaa 7800
gaccagcctg ggtaacatag caagaccccg tctctacaaa accctacaaa aaaattatcc 7860
agatacagtg gtgagcacct gtggtcccag ctactaggga ggctgaggtg ggaggatcac 7920
ctgagcctgg gaagtcgagg cgccagtgag ctgtgattgc accactgcat ccagcctggg 7980
tgacatagtg agactgtgta acaacaacaa caacaaaata ttttaaacat tatcatacag 8040
taaaattggc tttttaaagg tgtaccattt tatgattttt aagccatgtg tagagttgta 8100
tggctattgc cacaattagg atagagaaca gtctcgttgt tgtccaaact ccctcaattc 8160
accccttat cactaaacca cctccacccc taaccacaga tctgttctcc atccctatag 8220
ttttctctag actttaaaag attttatctt ataattggat taatattcct aaagttgaaa 8280
ttttaaattt gagtctggtt gatcctcatc attcccagat cccatatttt ctttttaaaa 8340
tttaaaattt aaatttttat tttgagaggc aggttcttgc tctgataccc aggctggagt 8400
gcagtggtgt ggtcctaatt ccctgcagcc tccaactctt gagcatcaac gatcctcctg 8460
cctcagcctc ctgagtagct gggactacag gcacacacca ccatgctcag ctagttttta 8520
ttgttattta tttatttatt tatttttgag acggagtctc actaactctg ttgcccaggc 8580
cagactgcag tggtgtgatc tgggttcact gcaacctctg cttcctgggc tcaagcaact 8640
ctcctgcctc agcctttcta gtagctgggg ttacaggcac gccaccatgc ccggctagtt 8700
tttttatttt ttagtagaga tggggtttta ccatgttggt caggctggtc tcaaactcct 8760
ggcttcaagt gatccgccca cttcagcctc ccaaagtgct gggattacag gcgcgagcca 8820
ctgtgcccgg cctaattttt aacttttcag cagggataag ggctcgctat gttgcccagg 8880
ctggtctcga actcctggcc tcaagtgatc ctcccatctt gacttcctaa agtactggga 8940
ttacaggcat gagccactgc acctggcccc agaccctgta tttttgaatt cacctactca 9000
ctcaaatgta tttgtaaccc tcaaaccagc atgctcagtg cctttctggt cattttagga 9060
cactcataag tacgagtctc aaatgtgagg tcaagtaaga gggcattcca ccttcttgct 9120
tcagccctta tgcgtcagat tcatacaatc tgcacactga ggattaaaac tagtcctttt 9180
tgagcaggcg cagtggctca tgcccagcgc tttgggagtc cgaggcgagt ggatcacgag 9240
gtcaggagat cgagaccatc ctggctaaca tggtgaaacc ctgtctctac taaaaataca 9300
aaaaattagc caggtgtggt ggcgggcgcc tgtagtccga gctactccgg aggctgaggc 9360
aggagaatca cttggaccca ggaggtggag gttgcagtga gccgagattg tgcctctgca 9420
ctccagcctg ggtgacaggg tgagactcaa aacaaaaaac aacaacaaaa aaacctgagt 9480
ccttttgtg gttatttggt gccacatttt tagcattttt gtgctttcag ttggtgatgg 9540
ggctgtttca aatgcccccc agggtgctga agccctgctc tctactcttc cttggctaag 9600
gagggctgtc accacccttg tggagaaaag gcagcgtggc ggggcacggt ggctcacatc 9660
tgcaatccca gcactttggg aggttgaggc aggtggatca cttgaggcca gagtttgaga 9720
ccagcctggg caacatggtg aaaccccatc tctactaaaa atacaaaaat tagctgggcg 9780
tgatggcgca cacctgtaat ctcagctacc tgggaggcta aggcacaaga attgctcgag 9840
cctaggaggt gaaggttgca gtgagccaag gcggtgccac tgcactccag cctgggcaac 9900
agagtgagac cctgtctcaa aaaaaaccca aaaaaacaaa aaaactccaa aaccaacaca 9960

-continued

```
cacacacaaa ggcatgtgtt acataaactt tgttcaggca tgagttctat tactgttggc  10020
cgtgagttcg gtgttaatga atcaacaata tagattcaat agtgtctttc aacagaaaca  10080
cacataaaac aaggctaggt attgatccat ggataaatgt gttgtggcca gaagttcgca  10140
ggtacttacc ctcgcatttt cctaggaaca atggttcagt attcactagt tcaacattca  10200
ggggaatttc acagagccaa actaccacca ataacaagaa tcggctgcaa gtggtttaaa  10260
actggtgaat ctgtggctca tacccgtaat cccagcactt tgggaggccg aggcaggtgg  10320
atcacctgag gtggtgagtt cgagaccagc ctggccaaaa tggtgaaacc ccgtctctac  10380
taaaaataca aaaattagcc gagcacggtg gctcatgcct gtagtcccag ctactcagga  10440
ggctgaggcg ggagaattgc tggaacccgg gaggcagagg ttgcagtgag ccgagactgc  10500
accactgcat tccagccagg gcaacagagc aagaccccat ctaaaaaaac caaaccaaac  10560
caaacaaaac tgtgggtttg tcattttccg tttagaatcc tttgaatgca aatgcccttt  10620
ttgttgtatt ttcatctgcg tggaaaccgc tgggttgata ccttttggaa agttcatgag  10680
atgtccaaaa accccctggcc catgtttcag ggaggggaat ccctgccctc tgccaacact  10740
ggtggcaggg agaggcagca gtggctctcg ggattttatt tatttcattt attcatttac  10800
attttttga gaaagggtct tgcactgttg ctcaggctgg agtgcagtgg cgcaatcaca  10860
gctcactgca gcctcgacct cctgggctca agtggtcctc ccacctcagc ctcctgagta  10920
gctggcacta caggcgtgtg ctaccacgac tagctaattt ttgtatttta gtagagatgg  10980
ggtctcacca tgttgcctat tattattatt attattatta cttttttga ggcggagtct  11040
cactctgtcg cccaggctgg agtgcagtgg cgtgatctca gcttactgca agcttcgcct  11100
tccgggttca tgccattctc ctgcctcagc ctcctgagta gcagggacta caggcgcccg  11160
ccactgcccc cggctaattt tttgtatttt tagtagagac ggggtttcac cgtggtctcg  11220
atctcctgac ctcgtgatcc cccacctcgg cctcccaaag tgctgggatt acaggcgtga  11280
gccactgcgc ctggccatgt tgcctattat tattattatt ttgagcagtc ttactccgtt  11340
gcccaggctg gaatgcagtg tcacgatctc agctcactgc aacctccgcc tccagggttt  11400
aagcaattct cctgcctcag cctcctgagt agctgggact acaggcatgt gccaccacgc  11460
ccagctaatt tttgcatttt agtagagatg gggtttcccc atgttgccca ggtgggtctc  11520
aaactcctga cctcaagcca cccacctgcc tcagcctctc aaagggctgg gattactggt  11580
gtgagccacc ttgtccagct ggcttgaagg attattatta ttattactat tattttgaga  11640
tggagtcgca ctctgttgcc caggctggag tgtagtggca cgatctcggc tcactgcaac  11700
ctctgcctcc tgggttcaag caattctcct gcctcagcct cccgagtagc tgggattaca  11760
ggcgtacacc accacgccca gctaattttt gtatttttag tagagacagg gtttcaccat  11820
gttggccagg ctggtcttga accccctgacc tcaaatgatc cacccacctc ggcctcccaa  11880
agtgctggga ttactggtgt gagccaccgt gccccgccgg ctcgcggggt tttagaaaca  11940
tattttgttt ccagcagaac aagctttgct atcctgcggt gccacgtaca gactggctct  12000
aagctcctgt tggagttcaa agcggacttg tgggaatgaa tgtttaattt cacatctggc  12060
attttcttcc agttccttag aagtaggata tctcatcagg tttatataaa agcccctgat  12120
gtatgttcag gaaaggcagg atgctatcat gagattctta tttcctttgc ctttgtggga  12180
atgtggaaac cataggtact gtctaaaaat taccctttt atcaatgcag gcaaaagtag  12240
tcagacagga agggactcga gagtagggat gcaactgctt ttttaaattg attttaaaat  12300
ctcatttatt cttatcatta gagacagggt cttgctctgt catcccggct ggagtgcggt  12360
```

ggtgtgatta tggctcattg cagccctgaa ctcctgggct caaatgattc tcgcgcttcc 12420
tcctcccaag tagctgggac tacaggcatg caccaccatg cctggctagt ttttttattt 12480
ttatttttttg cagagacagg gtctggctgt gttgcccagg ctggcctcga actcaagacc 12540
ttaagtgatc gtcccgcctc agcctcccaa agcactggga ttgcagatgt gagccactgt 12600
gcctggtggg atacaactgt tttctgactg cctgtgtatg tgtctgtgtg tgtgtgtgtg 12660
tgtttgtttg ttgttgtcat tctactctca aggatgtatc ttgttgtttc cttgcagaag 12720
atcagaaaag ggaggacctc atatgttccc tcctaattat acccagttac acggtctcca 12780
taccacctgt tacaaagtga ctttctggtc tggcaggact tctcttgttt ttcctcctgt 12840
cttctgtgtc ctgtctgctc ttgtctgtat aaatttcagg actcctgaaa tagcacggaa 12900
gccccccttct aatcctgtgg tttgatgttt gatattgtta ggattacaaa actatgtcat 12960
agactagagg agtcagacat tccagagttc acagaaggtg ttggtgtccg ggtggctgtg 13020
ggacacaggt gcccttccta gtccctggcc tttcatactg tgccccctgg agcccctctt 13080
tctttctttt ttctttttttt ttggagatcg agtctcgctc tgtcacccag gctggagtgc 13140
agtgcagtgg cacgatcttg gctgattgca acctctgcct tccaggttca agcgattctc 13200
ctgcctcagc ctcctgagta gctgggatta taagtgtgca ccacaatacc tgactaattt 13260
ttgggttttt tgtttttttt tttgagatgg agtttcgctc ttgttgccca ggctggagtg 13320
caatggcatg atatcggctc atcacaacct ccgcctcccg ggttcaggcg attctcctgc 13380
ctcagcctcc caagtagctg ggactacagg catacgccac catgcccagc taattttgta 13440
ttcttagtag agatggggtt tctccatgtt ggttaggctg gtctcgaact cctgatctca 13500
ggtgatccac ccgcctcggc tgcccaaagt gctgggatta caggtgtgag ctaccatgcc 13560
cggcctggct aatttttttat atttttggta gagacgggtc tcaaactttg gccaggctgg 13620
gctcgaactc ctgacctcaa gtgatccacc tgccttggcc tcccaaagtg ctggaattac 13680
aggcgtgagc aaccgcaccc agcctttgtt ttgttttgtt tttttgtttt ttgttatgag 13740
acggagtctc gctctgttgc ccaggctgga gtgcagtggc gcagtctcga ctcactgcaa 13800
gctccgcctc ccgggttcac gccattctcc tgcctcagcc tcccgagtag ctgggactac 13860
aggcgcctgc caccacgccc ggctaatttt tgtattttta gtagagacgg agtttcacct 13920
tgttagccag gatggtctca atctcttgac ctcgtgatcc gcccgcctcg gcctcccaaa 13980
gtgctgggat tacaggtgtg agccaccgtg cctggccttg ttttgttttt gagacagggt 14040
ctcctcgcac tgtcgcctag gctggagtgt agtggtgtga tgtcaggcct ccgcaatctc 14100
cacctcccag gctcgagcaa tcctcaacct cccgagtagc tgggactaca ggtgcacacc 14160
accacaccca tccaattttt ttttttttgg tagagatggg gttttgctat gttacccagg 14220
ccaatctcaa actcctgggc tcaagcagtc cacccacctc agcctcacaa agtgctggga 14280
ttccaggcgt gagcctctct ttctatcatt ttcttctctc agttgtctcc gtgctacctt 14340
tcctgcaata tcacctgttg tcactgcgtc caccagcatc cgtacctgtt cccccatctt 14400
cccaatgccc acgggaccca catccctgag tatcccaaag ccctcacaga ctcaatatgc 14460
tgccaactca gcctgttgtt cttgccactc taaactgttc ctatctcgaa tgcttcaggc 14520
tcattgacga tccctcctca ctctcttctc cctcttctct tccatttctc ctgggtatga 14580
agtcctgttc acacaaactg cccctggttt ctgtggtgct atgcatgctg tcttcagtac 14640
cttcttcatt ctgctgccag aaggctgttt ctctctttct tttttatttt ttaattttat 14700

-continued

```
ttttatagac atggggtctt actgtgttgc ccagattggt ctcagacttc tggacttaag  14760
tgatcctcct gcgtcagcct ccccaagggc tgggattata gatgtgagcc actgtgccct  14820
gtctagaggg atatttattt tattttattt tattttattt cttttctttt tttgagatgg  14880
agtgtcactc tgtcacccag gctagagtgc agtggcgtga tctcagctca ctcaacctct  14940
ccctcctggg tttaagagat tgtcctgctt cagcttcctg agtagctggg attacaggtg  15000
tgcaccacca tccctggcta atttttgtat ttttagtaga gatgaggttt ccccatgttg  15060
gccaggctgg tcttgaactc ctgacctcag gtgatcctcc cacctcaggc tcccaaagtg  15120
ctgcgattac aggcatacgc caccataccg gactcatttt tgtattttta gtagacatgg  15180
ggtttcactt tgttggccag gctggtctca aactcctgac ctcaggtgat cctcccacct  15240
cagcctccca aagtgctggg attacaggca cacgccacca caccaggcta attttcatat  15300
ttttagtaga catggggttt caccatgttg gccaggctgg tctcaaactc ctgacctcag  15360
gtgatccacc ccccttgacc tcccaaagtg ctgggattac aggcgtgagc cactgtgccc  15420
agcctgtgtg gctctctttt ggttaccctg tggtatcctg ttttctcaag ctcatcctcc  15480
ctggtgggtc catgatccct ggaaattgtt ggtcttctcc ggccttttga aattgctgcc  15540
ttatgaatgt ccagagttgg gtatctgcct ttctctccca aggaggaaga atcctgaggg  15600
ggcatctttg cttttaggtc ccagggcttt cactgacttc ctccttgctg gcttcttggt  15660
ttgttccaaa gatgtcctcg gtacatcttc tgagactaat gacatgataa gtttctggaa  15720
ggactatgat ctggatgatg agggtttcat cacagtcctc tttcagttct gtcctacaga  15780
ttacacttgt tttcttcctt catcctttgt cttcactggt tcactgtttc catctgcatt  15840
cttctgttct catttctttt tgttgttgtt ttattttta ttttttaatt tattttttaa  15900
ttttttgag accgagtctc actctgtcac ccaggctgga gtgtagtggc acagtcttgg  15960
ctcaatgcaa cctctgcctc ccaggttcaa gtgtttctcc tgcctcagcc tcctgagtag  16020
ctgggattac aggcgagcgc taccgtgccc ggctaatttt tttgtatttt tagtagagac  16080
ggggtttcac catgttggcc tggctggtct cgaactcctg acctcaagtg atctgcccgc  16140
ctgggcctcc tgaagtgctg ggattacagg cgtgagccac cgtgtccggc cttggttttt  16200
tttagaaata gtgtctcact ctgtcaccca ggctggagtg cagtggtgca gtcatagctc  16260
actgcagcct caacctcttg ggctcaagca attctcctgc ctaagcctcc tgagtagccg  16320
ggagcacaga cgcgcctcac cacgcctggc tatgttttgt atttttagta gaggtagggt  16380
tttgccagtt gcccaggctg gtcttgaact cccggactca agcagtccac ccgcctatgc  16440
ctcccaatat gttgggatta caggcatgac cactgcaccc ggccaacatc tctgcagttc  16500
tttgttttag tactttgtcc tttagctctg gtggtagctt atcacagtta tttaggtgcg  16560
tctttccttt acttgctgta agagtgcaac cttatttgtc ttgagagtcc ccctgggcct  16620
ggcacaatgt ctggcccacc gagatgccca gcaaacgttt gctgagtgaa tacaggaatg  16680
atttccatgt agctgacttg ccgggtccag aacctgcatt tgatccagac gcctccattc  16740
cttctcgcag aggtagattt gaaagctatt cttgcaggca ggtggagaat cttaaggatc  16800
tctgacaccc cagtgtgtcc aagctctaat ttctggaggt aataaatctg ggaatggatt  16860
ccatctggct cagatgggag acagaacagg tatacacagc cagagacccc agttctcatc  16920
tcttctttgt aggtttcatt atgctgttgt catcatttaa aggaaactga ggccaggcac  16980
ggtggctcac acctgtaatc ccagcacttt gggaggtcta gacgggtgga tcacctgagg  17040
tcacgagttt gagactagcc tggccaactt ggcaaaaccc tgtctctact aaaaatacaa  17100
```

aaattagctg tgcgtggtgg cgggcgcctg taatctcagc tactcaaaag gctgaggcag 17160
gagaatcgct tgaacccggg agatggaggt tgcagtgatt cgagatcacg ctactgcact 17220
ccagcctggg agacagagtg agactccgtc tcaaaaataa aaataaataa atgaataaat 17280
aaataaaaag gaaactaagg cgtgcagagg ggttgaagat gttgtccagg atcacacagt 17340
tgacaggtga cagagctggg ttgggaagcc agattcgtta gatttctagt gtgccccaaa 17400
actggtatag gtggtggcct gacaccagaa cccaagactt gttgaggcag gacctcctga 17460
atttaagagg aagcagtttg aggactggaa agaatgtgga aagggacgtg tgggccccag 17520
aataggtcag cagggagcat tttaagaatg ctgttactgg ccgggcttga tggctcacac 17580
ccatactccc agcacactgg gaggccgacg caggactgct tgagcccagg atattgagac 17640
cagcctgggc aacatggtga aaccccatct ctacaaaaaa tacaaaaatt agccaggcat 17700
ggtggtacgc agctgtagtc ccagctactt gggaggctga ggcaggagga tcacttgagc 17760
ccaggaattt gaggctgcag tgagctatga ttgcaccact gcactccagc ctgggcaaca 17820
tagcaagact ctgtctcaaa aaaaaaatcc tgtaactgaa gaacaaggac ctttatgatt 17880
gaaaacagga agtagaaaac tcttagcatt gtaaaggatt tcagaatctt ctagaaagtt 17940
ctttctctgc cctgctccca acccatctcc cctgctgttt tcatgatgga gagaaaatca 18000
gggaagaaag gaacacttcc taagatggct ctcatgtccg ccttctctcc ttctggaaaa 18060
ttctcagatt caggaccagc acggtccaat acagctctgc tttgatggaa atactctgta 18120
tctgctctgt ccaatatggc agccaccatc cacgggtggc tcttgagccc tggaagttgt 18180
ggctggtaag actgaattct tttttttttt ttttgagatg gagtctcgct ctgtcatcca 18240
ggctggagtg taatggcaca atctcggctc actgcaacct ctgcctccca ggttcaagcg 18300
attctcctgc ctcagcctcc ctagtagctg ggattacagg catgcgccac tcccccgacc 18360
ccgctaagtt ttgtattttt agtagagacg gggtttcacc atgttatcca ggctgatctc 18420
aaactcctga ccttgggtca tccacccgcc ttggcctccc aaagtgctgg gattacaggc 18480
gtgagccacc gcacctggct gaaactgaat tttattttca ctttaattca ttgaaatgtc 18540
aatgtaaact tttatttaat tcatggaaat gtaaaaaaaa ttagtactca gttctgttac 18600
tggaaaactc tcccatatat ttggaacaac ttggttatgt gaacttgagg tagtaggcgg 18660
gactcgtctc cagaggcggg gatccagccc tggaccaaat ggaggactag ccacaaggac 18720
agggctggcc gggcgcagtg gctcacgcct gtaatcccag cactttggga ggccaaggca 18780
ggtggatcac ctgaggtcag gagttcgaga ccagcctggc caacatggtg aaaccttgtc 18840
tctactaaaa atacaaaatt atctggatgt ggtagtgcat gcctgtaata ccaactactc 18900
gggaggctga ggcaggagaa tcacttgaac ccaggcggca gaggttgcag tgagccgaga 18960
tcatgtcatt gcattccagc ctgggcaaca gagtgaaact ccctctctga ccaaaaaaaa 19020
aaaaagtgct gtctaacacc accagctcac cctcgaattc tttcctgggt gaagccaaaa 19080
accctcccgg ggtaaggctc aattttgggg cttgcctctt ctacatcaaa cctacatttt 19140
cgatgatact ctttataaaa tctacataga caaatcaatt tttttttttt tttttgaga 19200
cacagtctca ctctgttgcc caggctggag tgcagtggcc tgatcttggc tcactgcaag 19260
ctccgcctcc tgggttcacg ccattctcct gcctcagcct cccgagtgta gctgggacta 19320
caggcacctg ccaccatgcc cagctatttt ttttttgtat ttttagtaga gacggggttt 19380
cacatggtta gccaggatgg tcttgatctc ctgacctcgt gatccacccg actcggcctc 19440

-continued

```
ccaaagtgct gggattacag gcgtgagcca ccacgcctgg gcgacaaatc aattattttt  19500
aaagaaaaat gagcctccgt ttcgagatgg gctgccaggg taaagcacac accacatctc  19560
gtaggcgtca tgggaaaaaa atcctgcaga ccagggatcc ccaaccctta ggccacagac  19620
cagtagcagt ccatgtcctg ttaggagctg ggctgcacag tagaggtgag cagagggcag  19680
gtgagcattg ccgcctgagc tccgcctcgt gtcagaacaa tggcagcatt agattctgat  19740
aggagctcga atcctgtcgt gaactgtgca tacaagggat ctaggttgcc tgctccttat  19800
gagaatctaa ctgatgcctg aggatctgag gtggaacagt ttcattctaa aaccatcacc  19860
acccatcccg tgttcgtgga aaaattgtct tctaccattg gtccctggtg ccaaaaaggt  19920
tggggaccac tgctgtggac tatctcatta atcatttttt ttttaggatt gattatatgt  19980
gggaattatt tatttattta tttattttga gatggagtct tgctttgtta cttaggctgg  20040
agtgcgacgg gatgatctca gttcactgca acttccatct cctgggttca agcgattctc  20100
ctgcctcagc ctcctgagta gctgggatta caggtgtgag ccatggtacc tggcccattc  20160
ggcatatttt agtacggaga tggtggtcag gcacggtggc tcacgcctgt aatcccagca  20220
ctttgggagg ccgaggtggg cggatcacct gaggtcagag ttcgagacca gcctggccaa  20280
catgatgaaa tcccatctct actaaaaata caaaattagc caggtgtggt ggcacacgcc  20340
tgtaatccca gctactcggg aggctgaggc aggagaattg cttgaacccc agaagtggag  20400
tttgcagcaa gccaagatca tgccactgca ctccagcctg ggcaacagag taagactcaa  20460
gtctcaatta aagaaaaaaa aaaaaagaaa aaagaaaata ttagctgtca cttagcaccc  20520
tcttcctcat tgccttttc tacctgtaca aagagtggcc attaaccagg tacccattat  20580
gaagaacttg aagcatcctt cacgcccact cagagatgtt aaaagccagc agaagtcctc  20640
gtgtctattt ctgccttcat ttctaacatc ctctgggtat tttctgtccc agtggtaaac  20700
tgctctattg tctttcacta atagggacac atacggcttt aatgaattaa gagttagatt  20760
cataggatat ttaaaaagaa aagcaattct tgattgttcc ctacaattat agctgtttaa  20820
tctttactca taacaacttt agtgagacag aattcacatg acatacaatt cacccatttt  20880
aagtgtgcag ttaggtggtt ttgaggacat ttacagttgt gcaactgtga ccacagtcag  20940
ttttagaata tttgcatcat cttcaaagaa accctgtacc ctctagctac tactttccat  21000
cccccatttc cctagctctt ggcagccacg aatctatttt ctgtctctat ggatttgcct  21060
ctttcggatt tttttgtatg aatggagtca gacaacatgt ggccttctct gtttgacttc  21120
ttttatggag aaggttcata cctgtaatcc cagcactttg ggaggccaag actggaggat  21180
tgcttgagtt caggagtttg agagcatcct gggcaacata gagagaccac tatctctaca  21240
aaacaaattt aaattagctg ggcatggtgg tgcatgtctg tggttccagc tatactggag  21300
gcataatttt gttttgtttt tgtttgtttg tttgtttttg tttttgtttc gtggggtttt  21360
tttggttttg ttttttgttt tttgagatgg agttttgctc tgtcacccag gctggagtgc  21420
aaaggcacga tctcagctca ctgcaacgtc cgcctcctag gttcaagcca ttctcctgcc  21480
tcagcctccg tagcagctgg gattacaggc atgcgccacc ccgcccagct aatttttgta  21540
tttttagtag agacaggttt tcaccacgtt ggccaagctg gtctccaact cccgacctca  21600
ggtgatccac ctgcctcagc ctcccaaagc gctgggatta aaggagtgag ccactgtggc  21660
tggcctttta tttacattta tttatttatt tatttagaga cggagtctca ctctttcatc  21720
aggctggagt gcagtggtgc aatcttggct cactgaaacc tccaactctc tggttcaagt  21780
gactcttctg ccttagcttc ccaagtagct gggactacag gcactcgcca ccatgcccag  21840
```

ctaattttt ttgtatgttt agtagagatg gggtttcacc atgttggcca ggatggtctc 21900
aatctcctga cctcgtgatc cgcccacctc ggcctcccgc agtgctggga ttacaggcgt 21960
gagccactgc ggccagcctg tatttacttt tgagacaaga tattgctctg ttgcccaggc 22020
tggagtgcag gggtacaaac acagatcact gcagtcctga cctcctaggc tcaagcgatc 22080
ctcctgcctc agtctcccgt gtagctggga ccagagacac acaccagcat tcctagctaa 22140
tgttttaaat ttttatagag atggagactc gctatgttgc ccaggttggt cttgaactct 22200
tgggtttaag caatccttcc gtctctacct cccaaagtgc tgggattaca ggcgtgagcc 22260
actgcactca gcctcagcta ttatgaataa tgctgctata gacatttgtg tacacgtctt 22320
tgtgtggacg tatagtatca tttctcttag gtagttacct aggagtggaa ttgccaggtc 22380
atatggcaat tcttggttta atattttgag gaactaccag agtgttttcc acagtggctg 22440
cactgtttta catccccatc aggaatgcaa aaggatacca gtttctctac attttatttt 22500
ttctttgaga tggagtctcg ctctgtcgcc caggctggag tgcagtgatc ttggctcact 22560
gcaacctcca cctcccaggt tcaagtgatt ctcctgcctc agactcccaa gtgtctggaa 22620
ctacatgcgc ctgccaccac gcccagctag ttgtttttttg tatttttagt agagacgggg 22680
tttctccgtg ttggccaggc tggtcttgaa ctcctgacct caggtgatct gcctatcttg 22740
gcttcccaaa gaactgggat tacaagtgtg agccacggtg cccggcccat ttctttacat 22800
tctttgcact tgtaattgtc actctttttg gttttagcta tcctagtggg gataaagtgg 22860
tatctcactg tggtttgaat ttgtatttct ctaatgtcca acagccagtt aatctttcct 22920
tttttctgt ttttttttg agacagagtc ttgctccatc gcccaggctg gagtgcagtg 22980
gtgtgatctc ggctcactgc aagctccgcc tcccgggttc atgccattct cctgcctcgg 23040
cctcccaaat agttgccact acgggtgccc gccaccacgc ctggctaatt tttttgtatt 23100
ttttagtaga gacggagttt caccgtgtta accaggatgg ttttgatctc ctgacctcgt 23160
gatcagccca tcttggcctc ccaaagtgct gggattacag ccatgagctg gccaccacgc 23220
ccagccgttg tgttttttta atcgagacga ggtctcactc tgttgcccaa gctggagtgc 23280
agtggtgtga tcacagctca ctgtaacctc ctattcctgg acccaagtga tcctcctgtc 23340
tcagcctccc aagtagctgg aattacaacc acatgccacc atgcctggat atttaattat 23400
tattattatt ttttagagtt ggggtcttgc tatgttgccc aggctgactt taaactcctg 23460
gcttcaatcg atcctctcac tgtggcctcc caaactgctg ggattacagg catgagccac 23520
tgtgcccagc cctagttaac ctttgaatgc atattcatgt ctgattttgg ttctgccata 23580
gcctggggag gatggcggcc aagtgttctt tctacctgca gtgtgtgtgt gtgtgtgtgt 23640
gtgtgtgtgt gtgtgtgtgt gagagagaga gagagagaga gagaaatgaa atatagtgtg 23700
ggactcaggg ttgagaagcc cagggctatg gccaaatcta agattaggat gccagccagg 23760
catggtggtt tatgcccgta atcccagcaa tttgggaggc tgaggcgggt ggatcacgag 23820
gtcaggagat caggatcatc ctggtcaaca tggtgaaatc ccgtctctac taaaaataca 23880
aaaattagct gggcgtggtg ttggacactt cttgggaggc tgaagcagga aaatcacttg 23940
aacccaggag gtggaggttg cagtgagcca agatcacggc actgcacttc agcctgggca 24000
acagaacgag actccacatc aaaacaacaa caacaaaaac cccacaagaa tttcatagaa 24060
acaatgagta attttttttta gggtaagtta tgtcccaaac attacatggg atatacttat 24120
cctcaaaaag gtattattgc ttatctgaaa ttcaaattca actaggcatt ctgcattttt 24180

-continued

```
ctttgctaag tctggcaacc ctgccagtca ctggtgagtt gtgtgtcctt gagtgatggt  24240
ctttgcctct tggagcttca gttttctcat ctatgggatg gggacagaac ttgctgggag  24300
gcaccaatgg cacgcggggt tctttgacat ctctggatgt ggaagctgtt gatgtgactg  24360
actgggagcc tcagactggg gttgggtccc tgactaggag gggtgggggg gctgggactg  24420
gcatccttgt cctcttgaag ctgcctccca gcctgagctt ggtccctgca gggttcctgc  24480
ttggttcaga ccccaggcag ccagtgttga ggggagggtg gagattaatc catagttgtg  24540
tactggggct ttcctccaac ttcctagcaa gcaagtgtgt gtgtgtgtgt gtgtgtgtgt  24600
gtgtgtgtgt gtgtgtgtgt gtgttttctc gacttagcct aatccatttg ctgcatggaa  24660
tgtgatccag gatcactgct acttttttt tcccatttgt ttgcttttgc tgtgttttgt  24720
cgttgttatt gtttttteta atttgtgctt cttttgtggg taattctcag ggtggatttt  24780
ttttttttt agaggattta ctattcttct ttagaacaat ctgttttcct caaagatatt  24840
ggtggaaggt ttagtgtttt ggaacaaaat aagcaggggt tgtatactga gccttatatt  24900
ctaggtgctg aggactgtgg tgtgtgtgtt ggggaggcgg tgtgtgtgtg tgtgtgtgtg  24960
tgggtgtgtg ggtgtgttgg cagagagaag ccatctaaag acttcaattt tgaaaaacgt  25020
taactcaggt gtaagggaca caaggaggag aaacacgcaa ataggtgtgc caaggaaagg  25080
aaatcaggga cggctgcctg gaggaggagg cagcatttga actggatatc ttgaagcatg  25140
atgggctgga tttagaaata gggagctaag gtacaaagca cttcgccagc caaaagatag  25200
actagcctag agatgactgt tatatgtttg gggaataaa caacagcaag aagaacaaca  25260
acaacaaaca acaaaatagc tgacattagt gcagcactta ctatgtctca ggcactgttt  25320
gagtgcttgc cctgagttgt ttcacttctt cttccatata agccatgtta cagaggagga  25380
taggagtctt ggagttgtgc aagagttgtg ggcaggcctg tttagtggtg tgcaggggat  25440
gtaggggcag aatcttgagg gaagtgcagg atgatgggga gccatggtgg gcgttggggc  25500
ctgggaggga ccgccttcag gagaatgaga actcagggca tttgggcaat ggagatcggg  25560
ctccctggga agccctcacc acacccaggt aaaaggtaat taggtcttga ttgcaggtca  25620
ggagagcagt ccgggaagga aagtcagcca gcgaggtggg aggattgaca aaacaaatac  25680
atttagcttt ccttgcccca tttctgaccg cgggcacctt tatccccgta aattatctcc  25740
tgaagatctt ctatgttgac gcactggaga cagttcccct ttctccttct gcacctgccg  25800
cgttactcaa tcccctgtaa tcccattgtc ccgactgcat catttcagag gtggtgattt  25860
taaggatttt aacagggctt gccaaaagaa ttattttctt ggcgttttga aagtaattac  25920
ttaggcatgg gtactttaca gagaaagcta ctcatcccgg ctggctgcag agtttacagg  25980
gcccgggatg aaaacacagg gcccaggttt cctgtccatg aagccggctc tgcccctgat  26040
ccttctgatg catccaccgt gcgtctgctc acctgtcttg ctttctgttc attttctctt  26100
gtagtgtgtc ccggcatgga tatccggaac aacctcacta ggttgcatga gctggagaat  26160
tgctctgtca tcgaaggaca cttgcagata ctcttgatgt tcaaaacgag gcccgaagat  26220
ttccgagacc tcagtttccc caaactcatc atgatcactg attacttgct gctcttccgg  26280
gtctatgggc tcgagagcct gaaggacctg ttccccaacc tcacggtcat ccggggatca  26340
cgactgttct ttaactacgc gctggtcatc ttcgagatgg ttcacctcaa ggaactcggc  26400
ctctacaacc tgatgaacat cacccggggt tctgtccgca tcgagaagaa caatgagctc  26460
tgttacttgg ccactatcga ctggtcccgt atcctggatt ccgtggagga taattacatc  26520
gtgttgaaca aagatgacaa cgaggagtgt ggagacatct gtccgggtac cgcgaagggc  26580
```

aagaccaact gccccgccac cgtcatcaac gggcagtttg tcgaacgatg ttggactcat 26640
agtcactgcc agaaaggtac gccggggata cagggttcta agcagtgtct cgtgccttgt 26700
tctagaaagc ttaaaatgtt ttatggctta aaaatgttaa atggtcatta ggtaggggcc 26760
ggggaatagt gggtggtggc attcactagc ccagggagtg gcagacattt tctgtaaaga 26820
ctcagatagt agatacttca gattttgcag gccatatggt ctctgatgca acgactcaat 26880
tctgccactg tattggacaa gcagccacag gcatgcataa atgtatgact gtggctgtgt 26940
ttcaataaaa ctttatttac aaaaacaagt cgtgggccgg attttgctcg agggcagcag 27000
tttgccaccg cctgtgctag tcagtgaatg ttcttcttgc ttgggagagg aaaaggagtg 27060
gaaaactgta gattcggttt ttttaaaaaa atagtttagt tcttatctga ttatagaagt 27120
gatattgctt ataatagaca tttggaaaaa gacacttgta aacgaaaaaa aagcaaaaca 27180
ttcatcttat tccacaacgc atgtcgccga gagtagttta ttgggggttg ttccttctag 27240
tgatcttcag gaatctgtcg tgtctactga aggtttcctt aaccattcct gttattgggc 27300
attaagatga tttccaggcc gggcacggtg gctcaggcct gtaatcccag cacttgggga 27360
ggctgaggcg ggtggaccac ttgaggtcag gagttcgaga ccaacctgac caacacggtg 27420
aaaccccatc tctactaaaa atacaaaatt agccgggcgt ggcggtgcac gcctgtagtc 27480
ccagctactt gggaggctga ggcaggagaa tcacttgaac ccgggaggcg gaggttgcag 27540
tgagccgaga ttgtgccatt gcactccacc ctgggcaacc agagggaaac tccttctcaa 27600
aaaaaaaaaa aaaaaaagat aatttctagt tttcacaaag agagtgatga acattttaga 27660
gtcaaagctt tatctagcag ttgtttcttt aggcttgctt tccagaagtg caatttctgg 27720
gtcagaggct cttggtgcag attgacaaat ggtgttccgg aaatgttgtg ccaacggcca 27780
ctcctcctag ctttggagga gagggaacac cttggccagc tttgagtgtt atttgaaaaa 27840
tctttcataa tttactgcgg gagggaggag ctgacgtgtt gtcattgttt ctatttgcat 27900
ttctttgatt gctatcgggg ttgaaccttt taaaacatgt ttatttatca tttgagtttt 27960
ctcttcctgt tcatatcctt tgcccatttg tcttttagta cctcagtagc ttttgcaaaa 28020
ttaatctgta tgtggttttc atcagtgaag gctactaacc ctttgccaat tgcattttgt 28080
tgtttttgtt gttcagtggt ttaaatgctc tgggaagtgt tttgctggag aagcttaaaa 28140
tgtttatgga gttcagagct ggatttcagt gtgccacttc tgtactttac acttagaaag 28200
tcttcttcta cccatgaaag gtttttttc tctacatttt atattttaat ttttttttt 28260 tttttgagat ggagtttcac tcttgttgtt aagactggag tgcgatggtg caatctcggc 28320
tcactgcaac ctctgcctcc cgggttcaag cggttctcct gccccagcct cccaagtagc 28380
tgggattaca ggcacccacc accaagccca gctaattttt gtattgttag tagagacgag 28440
atttcactac gttgaccagg ctggtctcga actctcaggt gatccaccca cctcggcctc 28500
ccaaagtgtt gggattacag gcgtgagcca ccgcgcccag cctatatttt aattattatt 28560
atctaaaaaa attcatcctc actacttgag atctgtttgt gtgtgtgact caacgggcgt 28620
ttcgtttctc tcccaaatag ctaactgggg gcctcagaca gctgttgatt atagaaatct 28680
acctctttgc cattgctttg gggtctgttt ctggtgtgtc catagatctg cctctccatg 28740
ccacagagcg gtgactgttc tgatcatggt agtgactgtt ctgatcatgg tagttttatc 28800
atgttttcat gctcaaggag gcaattccac attcacacat tacttgtttg ttgtttcatg 28860
gacttctttt cacatttccc tgggaagaac tagggaacat gcgatggagg tgggaagaag 28920

-continued

```
ttaagtgggt ggcttgaggg ttgtatcaca aaagatagaa gggaggggag aaaggaggat  28980
cttcttatct gagcccaacg ctctggggaa gccacccaga gtgagtgagt ccttaaatag  29040
acctaaatag aatccttgga attgtctgtg aggactccct tggagccccc agcatgagtc  29100
cttccatggg acatgttgga tggttggaaa tcgggagtgg gatagttgaa aaaggaagat  29160
gggttagtga agggtggtgg gagaggggac cgttattatt gcactgtgga aaaatcctga  29220
gaatattgta ggtcaggggc aaggagaagc taaactatga ccagagaggt tacttaactt  29280
gcccagagcc acacagctaa taaaagacag aactggggtt tgtgccaaat ttatgcaaga  29340
catacaccag aataaaagct atgatttttt ggaggagtgg gaaggatgtc ctctctgttt  29400
agaaacaagt gagctgcttc tagctgggac accaggggaa acagtgaaca ttcttttatt  29460
ctattactga gttttccaaa tgtagtgctt gtttgaaaag ctctaggcct acctatcttg  29520
agatataatt taagacattc ctctatgaat ttatttttgt atctgtttta gacaaaatat  29580
ccagaatggt gttatctgca attgagtctc ctgctccctg ctgggtgttc agttgttgtt  29640
gctgttgttt gtttgtttgt ttgtttttga gacagagtct cgttctgtca cccaggctgg  29700
agtacagtgg cacaatctcg gctcactgca acctccacct cctaggttca agcaattttc  29760
ctgcctcagc ctcccaagta gctgggatta caggtgtcac cacatccggc tacttttttt  29820
tttttttttt tgagatggag tttcgctttt gttgcccagg ctggagtgca atggcatgat  29880
cttggctcac cgcaatttct gcctcctggc ttcaagcgat tctcctgcct cagcctcccg  29940
agtagctagg attacaggca tgcgccacca cacccagcta attttgtatt tttagtagag  30000
atgggatttc tccatgttgg ccaggctggt ctcgaactcc cgacctcagg tgatctgccc  30060
gccttggcct cccaaagtgc tgggattaca ggggtgagcc accgtgcctg gccaacacct  30120
agctaagttt tgtgtatgtt gtagagacag ggtttggcca tgttggtcag gctggtctca  30180
aatttctgag ctcaagcacc tcggcttccc aaagtgctgg gattacatgc atcggccact  30240
gtgcctggct gtgcctggct gtgcctgatg ttttgagtga attaaaaatt gctttgctat  30300
taagaaccag gcttttgtgt ccaggaggtc gaagctgcac tgagccctgt tcatgccact  30360
gagctccagc ctgggtgaca aactgagact ctatctcaaa aacaaaagaa aacaaaaaca  30420
aaaatgaaca caaaacaaaa caataaaaag aaccgggctt gtttttccag tactggggtg  30480
tttgttaccc ggagaaggtg cgactaacac ttcccggggt accgggttcc tggcatgtgg  30540
tatatatctc agccatccat tagtagcagt atccccaggg ggccaaaaaa tgattgtttt  30600
ttgaactgtt gcccctgtct ttgagagcaa ctcagcttca gctttctttc ccctcttcaa  30660
tttcttgtat tgtgataaaa tacacataga ataaattttt catcttaact tttttttttt  30720
ttgagatgga gtcttgctct gccacctagg ctggggggca gtggtgtgat ctcagctcac  30780
tgcaacctcc gcctcctgga ttcaaatgat tctcctgcct cagccttccg agtgactggg  30840
acttataggc accagccacc atgcccggct aagttttgta ttttcaggac agagggggct  30900
ttgccatgtt ggccaggatg gtctcaaacc cctggcctcg agcaatacac ccacctcagc  30960
ctcgcaaagt gctgggatta caggtgagtg ccaccgcgcc tggccccatc ttaaccattt  31020
taagtccaca gttttcagtg gcattaagca cgttcacgtg gttttgcaac catcaccacc  31080
accatctccc aaactttctc atcctcccaa actgaaactc tgtccccatg aaacactcac  31140
tccaccatct ccctctccca gccccctggc acctaccatc ctattttctg tctctatgaa  31200
tgtgatgact gtagggacct cctgtgagtg gaatcagacg ggatttatcc ttttgtgcct  31260
ggcttatttc actgagcatg ttgtcctcaa ggttcatcca cgtggtagcc tgtgtcggaa  31320
```

attctttcct ttttaaggct gaatcatgtt ccattgtatg gagggagcac attttgcctg 31380
tgtattcatc catctacggg cacttggtcg ctttcacatt tctgccattg tgaatcaggg 31440
ccactgctgt tgacgcatct agcttttcaa tgcctgcatt aaccttgttg ctgaggcttt 31500
aggaaactta tttatttatt tattttttga gacggagttt tgctctcgtc gcccaggctg 31560
gattgcaatg gtgcgatctc agctcactgc aacctctgcc tcccgggttc aagcgattct 31620
cctgcctcag cctcccgcgt ggctcggatt acgggcacct gccaccacgc ccagttaatg 31680
ttttggattt ttagtagaga tggggtttca ccatgttggc caggctggtc ttgaactcct 31740
gacctcagat aatccactgg cctcggcctc ccaaagtgct gggattacag gcgtgagcta 31800
ccgcgcccag ccttaggagg cttatttgat gtctgatggg atttttgaat acagaataga 31860
ttgagccttc agaggatact cccctgtctt aggtgacaga aatgggctgg agaaaactat 31920
ccatcaaccc ctcttttccc ccagagtctt ttcagatact tctgtgaaca tccgtagttg 31980
ctatttttgt cttccacact tggcagcttc tggaagcatc aggggaatgc atcaacattt 32040
aggatgaagg tgctggtttg tcctttggac ctagtttaag caattccgag caacatccac 32100
cccttcttct acctgtccct taagcacttt ttacagggag accaaaaaaa ggctttcaat 32160
ggttaagggg gccgggtgtg gaggccccac acctgtaatc ccagcacttt gggaggccga 32220
ggtaggtgga tcgcttgagg tcaggagttc gagaccagcc tggctaacat agcaaaacgc 32280
tgtctctact aaaaatatga aaattagcca ggcgtggtgg tgggcgcctg taatcccagc 32340
tacttaggag gctgaggcag gagaatcact cgaacccgag aggcagaggt tgcagtgagc 32400
tgagatcgtg ccattgcacc ccagcctggc cgacagagtg aaactccatt ttttaaaaaa 32460
agaaaaaaaa atggttaggg gaattaaaag aaaaacaaaa aaacatggca tgtgctaatg 32520
atccatagcc tggacaccct ctctccatta tcctgcaatg gatttggggc aaagatacca 32580
ggagaggtcc aatgcacgaa gccttacatg ggaagagtgg agacggggtc tatgcagttc 32640
gtttattgac tgcctactag gtgtcatgtt ctggggcgct cagggcatag gaagggagcc 32700
agcctttgcc tcctcagagc ggccagtcta gtggcaaatg cagatgttca cgatcaaacc 32760
aagtacactc agaagagggg gagagttaga gggagatcta cattagttca gccagctgga 32820
cgcggtggct catgcttgta atgccagcac tttgggaggc cgaggagggc agactgcttg 32880
agctcaggag ttcgagacca gcctgggcaa catggagaaa ccccgtctcg acaaaaaata 32940
caaaaattag ccaggcatgg tggcaggtgc ctgtaacccc agctacttgg aaggctgagg 33000
tgggaggatc gcatgggccc cgggggcgga ggtcgcagtg agctgagatc acaccactgc 33060
actccagcct gggcgacaga gtgagactcg gtgagactct gtctttaaaa aaaaaaaaaa 33120
gaagttcttt gaggcaagca gcaccggctt ccagtctcgt tttaccattg actggtcaca 33180
agctggttca agcctcagtt tctccatctg aaaaatgggg gtcattatgg gacctgcttc 33240
ttagggtggt ggtgtggggg ttgaatgaga tggtgcaggg ggaggcactt aacctagcct 33300
caggtgctcc gtgagtgtcc tggaagcttc cagtaagtaa gcaccatggg cccaccctat 33360
ctgggcagac tagcttccag gtgaatatct accagggctc agcctcattt ctgactttgg 33420
ttttgaggca ggcagaggaa catgtatctt gcgacctgct gatgagggat gggtgccaca 33480
cctccagccc cagagggaag accaccctga tttttgggtg ccaacagcat gggatgctct 33540
ggaaattctc agctctgggc attttgaggg gaccagaagc cacagggctt gcctgaccag 33600
ctgctttagc caaacccact ggcattttct ttctgggagg tcaccccagc tgctcactgc 33660

-continued

```
cggccagagg ggtgggtgag gccgggacat gctgggtgcc aggggaaacc aacccgagat  33720
gccacatatg gacgtcggca ccaaagcagg agggggaggc tgaaagcagc aaatccctcc  33780
tccctgggtc tgagattaca gctccgagtc aaagtctctc aaagtgtggt attgtgccta  33840
ccacattaaa tatcacgtat ttaaatgcac gagtttaaat gcatgctctt ggagggtttg  33900
atttttggca gaatttttag ctgcctatgg aaactctctg cttctttttc ttcttccatt  33960
taaaaagttt gccttgatat tttatttttt tacattttta tttagttttt aatatttttt  34020
taaattgaga tgggagtctt gctatgtggc tcaggtcggt ctcaaactcc tggactctaa  34080
ggaatccccc cacctcagcc tctcaaagtg ctgagatttc acatgtgagc caccacgctg  34140
gacttgactt gattttgttt tctttttctt tttttttttt ttgagacaga gtctcgctct  34200
gttgtccagg ctggagtgca gtggcatgat ctgagctcac tgcaacctcc gcctcctggg  34260
ttcaagcgat tcttctgcct caacctcctg agtagctggg attacaggca cgtgccacca  34320
tgcctggcta atgtttgtat ttttagtaga gatggggttt cgccatgttg cctaggctgg  34380
tcttgaactc ctggcctcaa gtgatccgcc tgccttggcc taccaaagtg ctgggattac  34440
aggtgtgaac cactactctg ggcttgcctt ggtattttaa caatcggaat tgtctttgtg  34500
gcaaatgctg atttcatgcc agccgtggtt ctgggtgctt tgattaggat attgcatccc  34560
atcttcccaa caatcttatt tattgttgag accactaagg cttcgagagg ttaagcaact  34620
tctacttcca acactgcccc gcccacccct tccgccgcgc accccacaca catgggtagt  34680
aagtagtgga gatgggattt gaagctgggg attctggctc agaatccaag ctctttacct  34740
ttgtgtctta tagatgtcat tgcgggaagt tggtgaaatg caggaaactg taaaaagaaa  34800
ggaaggaagg agggaaggaa ggaaggaggg aagaaagaaa agaaaaggaa ggaaaaaagg  34860
aaggagggaa gaaataaaag gaaagaaagg aaggaaggaa ggagggaagg cgggaaggaa  34920
agaaggaggg aaggagaaag gaaggaagaa agaaaggaag gaaggaggga aggaaaggag  34980
ggaaggagaa atgaaagaag gagtgaagga aggaaggagg aaagaaaaaa aggaaggagg  35040
gaaggaagga aggaagaagg aaaggaagga gggaaggaag gaaggaaaga aggaaaagaa  35100
actggagagg aaatctagaa tttgcccctg ccaacatgtg tgttgcctct tcttatcagc  35160
cttctcattc tgtcttgact tagggcctct cctatcagac taagctctcc tgaaggcagg  35220
gactttgttg tatctcaagc acctgtcata gtacctggct cacagttgac aatgacatcc  35280
ttaacactca tcaatagcta gtgtttactg agcacttact atgtgctaag caatgcctta  35340
ggggatccca tcacagccta tgagggtttg ttatcctcat tttacagaag agggaactga  35400
ggcatggcta ggaattatga gacttgctct aggagaccta gctggggaat ggtttgactt  35460
cagacttgtc tgacgtaagg cctttgccca gtgatcagca aactacgacc tgtgggccaa  35520
atccagtccg ccagctgcta tttttgtatg acctatgagc taagaatttt ttattttatt  35580
tttattttta gagatggggt ctcactctgt cgcctgggct ggagtgcagt ggggtgatca  35640
taggccactg ccacctcagt cagcctcctc agtagctgga accacaggca ggcaccacca  35700
cgcccagcta atttcttttt attttttag tagagatggg gtcttgctat gttgcccagg  35760
ctggtctcaa acaattgggt tcaagcaatc ctcctttctt ggcctcccaa agtgctggga  35820
ctataggcgt gagccactgt gcttgcctgg cttaagaatg ctttttcaca tttttggccg  35880
ggcatggtgg ctcatgcctg taatcccagc accttgggag gccgaagcgg gcagatcact  35940
cgaggccagg agttcaagac caccctggcc aacatggaga aaccccatct ctactaaaaa  36000
atgtacaaac attagctgag cgtggtggcg ggcacctgta atcccagcta ctcaggaggc  36060
```

```
tgaggcagga gaatcacttg aacctgggag gcggaagttg caatgagtgg agattgcgcc  36120
actgcactcc agcctgggtg acagggtgag actctgtcta tatatgagct ggacattcag  36180
cattcaggga tagaggctgt ttcagtggga cttgggagca ccacggcctg aggccataca  36240
gcccagctgc cctttgctgg tacttccttc cttccttccc tctttccttc ctttctttcc  36300
ttttctttct tccctccttc ctttcttcct tccttcctta ctttttgaga ctctgtctca  36360
aaaaagaaaa aaagaaaaaa aaatgtgggg tagagcactg tactgaaaaa aattccacag  36420
tagttgtaat tcatttttca ctcagatgat tagcattttt tttttttttt tttggagctc  36480
tctgtttggg tggaggaggg cagtatatgt acaaggcaag gcccccactc caccctcctc  36540
cctcctccca ccccgccttt ccccttcgag tgagtcatcg aacccgtgct tctagacgtg  36600
tttggagcag agcacctgga aatcatgatg ttctctagat aacagggaat attgataaat  36660
tcccttgtgg cgatgtcact gtcgtccata cagaagacag gaaagtgtaa cgcctgcaca  36720
cggggatcca acaaaaagaa aaagataagg tgggggaggc cgggcacggt ggctcaggcc  36780
tgtaatccca gcactttggg aagccaaggt gggtggatca actgaggtca ggagttcgag  36840
accaccctgg gccaacatag tgaaaccccg tctctactaa aaatacaaaa attagctggg  36900
tatggtggtg ggcacctgta atcccagctg cttgggagac tgagacagga gaatcgcttg  36960
aacccaggag gcggaggttg cagtgagccg agattgtgcc actgcactcc agcctgggtg  37020
tcacagcgag actccatctc aaaaaaagaa aaaaaaaaaa aaaaaaaaag gtagggtaga  37080
gcatgtaacg tgaatgatgg cccacttgaa tctctcattc gtctttcttc ccttttatgt  37140
tgtcaaagat ctttaaaaaa aaaatctagg agagaaacaa acaaaaaaaa ctgtactgaa  37200
aaaaattcca cagtagttgt aattcatttt tcactcagat gattggcatt tttttttctt  37260
gtttttttctt tttgagacaa gggtctcaac tctgttgtcc aggctggggt gcagtggcgc  37320
aatcttggct tacttccgcc tcctgagtag ctggaattcc aggcacgcac caccatgctg  37380
gctaattttt gtatttttttg tagacatggg gtttcaccac gttacccagg ctggtcttga  37440
actgctgggc ccaagcaatc cacctgcttc aacctcccaa actgttgcat tatattatag  37500
gtgtgagcca ctgtgccagc caggattgga attatttatt tatttattta gtgagatgga  37560
gtcttgctct gttgcccagg ctgaagtgca gtggcgcaat ctcggctcac tgcaacccct  37620
gcctcccggg ttcaagtgat tctcctgcct cagcctccca agtagctggg actacaggcg  37680
cccaccacca cacccggcta attgttgtgt tttttttgta tttttagtag agacagggtt  37740
tcactatgtt ggccagggtg gtctcgaact cctgacctca ggtgatcctc ccactttggc  37800
ctcccaaagc gctgggatta caggcgtgag ccgccatgcc cagcccttat ttattcattt  37860
ttattttatt ttaaaataaa ataaatttta aaaatttgat tgaaattttt taaacaaact  37920
tttcactttg gagatgattg gattttgtag agcaggaaag aacaagtacc ctagagagta  37980
tgtttctggg ctcccggctc ctcttccggg ggttgaagat gaattgccgt tggcctttgt  38040
aaaagaggag agattgttcc agattggagt ggcagagatg tgctttggtt tgggtggcaa  38100
ggatcacaaa gaaagaagat gaggttgggt gtggtgggtc atacctgtaa acccagcact  38160
ttgggaggcc gaggcaggag gatcacttga acctagaatt cgagctcagc ctgggcaaca  38220
tagcaagacc ccatctctac aaaaaatttt aaaaaattag ccaagcatgg tgctgtgtgc  38280
ctatagtccc agctactcag gagtctgagg tgggaggatc gcttgagcct gggactttga  38340
ggctgcaatg agctatgatt acaccactgt accccagcct gggtaacaga gtgagaccct  38400
```

-continued

```
gtctcaaaaa caaacaaaca aaaacagaag gaaggaagga aggaaagaaa gaaagaaaga  38460
aagagaaaag acaagacaag aaaaaaaaaa aaaaagaaaa gacagggtga gagggaaggg  38520
tattcgggtg gatgaaatgg caaagagaag gccaagaggc gttttgtggg caagagtgaa  38580
gagggtgcct catgccggga agggaggctt ggaccagtgc agggtcctta tgggctccaa  38640
tgccgtcatg aaggtcacac aggggctgtg tttaggaggg gctgtttcca ccaatactga  38700
gtggacagcc ttgctgagcc aggctttttg ttgcgtcccc gaagtccttg ctgagtcagg  38760
gaggaagtca aagtaactat caggttagat aagctgatgg gtgggcagaa agtgttttgg  38820
tgggttcaag gctgcgctga aagatggtag accagttgac cgtgtggtca cttggctgcc  38880
ccagagatga tgctgtctaa atcttgagtg gtgaagataa cgaatttaca attcccacca  38940
ttgcctggct tcctggagcg ggtgggtgcg gggaccgggg aggggggccg ggggaggctg  39000
agggctatca gttgaaactg accttttggc ccaatccttt tgggaagaag gcgggtagag  39060
ttaaaatcca tcgtaatgga aaggcggctt tccctttggc tgtctgctaa cttggtgact  39120
ggcctgacaa gtttttcttt tccttcctcc tacctgatac tcactgaccg gttacttccc  39180
atgtcacccg accctttgtc agaattaaaa tctgttcttt gtgactgaac acctgaaatg  39240
ccccggggag gacccaagga agtcagcgag cgcctgtgcg tcaggctggc agcccaggtc  39300
cttcagtgat ctgtttctct caatgcgcct gtgtcagata gaaccgtgca tttcccagta  39360
aaaggaggtg atgtgtgtgc tggagtttca agattgtacc ccttatccta tctccccttt  39420
cctctgtctt ccctctctac ttttttattt tgttgtttgt ttgtttgttt ttgagatggg  39480
gtcttgctct gtcacccagg ctgcagtgca gtggtgcgat catagctcac tgcagcctca  39540
gccttttggg ctcaagcaat cctccagcct cagcctggcc agtagctgga actatgggtg  39600
catgccacca cgcccagcta attttattta cttatttact tatttattaa agagatggag  39660
tcttgctatg tttcccaggc agctcacaaa ttcctgtcct caagtgaccc tctcgcttca  39720
gcctccccca ttagctaaga ctacaggtgc gcaccaccat ccctggctaa tttatttttt  39780
aaatttttct ttttgtagag atggggattt tgctatgttg cccaggctgg tcttgaactc  39840
ttagactcaa gcaatcctcc cactttggga agcccaaagt gttaggatta caggtgtcag  39900
ccaccaggcc gacctgtttg ctcattttc cttttccttt tttcttttct tttcttttt  39960
cttttttttt ttgagatgga gtttcgctct gtcacccagg ctggagcaca gtgacacaat  40020
ctcggctcac tgcaacctct gcctcccagg ttcaagcgat tctcctacct cagcctcctg  40080
agtgctggga ttacaggggc atgccaccac gcccggctga tttttgtatt ttttagtgaa  40140
gacggggttt caccaggttg gccaggctag tctcaaactc ctggcctcaa atgatccacc  40200
agcctcagcc tcccaaagtg ttgggatgac aggcgtgagc caccacactc ggcccgtttg  40260
ctcattttta aacataaatg atgtcaagag tgggaagcaa acaagaaagt gttgaaagca  40320
ttgctctcct ctgctccctg gttacctatc atcctggggc ccgaggagtg gctgcagatt  40380
gggccacctt cctccaatca caggtttggg aagtggacca aagtctttca acacactgga  40440
cttagcatga tcatcaaatt tgcactggag gggccaggca cacgcctgta atcccagcac  40500
tcggggaggc tgaggcgggc agatcacttg aggtcaggag ttcgagacca gcctggccaa  40560
cgtggtgaaa ccccgtctct actaaaaata caaaaaataag ccgggctggt ggttggaacc  40620
tgtaatccca gctactcggg gggctgaggc aggaggattg cttgaacccg ggaggtggag  40680
gttgcagtga gtcgagatca cgtcactgca ctccagcctg ggtgacaaaa gcaaaacctc  40740
gtatcaaata attaaataaa taaataaaca aataaataaa taaaaaatta cactgtaggg  40800
```

catgtggtag gtgaagccca ccattgtcaa gtacctacct agagggtttg gggtagaggg 40860
tcctgtggct tcttctattt tttttttttg gcggagtctc actctgtcac caggctggag 40920
tgctgtggca cgatcttggc tcgctgcaac ctccgcctcc cgggttcaag ggattccccc 40980
gcctcagcct cctgagtagc tgggactaca ggcgcccgcc accacgcccg gctaattttt 41040
ttgtatttta gtagagacag ggtttcacca tgttggccag gatggtctca atctcttgac 41100
cttgtgatct gcccgccttg gcctcccagg gtgctgggat tacaggcgtg agccaccgcg 41160
cctggctgtg gcttctttat cctagaagtt tctttgcctc tcgttttgtc ccaggcgagg 41220
agggtcttgg atctttaatg actccatggc ttattgagtg tagcccagaa agaatggttg 41280
tttaataggc tttattaccg agtgtttcca agggcttacc tggggaagga aaacattttt 41340
actcggaggt ctgataagga tgggctttaa agcgctggca gctagtcatg tccacacgcg 41400
gtgtgcgaag cacggcgttg tttactgacc acctgcaaag cccgtcggct ggtgaacaag 41460
gctcttgtcc caggctgcct cattggtggt gatgatgtta agagtttcct catttgcaaa 41520
taaattgact aacctagcag acgggtttga tccaaagtgg tcaagattcc ttttctttaa 41580
atttgttttt tttttgagat ggagtcttgc tctgtcaccc aggctggagt gcagtggcgt 41640
gatctcagct cactgcaacc tcctggattc aagcgattct cctgcctcag cctcctgagt 41700
aactgggatt ataggtgaac accaccacgc ctggctactt tttttgtatt tttagtagag 41760
atggggtttc gtcatgttgg ccagaatggt cttgaactcc tgacctcaag tgatccaccc 41820
acctcgacct cccaaagtgc tgggattaca ggcgtgcgcc actacgcact ggcaaatttt 41880
tgtattttca gtagagacag ggtttcgcca tgttggccag gctggtcttg aactccggac 41940
ctcaggtgat ccacccacct cagccaccca aagtgctaca attacaggcg tgagccaccg 42000
cacctgggct attttcactt ctttcgaagt tatacctagg agtggaatcg ctgggtcagt 42060
tggtaattct atatttaatt aatggaatca agatttcttt ttcttttctt tttttggttt 42120
tactttaaaa aattctatct tattacataa aaaaaccaca ggttcagaaa agccacacca 42180
aacaaatgaa tagcctaatg gttcactcta acgtcaacac tcatataatc cctaactctg 42240
gttgagaaat agtactttgc cagaacaccc cctccaaaag ccatgccacg gaccacatcc 42300
tagtcacagg cctcttcccc cagagtagtc actgtcctgt cttttgtaga catcacttcc 42360
ttctttctgt atagttttat cacccaagtg tgaatctgta gacaaatatt tagctttgcc 42420
cattaaaaaa aaaaattgat ggccgggcat ggtggctcat gcctgtaatc tcagcacttt 42480
gggaggctga ggcgggagga tcacttgaag ccaagagttg gagaccagcc tggacaacat 42540
agtgagaccc catctctact aaaaataaaa taaaaaatta gccgagcatg gtggtgcatg 42600
cctgtagtcc cagctactcg ggaggctgag gtgggaggat cgcttgagca cagaaggttg 42660
aggctgtaat gagccgagat tgcatattgc actccagcct gcgtgacaga gcaagaccct 42720
ggctcaaaaa ttaacacaat aaaataaatt gatgtgtttg tttgggtctc tagcagtggt 42780
tttgaactga gggtgatttt ttttgtctcc caggggacat ttggcaatgt ctggagatat 42840
tttttggttg tcacaactcc agggaatgtg tgtgtactgc tttcattgag cagatggagg 42900
ccagggatgc cgttcaacgt cctgcaatgc agagacagcc cagccacaaa gaatgatcca 42960
gccccaaatg tcaatagtgc tgaggggcag aaagcctggt ccacaggttc tccctccatc 43020
cctttccttt taccttctct ctgttgaaga gctgggcttt ctggcttggg gtgcagtccc 43080
cagtctgagt gttgctgatc gtacgttcct gggacagttc tgcttgcccc tctgagctcc 43140

-continued

```
agactcagag ctagggtcac actcaggttc tacctcttgg actgacttta tttaacaagt  43200
accatttcag cactctctgc agtcagctgt tttcaaaggc gaccatgctt gatgctgttc  43260
gtttgcacat ggctctgagt ggtggtgtgt tctttgattt tttttctttt tcttttgttt  43320
taaagaaaaa cacaccgttt tttaaacacg gttgcccgaa ctctcatctt cttcctccct  43380
gccctccctc cctccctcct ctccttcctt ccttccctcc ctccttcctt ccttttttctt  43440
tatttcctcc cttccttcct tctctccctc cctctccctt cctcccttta tccttctctc  43500
tttccttcct tccttctctt tcttttcttt ctttcttttc ttccttttct ttcttctttc  43560
ttttcttctt tcttccttgc tttcttttta tttcttacct cccttccttc tctcccttcc  43620
tctctccctc ctccttcctc tttccctttc tccctcctct ttctttttct ctctcttcct  43680
ttcattttc tcccctcccc tccccttctt ctcctcccct ccttccccctc tcctccttcc  43740
catcccctct cttccctttt cttcctttcc ttcttttccc tccctctctc tttcttttct  43800
cctttccttt cctttccctc tcttttcttt ctttcttttc tttcgacagg gtcttgctct  43860
gtcacccagg ctggagtgca gtagcatgat catagctaac agcagtctgg aactcctggt  43920
ctcaagccat cctcccacct cagcctccag agtagttggg actacaggcc cctgtcacca  43980
tgcccagtta ttttatttta ttttttttttg agacagagtc tggctctgtt gcccaggttg  44040
gagtgcagtg gtgcgatctc agctgtctgt aacctccacc tcttgggctc aagtgattct  44100
cctgcctcag cctcctgagt agctgggact acaggcacct gccaccacgc ccggctaatt  44160
ttttgtattt ttagtagaga cggggtttca ccctgttagc caggatggtc tcgatctcct  44220
gacctcgtga tccaccctcc ttggcctccc aaagtgctgg gattacaggc gtgagccacc  44280
gcgcccagcc gctaattttt ttttaattta ttttttgtac agatggagtc tcactatatt  44340
gcccaggctg gtcttgaact ccagggctca agcagttctg gcacactagc ctccccccaat  44400
tcaatgggat tacaggtgta cccatttttt aaaaatgggc cagactaaat atttgtctag  44460
agatccatac ttgagtgata aagctatatg aggttccatc tgggaattcg gttctgcggt  44520
aaaacggtgc cgacgggcct cccttttttt agtgtctgac aaacagggca cagaccgaac  44580
ttcataacaa aactttgtgt tcttgacgaa ggcaagtttt gctaagaaaa ttatttttat  44640
aagcgagaaa ggtatgaagg ttatttgcaa aggaatttta ctggggtgag aaaaaaagca  44700
agaggtttac cttaggattc ctggtggtaa agaagatgga atgggcagaa gacgtcatca  44760
cagatgtcac ggggagagcg atagctgaac ctctgaaagg aaagaggttc ccagggaagg  44820
atgaatttga tgcaggaaaa aagttagagg atggtcttaa atttgtcaat gtagttcaga  44880
ggaaagtgta attcttcaca gacttttagt tttgaaagga tggcttcaaa agatactggg  44940
ggacatgggc gcagtaactc acgcctgtaa tcccagcatt ttgggaggcc gaggtgggcg  45000
gatcatctga ggtggggagt tcgagaccag cctgatcaac atggagaaac cctgtctcta  45060
ctaaaaatac ttaattagct gggcgtggtg gcgcatgcct gtagtcccag ctacgtggga  45120
ggctgaggca ggagaccatc gcttgaacct gggaggcaga gtttgcagtg agccaagatc  45180
acgccactgc actccagcct gggcaacaga gtgagactcc gtctcaaaaa aaaaaaaaaa  45240
aaaaaattct ggccaaccgg gaatagtcca ggataatcca ttcttcagaa cttgttcttg  45300
ctaactcagt taagtgtcga atggcgtggg ttgtctactg tattttagag gacattagaa  45360
tatttatgaa gggctttccc aggtttactc ataacttcat tttcctcatg ctatttgtcc  45420
cttaaagtct ttctgaaatc tttcagttgc cacttcttct gggtgggtgg gtatgtatgt  45480
tgagggtcat gctttttttt tttttttttt tttttgagat ggggtctccc tctgtcgccc  45540
```

```
aggctggagt gcagtgatgt aatcacacct cactgaagcc tcaacctctc aggcttaagt  45600
gatcctccca cctcagcctc ccaagtagct ggcactacag gcatgaacca ccgtgcctga  45660
ctaattttta aaaaatattt ttgcaaaatt agccaggcgc ggtggtgcac gcctgtagtc  45720
ccagctacct gggggactga ggtgggagga ttgcttgagc ctgggaggtt gaggctgcag  45780
tgagccaaga tcatgccact gcactccagc ctgggtgaca gagcgagacc ctgtctccaa  45840
aaataaaaaa ataaaaaata aaaaataaaa gatggagtct tgctgtgttg cccaggttgg  45900
tcttgaactc ctgggctcaa gtgatcctcc tgccttggct tcccaaagtt ctggaattat  45960
aggcatgagc cactgcacct gtctgggtcc tgcttttggt agtgatatag aaccaactta  46020
gtgaaattct agaatgacgc tgtccactaa ggtagctctg ccagccacag ccacatgtgg  46080
caatttaagt agaaattcat taaaattaga tatttgtccc tcagttgtac tcaccatatt  46140
tagacaatgc agacagacaa tgttgctatc actgcaaaaa cttgtattgg gtacctctgc  46200
cttagaactt ttcattccat gatgaaagat tgttctggag tcagacaggc ctgcatttga  46260
agcctatatc tgttttgtga ccttgggcaa attgtctagc ttttctgaat gtctgttttt  46320
tcttctatca tgaggacatg ataagggaac cagtctccaa ggttttcctc agctttgaac  46380
tggtatatcc cctctttcga taaaaataaa aatccagttc ctcttcccta cttggagttt  46440
gttctttttt cctctaaata taaaatatac cgttgaatgt tttttcaacc tctccacccc  46500
ttgagagtcc ctggaataga gaggaaggag tggcttggga aagttgatca caacaaagag  46560
gctattatag gtacatctaa tcgagaagag gaacaaggaa ggagtaggtg tgttgaccgg  46620
ggctcagagt gtcttgtctg tgggtcacca agaatgagga atgtgtcagc tccttcctgg  46680
cttctcctct ctgggaacag agaacagtgc attgcagctt aagtggagta aaatgggtgt  46740
gggtttggag gaagtggatt aaggatgggg aaggggccgt gggagagaac cccagcctga  46800
gtttgtcttc ctggctcagc actgagtgtc tcagtcaaca catgaatgcc agtaatggga  46860
atctatttgg attcacttaa gccatgaggt gggggcagtg tgttaactgg ggcaacacag  46920
ggctctcagc ttgaatcagc tagcttttgc tgtgtagcaa accactctga aacacagacc  46980
ttggaattta tattcaagtt taatcatgga gcttgtatca gctagctttt cctgtgtagc  47040
aaaccactct gaaacataga actaggaact tgtatccaag ttcattcatg gagcttgtat  47100
cagctagctt ttgctgtgta acaaaccacc ctgaaacata caacttggaa cttgttgtat  47160
ccaagttcag tcatggagtt tgtatcagct aatttttgct gtgtaacaaa ccaccctgaa  47220
acatagaact tagaacttgt tgtatccaag ttcaatcatg gagcttgtat cagctagttt  47280
tgctgtgtaa caaaccaccc tgaaacataa aactgggaac ttgttgtatc cacgttcaat  47340
catggaactt ttatcagcta acttttgctg tgtaacaaac tactctgaaa cgtaatggct  47400
taatcaacaa tcatgtactt agctcatgat tctttgggtc gctgggcaag ttttcttgtt  47460
tagacccacc agctgaccac aaacacaggc tcttttctct ctcatgtctg ggatcaacca  47520
gtgggttgtc tggtagctgg atggtctagc atggcctcac tcacatgtct ggtggttggt  47580
gctggctgtc agctgggagg ccttggtttt cttccctgta gctgctcatc ctccagttgg  47640
ctagtttggg cttagattac atgatagtct cagcgttcca agagtggcaa gagatcaatt  47700
tccagtacaa aagtgccttt tgagtttctg tttgcatctt gtgtgctaac atcccattgg  47760
ctaaggtgag ctgggaggga aagggagaat atagtcttta cctgttgatg gaagaggaag  47820
aatttgtggc cctgtttgcc atctgccaaa gaaccctgga gtgggaaaca gtggggctca  47880
```

-continued taaaacattt ttttaaaaac ctcttatttt aggttcatga gtacaataac attttaatca 47940
gaatttggag ctcaattgga catcaggact gtgtatggtg tgactgagga cattaaatga 48000
tttttttttg agtaggaatt taactttatg aattccactt gttgaataac caattccttc 48060
cccagtaatt cttgatgttt tcttcatcag gtattaaatt caaccaaaac catgaatttg 48120
cttttgggat atcaattcta tttcaagtcc tctgtgtctt aatcttatcc cagtaccata 48180
ctgtttatag atttagaata tgtgtttttt tagttttgtt tttgttgtcg ttttgttttt 48240
aaagaagtgg ggctcggctg ggcgtggtgg ctcatgcctg caatcccagc attttgggag 48300
gccgaggtgg ctggatcact tgaagtcagg agttcgagac cagcctggcc aacacagtga 48360
aaccccgcta ctataaatac aaaaattagc cgggcatggt ggcacatgcc tgtagtccca 48420
gctacttggg aacctgagac aggagagttg cttgaacttg ggaggtggag gttcaatgag 48480
ccgagattgt gccactgcac ttgagtctgg gtgacagagc gagattctgt cttcaaaaaa 48540
agaatggggg ctcactgtgt tgcctaggct ggactcaaac tcctgggtgc aagtgatcct 48600
ccttagcctc caagttgctg ggactacaag ctcatgcctg gtaagaacat gctttataaa 48660
gtggcaaatc tagtttttc cctattacac cttttagaag agtgtttcct tttctggttg 48720
aactaaatat ttccctcctc tcactctcat ataaaaccca ttgagggctg ggcgcggtgg 48780
ctcacgcctg taatcccagc acttggggag gccgaggcag gtggatcacg aggtcaggag 48840
atcgagacca tcctggctaa cacggtaaaa ccctgtctct actaaaaata caaaaaaatt 48900
agccgggcat ggtggtgggc acctgtagtc ccagctactc gggaggctga ggcaggagaa 48960
tggcgtgaac ttgggaggcg gagcttgcag tgagccgaga tcatgccact gcactccagc 49020
ctgggcgaca gagcgagact ccatcttgaa aaaaaaaaaa aaaaaaaaag caaaaacaaa 49080
aacaaaaaaa cccattgaga tattgattta aaaatttaat taaaaacata acccatttcc 49140
cagaggaaaa aaagtgcagc tcgctgccag cactccttta attttacata aacatgttct 49200
ttgaggctga agcaaatctg actgattttc aatatgagaa aatataaaac ggttcttgga 49260
gttatttcta aacagaactt gtctctaatc ttaatgtaac agaaatgtct ataatgttac 49320
attaggatta gagaatagat tattcttggg acaaatggaa aaatgggtta aaatccataa 49380
attaagaaat caatactttc gtatttttcc tttccgggca ggtatgggat ctccttttcc 49440
atttgctcaa atcttttttt ttctttttga gacagagtct cgccctgtca cccaggctgg 49500
agagtagtgg cacgatctcg gctcactgca acctctgcct cccaagttca aacaattctt 49560
gtgcctcagc ctcctgagta gctgggatta taggcacaca ccaccatgcc cggctaattt 49620
ttgtattttt agtagagacg gggtttcacc atgttggcca ggctggtctc gaattcctgg 49680
cctcaagtca tctgcccact tcggcctccc aaagtgctgg gatgacaggc atgagccact 49740
gcgcccagcc aatttgttca aatcttttat attgtccttt cttcatcttt atcctgtatt 49800
atttttgtga cgatggttcc tgatttctgt atcacagagt tttgttgtgt tagttatggc 49860
tactatgaat agcatattta ccctgaatcc agatacttta gtgaaattga ttggtaggtt 49920
tttaaattgt tttattcatt gtgtgcaatt tcgtcctcta caaattatgg tcatttaaaa 49980
aaattatgtc tgctcagttc tggaagcatg aaaaaaatta tgtctaaaat catacctctt 50040
gtttcggttt taaatcttat tctattgacc agggcttcta gactaacatt aaatatttaa 50100
caatggtatt atccgacatc tatgtttaat agatttccta atataaaatc atccttgctt 50160
tcctgtggta aaacctactt ggttgtgatg aattattctt tcagcataat gttgaattcg 50220
atttgctagg tttgctttgt ttcgttttct gaattcttgc catctgtgtt catgagtgaa 50280
attgggctat gtttttggtt ggttttattt tgcaatgtct tcatcagttt ggattattta 50340
ttgtgttcta gccacataaa atgaaatagc aggtaactga gtattcattg acaaatttta 50400
tggtgccata actttggggg ggaagcaatt ctttgataac ttaagaaaaa atttaggcca 50460
ggtgcggtgg ctcatgcctg taatcccagc actttgggag gctgaggcag gtagatcact 50520
ggaggtcagg ggttcgagac cagcctggcc aacatggtga aaccccgtct ctactaaaaa 50580
tacaaaaatt agccaggtgt ggtggcgcac gcctgtaatc ccagctactc gggaagctga 50640
ggcaggagaa tcacttgaac ccaggaagcg gaggttgcag tgagccgaga tcgcaccact 50700
gcactccagc ctgggcagta gagctagact gcatctcaaa aaaaaaaaaa aaaaaaaaaa 50760
aaaaaaccaa aacagtgtgt gactggctgt gacgtaaggc agtcagacct ctccttcgaa 50820
atgggccgtg attcatcttt atttttgtag ggctgtgtca cgttagaacc actacagcaa 50880
aagttttcat tggaaatcta ataatgtttt tttagtctgc catctggagt ctgtgctcct 50940
tgtatgtctt tattgttcaa gactaagagt ggtgtgtgtg tctgtgttgg ggggatgggg 51000
tttggtaatt ttgctaacat ggctctaaga atctgtcccg cttcccaaaa cctcattttt 51060
ctctgcttta gcagtagccc aacactgaaa acagagtact gctttttag aggagttctg 51120
atttggattc cttttctttc ttttttttta ggccaaaatt ttcatttata aatagcttct 51180
gtggtacaca acatgcaaat atttttggtt tcatgatatt acaccagagt tgcagagttg 51240
tagctgtttt tttttttttt tttttgaggc cagtctcgct gtgtcaccca ggctggagag 51300
cagtggtgcg atcttggctc actgtaacct ccacctcccg ggttcaagca attctcttgt 51360
ctcagcctcc tgagtagctg ggattacagg cgcccacacc acacctggct aatttttgtg 51420
tttttagtag agacggggtt tcaccatgtt ggccaggctg gtctcgaact cctgacctca 51480
agtgatctgc cctcctcctc agcctttcaa atgctgggaa tacaggcatg agccaccaca 51540
cccggctgaa cttttattat tttaaaaaca tttttattta tagtaaaagt cacacataaa 51600
atgaaatttg ctgtttttag aaagaatgtt taaaaagatg tgtaccatgt tgcccagtac 51660
agtggctatt cagaaacagc catagtacac cacagcctca aactcctggg ctaaagggat 51720
cctcaagctt cagcctccca agtagctggg gctacaggaa cacaccacca catctggctt 51780
gcctccttct ccttctcttt ctccttttcc ttctccttct cctcctcctt cttctttttt 51840
tttttttgag acaagagtct cactctgtca cccaggctag agtgcagtgg catgatcttg 51900
gctcactgca atttctgcct cctgagttca aagcaattct cctgcctcag cctcctaagc 51960
agctgggatt acaggtgcat accaccatac ctggctaatt tttgtacttt tagtagagac 52020
ggggtttcac catgttggcc agtcccgaac tcctgacgtc cagtgatcct cctactgcgg 52080
ccttccagag tgcacaggca tgagccactg tgcctggctt gtttcttctt ttttttaaat 52140
ttaatgagtt taggcagggt ttctcagcct caacagtgtt agcattctgg gctgaacccc 52200
tctccgtggt ggggactgcc ctgtacatta caggaagctt agtagcatcc ctggcctcca 52260
ctcaatacca gtagcaaccc caagtcatga caaccaaaaa tgtctccgga tactgccaag 52320
tgctgggatc acaggcatgt gccaccatgc ccagctgatt tatttttatt ttattatttt 52380
tgagacagtc tcgctctgtc gcccaggctg gagtgcactg gcacgatctc agctcactgc 52440
aacctctgcc tcccgggttc aagtgattct cctgcctcag cctcccaagt agctgggatt 52500
ataggtgcac gccactatgc ctggcaaagt tttgtatttt tgtagagacg gggtttcacc 52560
atgttggcag gctggtctcg aactcctgac ctccagtgat ccacccgcct gggcaatata 52620

-continued

```
gcaagacccc atctctacca aaaatttaaa aaaatttagc cgggggtggc ggcatgttct  52680
tgtagttctg gctactcacg aggctaaagt gggaggatca tttgagccca ggagttggag  52740
gctgcagtga gctacgatca caccactgca ctccagcctg gacaacaggg caaggcctca  52800
tctcttaaaa aaaaaaaaaa aaacaaaata aaataaaaag tgaataagtg aaagtaataa  52860
aatgtaagat acagttggag ttctctttgt catcttccct tgctatattc tcctcccttc  52920
ttcccagagg taacaactct cttaggtttg gtacataaac ttccagccct gcatgtattt  52980
tgacacataa ccttgtacac acgtcaatgc cagatacagg ttcagtatcc cttattcaaa  53040
atgcttggga ccagaagtgt ttcccacttg ggattttaga atatgtgcgt atatgtaatg  53100
agatactgtg gggctgagaa cgaggtctaa acgttaaatt catttatgtt tcatgtacat  53160
cttatacaca tagcctggag gtaattgtat acaatatttt cagtaatatt gtgcgggaaa  53220
caaggttttc accgccctga ctgtgacctg tcacaagagg tcaggaatgg aattttcttc  53280
cactgctatc atgtcggcgc tcaaaaagtt gaattttgga gcatttagga ttttggattt  53340
tcgggccagg aaattttgga gcatttaaga ttttggattt tgggttatct tcagttgttc  53400
tttaaatcta tttatttatt tatttgtatt tgacaacgag tttcactctt gtcaccctgg  53460
ctggagtgca atggcgcaat cttggcttac tgcaacctcc gccttgcctc aagcaattct  53520
gctctctagt ggctcagatt acaggtgtgc accaccacgc ctggctaatt tatgtatttt  53580
tgtagagatg gggtttcacc atgttggcct ggctggtctc aaactcccga cttcaggtaa  53640
tccacctgcc tcagcctccc aaagtgctgg gattacaggc atgagccacc acgcctggca  53700
taaatctttc tttaaatctt tcgctgctgt aataaaatat acatcataaa atttgccatc  53760
ttatttattt ttcagtatac agttcactgg tgttaaacac tgccatttat attgtaatac  53820
acttttgagt attctaaata tctgcatata ttgggaagct aagtagtact atcccttagg  53880
aagccattgt gtattttgca cgtaaagcac atttcagttc tgactggcca cacgtggctg  53940
gtcctgctgt aatggatcta gtctttaaaa atactccgcg agagcttgca gtgagctgag  54000
atggcgccac tgcactccag cctgggcgac agagtgagac tccgtctcaa aaaaaaccaa  54060
aaaacaaaaa actctgcgat cttcctcacc atgcacacat atgatatttt tgtgattgtg  54120
attccaattg ctacacctgc tgcatgagtt cttaagccaa atgctttttt ttttcctctc  54180
agccactatg ttctttaagt ttatgcctct tgattcagta ttgctagttc attcttttaa  54240
gtgctacata gtatcttgta tgaataagcc acatgctact caccagctcc cctagtggga  54300
ggcattgaga ttgtttccgg tttgtttctt ttataaacaa tgctgcaatg aacatcttgg  54360
tgtccatctc ctcctaccca tttgtgaatg gttttctagg attgatgttc agaattgaag  54420
tcacagggaa tggagtatgt gcatttttag atctagtata tactccccga atggtctcca  54480
aggtggctgt gacagtttca ccagtgatgc attaaggtat atgtcaaatg tgggcaaggc  54540
tgcaggaaaa ttatgttaat tccagtgcat ggaaattggt atcctatggt attcttttgc  54600
atctccctga ttcctggtaa gactgggaat ctctctgtat gcttcttagc catgtcttcc  54660
tacctcttcc tcctctttcc ctgggagctg ttttggggtg ggggggctgg gccttttttct  54720
tcagggactc tgcattggca acgtcacaaa gaggtgcaca agggattgaa gtgtcggaaa  54780
tgctttgctg ctgtcattgc atttctttac ccagcatttc aattgtgctt tgctttgctt  54840
ttctcacttg aaattgtggc cagatagaaa cccagttaga ctaataagca tccatctttt  54900
taaatctctt tgagatgctg atgtttggat atcttcagtt gctcttcttt aaatctgtaa  54960
ttttttttt gtagtaataa taggacatgc atcataaaat tgaccatctt aacctttttt  55020
```

```
tttttttttt tttttttga gaattcatct gttgatggac atttgggttg tttccgcctt 55080
ctggccattg taactaacgc tgggaaaaac acgggtctac aaatatctgt ttgtggctgc 55140
ccaagttttg ggacacata gtggaagccc accccttcct gattgaagca tggggcccat 55200
tgagagactt agcccatagg agcctctttc cagtgaggaa tatggaggga atggagggca 55260
gtacaaaagt tctccggcct ggacccttgt gattctttga aggctgagac gagagatgag 55320
actcatggct gggttcactt tttggttcac tttccctttc cttttttttt ttttttttt 55380
tttgagatgg agcactctgt tgcccaggct ggagtgcaat ggcgtgatct cagctcattg 55440
caacctctac ctcctgggtt caagtgattc tcctgcctca gcctctcggg tagctggaat 55500
tacaggtgca tgccaccacg cccggctaat ttttgtattt tttagtagag atggggtttc 55560
accatgttgg ccaggctggt cttgaactca tgacctcaag tgatctacgc acctcagcct 55620
ctcaaagtac tgggattaca ggcgtgagcc actgagcctg gcctcttttt ccattttctg 55680
ttgcatcaat ggaaagtcca tctcctgccc gtggacgttt tctatgttga tgtggaatgt 55740
ggcatttgtc caggaacttg gtgctttttt tttccctcta ttatttcatt tgcttttgga 55800
ttttgagaga tggagaactt ccttagtgtg ggagggaaac agttatggat ttactttatg 55860
attctacatt caatcctggt ctcttcaaat gatttcaggg cttgtttggc caggtcaagt 55920
ctgttctagg aggattttct ttccatcctt cctctgggaa atgaatgagt ataaaaacat 55980
gcccaagatg gagggaaacc tccccttccc tttttttgcct ttttcttcct ggttttgtac 56040
ataactgaac attttgattt tgggatgaga ggatattagt tcattctcac attgctataa 56100
agaactatct gagactgggt atttttaaa tttttaaaaa tttaatttaa tttaatttaa 56160
tttaatttta tttatttatt tttttgagat ggagtctcgc tctgtcaccc aggctggagt 56220
ccagtggcgc catcttcgct cactgtaagc tccacctccc gggtttacgc cattctcctg 56280
cctcagcctc ccgagttgct gggactacag gcacccgcca ccatgcctgg ctaatttttt 56340
gtatttttaa atagagacgg gatttcacca tgctagccag gatggtctcg atctcctgac 56400
ctcatgatcc acccgcctcg gccttccaaa gtgctgggat tacaggcgtg agccaccacg 56460
cccagcctat ttatttattt ttttgagaca gagtctccct gtgttgccca ggttggagtg 56520
cagtggcatg gtctctgctc actgcaacct ccacctcccc ggttcaagcg attcttctgc 56580
ctcagcctcc tgagtagctg ggattacagg tgcctgccac cacgcccggc taatttttat 56640
agttttagta gagacggggt ttcaccatat tggccaggct ggtctggaac tcctgacctc 56700
gtgatccacc tgccttggcc tcctaatgtg ctgggattac aggcgtgagc caccgcgtct 56760
ggcctgtttt tttgtttatt tccataggtt ttgggggaac aggtggtatt tggttatatg 56820
agtaaattat ttcgtggtga tttgtaagtt ttggtggatc catcacccga gcagtataca 56880
ctgaacccaa tttgtagtct tttatccctc actcacttcc tatcctttcc ccctgagtcc 56940
ccaaagtcta ttgtatcttt tttttttttt ttttgagaca gagtctcacg ctgtcaccca 57000
ggctggagtg cagtggcgcg atctcggctc actgcaagct ctgtctcctg ggttcatgcc 57060
attctccttc ctcagcctcc cgagtagctg ggactacagg cgcctgccac catgcctggc 57120
taattttttt gtatttttag tagagacagg gtttcaccgt gttagccagg atggtctcga 57180
tctcctgacc tcatgatccg cccgcctcgg cctcccaaag tgttgagatt acaggcatga 57240
gccaccgtgc cgggccttgt atcattctta agactttgca tcctcatagg ttagctccca 57300
cttatgagtg aaaacataga tgtttggttt tccattcctg atttacttca cttaggataa 57360
```

-continued

```
gagtgagact aagtaattta taaagcgctg ggattagagg cgtgagccat ggtgcctggc  57420
caatgtctgg catcttttct ttggtgtaat gttttgagat tcatccatgg ttttgcattt  57480
atcaatagcg tatttctttt gtgttgttca gtagcattcc attgtgtgga gagacgacat  57540
ttagtttcac cattttagct gttgagagac atttgggttg ttttcaactt ttggctatta  57600
ttcataaacc tgcatgaacc tgttatacac aattgtgtag gagtctttta tgtggaccaa  57660
tgccttcata tctcttgagg ttatatcctg gagcagaatg gatgagttgt gtagtagaag  57720
tgtgtataag gagtgggcag gccaggtgcg gtggctcatg cttgtaatcc tagcactttg  57780
ggaggctgag gcgggtggat cacttgaggt cagcagttca agaccagcct ggccaacgtg  57840
gtgaaacccc gtctctactc aaaatacaaa aattagccgg gtgtggtggt gggcacctat  57900
aatccaagct atggtgggag aattgcttga atccagcagg tggaggttgc agtgagctga  57960
gatcgcacca ctgcactcca gcctgggtaa caaagcaaga ctctgtcttt aaaaaaaaaa  58020
aaaaaaaaag gaaaggccag attgttttcc taagtggttg gagtctgtta tatttccacc  58080
agcaatgtat gagagttcta attgctccac atccttagca gcacttaata tttattgtca  58140
atctttatta ttattattgt tattattatt tttagagata ggatcttact ctgttgccca  58200
ggctggagtt cactgcagcc ctgaactcct gggctcaagt aatcctccca cctcggcctc  58260
ctgagtagct tggattacaa gcacacatca ctacacccag ctaattttat ttttgtaaag  58320
atgaggtctc actaccttgc ccaggctggt cttgaacccc tgggatctca agcaatctcc  58380
ctcctcatcc ttccaaagtg ttggattaca ggcgagagct gcagcgcctg gcccctttca  58440
ctttcttaac agtatctttg aaaagcagct gatttttcac agggtgttgt aattaattta  58500
attagctcca cactgtggct ttgaaaatct tccgtaagct ctagcgccag acacatggat  58560
atttgcagaa tcttattttc tagagtcctg gaaattttct ttcctgtgag agagttgaga  58620
gcgataattt tagggtggtt attcatcttc agacacaagg agtaagaatg tagggagttc  58680
gtgactgtgt ttggagaggg gagagcatag cagtggtcta atgatcttct cagggttctc  58740
aaagggtgga cgagctgcag gttgaaactt gccttgcttt tagactgttg actgagtttg  58800
tagttaagca gataagtgcc aaaggagaag tcagggctga ctgattgcaa gtgatgattg  58860
aatactggcc ctcacaacca tctgtgaaaa gtctatttcc agaaattttt tttattttgt  58920
tattattatt attattattt tttgagacgg agtctttctc tgtcgcccag tctggagtgc  58980
agtgatgcaa tttcagctca ctgcaagctc cgcctcccgg gttcacgcca ttctcctgcc  59040
tcagcctccc aagtagctgg gactacaggt gccctccacc acacctggct aatttttttgt  59100
atttttcgta gagatggggt ttcatcatgt tagtcaggat ggtgtcgatc tcctgacctc  59160
gtgtccaccc gcctcggcct cccaaagtgt tgggattaca ggcatgagcc actgcgccgg  59220
gcccagaaat atttttaaga agagattttt gaaaaaccct tgttttcatg atgggaggat  59280
atgaaaagca gtgttttgaa atctcctcct tagatcctga tactcggaac tgtcgattct  59340
cccattttca ttttctcctg gatagattgt acacttgtgc cttggtatct tcaatgattc  59400
caaaaccccc ctggggatcc agtccctgac ataaaatggc gtagtgtttg tacataacct  59460
acatacatcc tcctgtatac tttaaatcat cttggtctgg cagtgtggct cacacttgta  59520
atcccagcac attgggaagc agaggtggga ggattacttg agcccaggac ttcaagacca  59580
gcctgggcaa catggcgaga cccccatctc tacaaaaaat ttaaaaatta attgggtgta  59640
gtggcatgtg cctgtagtcc cagctactca ggaggctgag acgggaagat tgcttgagcc  59700
agggagttcc aggctgcagt gagttatgat cgcaccacta cactccagcc tgggcaacaa  59760
```

agaaagaccc catttccatt taaaataata ggggccagat gcagtgactg atgcctgtaa 59820
tcccagccct ttgggagcct gaggtgggcg gatcatcact tgaggtcagg agtttgagac 59880
cagcctgccc aacatagtga aaccccatct ctactaaaaa taaaaaaaat tagctggaca 59940
ccatagcgcg cctgtggtcc cagctactag ggaggctgag gcaggagaat cacttgaacc 60000
tgggaggtgg aggttgcagt gagccgagat tgcgccactg caccactcca gcctgtgtga 60060
cagaatgtga cagaatgcgg gcacatcacg agatcaggag atcgagacca tcctggcgaa 60120
catggtgaaa ccctgtctct actaaaaata caaaaaaatt agccgggtgt ggtggcgggc 60180
gcctgtagtc ccagctgctc aggaggctga ggcaggagaa tggcgtgaac ccagggggcg 60240
gagcttgcag tgagcggaga tcgtgccact gcactccagc ctgggcaaca cagcgagact 60300
gcgtctcaaa aaaaaaaaaa aaaaaaaaaa aagacagaaa aagaaaaaac aaaagacgtt 60360
tagctttcct gggtgaccca gtgttgcagg gattggccat ccttggtata aggcatagga 60420
tgtgcagggt agcaggacag cagagtgggc agtgtgtggg gtttctttca ttgatagggt 60480
ggttcccagc actcggggtc agggcttgct tgtagaagtt tctgaaaagt tgcagtcatg 60540
tttcatttct ttctcccccct acctagcaca tgccaggcca cacagcatag tacgatggtt 60600
tggaaccagg cttaacctgt tagtagccgt ggggctctgg gcaagtccac tggagttctc 60660
cgggatctgt ttcctctttt gtaaaatggg aaccaaaagg tatcacaggc tgggcatggt 60720
ggctcacgcc tgtaatccca gcactttggg aggctgaggt gggtggatca cctgaggtca 60780
ggagtccaag accagcctgg ccaacatggt gaaaccccgt ctctattaaa aatacaaaaa 60840
ttagccaggt gtggtggctg gtgcctgtaa tcccagctac tcaggaggct gaggcaggag 60900
aatcacttga acccaggaag cggaggttgc agtgagccga gatggcgagg tggcgccact 60960
gcactttagc ctgggtgaca gagggagact gtctcaaaaa atcaacacca aaaccaaacc 61020
caacatgtat cacaagctcg ttgtgaggat cagagaagag gatacgggaa tgataaacat 61080
ggtagttaca ttgttgctag cattgtagtt atattgcagc tgtacattgt gacctattgt 61140
agctactgtt atttctttga ttaagtttag caactgaaat tttttttttt tgagacggag 61200
tcttgcactg ttgcccaggc tggagtgcag tggcgggatc tcggctcact gcaagctccg 61260
cctcccgggt tcacgccatt ctcctgcctc agcctcccaa gtagctggga ctacaggcgc 61320
ctgccaccac gcctggctga ttttttgtag tttaagtaga gacagggttt catcttgtta 61380
gccaggatgg tctcgatctc ctgacctcgt gatccaccct cagcctccca aagtgctgag 61440
attacaggtg cgagccactg ggcccggcca acaactgaaa tatttaacat acaataaaat 61500
gcacatggcc ggggtgcagt ggctcacgcc tgtcatccca acactttgac aggctgaggc 61560
aggcagatca cttgaggtcg ggaatttgaa accagcctgg ccaactacta aaaatacaaa 61620
aattagccag acgtgatggt gcgttcctgt aatcccagct actcaggagg ctgaggcagg 61680
agaatcgctt aaacccagga ggcggaggtt gcagtgagcc aagatcaggc cattgtactc 61740
cagccggggt gacagaagga gactctgtct caaaataaat aaaataaaat aaaatgcaca 61800
gatctgaagc attgagttca atgaattttg acaaaaaata tatgcacctg tgtaaccacc 61860
actgaaaaca aaatggagga cattgcctca tcccagccct ttccagtgaa ttcccagtac 61920
ccccgggaat gaggtgttac aatgattact atcaccattg ttgattatta ttgtttagtt 61980
tggttttatt gaagaagcgg gtagagaaag aaatagttag cctcatgcaa aaagtagggc 62040
atatgagagc ctgagatatg gcttaagaag agtattgttt gagaagtttg gctgagtgtg 62100

-continued

```
gtggcttatg cctgtaatcc cagcacttcg ggaggctgag gtgggagaat tgcttgagct  62160
caggagttca agaatagcct gggcaacata gtgagactct gtctctataa ttaaaaaaaa  62220
aaaaagagac agaaaagttt aaggtatgtt ggcaggtagt cctagatggg gtttactgcc  62280
aggagcagtt aggattcaaa gagcaaaaat ttgagggtaa aaggatgtat ggcaggttgt  62340
tggtggtgga tatatagccc caacatccag tcactttaaa ctcttatcaa gacaacacag  62400
ggccgggtgc cgtggctcat gtctgtaatc ccagcacaat gggaggccaa ggtgggcaga  62460
taactggtgg tcagcagttc gagaccagcc tgaccaacat ggtgaaaccc tgtctctact  62520
aaaaatacaa aaattagcag ggcgtggtgt tggggacctg taatcccagc tactcaggag  62580
gctgaggcag gacaatcact tgaacctggg agatggaggt tgcagagagc agagatcaca  62640
ccaccgcact agagcctggg cgaaagagag agactccatc tcaaaaaaaa aaaaaaaaaa  62700
aaaaacaaaa aacaccacca aaaacaagac aacacaaagc gtttgaacga aaacagcatt  62760
tgcagatgca aattcaggat ccgaaattaa ttcttccccc ctctttgctg agctgccaga  62820
atgttccaag gagatccctc ctttccagtt tcctccgtgg cgcacaggct gtgccgagta  62880
agtgggcaat tgtgagtttc tggaaatcag cgagctggtg tggctcctgg ctcctggctc  62940
tggccaaggg agttggcttc cctgtgtcca tgccaggagg ggaggctgga ggcttctaaa  63000
ggccgcagct ccgctgtaga cacgcgcctc cttggcactg gctttgttga aatctgtccc  63060
tagatagtct ctcttctgca cagacctctg aggtttttcc atactgcaaa gggccttgct  63120
gcaggaggaa cagtctgacc taatctctcc tagaggaggc cttgagctaa tattttttat  63180
ttttttttta tttttgagat ggagtctcac tgtcacccag gctggagtgc agtggtgcaa  63240
tctcagtcca ctgcaatctc cgcctctcgg attcaagcga ttctccctgc ctcagcctcc  63300
caagtagctg ggattgcaga tgcccgccac cacacccggc taatttttgt atttttagtc  63360
gagatggggt ttcaccatgt tggccaggct ggtctcgaac tcctgacctc aggtgatcca  63420
cctgccttgg cctcccaaag tgctgggatg acaggcatga agcacctcac ccagccaagg  63480
taatatttct gaaaggtgga gtaccatgct atgagctaga cacttggtgt ggtttatcct  63540
gtcatcgcct cagtgacctc accaggtgga cactgttagg attcctaatt tgcagaggga  63600
gaagttgagg ctgacagaaa ggtcagcact gtgctcaaag tgatccagct gctaccaaga  63660
tgaactgcag gctttgctct gagctcacag cctgacctca gtctagagct gggaatcttt  63720
ctctccctca ttgctacacc tgatcaatta ctgagtccca tccctttaac tgcttacatg  63780
gccttcaaat ccatcttccc tacctaagct gcccattcat tgacctgtgc cttctgtcca  63840
tctgctgaga gccaggtgct gtgcgagcct ctgagaatgt ggccgagaac aatatggata  63900
aaagttctga gccgggtacg ctgactcatg tctgtaaacc cagtgttttg ggaggttgag  63960
gcagaagact tccttgaagc caggagtttg aggccggcct ggacaacaca gcaagacccc  64020
atctttacaa aaacaaaaac aaacaaacaa aaaaaagaaa aagaaaaatt agctgagcat  64080
ggtggcactg acttgtggtc tcagctactt gggaggctga ggtgggagca tcacttgact  64140
ccaggagttc gaggctgcag tgagccatga ctgtgccact gcactccagc ctgggcaata  64200
gagcaagacc ctgtctcaaa aaaaaaaaaa aaaaaaaaaa gactgtaaat gtatcctcca  64260
gagtaattct tctttttcat ttttcaaaag catccttgct ttgtttatgc ttccaaaagt  64320
ttaaaaactg tagctaagtt ccaagaaaga aaaagggaag caaaggaaaa ggaaaacaca  64380
gacccagagg ccctttatgg ggttgattgt atgtgaagtc cataaattga tggagagaag  64440
gagcaccttg gcagtattta cttgtactct cctatgtcat ggatttcctc tccattttcc  64500
```

caagggttct ttcctgttct tagaaatgtt ttgtgatttt gcttcagaca cagtttgtct 64560
acttcttgta agcattgttc ttagattgct ggctttatat ctatcactcc cttgctcatc 64620
tgcccatcca tctatccatc catccatcca tccatccatc catccatcta tccatccatc 64680
catccatcca tccatccatc atccctccat ccacttgctc atctgcccat ccatccatcc 64740
atctatccat tcatccagtc cattcaccac ccaccatcta ttatccatcc atccatccat 64800
ccattcatcc actcacccat tcatccatca tccatccact cacccatcca ttcattcagt 64860 caccccttcat ccattcactc acccatccat ccatccactc atccaatcac ccatccatcc 64920
atacatccac tcatccattc atccatccat acatccactc atccattcat ccatccatcc 64980
acccacccag acgtccatcc atccatccat ccatccatcc ttctgtctac tctgccaaca 65040
atccacacac ctgtccctcc atcccttcca accactcacc cagcaatctt ctcatccatc 65100
tatccaccca tgcatacatc cacttattca ttcatccatc cctccaccca cccattcatc 65160
cacccatcca tgtgtccatt catctctcca tctatccgtg tgtctatcat ctaatataag 65220
ggagatgttt tgaagtatta aaagtgatta ttttgtagca taggggacag ggattgtgtt 65280
ttctttactt actgctacct tattaaatgc ttactagttc taaaagccct gcaattgatt 65340
cccttcaatt ttccaactct ataattgcag catctgcaga taatgatgac ttcttgcctt 65400
ttgccaataa ttagaccagt tattgctgtt aaccttgtta tggcaggaac ttccagaaca 65460
gtgttcagtg acgcagctga atatggtcag cccagtctca tttctgattt gagtggaatg 65520
cctcaattgt tttactgcag aggataatta tataattgtt aatactcttg accttcctgt 65580
ctttagcctc actgagtaaa tggggtgtga tcatgaaatc ttgattgtct catagatgca 65640
agagacataa acgacatttg tctgtgtata atgacagcag atttattttg ctaagctgtt 65700
aagctgttaa aataagcctt taagcccccg cctcaatttt ccagcagagt ggaatgttat 65760
tttgttgctt ctggccaagt gtcgatattc attttagggc aggtcttcat ggaaagtctg 65820
ctggactata ggtctggata cttgccggac cctgtgtcat cactaaagtt agggtgcgtt 65880
tcagaaccac cctgtaccac agtgaagagg gacaaatggc cttagggagc aggacccatg 65940
ggggccctct ggggctgttt cttgtgccct gagagaggcc ctagatttgg gacagtctga 66000
tttacctccc ctcccttttt tttttctggg tgatgctacc ctggtttctg tgttgaaata 66060
tgaccctagt gtgaaggtcg cggtctcaga ccatcttgtt tctggtatgt taagaaacag 66120
aaaaacacct tttaggacac aatgttaacc attgaggata catatcagtg ttctggaaaa 66180
acaaaaacaa aaacaaaaca atctgtaccg cgactgtggt tttcatcagg gtgggctgcc 66240
tttccgatcc ataaccctgt gtggcttgat ggagaacatg ttttgtaact tgcaagggca 66300
tctgcaatag ccgggtcctc ttggtgaaag gggaggaccc acattaggtc taagctggct 66360
ggagtcgatg caaaactctc acatgctttg gaaaaagcac gtgatctttc gacgagaatg 66420
caaatgttga ccgggtgcag tggctcatgc ctgtatttgc agcatttggg gagactgagg 66480
caagcggatc gcttgagtcc agaagtttga gaccagcctg ggcaacttgg tgaaacccca 66540
tctctacaaa aaatacaaaa attaaccagg tgtggtagtg catgcctgta gtcccagcta 66600
cttgagaggc tgagttgaga ggattgcttg agctcaggag gttgaggctg cggtgagctg 66660
tgatcacgcc actgcactcc agcctgggca acagagccag accctgtctt taaaaaaaaa 66720
aaaagaatgc aaatgtttgc ttgattattc agctggtatt tgacacacag ttctttgttc 66780
cagagggact gtccagcaac aaatagtgaa ttcgttaatt tttcacacca aacctattga 66840
aaataaccag aaaaggtata tgctggaaaa ctcagtgttc tagaaacatt catgtttgcc 66900
atcccaagag caaaagtcat ggaatgcctg atgcttagtg ttaagaggaa ggaattccac 66960
acagcctgtg gctagctttt cttatttcat tggtgtccaa gacaagattt gaactgttta 67020
ctaaaggaaa ttagcatcat aagtctcctc tggcatatat ttccagcatc caagtggagc 67080
tgctgagatc ttgctcaaga gtagcaaaat tggcaggagg aggagggcat tagtttttac 67140
atcagcttaa agaatttttt ttatcagcca tttttgcaat ttggaaacct gtttggagta 67200
ggggtatatg gagatgaaat tgggctgttt ctaggattca cctcctcctt caggcatttt 67260
tttttttttt ttggaaacag ggtctggctc tgttgcccag gctggtgtgc agtggcgtga 67320
tcatggctta ctgtagcctt gacctcttgg gctcaagcaa tcctcccact tcagcttccc 67380
gagtagctgg gaccacaggt gtacaccatc gcacctggct aatttttata tattttttgt 67440
agagatgggg tctcactatg ttgccaggga tggtcttgac ctctcaggct caagcaactc 67500
tcctgcctcg gcctcccaaa ttgctgggat tacaggcagg agccactgca gttggtactt 67560
agagttgttt tttttttttt tttttttccc ttgagacgga gtctcactct gttgccaggc 67620
tggagtgcag tggtgcgatc ttggctcact gcaacctcca cctcctaggt tcaaaccatt 67680
ctcctgcctc agcctcctga gtagctggga ctacaggcac acgccaccat gcccagctaa 67740
tttttttttg tatttttagt agagatgtgg tttcaccatg ttggccagga tggtctcgat 67800
ctcttgacct cgtgatcctc ccacctcggc ctcccaaagt gctgggatta caggcgtgag 67860
gcaccacact aggccgatcc tcagacattt ttaattttcc ttttttagtg ttacagccag 67920
ccatttgaaa aatgagactt ccccctaacc ttgtgtcaaa ctcagagacg ttgtcatctt 67980
ggctttgatg tggtggagga gaggggcttc tcattccggg acggggtttc tccacctggg 68040
gcctgcggat actggggctg gattgttctc tggggtgggg ccgtcctggg cactgagggt 68100
gctagcagca tccctggctt ccacccattc catgcctgga gcgccgcccc cgaggcatgg 68160
caaacacaaa tgtctccaga cactgccagg tgtctcctgg tgggcagaat cgcctccatt 68220
tgaggacccc tggaccaggg tgctggaatg ggggtgaggg gcactctgca attattctct 68280
gctctttttt tgaggggggg gaaatggaaa ccaagagccc atcatcagcc tcgtggctct 68340
gtggtttgac actgccatgc taccgacaaa aaccacgtcc ctagacttgg gggaccaagg 68400
aatctggagg aatatgatga tagtcattta atgaaggtgg gtttatgtat tactcaagtg 68460
ctgggctggg gagtcaggac atagccacag ggaagaaaac agaaaggtcc ttccctcttg 68520
gaagcccctc ttgaaacacc taattggtga catggtacac tggagaatca gagagtgtca 68580
ctcaagcatt ttggcttggt ggtggggcgg gggtggcggg tcaggcactc aagcacccct 68640
aagctgatct ggagaaagtg tcggggaagg ggaacattag cgtttctccc tgaggaatca 68700
tcttacacct ataacggcaa ctggcccaca gtaacattga tggagcaagt gtcttcttgt 68760
ggctcggccg ctcaatagct gtgtgaccat gggcaggtta ctgaacctct ctgtgcctca 68820
gtcttctcct ctgtaaaatg ggaacatcta ggattgttgg gggaaataaa tggttaataa 68880
ttggaatagt gctgggtgca taggaaactc taagtgttac acagcatgtg gccacaacct 68940
cccctctccc ctcctctctc ctctttgctg ctgccctgct gccttaatgg gatactcccc 69000
tctctgtctc tgtctgtctg tctgtctgtc tgtctctctc tcatcccctt ttctttcctc 69060
tgttccccca cccccacctc tgatgcagtt tggaccaagt tttcttcagc cagctaattt 69120
agagacaaga acctggatat ttattgggcg tttgggggac ttccttacag ccctaggtct 69180
ctgtgaaaag ggccctggat tatctctgca aaagcccacc tgctattggt tagccaggac 69240

-continued

```
tgtctccact ttcagacacc agcttcatcc aaacactctt tgctgtattt ataaccacgg  69300
tgcatttcct cgggacgcac atcttacggc ttcttggccc cttcgcccag ggtgcactgc  69360
ctggaccatc gccctccggc agagacagtg tctttctttg tatgttctcc ttcctctggt  69420
cgagatgtgg cttggtcacc tggagtgggg ccgtcggcaa gtcgcctggg cttcgtggag  69480
gctcgctgcc cccatggcgg aaagctcggc cacacaccct gatgtctcga cacctttgag  69540
ttgcccatga atgggttttc agagcttccc gtgtttactt cgctgcacgc ctctgtttgt  69600
gctctgggga aattcttggc agaggaaaag ccaattggaa aacagccctg cttggtgtca  69660
gggcttgagg ttgagggaga aagactgaaa cggagatttg catgagctgg tttgagcatg  69720
tcacaagact ttgtctttaa aaaaaaaaaa aaaaaaattg gcctggtgtg gtagctcact  69780
cctgtaatcc cagcactttg ggaggctgag gcaggcggat cacgaggtca agagatcgag  69840
accatcctgg ccaacgtggt gaaaccccgt ctctactaaa aatacaaaaa ttagctgggt  69900
gtggtggtgt acgcctgtag tcccagctac tggaggctga ggtgggagaa cggcttgaac  69960
ccaagaggga gaggttgcag tgagccgaga tcatgccact gcactccagc ctgggtggca  70020
gagcgagact ggtctcaaaa aaaaaaaaaa tttttttttg ttccagtcta ttctggtggc  70080
ttagaggagg gaagatggga aattttgggt ttaatagagt aatatccatc aggttgaggg  70140
ctttgaagca cctgggaata tccataagtc actactgagc accagctgta tagagttatt  70200
gagcatgtat tgtctcccag gcacatggtc ctcacaacaa tcttttcaca gagctaggat  70260
ttgaacccac agtctctctg gcttcagaac cctagctttt cttgctatac tctgccttac  70320
agaggaaggg aacttttgta ctgggttttg aagggtgaat aggagttcaa tgaagaagca  70380
gcacattctg tgctaaattt ggcttcctga tcctcctaga attggccaga agccaatatc  70440
tggaggccaa aattgggtca ctagggtgac caactcatca cagggccctg gattatctct  70500
gcaaaagccc acctgctact ggttagccag gaccatcaca gtgtgcccag gtaaccctgc  70560
gtttcacccc aaagcagaat tttacaccag agcctggaca ccagttgaat tttctttaac  70620
tcatttctgt caatggttac ctccaaaaat gctcccttgt gtctttatgc tgggcttctt  70680
tctctagata cttccatttc ttggtttggg tgaaaatcaa atgaggtaat taatgcttgt  70740
gacatgtaaa gtgtagtgag tggcacatgg taacctcttt agttttagcc agttggtttt  70800
ttttgtttgt ttgtctttga gacagagtct cactctgtca cccacgctgg agtgcagtgg  70860
cgcagtctca gctcactgca acctctgcct cccaggttca agcaattctc ctgcctcagc  70920
ctcccgagta gctgggatta caggtgcacg ccaccacact gggctaattt ttgtattgtt  70980
agtagagatg gtgttttgcc atgctggcca ggctggtctc aaactcctga cctcaggtga  71040
tccgccctcc ttagtctccc aaagtgctgg cattacaggc atgagccaca gtgcccagac  71100
agttttagcc agtttttcac tggcctccct ctttgccttt tttgcaaggg agctggcctc  71160
cctgtccctg gagtaagcaa acttccttat acctatagct tcctctaagg aagcgtagtt  71220
acctacagcc tggccctccc caaggacaca gctgtttcct ccaccaagag caaggagtgg  71280
acataatcac tgccaaatag ggaagccagg ctggacaccg tggctcatgc ctgtaatccc  71340
agcactttgg gaggccgagg tgggaggatc acttgaggcc agggattcaa gaccaacctg  71400
ggcaatgtag caagaccctg tctctaaaca aataaaaaaa ttagccagct gtggtggccc  71460
atggctgtag tcccagctac tccagaggct gaagcaggag gattgcttga ccgcaggagt  71520
ttgatgctgc agtgagctac ggtcacacca ctgaacacca gccaggacaa cagagcaaga  71580
```

```
ccctgtctct taaaaaaaca aaaaaataag gaagccagat gggtgctggg tgtacgggac  71640
acatgtcaaa agtcagacct ctatctgagt aaggaaacag gttcagagtc aggattaaag  71700
accaagacag cttgaggtca tcagaggcca ggaatttcca tacaggctgc ggtccaaagt  71760
gccaagctgg gctagataga tgttggggaa gagtctctgt cgccctcttt ccttccccgt  71820
taatgctatc agctgagcat gggtcactcc tgattttttt tttttttttt tttaccgagg  71880
acataggctc agagtgtctt ctagctttca acccacccca gactctgact tagcctttcc  71940
caaatggtgc tgtgcagaaa aatgaaaaaa ttgctaggag gatcatgtgc ctggtggata  72000
gtacatgctt gatagctgta aacagttggt gctcaatata tcgtggcttg tggatcttcc  72060
cagctgcttc agaaccccaa gcctgctgta taattgtact tgatcccgac aacagccctg  72120
ccagatgggt gttactctga ttcctgtgtc ctggtaagtg gacggggggc ctggagtagc  72180
tgaattgcct agagaagggg acatagctag aaaggaaaag ttgaaaccca gtgtgatgcc  72240
agagtccatg caaactttat cctgaaagga gggatctctt tttttttttt tctgagatgg  72300
aatctcactc tgtagcccag gctggagtgc agtggtgtga tctcggctca ctgcaacctc  72360
cgcctctcag gttcaagcga ttctcctgcc tcagcgtccc aagtagctgg gattacagac  72420
gtgtgccacc acaaccggct catttttgtg tttttagtag ggacggggtt tcgccgtgct  72480
ggccaggctg gtctcgaact cctgacctca ggtgatccgc ccgcctcggc ctcccaaagt  72540
gctgggatta caggcgtggc cactgcgccc agccttcttc ttcttcttct tctttcctcc  72600
tcctcctcct cctcctcctc cttttttttg acagagtctc actctattgc ccaggctcga  72660
gtgcagtggc acaatctcag ctcactgcaa cctctgcctc ctgggttcaa gagattctcc  72720
cacttcagcc tcccgagtag ctgggattac aggtgcgcaa caccacagcc ggttaatttt  72780
tgtgtttttg gtagaaacgg ggtctcgcca cgttggccag gttagtctca aactcctcac  72840
ctcaagtgat ccgcccgcct cagcctccca aagtgctggg attacaggcg tgagccactg  72900
cgctcggcct ggtgaagacc ttcttgccgg tggggactct gcagagtcct gacagggagc  72960
agggcatcac atggcgaggg agctgagagt gtcagctcag gtctctcttc ctcttcttat  73020
aaaaccacca gtcccactcc tatgataaac cattaatcca tgaatggatt aatccactta  73080
tgaggacaca gccctttttaa tcacctctga aaggccccac ctctcaatgc tgccacatga  73140
ggaattacat ttcaacatga gttttggagg ggacaaatat tcaaatcata ctattatgtt  73200
accagtaaaa tttaaaatat aggaataata attgccgatg tgtggcagac ttaccaaata  73260
ctagaccctg tgctaagtgt tttatatcta ttattttatt taattttctt ggtcactgca  73320
taacatatgc tctgttagtc ccagtttttc gaatgggcat aacaagaccg aacctaccta  73380
gagttggcac aagttgtaaa aataggatcc gtggccgggc acagtggctc acacttgtaa  73440
ttccagcact ttaggaggcc aaggcgggag gatcacctga ggtcaggagt tcgagaccag  73500
cctggccaac atggcgaaac cccgtctcta cttaaaatac aaaaattagc caggcgtggt  73560
ggcgcgcctg tagccccagc tcctcgggaa actgaggcag gagactcgtt tgaacccggg  73620
aggcggaggt tgcagtgagc caagatcgca ccactgcact ccaggctggg cgacagagcg  73680
agactccatc tcaaaaataa aataaaacaa aaaaatagga ttcacttttg ccaccaactt  73740
gaaaaggagg caaacacaag attactcatc tctggagagg aggcattcag atttgcctac  73800
tcagcattcc tggagataga accagatttt gcatgggtta gaatcatatt ttgcttggga  73860
agccactcag acctcattgt gtggactcta ttcccagagc cagcttcctt tattccttca  73920
gactcttatg attggctcag gggaaggcac atgactcaga ctgggccaat cagctttctt  73980
```

-continued

```
aattcctcca gcctccatga ttggttcagg ggtgggcatg tgaccccaga aggttccata  74040
agattcagtt ctgggacttt agtgggagtg atagagagat ttttccttgc taaatcttcc  74100
ttgctgtgaa gctataatcc aggtgccacc atgtagagac cacgtgtctc agacttctga  74160
caccatagaa ggaagcagga ctgcgaaaag gaaagggaga gagatggggt ccccatgaca  74220
tcatttgaca cctggatcta gctgtacctg aaagtgtcct tgtcctatga cttgttagtt  74280
aaatgagcca gcaatcgttc ttttcttttt tttcattttc tttctttccc ttccttccct  74340
ccttccctcc ttcctttcct ttcttttcct ttccctccct ccttccctcc ctcccttcct  74400
tccttctctc tctcttccct cccttccttc cttccttctc tctcccctt ccctccctcc  74460
ctcccttcct tccttccttc tttccttcgt tccctccctc cctccttcct tccttccctc  74520
cctcccttt ctctctctct ctctcttctt tctctctgta taactgagct ttctattctc  74580
acaaactgaa agaggtcttg ctaatccaag gcatgacaat cagagcaaca tgtgaagccc  74640
aaagagctgc agagctcccc tccatggctt ccagccccgg gggtggtcag tgaaagtaac  74700
tggagcccgg agcttcagag gccagtgtgg aggttggaaa ggttgtggtc aggagagagt  74760
aatatatctg gtccctgcaa cagacacccc tgcagtttta tcctgaatcc tgggtaattt  74820
ccccaggtcc tgggaagcct aataaagccc ctactcagat gttggattgc aagtcctttt  74880
tgtttgtttg ttttttaaat ccactttaaa tatgtctgaa aaccacacac agagtgactg  74940
ctgcacagaa gagcgaatgg ttcatgcctt cttctttgct gccaccaaca agtcagttac  75000
ctacttctct gacatgggac ccttggctgg agctcactgg ctgccttcct gccacctgta  75060
agcctcggca cttgctgttc cctctaccta catgcttttc cctgtgatac ttcctcatac  75120
gatttcctca gattatcttt gctcaaacaa caggcaaggg ctgggcctta atctcacacc  75180
tgtaatctca gcactttggg aggccaaggc aggtggatca cctggggtca ggagttggag  75240
accagcctgg ccaacatggc gaaaccccat ctgtacaaaa aatatacaaa aaattaacca  75300
gatgtggcag cgggtgcctc tgatcccagg gacttgggtg gctgaggcag gagaatcact  75360
taaacccagg aggcagaggt tgcagtgagc cgagatcatg ccactgcact ccagcctggg  75420
caacagagcg agacttcgtt tcataaaaac aaagaaacaa acaaacagaa aaaaacaaca  75480
aaacaaacaa acagaaaaaa ccaacaaaac aaaaaacaag aggcaagaag ttcagtgtgc  75540
agaatctctg agaaaaaccc atggttgtta accccaggtc tgccccttt gagcagggtg  75600
acattaggca actgatttga tttctcttag atgaaatttc ctcactccct gcctattcaa  75660
ccacagtact gaggacattt ggagctggat tatctctctg gtggcagctg tcctgggcat  75720
tttagggtgt ttactagcat ccctggcctc cccccactag ataccagtag cactcccacc  75780
ccacactggt tgcaacaacc agaaatgtct ccaagacact tccacgtgac ccccgggggg  75840
tcagaatttc tcccctcccc cctgtgtttt cctatggagg tggaacgtgt ttatttcttt  75900
gctcaccgtt ttgcaatctc tcttccccg ccacaaggca gggactcttc tatctccgtc  75960
accatcccat cctcccacag tggagacagc tctggggact ctcctgagca gcagattctt  76020
gggtgccaca ttctgttcca ttcctgggga atttatctct ttactgagtg atgggtacat  76080
gagaactttc tgtgtcaccc ttgcatcttt tctgttttgt ttttacaaaa gaaaaaaaag  76140
aaggccgggt gcggtggctt acgcctgtaa tcccagcact ttgggaggcc aaggcgggtg  76200
gatcacgagg tcaggagatc gagaccatcc tggctaacac ggtgaaaccc cgtctctact  76260
aaaaatacaa aaaattagcc aggtgtggtg gcgggctcct gtagtcccac ctacttggga  76320
```

ggctgaggca ggagaatggc atgaacctgg gaggcggagc ttgcggtgag ccaagatcgt 76380
gcccactgca ctccagcctg gcagacagag cgagactccg tctcaaaaaa gaaaaaaaga 76440
aaaaagatat cactcgatga ctgctaccga aacattctgt ggctgggaga ggaaaatacc 76500
agaaagggtg aatgtggtcg gttgaatgat gcctctccct tcccccagag atgcccacat 76560
cgtaatccct gtcacctgtg aatttggtac ctcacttggc acaaggctct ttgcagatgt 76620
gattaagttg aggatcttga gacgggggga tgatcctaga ttatctggtg caccaaatgc 76680
catcgcaggg atccttttca aggaaagagg gaggcaagag attgaaatgc tacggccaag 76740
aaaaaggagc tgccttaaaa gctggattct ctctggagcc tccagaagga accaaccttt 76800
gtaacatctt gattttagcc ctgtaagact cattttgggc ttttcaccac caaaactgta 76860
agaaaatagg caggccatga tggttcatgc ctgtaatgcc agtactttgg gaggccaagg 76920
tgggacgatt tcttgaggct aggagtttga gaccagtgtg ggcaacatag caagacccca 76980
tctctacaaa aaaaaaaaaa agaagaagaa gaagaagaaa aattagctgg gcttggtggc 77040
acacatctat attcccagct acttgggagg ttgaggtggg aggattgctt gagcccagga 77100
gttcgaggct gcagtgagcc atgattgcac cattgcactc cagcctaggc aacagagtaa 77160
gatcccgatg caggagaaaa taataaatgt atgtcgtttt acatttgtgg gcgtttgtga 77220
cagcagcaat gggaaatgga tacggtgaga aacccagcac ctgggcctgg aaacccccctc 77280
tgggcgggtc tctagccagg ggccaacagg agtcagagca gggccttggt gagaggtgga 77340
tacggggccc cagcatcctg atggccttgc tgtggcttct ggggacacct gcagtggctc 77400
cattacaccg tggcaatttg ttccttccca gaccccctgg atacaagggg cctgcatttt 77460
cgaacccaga gcccggggac atcccccgtg gttccctgtt accctctgga tgtctgtcct 77520
gctactatgc acctctcccc aactcctggt acacagtggg agttcagggg ccgtctcatt 77580
tgtaccgcat aacatcacgg aggtccaaga cgccatgtaa tattctgttt aggatttcag 77640
aggcacagtc agttacatcc atcttctttt tgtctttgag acagagtctt gctctcttgc 77700
ccaggctgga gtgcaatggc acgatctcag ctcactgcaa cctctgcctc ctgggtttaa 77760
gcaattctct tgactcagcc tcccaagtag ctgggattac aggtgcacgc caccacacct 77820
ggctaatttt ttgtactttt agtagagacg gggtttcacc atgttggtca ggctgatcta 77880
gaactcctga cctcaggtgg tccactcacc ttggcctccc aaagtgctgg gattataggc 77940
gtgagccacc gtgcccagcc tgcttccatc ttcttagcca cttttccctc aggtgagacc 78000
atgagattag gaacctgttt caattcccgt cggaatttcc caacagagct ggggctttgt 78060
gattcgaata tgttcagaga aggaagcaga aggaagcaga aatgaaggat gttatcagaa 78120
aaggagactc agggttgggt gtggtggctc acgcctgtaa tcccagcact ttgggaggcc 78180
aaggtgagtg gatcacctga ggtcaggagt ttgagaccag ccaggccaac atggtaaaac 78240
cctgtctcta ctaaaaatta caaaaattag ccaggcgtgg tggcatgcgc ctgtaattca 78300
agctactcgg gagactgagg caggagaatc acttgaaccc gggaggcgaa ggttgcagtg 78360
agccaagatc atgccactgc actccagcct gggtgacaga gcaagactcc atctcaaaaa 78420
aataaataaa taaataaata aatacaggaa aaggaagctc ggtagttttc aggggctgct 78480
ggcgtttcca agctttaggc atttgcttt gagtcttttt ctgtctttcg agtcatcctg 78540
aagtggaacc gagagaggac tgagtgggtg gagggggtgg tggtggggac ggctgtctgc 78600
tctgctggaa ttgagagtct gggagatcat tgtggtgttt ttggagtgat tcttaacccc 78660
agatatagac agtgacacaa ggggcataaa tacgaggaac agtgaccttc cctggtgtcc 78720

-continued ttgtttgaag catttgacca tctgggcaag gcctgggagt gtctgaactg gctggtgctt 78780
ccatgaacaa gcacagactc agagcccatg gtcctgggtt cgaatcctag ttcttccact 78840
tctttgctgt atgacctttg tctacaaaaa ataaaaattt agccaggcac agtggcgtgt 78900
gcctgtagcc ccagctactc gggaggctga ggcaggaaga tccattgagc ccaggggtcg 78960
aggctgtagt gagctatgat tgcaccactg cactccagcc tgggcaacag aagcagaccc 79020
tgaagaaaga aagaagctgg gaagacaggg aagaaggaag gaagaaagga gggagggaga 79080
ggggaaggaa ggaaggaaaa aaaagggagg gaacaaggaa ggaaggaagg aggtggggac 79140
ggagggaaga aggaaggaag gagggaggga aggaaggaaa gggagggagg ggagggagga 79200
gggagggagg gaagaaaaaa agggaaggga aggaactttg gaactactga acatctctgt 79260
ttcctcatct ataaaaagag ggataagtca tcatcatatc ttcctctatg gtcattgagt 79320
ggatgaaata agacagcatt tgcaaatccc ctaatgcata cctggcccct gattttgttc 79380
cttgggctgc agcgatgata gaggtttaaa acctccaaac gctgtgttga aatctctcac 79440
gtggacaacc agcccaccag cagagaatgt catttttcca tcctgggtaa acagggtaga 79500
gaagaatgag gacctcaggc caggttagag agacctcgct tggtgacctt gggaaggctt 79560
ttaactttta actttaatgc taacatctgg ttccctccag ttaggcagtc ggcggcctag 79620
ccgtcttgtc ttgaagtttc tcttgccttc catcatgggt ttatttgttc agcaaatgtt 79680
tatggagggc cagcacaggg gggaataaga actagagttc tgggaggacg tgtgaagaaa 79740
caagttccga gccccaggga ggaaagaggt cattgcctcc ctctggggaa aatgtctctt 79800
ctcatacctg gttcacttct taaatggaat ttccccettc agatgagtaa ggcgtttaat 79860
cacaaagaga aaacaccttc atcacatagc catccttaaa aggcatttat tgtgaagctg 79920
gttcatagac ttctcgccca ggttgctaac agccaacctg tctgggtttt gggaagttaa 79980
agtgtctgta tcccatttcc tttttttttt tgagacaaag tcttgccctg tcacctagcc 80040
tggagtgcaa tggcacaatc tctgctcact gaaacctctg cctcccgggt tcaagcgatt 80100
ctcctgcctc agccctcccg cgtagctgag attgcaggcg tgcaccacca cgcctggcta 80160
attttttgta tctttactag agatggggtt tcaccatgtt ggtcaggctg gtctcgaact 80220
cctgacttcg tgactcacca gcctcagcct cccaaagggc tgggatgaca ggcgtgagcc 80280
actgtgccca gccagttctg actttttaac ttgtgatttg acttttcctg tctgaagtct 80340
ttctctgctg gacgtgagtt gttgaaggtg ttgcttttct ttgtagacaa ttagaggcgc 80400
tcatgcactg ggctatggac aataatactt tgaagatgtg caaatgattt gcaacctttg 80460
ttgcataaat tatccctctg agatgctgtt tggcttgata aataaaggac ctgcaagaga 80520
gaatttatct tgagcattcc ttgggggaga gaagcaaagg ggaagtgaat gctgcataat 80580
aattctttgc atactttatg gagggtgggt tcctgcagtg ccctgtaggg tttttttgttt 80640
gttttttttt ttttttttg agatggagtc gctctgtagc ccaggctgga gtgcaatggt 80700
gcgatcttgg ctcactgcaa cctccgcctc ccgggttcaa gcgattctcc tgcctcagcc 80760
tgccaagtag ctgggactac agacgtgctc caccacgccc agctaatttt tgtattttta 80820
gtagagacag ggtttcaccg tgttagccag gatggtctcg atctcctgac ctcgtgatcc 80880
gcccacttcg gcctcccaaa gtgctgggat tacaggcgtg agccaccgcg cccggccccc 80940
tgtagtggtt taaagcatct tcactgttat tctaagcctc acattttaaa cagagctgaa 81000
aaaggactct aattgctggc ctgggatcct tgtgtgctgt aggaattcac tgagggggcg 81060

```
gggctggaga gggctgctag agggtggtac agaagcagat ggaactttct ctctggctgg  81120
acacagtagc tcacacctgt aatcccagca ctttgggagg ctgaggttgg tggatcacct  81180
gaggtcagga gttcgagacc agcctggcca acatggtgaa gccccgtctt tactaaaaat  81240
acaaaaaatt agcaggacgt gggggtgggt gcctgtagtc ccaactactt gggaggctga  81300
ggcaggagaa tcgcttgaac ccgggaggta gagcttgcag tgagccgaga tcatgccatt  81360
gcactccagc ctgggcaaca agagtgaaac tccatctcaa aaaaacccaa aaataaattt  81420
aaagaaaaat tttctctctg attctgcctg cctgcctgct agactggaag caccatgagg  81480
tcaaggtcca cgatgtcttg tcgctattga agcgcctcca aaacatggca gaccctcagc  81540
aaatcttgga cagatgaatg ggcattcgat tcaacatgtg tctgctaggt gggagctgag  81600
cgggaatcgc agggcttggg tcccggggat gatggggaat ggcagtgtga ctgtggggaa  81660
gccaggggaa tggggtgctg gagcccccaa agctataaat cagggcctga tgaacagaca  81720
gacagatgga ccaacttaac catttcagcc ccatcggctt tgatgatttc cctctggctc  81780
tggcaagagt ctcgctcacc aagtggttct caccctaggg tgggtctgga tatttctggg  81840
gacatctgtg gttgtcacac gtcggggtgg ggggagatgc tcctgacatg gagtgggtgg  81900
aggccaggga tactgctcag caccctgcaa tgtacaagac ggcccctccc cagatgaaga  81960
tccgactctg aataccacca gtcctgaggc tgagaaaccc tactttaaga taacagtgat  82020
gggggaatta tccaccccag agtctgagtc tgtgacttgg gaaacggccc cggcattacc  82080
aggtgttgaa ttcgtgagaa tacaaggaga aggcgtgtag cccgtgaccc agtcctgccc  82140
cagacaaacc gatattccct ccaaagctct atttggcaga agaagtgttt tcgttccctc  82200
ttgcctgtgg tatctcccct gataagcgtt gtggattgtt ccagaccgtg ttgacgggga  82260
cagcttcctt ctccgcggct gccggccctg accctgcagc tttcagtctg tgggagtaga  82320
gtcagctgtt gagcagttta ctctgtccct gtgtcaatgg gattgtgcat gttttggttc  82380
ctgaggggtc attgatggtg cacttttctt ttgttgttag tcaatttaat ttgttactaa  82440
taataaaatc tggaacttac ctgaccccaa aggcccaggt cgttaagaat gcttggtgga  82500
atgcacgtcc ttttcaaata ccggctcctt tggaaaacac agaggatgga gtgaaatcct  82560
tacctggatt gtactggcag tgggatgaca gcgtcacctc ctgaaaatgg aatgtagctt  82620
attgctaaat aagacagcgc agtgcctccc tcgcacctgt catcttggtg cttagagagg  82680
ccaaggtggg aggaattctc gaggccagga gttcaaaacc agcctgggca atacagaaag  82740
agcctatttc tactacaaat ataaaaatta gctgggcatg gtgacatgca cctgtagtcg  82800
cagctacatg ggaggctgag gtgggagaat cgcttaagcc caggaagtcg aggctgcagt  82860
gagctgtgac ttgctactgc actccagccc atgcagctga gcgagatcct ctttcaaaca  82920
aaccagccaa ctaacaagca ggccccaagg ggacaatttt tctggaatta cctgattgta  82980
tcaagaacag tttgatcaac acctgtaatc ccagtacttt gggaggacgg atcacttgag  83040
gtcaggagtt agagaccagc ctcgccaaca tggtgaaacc ctgtctctac taaaaatata  83100
ataattagct gggcatggtg gtgggtggct gtaatcccag ctacttggga ggcagaggca  83160
ggagaattgc ttgaaaccgc gaggcagagg ctgcagtgag ctgagactgt accactgcac  83220
tccagcctgg gccacagagt aagactctgt ctctctctgt ctctctgtct ctgtctctct  83280
ctctccatat atacatatat atttatatat ataacttatc ttgaagacgg ttttggcacg  83340
ccttaacttt tatgccagag gccagtgcct tgcttgtgtc accctggttc caagaatctg  83400
catagttttt cccagcccat tctacagaca gggaaactga ggaccaggca cactaggttc  83460
```

ccctccagga gtcgcacagc gaggagaaag tggagccatg acttgatgcc aaacactgag 83520
actccagaac ccatattttc tcagctctta ggtttttgtc aatttcctaa atttgtgtgt 83580
gttttagtgg ggctgagttt ctcctgttaa tttgtttatg gagaggagac actcttgttt 83640
actttttttt tttttttttt gagacagagt ctctgttgac caggctgcag tgcaatggct 83700
caatctcggc tcactgcaac ctccacctcc tgggttcaag cgattctcct gcctcagctt 83760
cccgagcaac tgggattaca gtcacacacc accacacctg actaattttt gtatttttag 83820
tagagatggg gttttcccat gttgatcagg ctggtctcaa actcctgacc tcaggtgatc 83880
cacccgcctc ggcctcctaa agtgctgaga ttacgggtgt gagccactgc gcctggctct 83940
tggcgttctc ccttagtaat acttcttggg ggtcattttg aatctctgtt tcttctgtgg 84000
tcacgttcat ttggaattta cttattcaac ccacaaccaa tagacatttc cagccctttg 84060
ttagtataaa cagaacttct ctttgacttt cacagcgttt ttgttctgga ggtgctatcc 84120
ttgattgcta agacacccac gacattgctc ttggaattgg agtagggtgg atgaaatagt 84180
attcaaagat gggggtggtg caaatgttct gtatttcaac ctgtacatta gtcaagtgtt 84240
atttttaccc tcatgtacat ctattatgga ataaaataca tgactttggc caggcgtcat 84300
ggctcacacc tgtaatccca gcactttggg aggctgagac gggaggatcg cttgaatcca 84360
ggagttcgag accagcctgg gcagcatagc aagacccctt ctctaaaaaa aaaaaaattag 84420 ctgggcatgg tggtgtgtgc ctataatccc agttactcga gaggctgagg caggaggatc 84480
agttaagcct gggaagtcga ggctgcagag agctgtgata ggcagcctgg gtgacagaga 84540
aagaccctgt ctcaaaacaa aaaacaaaac aaaacatgac ttttatggag ttgagctcaa 84600
cgtttgcata cacatgagga gcagaagctg gaggtttcaa ataaatatct ggcttctgca 84660
ggctgcctgg agagaggtga gagcgatgca ttggtcaccc agcctggagt gcagtggtgt 84720
gatcacagct cactgcagcc ttgaccttct gggcacaagc aatcctcctg cttcagcttc 84780
ctgagtagct gggaccacag gtgtgtgcca ctatgcccag ctaattttat ttatttattt 84840
agagatggaa tcttgctctg tcgcccaggc tggaatgcag tggcacaatc ttggctcact 84900
gcaacctctg cctcctgggt tcaagcagtt cccatgcctc agcctcctga gtagctggga 84960
tcacaggcat gtgccactat gcccagctaa tttttttttt taatggagtc ttgctctgtt 85020
gccaggctgg aatgcagtgg cgccatcttg gctcactgca acttccaact cccctgttca 85080
agcgattctc ctgcttctgc ctctcgagta gctgggatta caggcacgcg ccaccatgcc 85140
cagctaattt ttgtattttt agtagagagg gggtttcgca tgttggccag gatggtctcg 85200
atttcctgac ctcgtgatcc gcccacttcg gcctcccaaa gtgctgggat tacaggcgtg 85260
agccactgcg cccagcctaa tttttgtacc cctagccgag acagggtttt gccatgttat 85320
ctaagctggt ctcgagctcc tgggctcaag cgatccaccc gcctgggcct cccaaagtgc 85380
tgggattaca ggtgtgagcc actgcgcccg gccacagctg ttgttttctc actggcttga 85440
gaattgttct cttaagctgg tcaaggttat gacggtttgt gtggcctgtg cacgtgtgtg 85500
tggtcaaatc ccatttttct aaagcaaagt ttctatttgg gtatctgctg tttaattttt 85560
cagggatttt ttttttccgg ttgctaagga aagtacatta aattttatct ttgtatcctg 85620
tagaactctt tgtgaataat acacggccag agggaagata ggctgaggaa acagatagga 85680
aggaagttca aggggggat ttctatgtga gaaccaagaa acacctttga tctttagatt 85740
tcaaagtggg aagttcaagg tgaggtgggc gtggaattag gagtaaaccc aagaagagcg 85800

-continued agtgggcggt tcctcctggc agccacagaa tagttacgtg gcatgaggtc agtagcatct 85860
cagagggtgt tgttgtcttt gacttagatg agttccaaga agcagaagtt cgtgagccaa 85920
acacgaggtg gttttctggg gggtacaagg gctggaagag gggccagctc ttaaccacaa 85980
atccctttcc atgcccaagg ccaagctcct tgtaactctt ttctttcttt gcctccctcc 86040
ctccctccct ccctccttcc cttccttcct tccttccttc cttccttcct tccttccttt 86100
ccttccttcc ttctcaaaca aggtctcact ctatcaccca ggctagagtg caacggcaca 86160
gtcatagctc attgcagcct caaacccctg tgctcaagtg atcctcctgc ctcaggccct 86220
caagtagttt ttaaacttgt ttgtagagat gggtcttgct atattgccca ggcttgtctc 86280
gaacttctgg tcttaagcga tcctcctgcc tcagcctccc aaagtgctgg gattacaggt 86340
gtgagccact ggcccggccc attctccttt ctttagccag gctagggaga cataagtggg 86400
gaaactcatg ttgtttttg agatggttgc tttattctcg tgatattttc cctctttcca 86460
acttccttga gccctcccca gcctcctctt agtgtctgtg tgtgggtgag ggggctttgg 86520
tataccttct gctttgggtc tcattcattt taatttttta ttttgttttg ttttgttttg 86580
ttttgagatg gagtctcact ctgttgccca ggctggagtg cagtggcacc atcttggctc 86640
actgcaacct ctgcctcccg ggttcaagcg attctcctgc ctcagcctcc cgagcagctg 86700
gggattacag gtgcatgcca ccatgcctgg ctaatttttc tatttttagc agagacaagg 86760
tttcaccatg ttggccaggc tggtctcgaa ctcccgacct caggtgatct gcttgcctca 86820
gcctcccaaa gtgctggggt tacaggcgtg aaccaccgtg cctggccacg ggtctcattc 86880
attttagttg gagcccaaat tcactggtgg ttcaagttcc caatcattct cggcattcta 86940
taatcacagg cctcagagag taatgctccc aatggccctc aaattatggt ttccttagga 87000
ggctattaaa tcttgatttc tgagaggaaa attggggatt ttgtgttttc ccttttagac 87060
ttgagtgttc tgttactgtg gatgagctct tctagaaact tccaagcagt ttcaaagggg 87120
atttagatgt catcaggaag tgtggttgac aacgtgatat ttgggcttta gaaaaacagc 87180
gtgtcacccg ttttatttat tccttgatga ctcttttttt gtttgttttt gttgtggtcg 87240
ttgttgttga gacagggtct cactctgcca cccaggctgg actgcactgg tgcaatctct 87300
gttcactgaa acctcctcct cctgggttct tgcaaataga cagtcccatt tggtggtgac 87360
gggagacagt gacagatcat caagcattag attctcataa agagcgtgca acccagatcc 87420
ctcgcatgca cagttcacaa tagggttcac gctcctagga gaatctaatg ctgctgctga 87480
tctgacagga ggcgcagctc agatggtcat gcaagcaatg aggagtgact gtaaatacag 87540
atgaagcttc catcgctcgc ccgcccctcg tccactgctg tgcagcctgg ttcctaactg 87600
gctggtttga aactagactg ggcaacatgg ccaaaccccg tctgctcaaa aaataccaaa 87660
attagctgag tgtggatcac aagtgtgtgc ctgtagtccc agctacttgg gaggctgagg 87720
tgggaagatt gagtgagccc aagaggtaga agctgcagtg agctatgatc acacccactg 87780
cactccagcc tgggttacag aatgagattc tgtctctcaa ctccctgagg ggtgggggac 87840
ccctggttta atccatccaa ccctctcttc ccatgaaata aaggaagttg tgagtgctat 87900
tttgtgcgtc atcccctcca gtattcaagt cagcccaagg tacttcgatg gttcccgtct 87960
gcacatgggg aaaccgaggc acagaaagca gactcatgtg accaggaagt agctgtgtct 88020
gctcgaaact caggtcgacc tgataccata agtccttgca ctccacgtgc tggctattga 88080
agctgtggct cgcaggtctg atgggagagc ctcagacagt gtctcactct gtcacccagg 88140
ctggagtgct gtcatgcagt cataacccac tgcagctttg acctcctggg ctaattgatc 88200
ctcccacctc agcctcccga atagctggga ctacaggtgt gcaccacaat gcccacctaa 88260
tttttgtatt atctgtagag atgggcgtgg ggggtgtgag gggtcttgcc atgttgccca 88320
ggctggtctt gaactcctga cctcaggtga tcctccagct tcagcctccc aaagtatcgg 88380
gattacaggc atgagagagc cactgcagga agccaagaga gcagatttgg acaatgtaga 88440
atttctccac gctcctccta ctgtccccat cttaggcctg gctactgcgg gactgacagg 88500
catggctggc tgtccatccg ttccttagtt tgattgcatg gcagacatga ggaaggaagg 88560
tgagaactga gctagaaagt tggcatttgg tgctctggtt tctcaatgca agaaagtaac 88620
actttggctt ttatagaata accttctgag gaaattaaca acccgggcgt ttcagccccc 88680
tgtgaacttg attggagcat ggtcacaatt tgtaacgaaa tgtgcttgca tgcccagtgc 88740
taaagatttc tctctgtcta ccctctaggc tgtggaaagg tctgttctaa ccattagctt 88800
gtatctggag ctcagatggt gccggacact ccgtaggagc tcagatctgt tgatagaagc 88860
cactagagaa tgggacaagc aacaggaggt gttttgctgc ctagtaaact ttttttgaga 88920
tgaagtttca cttttgttgc ccaagctgga gtgcagtggt gccttctcgg ctcaccgcaa 88980
cctctgcctc ctggcttcaa gcgattctcc tgcctcagcc tcccaagcag ctgggatgac 89040
aggcacccgc caccatgccc ggctaatttt ttttgtatat ttagtagaaa tgaggttttg 89100
ccatgttggc caggctggtc tcgagttcct gacctcaagt gctctgcccg cctcggcctc 89160
ccaaagtgct gggattacag gcgtgagcca ctgcgcccgg ctctacccat ctttcttaca 89220
tgatgatgtt cagcagccag cctgataggg gagcattgtt tgtccttttt ttccttattg 89280
cattttcccc gcataggtgc cagggctcag tagcataaat ccaggtagaa ctgggaagtt 89340
ccaggtatct gggctgtttg ctctggtgga caaagagcag ctgcaaggtg ggtcttgatt 89400
agccagtgaa gtctgaggat ccagagggaa acttattcct ttcttttgtt gaaatcaaca 89460
tgagcaggaa atggatcttt cccccaatca gagaacttca catgtttttc taatagaata 89520
gcagtgtctg aggtatatac acggggagtg gcccccggg aaaacgaggc catgaggctc 89580
ctggcatgga gatgacacac gaagactctc gtaacttata gaggggaaaa taaagcagtc 89640
attccaggct gggcatggtg gctcacgtct gtaatcccag cactttggga ggccgaggca 89700
ggtggatcac ctgaggtcag gagttcgaga ccagcctggc caacatggtg aaaccccaac 89760
tctactaaaa ataaaaaatt aaaaaaaaaa attagttggg catggtgctg ggcacctgta 89820
atcccagcta ctcaggaggc tgaggcagga gaattgcttg aacccgggag gcagagattg 89880
cagtgagccg ggagcctgta atcccagcta ctcaggaggc tgaggcagga gaattgcttg 89940
aacccgggag gcagagattg cagtgagccg ggagcctgta atcccagcta ctcaggaggc 90000
tgaggcagga gaattccttg aacctgggag gcagagattg cagtgagcca agatcacacc 90060
actgcactcc agcctgggtg acaagagtga aactccatct gaaataaaat aaaatataaa 90120
agttaaagca gtcatcctgg cttttaggaa cccgcagaat caggaggtaa gctaaaagtc 90180
gtctcccttt tgtcacgatg gaatgtgaaa taggtgcatt ttccttctga cttatgattc 90240
tgtttcacgg tgcctctgca gaaattcagt acgtccccat gggcacctgt gtccttcagg 90300
agttgaggaa attttctcca ttccttgtcc ctgtccctag actctgccag ctcgtgcatg 90360
tagaagctcc cgggaaaact gtcaacctgt gcacattcaa gaccgccata tacttgttat 90420
tgaaaagcca tcagtcatgt gagcagaact tttttatggt tgagattgtc cccagggaaa 90480
cccgccttgc aattcagacc ttccacggag atcgattcca aactctcatc ccgttcccac 90540

-continued

```
ttcctcgttc ccatggaggc tgcggttctc tctctctgtg ccgcttacag attgtcatac  90600
ctatttccaa aaatgacaca gaaaacttca acgtgtggct aaatttgaac agagaaaaat  90660
aagcaaagaa ttcaaggcgc gaggcgtttt cagggagaga gggagagctt ttgcatggtt  90720
tgaagggatg atctttaatg agttgagggt cacctagaat agaattaaac tgtagagagc  90780
aaattgttgg aaatgcaagg agaaacttcg gagaagactc caacacagcc tggatctggg  90840
agatgagact caggtaacaa aaagtttgaa taacatggtt aataagattg tggtaacaga  90900
taggactgaa ctttgcactc tgcaaacaat atacatttta aagtgctctt ggaatagtta  90960
gaaaaatcaa tcatctgtta aatctgaaaa aaaaaaaaaa aaaacaacaa aaccccaccc  91020
caaaccaata cattccaaaa aagcagacat tgtacgggtt ctaatctctg gctgcaagta  91080
agcataactg gaattaattt ttaaaagctt aactgaacaa gcatgtaaga gagactccta  91140
ccacttgata attaaaaaga aaatgaaaac caaaaaaaca aaaacaaaaa aaccgaaaag  91200
ggctgggcac catggctcac gcctgtaatc ccagcacttt gggaggccga ggcgagcgga  91260
tcacctgagg tcaggagttc gagaccagcc tggccaacat ggtgaaaccc cgtctctact  91320
aaaagtacaa aaattagctg agggtggtgg cgcataccct gtaatcctag ctacttggga  91380
ggctgaggca ggagaaccgc ttgaaccccg ggggcagagg ttgcagtgag ccgagatggt  91440
gccattggac tcttctagcc tgggcaacaa gagctaacct ccatctcaaa aaaacaaaaa  91500
acacaaaaca aaacaaaaaa acaaccaacc cctaagtctt aagttggagg atcgaaacac  91560
tgcaaggata gactatttga agatgacaat gatgtgaaca tggagacaaa ggcagaggtt  91620
taaatgatta tagaggaaat ttgcttgata atttattata tgaatataga gagaaatcac  91680
aaaaatgaga tgatgaatat tggaaataat aagcacagac gaactgatta gaaaacaaat  91740
agaactgaca aaatcaaaaa gctggatctt ttagagagat gctgctcagt agggtggcca  91800
caacccacgt gaaaattaaa ttaaaaattc attttctcag tcgcacgagc caagtttcca  91860
ctgcttaggg gccatgtatg gttagtgact actgaaatgg atagaacaga tacagaactt  91920
ttccatagct gctgaacgtt tgttggacag tgctgtttta gagggaggaa tcaataaaac  91980
agaaaaacta agacaaagga gggggagaga acaaatattg tagataaaat taagaatgaa  92040
ggcctagcgc ggtggctcac gcctgtaatc ccaacacttt gggaggccga ggcgggtgga  92100
tcacgaggtc aggagatcga aaccatcctg gttaacacgg tgaaaccccg tctctactaa  92160
aaatacaaaa aattagctag gcgtggtggc cgcgcctgta gtcccagcta cttgggaggc  92220
tgaggcaggg gaatggcgtg aacccgggag gggagcttg ccgtgagccg agatcgcgcc  92280
actgcactcc agcctgggcg acagagtgag actccaactc aaaaaaaaaa aaagaatgaa  92340
aatagatgta atttatttat tattgattga ttgattgaga cagagtctca cttggtcgcc  92400
caggctggag tgcagtggta caatctcagc tcactgtaac ctctgcctcc agggttcaag  92460
cgattctcct gcctcagcct cccgagtagc tgggattaca ggcgcccacc accacaccca  92520
gctaattttt gtatttttag tagagaagtg atttcaccct gttggccagg ctggtcttga  92580
actcctgact tcaggtgata cacccgcctc ggcctcccaa agtgctggga ttaaaaacag  92640
atgtcattta aatccataaa aaattgtaaa gacagctcta ctaacaattt tggaaatatt  92700
aaaaataact tcatttactg attcaagtgt tacttttatt tagcttaatt gtttctcttt  92760
accagaaatt gaggctctga atttgcccca gagaatgggt atgccattct ctctcataag  92820
ctgtactctc ttattatcag taatttctaa atagcctgta aaatttatat ggactcaaaa  92880
tgcaggaaac atcaataggt tgaaactcaa caacttgtaa aaagttactc ctgtacttaa  92940
```

ttgcataaaa tgtgtattgc ctacatgaat gagaataaaa acttccaaaa tgccccccaac 93000
aaacaggggt ttttgcacct tgccatgagt agctttctgg agcaagccgg agtggttaga 93060
gctgtgactc ggcaaccaca aacacaacca tttttgtgtg gaagtgtggc tcttcagcct 93120
ttttttttt ttttttttt tgagataagg tctcactctg ttacccaggc tggagtgcag 93180
tggcgtgatc ctagctcact gcagcctcaa cttcctggac tcgagcaatc cttctgcctc 93240
agcttcccaa gtagctggaa ctacaatcat gtgtcatcat gcccagctaa gttttatttt 93300
ttttaatctt taattttttt aagaaataga gatgaggtct tgctatgttg cccaggctgg 93360
tcttgaactc ctaggctcaa gcaatcctcc tgcctcagcc tccccattag ctggaactac 93420
acttgtgtat catcatgccc agctaatttt taattttta tttattattt ttttaaagag 93480
ataaggtctt gctctgttgc ccaggctggt cttgaactcc taggctccag caatcctccc 93540
acctcagcct ccaaagtgca gcctctatat cttgaactcc acacctcaaa cccagattgt 93600
ccacatgtga gcacctgtct ttttggtttg ctgtttctct cgtgagttgt atccagttgc 93660
ccaaggtgga aagttgggcg tcatccagca ggtaagtcct gacacctcca cctccccgat 93720
ggcttcagaa gccagcctct tcttttctgt ttcctctgcc tctcaacttc ctcatccatc 93780
taccataagc cagaaaaatg acccccaaat gtgaatccga tggtgttctt tctgcctgac 93840
atctttcttt ggcttctgct gtggggtaaa gtccaagccc cttggttccc tgtctttcct 93900
ctctggtcta atcttctatt cctctcatcc tgtactttgc ccttcatcaa ctctgaactg 93960
tttatagttc tctgaacata gcccgagtga ttcacacatt tgcatgtact gttcctctcc 94020
tgctgtgata aagggacagt cacctaatcc ccgcccctcc gttgcatttt tttttcccta 94080
caagatttat tatgcaccta ctgtgtgtat ggctctggga tgctgtaata agcaagacag 94140
acacatcttt cccttcacgg ggcgtatgtg tctcgtgcat actgggaggg cagggacagg 94200
gtctccattc atttctgcat tccaatgcca agagggtgtc agatctgggt gggtcgaggt 94260
agggaacagg taaacataac tcacagtgtg atgccgtgtt acagccaggc tgggttcctc 94320
acgcctgtga tggcagcgct ttggggagcc aaagtgggag gattgcttga agccaggagt 94380
ttgagaccag cctaggcaac atagagagac ccgctctcaa aaaaaaaaaa aaaaaaaaaa 94440
gctgtcgcag tggcactctc ctgtagtcct agctccttgg gaggctgaag cggaaggatc 94500
acttgagccc aggagtccta gactgcagtg agctatgatg gctccattgc actccagcct 94560
gggccacaga gtaagaccct gtttcaaaca aacaaacaaa tttaaaaaat caaacaaact 94620
cccactcccc caaactccat accacaccct ctcctggtct ctctgggaga cctggattcg 94680
agttctggca gagctggtta ttggcaaagt agcccctcta tgcctcggtt tctccaattc 94740
taatggtgat gattgcttga ataattgagt taatatgacc tcattgatgg attggaccgt 94800
gtgtgctgca aacagattac acactttaaa gtgtattcat gcctgtaatc ccaacacttt 94860
ggtagactga ggcaagagga tcacttgagg ccaggagttc taaaccagcc tgggcaacga 94920
gtccccatgt ctacaaaaaa atagaaaaaa ttagccaggc atagtgatgc acgcctgtag 94980
tcccagctac tcgggaggct gaggtgggag gatggcttga gcccaggagt ttgaggctgc 95040
agtgggcgat gatcacacca ctgcactcca gcctgaggcg acagagtgag accccccccc 95100
caaaaaaagt gtatttatgg gggtgaatgt taaatgagaa tgtccactcg ctgccttggt 95160
ttactggaac tgcaaattca atggggacac acaagttttc aaatgcatgc ggaatactgg 95220
ctggaggtta ccccaaaaac gtagcctgtg gattttaaga atgtatttat gagtatggtt 95280

-continued

```
ctcgttttct gggtgagtgg tgggtgagaa tagagggtgc actggcccgg cgagttcgga  95340
gatgcggacc ctcccccct gcaatgtgag gaattttgct gtgtgaccct agtgagccgc  95400
tgcacctttc tggacccctc ccgagggagg cctggggtca gggggcccct cggcagtccc  95460
gggagctgcc acgcggtgac ccgatctcct cccgggcaca cgcccagcgc cgcgcgcagc  95520
ctaagccacc ccggtggatg cttgatgagc ccttgcaagc tcggtttctc cttttcccta  95580
gctttttcca aagttccatc cgtggcagac tcgacctgcg gggtctgcag ccacgagggg  95640
ccctcccagg gcgccctttc ctctggccgg gaccgcccgg cggcggccac tgcccgagcg  95700
ccagtctggg gagcggagcc cggcgcaccc ggggggcggg gccagcgccc ctgcagcacg  95760
cccgcccatt ggctgagcgc gagggcggcg ctgcggccgc cgcaaccgcc ggggccggat  95820
tccccggagc ggagtgcgcc ccgggctttg tgctgcgctg aggcctccgg ctcgaggggg  95880
cggagccttg agcgcctagg gctccctccc tcgcccccat gggcacacac gcagacacgg  95940
gcacacacgc agacacacac acacgcccat catggacaca cacacacgct cgcccaccat  96000
ggacacacac acactcccac catggggaca cacacacact cccaccatgg ggacacacac  96060
acacacacac acacacacac actctcactc tggaaccgac caatcctggg gctgcacaga  96120
cacacacgcg cacacactct ctctcgttct ctctctctct ctctcgttct ctctctctct  96180
cgctctctct cccactctgg aaccgaccaa tcctggggac acacacacac acacacacac  96240
actcccactc tggaacctgc caatcacaca cacacacaca ctcccactct ggaacctgcc  96300
aaacacacac acacactccc actctggaac ctgccaaaca cacacacaca ctcccactct  96360
ggaacctgcc aaacacacac acactcccac tctggaatct gacacacaca cacacacaca  96420
cacccaaaca cacacactcc cactctggaa cctgacacac acacacacac acacacacac  96480
acacccccac tcccactctg gaacctgcca atcctggggc tgctctagcg aggagacccc  96540
tgggaccccg cctccttccg ggcctctgcg tgcgcagtat atctcctaag agatccgcag  96600
catggagagg gcccgccccc gtggacggac tcactccctc cccactcact cactcactcg  96660
cttactcact cactcactct ctctccgaag agaagaagcc tgcggctccc gaagcgggaa  96720
ggccctctgg tactctgttc cctttctagc ctctatatgc gccgtatgtc tccaaagagc  96780
tgcgcagttc tattccaaag gcgtcatcgc gtgtggggcg gtattgtcag gcaaggaaaa  96840
ggggcgcttc cccgcttcaa ggacacgcgc tcctgcggtc gtcgctgctg accacgaagc  96900
tgtcaaaagt tcacctcctt ggctgccccc aacccctgcc cctttgccat taaatcattt  96960
actagattcc aactagagga atttggctcc ggggactcga acctctgagg tcagggtctg  97020
gggccagtgt gggagagaaa ggccttgaat ggaaacaaaa taaattactt taaggagttt  97080
ataaaactca cacttatagg gagagccgcg gggccctgtg gtcaatgtac cagcaggccc  97140
atgacgcaac tgttccgttt ggaaatttct ggaaagcagt aatttttgga atcataaatc  97200
ttgagtattt ttttttaaa ctttggaaag gtttttaaac tttttttttt taagtttttt  97260
ttaaacttcg gaaagtttta agctttggaa agaatgtaac aaaatgttat taacatatgt  97320
ggagctatcg aatcatttaa tggtggtttc tgtattttct gttttgtttt ttatcacata  97380
ccttcttaat taagaaaaac ccaaactaat ttgaacttta aaagggaggc aaacaaaaaa  97440
gtgtcagagt gactggattt ttgtgcgcaa gtcatttaac aatgcagcgc tgcgtctcct  97500
atttctctgg cttttaacct tgctttggac aaattggtcg ctttttgttt tgatgtcgtt  97560
tcaagcttac ggaaaaattg caagattata tctagatcaa tcaattgttt acgttttatt  97620
ctacttgttt tattaccttt ctaatatatt tatgcacaca cattatatac atttttttcc  97680
```

cctgaactat ttgagagtta gttgcaggca tgatacatac tccttaattc ttcagtggat 97740
atttcctaag aacaagaaag ttctgaggcc aggcgtggtg gctcatgcct gtaatcccag 97800
cactttggga agctgaggcg ggcggatcac ctgaggtcag gagttcgaga ccagcctgac 97860
caacttggag aagccccgtc tctactaaaa atacaaaatt agccaggcgt ggtggcacat 97920
gcctgtaatc ccagctactc gggaggctga ggcaggaggt tcgcttgaac ctgggaggca 97980
gaggttgcag tgagccgaga tggtgccatt gcactccagc ctgggcaaca agagcgaaac 98040
tccgtctcaa acaaaaaaaa aaaaaaaaag aaagaaaaga aagaaagttc tcttacataa 98100
tgatggtact ggtgccgttg tcaaaatcag gaaattaaca ttgatacagt attttaatcc 98160
aatgtcttct ataatcttat ctgttgtctc aatattgccc tatatagatt ttttttccta 98220
ggcgaaggtt ccaatctagg atcacacttt gcatttgaat gctgctgtct cttaagtccg 98280
cacaattcct cagttttctg tgtctttccc aacattggct tttatttatt tatttattta 98340
tttattttta ttttttttg aggcggagtc ttactctgtc acccaggcta gagtgcagtg 98400
gtgagatctt ggctgactgc aacctctgtc tcctgggttc aagtgattct cctgcctcag 98460
cccccaagta gccgggatta caggcatgcg ccaccacacc cagctaattt ttgtgttttt 98520
agtagagaaa gggtttcacc atgttggcca ggctggtctc gaactcctga tctccagtga 98580
tcttcctgcc tcagcctccc aaagtgctgg gattacacgt gttagccacc acacctggcc 98640
aacattggca gttttgaaga gcacaggcca gttattttat cgaatgacct caagctaggg 98700
ttagtaatat atggaaagaa agctacacaa atattttgtc tttttcattg cctcataatg 98760
ggaagtacgt gttgttgcct tgtcccacta ttgtgggcaa tgttacttga agtattttta 98820
actagaattt ttaagaagaa atacatttcc cgtaaggctc agtacccaag acatgcatat 98880
acctgaatga aaagtttccc acaacaagat ttactcttgc cattttctag tactgtggga 98940
tttttttcctt ttcttttccc cctgcaggag gggatgctgc tgggggctga ggacaatgct 99000
aaacctggat gtctcgagga caggggatgg ggtttttgtg tcatctatgt tctgatgctt 99060
tttcatttaa tacgagaaca ggtttcctat gatttggcac actgggacat tcgacatgtg 99120
tttgttgaat gaaaaaaaga aaaaagagaa atgctaacaa tttgttgaat agtccataaa 99180
agagcaaagc tggcctggcg cggtggctca cacctgtacc agcactttaa gaggccaagg 99240
cagacggagg tcacgtgttt gagaccagcc tggccaacat ggtgaaaccg cttctccact 99300
aaaaaaaaaa aaaaaaaaaa aatcagttgg tgtggtggcg tgtgcctgta atcccagcta 99360
ctcaggaggc tgaggcagga gaatcgcttg aacccaggac atgggggtta cagtgagcca 99420
agattgcacc actgcactcc agcctgggtg acagaaagag attttgtctc aaaaaaaaaa 99480
aaaaaaaaaa aagcaaagct attattaaaa cacactccac acttcacccc tgagccccat 99540
attgattttg taataaggca aagataattt ttttttcttt ttttgagatg aagtctcatt 99600
ctgtcgtcca ggctggagtg cagtggcacg atcttggctg actgcaacga ctgcctcctg 99660
ggttcaagca attctcctgc ctcagcctcc caagtagctg ggattatagg tgcctaccac 99720
cacgcccagc taatttttgt attttgaata gagagtgttt caccatgttg gccaggctgg 99780
tctcgaactc ctgacctcaa gtgatcttcc tgcatcagcc tcccaaagtg ctgggattac 99840
aggcgtgagc caccatgccc agccaacaaa gatgatttta agagaacctt tgtaaaagct 99900
ctcaccgatg cctgtcatta ttagaatatt tgggagtaga atcatgtaac tgatcaataa 99960
cattgtttac tgtctagcag aggcttttga aaaatgtatt tcctggctgg gcattgtggc 100020
ttacgcctat gcccagtttg ggagctcggg gagagcggat ctcttgagcc taggagttca 100080
agaccagcct gggcaatatt gtgagacctc atctctacca aatgtatata tacatataca 100140
aaaattagcc aagcatggtg gtgtacgcct gtagtcccag ctactcagga ggctgaggta 100200
ggaggagcac ttgaacctgg gaggcggagg ttacggtgaa ccaagatcat gccactgcac 100260
tccagcctgg gcgacagagt gagacactgt ctctaaataa ataaatgaaa gaagaagcta 100320
cttgaaaaaa atatgtattt ccaaatatat gtcagttttg acaggatagt acacatacat 100380
agtaaaaaat aaaaataaaa tagggcactt ttttgtgtcc ctttcagagg gacatatgtc 100440
ccatgtgtcc tccccctcc tgcccctaat ttttttgttt gtttttttat gagatggagt 100500
ctcactctgt cgccaggctg gagtgcagta gcgtgatctc agctcactgc aacttccgct 100560
ccccaggttc aggtgatttt cctgcctcag cctcccatgt agctgagact acaggtgcgc 100620
gacaccatgc tcagctaatt tttatatttt tcgtggagac ggagtctcac catgttggtc 100680
aggatggttt ggctctcctg acctcgtgat ccgctcacct tagcctccca ggcttagcct 100740
ccttagcctg ctgggattac aggcatgagc agaagaatct cttgaacccg ggaggcggag 100800
gttgcagtga gctgagatcg tgccactgca ctccagcctg agggacaaga gtgagactcc 100860
atctggggaa aaaaaaaaaa agaaaaaaaa gaaatactgc atcaaattgc acttgcctct 100920
tggtgcaaga ttcgttcctt tgctttgaac tgcctccctg aagcaaattg gtgtttctgt 100980
gactccctct gtctagggaa ggggtccttt agtggggaca ttgtctttct tggggagggt 101040
ccaccagagg actctgacac agcggtctcc tttctcctcc gtcaacttag ttagatttta 101100
gtccctgatc ttctcagcag tgtatagtga aaaagccacc gcagctgaaa gtttcaggaa 101160
gatgatagtt gcttctgtgt gctcacccag gagcttttgg gaggtttagg gagaactggg 101220
ggaaaattgg gaccagcagc tcaatgtggc tttgaagggg agacagcgga tggacacaga 101280
acttgcattt ttggagaggg gaggtctggg tagatgttcc ctacatacac agcagcactt 101340
gtgtgcaggt gtgagggagt gacagccccc ggacggtttg gcattttcct gcaagtctgc 101400
catcttgtct ggcagacata gcctgggctg ctgactgtcc ctaccccaaa ccagaatttg 101460
ggcaggaacg gacacttggg ctcattacgt gtcaatgagg gggatcaggt caggggcaca 101520
gggagaggaa agtcaacccc gtcctccact ggggctgttt ctcatcttgc atgacacgtg 101580
gctttcataa tgtcttcact ttgcggtctc tctcaccaga agaagctgct gttttgtggc 101640
tagttcatct gtgtcatgcc ctttccccag cctgggctgc ctgtgatttt tttcttttct 101700
tttcttttct tttcttttct tttcttttct tttcttttct tttcttttct tccctccctc 101760
ccttccttct ttctctttct tttctttctc ctttctttct ttttctttct tttttctttt 101820
ctttctctgt ctttcttttt ctttctcttt ctctctctct tatctttctt ctttctccct 101880
ctttcttttc ttttttctct ttctgtattc tttcttcttt ctctctttct ttccttcttt 101940
ctttctccct cccttcctgc ctctttcttt ctctttcttt ctccctcttc tttctttctc 102000
tctctctccc ctccctccct ccttccttcc ctccttcttt ctttttatct ctctccttcc 102060
ttccttcctt ccctccttct ttctgtcttt ctctttcttt tctctctctc ccttcctcct 102120
tccttccctc cttctttcac tctctctttc ttttctctct ctcttctttt taaagatagg 102180
gtcttgcttt attgcccagg ctggagtgca gtggtgcagt cacagctcac tgcagcctca 102240
aacccctggg ctgtagcaat cctcccacct cagtctcccg agtagctggg actattggtt 102300
tacgggtgtg caccatcaca cctggctaat ttttttattt ttgtagagac aggggtctgg 102360
ctattttgcc caggctagtc ttgaactact ggactcaaga gatcctcccg tgttagcctc 102420

```
ccaaagtgcc attacatgca caagccactg cgcctggcag gcttgtgatt ttcatgtgga 102480
gcttttcaca ttctgtctaa caatccgagt tcagaggaac cagtatgggg agcaagagta 102540
tgtggaaacg tccagcacca gtttagagga ctcccactca gctagggggt gcagtggcca 102600
ccccgagtgg cttttctttc ttttctttcc ctccttccct ccctccctcc ctcctttctt 102660
tctttctttc tttctttttc tttctttctt tctcttttct tttctttctt tttgagacag 102720
agtctcactc tctcttccag cagtggcaca atctcggctc actgcaaccc ccgcctcccg 102780
ggttcaagca attctgctgt ctcagcctcc caagtagctg ggattacagg cacctgccac 102840
cacgcctgta taatttttgt atttttagta gagatggggt ttcaccatgt cggccaggct 102900
ggtctcgaac tcctgacctc aggtgatcca cctgccacgg cctcccaaag tgctgggatt 102960
acaggcgtga gccaccgttc ccagcctcta tttttttaaa attgacaaat aataattgta 103020
tatgttacat atttatgggg taccatgtga tgttttgata tctgtttaca ttgtagaatt 103080
actaagtcat gccaatttaa aagctatcac ctcacatact tatcattgtt ttatggttaa 103140
aaatatctac atttttggca attttgaaat gtccagtgca ctattactta ttatagcaac 103200
cattgtgtcc aatacataac taaagcttat ttctcctaag tgaaattttg tagtttgatc 103260
aacatctccc tacagagttg gaaacacctg gaatgagctt atagtgttcg aaggatagtc 103320
ttcaaagaat tggttgggcg cggtggctca cgcctgtaat cccagcactt tgggaggcca 103380
agatgggtgg atcccgaggt caggagttca agaccagcct ggccaacgtg gtgaaacccc 103440
atctctacta aaaatacaaa aattagctgg gcgtgatgac gggcgcctgt aatcccagct 103500
actcaggagg ctgaggcaga gaattgcttg aacccgggag gcggaggttg cagtgagctg 103560
agttctcacc attgcacttc agcctggaca acagagtgag actctgtctc aaaaaaaaaa 103620
aaaaaaaaaa accaccaaag aacacaggtc agcatgttta tttaacccat tagtgaggga 103680
acagcaggat tataaagcca aaacatgtat agtcactgaa ataagaaggc agtgttagct 103740
gtgaggctgc ttaatgtccc ataggacaat aaaactgtaa tctttgggga tgattttttt 103800
cttttttttt tcggcaagga gagataggat ctcactctgt tacccaggct ggtctcgaat 103860
gcctgggctc aagcaatcct cccgcctcag cctcccaaag tgctgggatt acaggcatga 103920
gcctccatgc ccagctgaga gtatcttttc tctgagatga aaataatttg tagcatatct 103980
gtctgtaagt taactctaat ttccttgagt ctagttccta atagaaatag taaaatcggc 104040
caggcgtagt gggtcatgcc tataatccca gcactttggg aggccaaggt gggcagatca 104100
cttgaggtca ggagttcaag accagactgg ccaacatgct gaaacccagt ctctactaaa 104160
aatacaaaaa ttatccaggc atggttgtgg gtgcctgtaa tcccagctac tcaggaggct 104220
gaggcaggag aattgcttga acctgggaca cagagtttac agtgagcgga gatggcaccg 104280
ctgtacttca gcctggacaa cagagcaaga ctcggtttca aaaaaaaaaa aaaaaagtaa 104340
tagtaaaatc aattacaggt acatttaact agtgcaggtt gataaactat ctggcccatc 104400
acttgctttt ataaataaag ttttattgga cctagccatg cctcttcatg tacatatgtc 104460
tgtggctgct atcatgccat cgtggcagag ttgagtagtt tcaaccaaca ccatatgtcc 104520
tgcaaagcct caagtatttg cttgtggccc tttacagaaa aagttgacca actcctgtgc 104580
tgacaaatga aatagctcag ataggcctgt cagctagggc tccaacacag gattgcaaag 104640
tctcgcagcc tctggccttg tttgcaatgg ttggataatt tttcttccca ttgtctaggc 104700
cggaaggact tatgtgtttg agaggtttgt gttaggccat tgatgacgcc tcttttgaat 104760
```

-continued gaaagggctg accctctgaa gtggctccag cccaggaaac aagccccttc ctcttgtgtg 104820
tgtgtttcct tgccagagtg ctggaactcc gtgggtcctg gatcattgtt gtctgccttg 104880
tatattgctt ccttcaattg aatttcagcc ctcaggttcc cacagacaga tcagtgttaa 104940
tgatgttgat aattatgata attatagata ccctctgtag ttaatttcta tcaagcctaa 105000
aaatgtctct atcaaagaat ctgatgtgtt actgacgtca tcctgtttat ttcttgcaac 105060
agccttaaga aggaaggaag ggactcttat taacaatccc ccctcccttt tttttttttt 105120
tttttttttt gagatagagt ctcgctctgt cacctaggct ggagttcagt ggcacaatct 105180
tgactcactg caaactcctc ttgcgttcaa gcgattctac tgcctcagcc tcccgagtag 105240
ctgggattat aggcaagcac caccacaccc gactaatttt tgtattttta gtagagacgg 105300
gtttcaccat gttggtcagg ctggtcgtct tgaactcctg acctcaagtg gtccacccac 105360
ctcagcctct caaagtgctg ggattacaag catcagccac tgtgcttagc cctattagaa 105420
cttcctaata ttcttgtttt tttttttttt ttggacggag tctcactctg tcagccagcc 105480
tggagtgcag tggatctcag ctcactgcaa cctccacctc ccaggttcaa gtgattcttg 105540
tgcctcagcc ttctgagtag ctgagtagct gggattacag gcgcccacca ccacgcccag 105600
ctaatttctg tatttttagt agagtcgggg ttttaccatg ttggccaggc tggtcttgaa 105660
ctcctgacct caaataatcc acccacctca gcctcccaaa gtgctgggat tataggtgtg 105720
agcccccgcg cccagcccca agataatttt caagagtgat ccatgccata aggaaaatgt 105780
aatgagataa tgtgttagct tatgaatgga gcaggaaggg cgacttctgc tggggaagtc 105840
agggaagatc tgtgtaagga cctgaaggat gcaaaggagc aagtcacaag gggacaaggg 105900
accagggtgc tccacccaga acagcttgtg caaggtccta aggtagggct gagcctgggt 105960
gtgtgtgggt gggaggtgca gaaaggaggc cagcctggga gaagaattta gcaagactgg 106020
cagggattag accccccaag gcctgtaggg agttggcttt tattctgtat gcctgaactg 106080
tctcgtctgg gagacggtag tcatctgtgg ctagtaaaca ttggaattgt gtcaggcaca 106140
gtggctcata cttgtaatct cagcactttg ggaggctgag gtgggaggat cgcttgagcc 106200
aggagttcga gaccagcctg ggcaacatag tgagacccca tttctacaaa aaattaaaca 106260
cttagctggg cgtggtggcg catgtccatt attccagcta cccaagaggc cgaggtggga 106320
ggatcacctg agcccaggag attgaggctg cagtgaactg tcactgtgtc actgtacccc 106380
agaacctaag tgacagagcc agaccccatc acacacccaa aaaagaaatc gttacacatt 106440
ttatccatat gacaaaatat cacaagtacc ccataaatgt gtaaaatatt ctgtatcaat 106500
gtaaaacttt ttaaaaattt taaactgaaa ttaaaatgaa atgcagttaa aagttttgtt 106560
ccttggtaaa aattggagcc ctggtacact gttggtggga atgtaaaata ctgcagctag 106620
gctgggcaca gtggctcaca cctgtaattc cagtactttg gggggccagg gtgagtggat 106680
cacttgaggt caggagttcg agaccagcct ggccaacacg gtgaaacccc gtctctacta 106740
aaaatacaaa aaaattagcg ggtgtggtg gtgggcacct gtaatcccag ctactcgagg 106800
ctgaggcagg agaattcctt gaacccagga ggtggaggtt gcagtgagcc gagatcgagt 106860
cactgcactc cagcctgagt gacagagtga gactccatct caaaataaat tttttaaaaa 106920
agaataaatc ctatattatt ccacttatat gaggttccta gagtcatcag agtcacagag 106980
acagaaagta aaatgggatg tcgggcgcag tggctcacac ctgtaatccc tgcactttgg 107040
gaggctgagg caggaggatc acgaggttag gagttcaaga ccagcccggc caacatggtg 107100
aaaccccatc tctactaaaa atacaaaaat tagctgggtg tggtggtggg cgtctgtaat 107160
cccagctact ctggaggctg aggcaggaga atcacttgaa cccgggaggc agaggttaca 107220
gtgagctgag atcgcgccac tgcaccccag cctgggcaac aaagcaagac tccatctcaa 107280
aaaataaaaa taaaaaaaaa gaaaagaaaa agaaagtaaa atggcaggtg ccaggagttg 107340
gggaggagga tgagtgtgac tgtttcatgg gggcagagtt tcagtttggt taaggtgaga 107400
aagttctgga gatgggtggt ggtgatggtt gcatagccac ataaaagtat ttaataccac 107460
tgaactatac atttaaacat gattacaatg gtgaatttta tgctatgtgt attttaccac 107520
aattaaaaaa aaaattggat ttcctagttg cactaagcac attcagaagc cacaggggag 107580
aagtggctac tatgttggat ggcccagata gagaacattt ccgtcatcgc agaaatttcg 107640
accagatggt gctgttcata tatggatgta gcttctgggg ccacttctgt tccctgagtt 107700
tggccggtgg gatccactgt gctgagaatc acagtctggg gatttggggt gaagaacact 107760
ccccaacttt ctttcttatt ttttgttttg tttcattttt tgttttgaga cagagtctcc 107820
ctctgtcacc aaggctggag tgcagtggca tgatctcggc tccctgcaac ctcccctccc 107880
aggttcaagc gattctcctg cctcagcctc ctgagtagct gggattacag acgcccacca 107940
ccacacccgg ctaattgttt gtatcatcag tagagatggg gtttcaccat gttggccagg 108000
ctggtctgaa actcctgacc tcaggtgatc cgcccacctt ggcctcccaa agtgctagga 108060
ttacaggcat gagccaccac aaccagcctt ttttttttcc ttccttcctt ccttttctct 108120
ctctctttgt ctctctctct cttttttttt tttttttttg acagaatttt gcacttgttg 108180
cccaggctgg agtatagtgg cacgatcatg gctcactgca gcctccacct cccagattca 108240
agtgattctc gtgcctcagc ctcctgagca gctgggatta caggcatgca ccagcacacc 108300
tagctaattt ttgtattttt agtagagaca gggtttcacc atgttgacca ggctggtctc 108360
aaactcctga cctcaggtga tccacccgcc tcgacctccc aaattgctag gattacaggc 108420
gtgagccacc acaccgagcc acatttgcat gtttaagtaa ctaacatgtc tcctccatta 108480
gaccttgtgc tcccaaaggc aggatctgca gccacttttt tccccacagt ggccacagta 108540
tctagattag tgcaagcaaa tgtctgttga agcaatcagt ggtttggggg caagttactt 108600
aacctccctg tacctcagtt tccccatttg taaaacaaaa aaataaagga gctaacagtg 108660
tatctacttc acatgtgggg tgcagcagca tgctggagtt ggcttgctgg agccagtggt 108720
gaaattttca ggcaatttgt gagccatttg ttaaacatag atattcataa aaattacata 108780
aacctacagt taaacaaatt acattaaaaa caaaagtttt taaattaaca aagcttttta 108840
aaagtaacaa atactcaaaa ctcaccacct cctaatatca tacgatgttt tcctattatt 108900
tgtgctgttg aggttattta ctacttttgt gtcaatagta gatacatttt gtgtatactt 108960
ataaatacta cttagaggaa tgctactgtg tatcttttgt cagcttatgt ttagtaactt 109020
catgttggtg gcctgaaatc caccactggt aggaatattt acaccatgga aatcggcaaa 109080
tgctatataa atctgggcct ccctgggccc ctccctcagg cagctgttaa acatttacaa 109140
gctcaccaat ggtttggagg cttaaaccag ttaatagatg tgtctgacat gtgggtaatg 109200
atgtagacgt gccgctttta ctgttagtgt ttggttggct ttcactgtct gatccagaat 109260
tgctgcatat gcagacagga attggacaaa gccatttatt tatttattta tttatttatt 109320
tatttattta tttatttccc tctctctctc tctctctctc cagtttgccc gaccatctgt 109380
aagtcacacg gctgcaccgc cgaaggcctc tgttgccaca gcgagtgcct gggcaactgt 109440
tctcagcccg acgaccccac caagtgcgtg gcctgccgca acttctacct ggacggcagg 109500
tgtgtggaga cctgcccgcc cccgtactac cacttccagg actggcgctg tgtgaacttc 109560
agcttctgcc aggacctgca ccacaaatgc aagaactcgc ggaggcaggg ctgccaccag 109620
tacgtcattc acaacaacaa gtgcatccct gagtgtccct ccgggtacac gatgaattcc 109680
agcaagtgag ttctggatgt gggtctgggg ggcagccgag aggagaagga acgtggggtt 109740
ggttgtgacg atgccgcttg ttaaaactgt gtgcaaaccc agggttaatt ggctatgagt 109800
gaggtctctg ctctcagatg ctacttttgc accctgtttt ggtcctgggc ttgggagtgg 109860
gagttgacta cctttttctc taaaggacca gatagtatat acttctggca ttgtgcccac 109920
cattcttttt tttttttttt gagatggagt cttgccgcaa gactcccaag ctggagtgca 109980
gtggcacgaa cctggctcac tgcaacctct gcctcctggg ttcaagcgat tttcctgcct 110040
cagcctccca agcagctggg actgcaggtg cctgccacca tgcccggcta atttttgtat 110100
ttttaataga gacagggttt cgccatgttg gtcaggctgg tctcgaactc ccaacctcag 110160
gtggtccacc tgccttggcc tctcaaagtg ctgtgattgc aggtgtgagc caccgcaccc 110220
agtctggcat tgtggacctc agttctaagc tttctgtggt tggcttcaga acaagaaaat 110280
ataataagga cagagtcctt ggttttccct aaaatcctcc acgtggcctg tcctcactga 110340
tgtagcttca tcattgtcac ataaaggata taccaaggtc tttcgtgtct tccctgacct 110400
gtagcctggt ggtgtgccaa gattagccca gaacatactg tctccaggag gaagagactc 110460
gcttctgcat tattctcagg gctttgctgt tctctgaagg acagtataat caaaccattt 110520
cctgccgttt gggtgagaaa tagcagggtt ttctctcttc gacagagtca gatttcctac 110580
gcacatcgca gactttctgt tcgtactgtg agcttcttcc atgagctatt ttggggccgt 110640
aactgagttg caaaaatctg tttcctggtt tttgtattga ggttttatgt tttgttttaa 110700
aacacacaca cacacacaca cacacacaca cacacaccac aaaacaacac aaaaacaaat 110760
cagaaacaga cacacatcaa gaggccttga gctgacctgc ttacgtaaag tatcttcctc 110820
ttcagacttg agaattagcc aagcgagagt gttggggtgg gaaattgtat ttccctgggt 110880
ggagagggcg ggaaggaaaa caagctgtaa tttcagttct tatgactctt tctttgagtg 110940
tttgtgaaac ctgcaagtac aatatgtttt gttttgctcg ttgttgataa aaacctacca 111000
aaaaaacctt ttggctttat tgaccaaaag ggtctataaa tcaccttttc ataccagaca 111060
gacttttgtt ttaggttttt tttttttttt ttggccagtg tattcccaag attgaggaaa 111120
tgaccatatt ccttttgatt catttctttc tttttaaaat cacaattgaa ataaaaaaaa 111180
tgggttaata tcttctggca agatgtttgt ttaaaagaca ttggccttaa ataaaaggca 111240
tttttccctc accttaacaa tggcctgaga aatatagcaa cctcctttga ttttctcact 111300
gatgatgcgg gagatgctaa aacagaaacc ctgagaaatt gaccgcacat ccttggtatc 111360
tgggaccttt cctgaacgga agaaaacaaa ggagaggggg gtgcattgtc accgtatttt 111420
attgcgtagg tttaaaaaaa ttaatatttt tatttctgaa gcttttaatt aattaattta 111480
tttattttga gacagagcct cactctgtca cccaggctgg agtgcagtgg catgatctca 111540
gctcactgca acctctgcct tccaggttca agccattctc ctgcctcagc ctcccaagta 111600
gctgggatta caggtgtgag gcagcaagcc tggccaattt ttttttgttt gtgcttttgt 111660
ttttttgaga tggagtttca ttcttgttgc ccagactgaa gtgcaatggt gcgatcttgg 111720
ctcactgcaa ctcagcctcc cgggttcaag tgattctcct gccttagcct ctaagtagct 111780
gggattacag acatctgtca ccatacccag ctaaattttt cttgtatttt tagtagagac 111840
cgggtttcat catgttggcc aggctggtct tgaactcctg acctcaagtg atccacccac 111900
ctcggcctcc caaagtgctg ggattacagg catgagccac cgcacctggc ctgaagcttt 111960
tctttttatc ttatgaaaga cttaatcgta ctgtggcatt ttctaatgtg gtttgatatc 112020
aaatagggcc agatgttttc ttccattctg gtggcttatc tgggaaggag ttcttgatgt 112080
tttcagagca gagttctggg aacccatgtt aaaaggcctt ggccaggcac agtggcttat 112140
gcctgtaatc ccagcacttt gggaggccga agtggacgga tcatctgagg gcaggagttc 112200
aaggtcagcc tggccaccac ggtgaaaccc cgtctttact aaaaatacaa aaacaaaaaa 112260
aaaattagct gggcatggtg atgcatacct gttatcccag ctactcggga ggctgaggca 112320
tgagaattgc ttgaacccag gaggcagagg ttgcagtgag ctgagatcac gccattgcac 112380
gttagccccc aggcaagtgt gacaagagtg aaactgcatc tccaaaaaaa aaaaaaaaaa 112440
ggtctcacca tctactgtcg ttccaaagta cctgctggga tgtaatagca cagtgctgct 112500
tcctgagatg agaaggacca gatatttgtg atgaataaat tttcaatgcg tatggggtat 112560
ccactgggaa ggggagaatt acctaaaatc cttgattctt cttggcctct ctcacttctt 112620
cctattaagc tgaggtctca aatttgtcta cacctccatc tatttcacca tcatgtctgg 112680
tctgacccag tccccttgaa caatctcttt gctcctgctt ccattctagt gacactggta 112740
aaaagtggcc acctgggcca ggcgcggtgg ctcacgccta taaccccagc actttgggag 112800
gccgaggtgg gtggatcacc tgaggtcagg agttcgagac cagcctgacc aacatggtga 112860
aaccccatct ctactaaaaa tacaaaaatt agccaggcgt gggattacag tgggcgcctg 112920
taatcccagc tactcgggag gctgagacag cagaattgct tgaacccggg aggtggaggt 112980
cgcagtgagc cgagagtgtg ccactgcact gcagtctcgg tgacagagtg agactctgtc 113040
tcaaaagaaa aaataaaagt ggtcatctga tcatatgcca tgtccttccc taaaaccctc 113100
cggtggcttc ccaagaccaa tggacagaat ccaaactcct catcgggagg gctcggccag 113160
ttctcattct catttcattc cggtgccccc tggccgtggt ggtcgttacc gcaggagctt 113220
ttcctgcaac ttgctacatc cgctttcctc tgtgcctttc aattagctgt tccctcttcc 113280
tataatgctt gtccctgcat ttgagaatga tccacttttt cccctcgtca tctagatggc 113340
agcttaaaag tcacctcctt ggcaaatcct tcccgtctga gtcaatcatc cgtgcactct 113400
ctgtcacatc atttagtttt aactcttcga tttgtcacta gctgatattt ttgtcttttt 113460
tttttttttt tgagacaagg tcttggtctg tcacccaggc tagagtgcag tggcacccac 113520
atggctcact gtggtctcaa ccccctgggc tcaagagatc ctcctgccac agcctcctga 113580
gtagctggga ctatataggc acacaccacc acacctggct aaaaaaaaat tctgtagtgt 113640
tgggggtctt gctatattcc ccaggctcgt cttgaactcc tgggtttaag tgatcctccc 113700
accttggctt cccaaagtgc tgagattaca gggcctgagc cactgtacct agcctttgtt 113760
gtcaatttat tcactctccc caaccagatg ataagctttg tgagtgtatc agctagctct 113820
tgttgcgtaa caaaaccacc tcagtgctta gtggcttaaa acactccttt aggagctctg 113880
atgatttcat gtgttgactg aaggtttgtc tggcctgggc ctgtttagct acggctgatg 113940
gtttagggga gcctcttgtg tctttgatgg tcagtggggg tctctctcca taagtctctt 114000
accccagcag ccaggaaggg cagacctcaa tgttcaagtg cttttcaagc ctcagcttgt 114060
atcacgtttg caaatattcc attggccaaa gcaagccata tggccaagcc cagattcaac 114120
aggtgggaac atagactcca cttcttggtg ggagaggctg caaagaactc atggtcattt 114180
ataatttccc actgggaaag catattatct gctttgttca ctcatgtata ccggcagctg 114240

-continued agaacggggg ttggccaagg gccagatagt aaatattttc agctctcagg gccatatggt 114300
ctctgttgga gctacttaac tctgcctttg cagcgtgaaa gcagggttag acgatgtact 114360
aaccaataaa tgtggccata ttccaatagg atattatttg caaaaacagg tggcctactg 114420
gatttggctc ccagcccact gtttgccaac tccaggctta gagcattgcc tgccacataa 114480
taagaataga ggcaataaaa gaagtcaaac atttggtcag tattttgttt ctgcctcagc 114540
tgttctgcca ctacctgggt gtacttgcaa caccgttctg acaccatcct cctccaaagt 114600
tagcatcaga cgccacaagt ttaaggctca gccctccatg agatttccct tgcttcagac 114660
actggcagca tcttggggat cccccagcca cccacacttc tgactaactg gctctaaatt 114720
gggggattcc cacaaactgt ttgggtttca taatttacta gaaggaactc acagaatgaa 114780
aataaacctg gccaggtgtg gtggctcatg cctgtaatcc cagcactttg ggaggccatg 114840
gtgggaggct cacttgagcc cagaggttcg agaccagcct ggacaacata gtgagatccc 114900
atctctacaa aaatttaaaa acattagcca ggtgaggggg tgcatgcctg tagtcccagg 114960
tacttgaggg gcttaagcag gaggatcgct tgagcccagg agttcgaggc tgcagtgagc 115020
taagattgtg ccagtgcacc ccagcccggg tggcagagca agatcttgtc tcaaatttaa 115080
aaaccctgct atacaattac agttttatta taaaggatac acatacggca agatctggga 115140
gagttctaga tgcagaattt ccatattgcc tcctcgtggc aacagcatgt atcaccctct 115200
tgacatactg gtgtgtccac cagctgggaa gtactactga gcttcagcgt ccagagtttt 115260
tgtttgtttg tttgtttgtt ttgagacgga gtctcactct gtcacccagg ctggagtgca 115320
gtggctcaat ctcagctcac tgcaacctcc acatcccagg ttcaaacaat tctcctgcct 115380
cagccccccg agtagctggg actacaggca tgcaccatca cgcacggcta atttttgtat 115440
ttttagtaga gacagggttt caccatgttg gccaggctgg tctcaaactc ctgacttcgt 115500
gattcacctg cctcagcctc ccaaagtgct aggattacag gcgtgaggca ctgcacccgg 115560
cccagtatcc agagttttaa ttggagtctc attccttagg cgtgattgat tgaaatcatt 115620
gaccatgtga ttcaacactg ccatttccag ccccctcatc tccctggagg tcctaaaagc 115680
cccaaccctc tgatcacagg gttgttcttt ctggtgaccg ccccccaccc tcatgttatc 115740
taggcacccc cccccccaca agtcaccccg acattcctaa cactcctaac aaaagcattc 115800
ctgtgactca gaaagttcca agggtttttg aagctctgtg ccaagaaccg ggatgaagac 115860
cagatacata ctttatgatc ctacagtcac aaaaatcact ctgaagagtt gaatacccag 115920
gagtgtgaga acaacagcag cagcaacaag gatgccacca ataaaaaatg acccttgtag 115980
caacggataa aattgcgttc tgtgtgcgaa gtgcttttgt ggtatgcttc attgagttcc 116040
tcatcacaag ctgtggcgtt ggtggtgtta ttttcagatg aagaaatgga gactgtaaca 116100
gttgggaatc ttgtggtttc atgcaccaga accccaactc aaattggctt aactggccgg 116160
gcacggttgc tcacacctgt aatcccagca ctttgggagg ccgaggcggg tggatcacct 116220
gaggttggga gttcgagacc agcctgacca aaatggagaa accctgtttc tactaaaaaa 116280
aaaaaaaaaa aaaaaaaata caaaattaga tggggcatgg tggtgcatgc ctgtaatccc 116340
agctactcgg gaggctgagg caggagaatc acttgaacct gggaggcgga gcttgcagtg 116400
agccgagatc gtgccattgt actccagcct gggcaacaag agtgagactc catcttaaaa 116460
aaaacaaaaa caaaaacaaa acaaaaaaac cattgactta accaagatta aaggagtttg 116520
ttggtaccca taaccaaaaa gttcagggag ttggttcagg tatagctgta tcaagaagct 116580
taagcgatgt acctgatcag tctccttcat ctttattttc ctctttgttg gttttgttat 116640
caggcagctt ctccctcacc cttcacccca tgctagcaag atggcaaaac ccttagatac 116700
tccagaagga agacaatttc cccttccagc atgttctagc aaaaccctca ctgcactgac 116760
ttaagttctg tacccaccac ctctgagccc ccacaggaat agaaggtggt gctcagcttg 116820
gcttggatct tgtgcccatc ctggatctag aagggctttg gcaaccaaga actgatctca 116880
gagaccccgt gttggggagg actggttccc aaaggactcc tgggggctgt gagtttgatg 116940
gcatcaggct gcaggctggc aaaaccaaag gctgcccaag tcacttgcca ttaaacatgg 117000
ggtcatgtta cagccgtagt tgcatcacat cccacacaga acagcaaatg tcctgtctcc 117060
ttggagtagc aggttgaatt ctgccacgtt ggggtaactg tcagttctgc cacatcaggc 117120
ccatcatctc aaggtaacgg cacattctta ttaccacatg cattagtcca tttctgcact 117180
gctataaaga atacatggaa ctgggtaatt tataaagaaa agaggtttaa ttggctgaca 117240
gttctgcagg ctgtacggga agcatagcag cttctgcttc tggggagacc tcaggaaact 117300
tacaatcgtg gcggaaagca aaggggaggt aggcacatct tacatgactg aaggaagaga 117360
gaaaggggga aggtgctaca tagttttgtt tgtttgtttt gagacagatt ctcactctgt 117420
cacccaggct gggctgcagt ggcacaatct cggctcactg cagcctccac ctcctgagtt 117480
caagcaattc tcatgcctca gcctccccag tagctgggat tacaggtggg caccaccaca 117540
cctggttaat ttttgtattt ttagtagaga cggggtttca ccatgttggc caggctggtc 117600
tcgaactcct ggcctgaagt gatccgctcg ccttggcctc ccaaagtgcc ggaattacag 117660
gcatgagcca ccatgcccgg ctggtgctac atacttttaa acaaccagat ctcgtgagaa 117720
ctcactcact atacactgcc aaggggtatg gtgccagacc attcatgaga actccgccca 117780
ccatgatcca gtcatctccc accaggcccc acctcccaca ttggggatta caatttgaca 117840
tgagatttgg gtggggacac agatccaaaa catatcgcca cgataatgct atgagtccca 117900
ttgctgtcac gcacagggta gatcatggtc ctgcctccat gggatatggt gtgaatccca 117960
tcactgtggg gtccagcagg agtcctgtcc catcactttg gggtaaaata tgagtcttgt 118020
cactttgggg taaaagcaag aggacctgca accatagggt aatggcataa ttctctcact 118080
taaggcagtg gttcttttct ggggacaatc tggcatcctc cctccccagg ggacttttgg 118140
caatgttggg agactttttt ttttttgag atggagtctg actgtgtctc ccagctggag 118200
tgcagtggtg ctatctcggc tcactgcaac ctctgcctcc caggttcaag cgattctcct 118260
acctcagcct cctgagtagc tgagattata ggcacgtgcc accacaccca gctaattttt 118320
gtatttttag tagagacagg gtttcaccat gttggccagg ctggtcttga actcctgacc 118380
tcaggtgatc tgcccgcctc ggactcccaa agtgctggga ttacaggcgt gagccacttt 118440
gcctggcctg gaggacattt ttaattgcca caacttgtgg gagggatgct actggcagct 118500
cgtgagtgga gcctagggat gccgctcaat atcctccaat gcataggacg ccaccccac 118560 taccacagtg gagaattact tggccccaaa tgtgaacaat gctgaggtca gaagaccttg 118620
ccgtagcatg atggacttat gccatcactt gagaccctgc atagtgtgct gtcttcccag 118680
gctgatcttg aactcccagg ctcaagcaac cctccctcct tggcctctca aagtgcagga 118740
atgacaggca ggagccacca cgcccggctc cagaatctac atttttaaca atcaagcgat 118800
atgtcctatt gcagatcggc agactgtgtt ttcagaaata tcatctcagg cagaaagggc 118860
cgggtgcagt ggctcacacc tgtaatccca gcactttggg aggccgaggc gggtggatca 118920
cttgaggtca ggagtttgag accagcctgg ccaacatggt aaaaccccgt ctctactcaa 118980

-continued aaatacaaaa attagccagg cacggtggcg ggcacctata atcccagcta ctgtggaggc 119040
tgaggcagga gaatctcttg aacccagaag gcagaggttg cagtgagctg agatcgcacc 119100
actgcactcc agcctgggca acagagcgag actctgtcac acaaacacac acacacacac 119160
aaagaaatac catatcaggc agaaagatgc ctgagatgtc tgaaggacct tggataccgt 119220
gacacccccc tccccttct ctttctctct ctctctgctc cgtccttagc ttgctgtgca 119280
ccccatgcct gggtccctgt cccaaggtgt gccacctcct agaaggcgag aagaccatcg 119340
actcggtgac gtctgcccag gagctccgag gatgcaccgt catcaacggg agtctgatca 119400
tcaacattcg aggaggcagt gagtgtctct gtgtgggcgt cgggggtgcc tgttgggctc 119460
catgtccctc tgagctgtga gcggggaaga aaagcagtgc agaccctgct gcgtgctcct 119520
acagcacttt taggatggtc gttcagtggc tcccccatgg atagaaccat gctgggagtc 119580
tgcctcaaaa cctgaaatga acagctcagt cttggcctta ctaaccttga gattctcatt 119640
ttctactttg ggagttgggg catcaggaat ctgcatttac atttattttt atttttattt 119700
ttatttttag agatggggtc ttgctccatt gcccaggctg gagtacagtg gggcaactct 119760
agctcactgt agcctcaaac tcttgggctc atgcagtcct cctacctcag cctcccaagt 119820
agctgggagt acaggcaggt gtcactgtgc cgggctaatt tttttttttt ttaatttttt 119880
tccagggcca ggttctcact atgttgccca ggctggtctc aaactcctgg gctcgagcaa 119940
tcttcctgcc tcagcctctc aaagtgcagg gattacaggc atgagccacc ccacctggct 120000
ttggaatcgt cgtttttaac aatcaagcaa tatgccctat tgcagaactg caggctgtgt 120060
tttcagaaat aaatctcagg gccgggtgca gtggctcatg cctgtaatcc caacagtttg 120120
ggaggccgag gcaggtggat cacgtgaggt gagaagttta agaccagcct ggccaacatg 120180
gtgaaaccct gtctctacta aaaatacaaa aaaattagcc aggcttggtg gtgcgtgcct 120240
gtaatcccag ctacgcagga ggctgaggca ggagaatcgt ttgaactcag gaagtggagg 120300
ttgcaatgag ctgggatcgc gccactgcac tctagcctgg gcgacagagt gagactccat 120360
ctcaaaaaaa aaaaaaaaaa aaaaaaaagc caggcgctgt ggctcatgcc tgtaatccca 120420
gcactttggg aggctgaggt gggcggatca cttgaggtca gaagtttgag accagccaac 120480
atggtgaaac cttgtctctc ctaaaaatac aaaaattagc tgggcacggt ggcacatgcc 120540
tgtagtccta gctacttggg aggctgaggc aggagaatca cttgaacctg ggaggcagag 120600
gttgcagtga gccgagatca caccactgca ctccagcctg ggccatagac caagactcca 120660
tttcaaaaaa aaagaaaaga aataccatgt caggcaaaaa ggcattcctt tgtttatttc 120720
tttagcgaac atgtactgaa tactcacagt gagtaaggga aagtccttac cttgatggat 120780
ttttgcgcat aagtaaatcg acagatattg taaggtcagg ttgtggtctg tgctgtgaag 120840
ggaagtgcag cagggtaata ggtggaatgg aaatgggcaa cttttcccta taaagggctc 120900
tttcatgaat atattcagcc tggcaggccg ggcagtctct gccgtaacca ctcaactctg 120960
ccgttgtaat atgaaaacag ccatagaccc atgtcagcta gcaggcatgg ctttgttcca 121020
ataaaacttt atttacaaaa caggtagaat ttggccagtg ggctgtcatt tgtcaacctc 121080
taaaatggag actaacaggg gttgctattt tttttttttt ttgtagtttt agtagagaca 121140
gggtttcacc atgttggcca gggtggtctt gaactcctga cctcaagtga tccacctgcc 121200
tcgccctccc aaggtgctgg tattacaggc atgagccacc agcaccaagc tgggggttgc 121260
tattttagag aagtctctgg tatgggaaag gagggtttga gatgatgatg gaacaagcca 121320
aggagatata tggtggaata atattctgag caacagacgc agccagtgcc aaggtcctgg 121380
ggcagaagta tgcttgaccc atttaaggaa tgctaaggac ttcagattgt gttctaagca 121440
tgatgagttt tgagctgggt atgtccagtc atttgcagcc tgagggttat cttctcacca 121500
tggagaatca tgagaagatt gaaatatgtc tatagaaacc cactggatat tctctccttt 121560
ccttagacaa tctggcagct gagctagaag ccaacctcgg cctcattgaa gaaatttcag 121620
ggtatctaaa aatccgccga tcctacgctc tggtgtcact ttccttcttc cggaagttac 121680
gtctgattcg aggagagacc ttggaaattg ggtacgtggg cctgattgtg tgtatggcct 121740
gagtgctaac taggaagttc gtgtattaga acaacttaag gattttttg gccaggtgtg 121800 gtggctgatg cctgtaatcc cagcatttta ggaggccaac gtgggtgaat cacttgaggc 121860
ggggagttca agaccagcct ggccaacatg gtgaaaccct gtctctacta aaagtacaaa 121920
aattagccaa gtgtgatagt gcatgcctgt aatcccagct acttgggagg ctgaggcagg 121980
agaatagctt gaacctggga ggcagaggtt gcagtgagcc aagatcacac tactgcactc 122040
cagcctgggt gacagagtga gactctgtcc aaaaaaaaaa aaagaaaaga aaaggaaaaa 122100
cttaaggatt ttttaaaaat caaataaaaa caaataaaaa acaaataaaa gtatatctgg 122160
caaaacctcg ggaaaaaaga acttggaatg tgcctaaagg tccatccagc caaaaattgt 122220
aaaagctttt ttatagtcat tcttgagaaa caaaagtggg agcagcccaa ccttggtgcc 122280
catcctccaa gggtacaggc tggaattttt gctaaatttg ctgtttgggc tgcattgtga 122340
gtagagtttg gcatgcataa aatgaacatt ccctcttagt cccggttgtc catcctaatt 122400
tctgggatgg actccatctc agtatattcc agtatattcc aaccttctcc ttgaggtcct 122460
agaaactcta ttagcaaaac agcagaaact caaactagct agatcaagat tgactcatag 122520
gcaggaggtc tgtggaagac ccagattctt tccatctttg tgctcctcat ggtcacaaga 122580
tggctgcctc agccccagcc tcacatctgt agaacagaca gcaaatgggg aaagggacaa 122640
aaggacatgt taatcaacat gagctggtaa gtgacttgag aaggtggtct aaacaatata 122700
gtttagacta tattatctgt actccagcct aggcaccaga gtgagaatcc atctcaataa 122760
aacaaacaaa caaacaaaca aaaaccttca atggctcctt tctccttatt aaggatggcc 122820
acatgttctt ggtcttggtc tggcatgcaa tatactagag ggtctggtcc attgcaacta 122880
cagctatttc ctgtcaccta ttggccaaaa caggctactt tgctcttccc tgaactcagc 122940
ttaggtgcct ctgtgttatc agtatttccc ctatttgcag aaattggttt ctgcaaaacc 123000
tattcctcag tccatcacag actcaccacc cctcttcaag actgagctga gcctccttcc 123060
tggccatgaa aacttcctca acttcctctg ttatccacat tcaacaaata tgtgttgagt 123120
atgtgccaag caagtggaga ggattaggca cgtagcactg aacaagatca actccgagca 123180
tggccacacc atcttggagt tgtagaagac cagccgttga atgactagat gtgtgtgttt 123240
tttccatagg aactactcct tctatgcctt ggacaaccag aacctaaggc agctctggga 123300
ctggagcaaa cacaacctca ccatcactca ggggaaactc ttcttccact ataaccccaa 123360
actctgcttg tcagaaatcc acaagatgga agaagtttca ggaaccaagg ggcgccagga 123420
gagaaacgac attgccctga agaccaatgg ggaccaggca tcctgtaagt cactggtccc 123480
caaccttttt ggcatgaggg accggtgtag tggaagatgg tttttccatg gactggtggt 123540
gggtggggat ggtttcagca tgattcaagt gcattacatt tactatgcac tttattccta 123600
ttatgattac attgtaatat ataatgaaag aattgtacaa ctcaccatca tgtagaatca 123660
atgggaaccc tgagcttgtg ttcctgcaac tagatggtcc cagctggggg tgatgggaga 123720
cagtgacaga tcatcaggca ttagattttc ataaggagtg tgcagtctag gtacctcatg 123780
tacacagttc acaatagggt tcacacccct gtgagaatct aatgccgccg ctaatctgac 123840
aggaggcaga actcaggtgg tcatgcaagc gatggggagt gactgtaaat acagatgaag 123900
cttcacttgc tcacctatca ctcacctcct gctgtacagc cctgttcgta acaggccatg 123960
gataagtact ggtctgtggc ccaggggctg gggacccctg ctgtaagtgg tccacaaacc 124020
agataatgtg gctgtcctct ctcatccatc acagtcaccc ccaggggggta ttacttccct 124080 ctaacaactc actgtgtgat aggctttctt actgagggca gattctgcac atttattaat 124140
attatcacta tgcttactgt gccatatagt accggatacg ggatgaagtc atacaagcac 124200
tgaatgaatg gatgaatgaa tgatggatga atggatgaca ccttcttata tgtgtatcag 124260
gctgatgctg aagacttcaa agttgagtaa aatacctatg tcagtctgca tctcctggga 124320
agtgactgcc aagttgaagt taggagtgca gaaaatgtat tgagggtaat attcataaaa 124380
tatgaaacag aggaagagct tcttttttttt ttttttttt ttttgggaca gagtcttgct 124440
ctgtcaccca gggctggagt gcagtggcgt gatcttgcct cactgcaacc tccttcccct 124500
gggttcaggt aattatctcg cctcagcctc cagaatagct gggattacag gcacatgcca 124560
ccaagcccgg ctaatttttt tttttgtatt tttagtagag acagggtttt gccatgttgg 124620
ccagggtggt cttgaactcc tgacctcagg tgatcctccc gcctcggcct cccaaagtgc 124680
tgagattaca ggtgtgagtc accacgctca gccatgaaga gccttttgac aatagcgtgt 124740
gtctgacctc tgtgaacaga gagcgggaag gagggaggat agggctggga gagtctcaga 124800
tggtgatgca tccctgagtc ttggccaaac ccagaaagag atcaaggcca cggttgtctg 124860
cagggaagtt ctgcattgca aagggacggc caggcatcta ccaagctcag tcataggtgg 124920
gggctgtcca gggagagtca ggttttggct ggaatgctac agcaggtcct gcagtttctg 124980
cagctgcagg ctgcctgctg actgcacttc cctgacagat tctaaacagt gagctgccaa 125040
gggcttctgg gataccttca tggggagtta gttacttatg tcaaaatgta gtgcaagggc 125100
tgggcatggt ggctcacgcc tggaatccca gcactctggg aggccgaggc aggcagatca 125160
cttgaggtca ggagttcgag accagcctgg ccaatgtggt gaaactccat ctctactaaa 125220
aaaaaaaaat acaaaaacta gctggacgtg gtggtgggtg cctgtaatcc cagctacttg 125280
agaggctgag gcatgagaat tgcttaaacc cggtaggtgg actgcactcc agccttggtg 125340
acagagcaag actgtctcaa aaaaaatgta gtgcaaggag agagagcgag gttggggtga 125400
ggtttaggag agggtttgtc ttctaggcag agagaattac ttagatgcgt ctctccgatg 125460
tctaatgatc tgcagggtct ctaaactcac ttggcatagg tttatttgca ctggagttgc 125520
acctccttcc aggtcagtct tacaagtcca tatgcgagac aacgttgtgt caggacaaac 125580
atcacccttg gaaatccctt cctccaataa ctattggccg gttgtccttc ttgcgcgggt 125640
acagactgcg cttattcagt tgactgtctg gctgagtcaa gtcattggct tacgtgagtg 125700
tgagtggcca agttgcaaaa ctggctctta cctttgaatc ttccccccatt catactcagc 125760 caggcacatg gggaggagac ccttaaggga atagcagcgt cacctctgcc ttctcacggt 125820
ccctccagga agtgtggggg tcccaggctt tggtctgaaa ctacactgaa atagctcatt 125880
tttgcctttt gttttaactt ttccaggtga aaatgagtta cttaaatttt cttacattcg 125940
gacatctttt gacaagatct tgctgagatg ggagccgtac tggccccccg acttccgaga 126000
cctcttgggg ttcatgctgt tctacaaaga ggcgtaagta gaagagttag agagacgctg 126060
aggaggcgag ggctggctgg ctctgtgctt gctacgtttg tgctccaatc tgcccctctt 126120
gggttcctgt ctatctccct cctcctcctg gaataaatat cttaggttcc tttttacaat 126180
ctcaccagtc gatggcatgc aaagtcaata gtgtctgctt ttatcaaatg cctaaaatgg 126240
aagcagacag ctttcccata gaagcccgga ctggccagtt tcctggggca atattctatt 126300
ttgccttgcc tgtgtatgtc tcatcagaca tccttagtag tcaggagctc agtctactaa 126360
gtggatgtta tcaaatgtat tgcttatcta tttttctttt ttatccccaa tttttttttt 126420
ttttttgaga cagagtcttg ctctgttgcc cagggtacag tgcagtggca gatcttggct 126480
cactgcaacc tctgcctccc gggttcaagc agttctcctg cctcagtctc ttgagtagct 126540
gagattatgg gcatacacca tcacacgtag ctaatttgtg tatttttgat agagacgggt 126600
tttgccatgt tggccaggct ggtctcaaac tcctgacctc aggtgatctg cccaccttgg 126660
cctcccaaag tgctgggatt acaggcatga gccaccgcac ctgaccagta gtaatattaa 126720
taatagttct agccctcaag atttaccttg tgccttgctg agcactgaca cacagtctaa 126780
tcttatcagt aacttgtgag ggagctcctg ctattactat tattacagat tgagtatccc 126840
taatctgaaa atctgaaatt tataatgctc caaaatccaa agctttttgt gggccgactt 126900
gatactcaaa ggagatgctt attggagcat ttcagatttc agatttttag attagagatg 126960
ctgaaccagt acaatgcaaa ttaactagta aaatgcaaat atttcaaaac cccaaaatat 127020
ccaaaatcca aaacacttct ggtcccaagc atttatttat ttatttattt atttatgttt 127080
ttgaaacaga gtctcccttt gtcgcccagg ctggagtgca gtggtgcgat ctcagctgat 127140
gctacctctg cctcccgggt tcaagcaatt ctcctgcctc aacctcctga atagctggga 127200
ttacaagcat ctgccaccat gcccagataa tttttgtatt tttagtagag acggggtttc 127260
accatgttgg ccaggctggt ctcgaactcc tgacttctgg tgatccgcca ttctcggcct 127320
cccaaagtgc tgggattaca ggcgtgagcc actgcacttg gccaagtctc aagtgttttg 127380
aataagggat gcccaagctg tgttttttca ttgagatgtc agggttgaca gttcctttct 127440
ctttggctgt tcccgagtta ttttttcttg tggcattaga ttgttgggtg agtaacatgt 127500
gaccctatgg gatgtaactt cccaggcctc atctgcacgg cactcagtgt gacggtcttg 127560
taagggtaac tgccttctgc tgttttgtct tgaaagccct tatcagaatg tgacggagtt 127620
cgacgggcag gatgcgtgtg gttccaacag ttggacggtg gtagacattg acccacccct 127680
gaggtccaac gaccccaaat cacagaacca cccagggtgg ctgatgcggg gtctcaagcc 127740
ctggacccag tatgccatct ttgtgaagac cctggtcacc ttttcggatg aacgccggac 127800
ctatggggcc aagagtgaca tcatttatgt ccagacagat gccaccagtg agtgtgtctt 127860
gggaatgtga attcgtatgt gaatcagacc tcttgctttt aataggctga tgcagtgagg 127920
ttgtataaaa tgctccttga tatggttatt ggcttttttt ttttttttag acagggtctt 127980
actttgtcac ccaggctaga gtgcaatgca gtggggtgat catggctcac tgcagcctca 128040
aactcctggg ctcaagcaat ccttctgcct cagcctccta agtagaagga actaccagag 128100
tataccacca tgtgtggctt tttttttttt ttttctttga gatgaagtct cactctgtca 128160
cccggactgg agtgcaatgg catgatctcg gctcactgca acctccgcct cccaggttca 128220
agtaattctc ccacctcagc ctcctgagta gctgggacta caggcatgca ccactatacc 128280
cagctaattt ttgtatttct tgtagagaca gaacgttgct gtgttaccca ggctggtctt 128340
gaacccctgg cctcaagtga tcctcctgcc tcggcctccc aaagtcctgg gattagaagt 128400
gtgagccacc ttgcccagtc agttattggc ttttaaagga gctgggtatt gaggcttata 128460

-continued gtttcagacg aggcagtagc aacaagccac ttgatgggaa tatttatatt tttcatccta 128520
ttatgaaaaa ttgtcaaata ttcacaacac agaacaaaac cccatagtta gccgcctccc 128580
agcttcagcc tttggtcatt tttgtttcat ctcgacgcct gttccctctt cccacttgtt 128640
acttcttttt gttttgttgt ttgttttggc ctggagtatt tcacagcaat ttaattatgt 128700
ttgtttgttt gagatggagt ctcactctgt cacccaggct ggagtgcagt ggcgccatct 128760
ggactcactg caacctccac ctcccaggtt caagtgattc tcctgcctca gcctcccaag 128820
ttgctgggat tacagcacac ttggctaatt tttgttttgt tttgttttgt tttttgagac 128880
agagtctcac tctgtcactg aggctggagt gcagtggtgt gatctcagct cactgtaacc 128940
tccccgtccc agttcaagtg attctcctgc ctcagtctcc caagtagctg caactacagg 129000
cgtgccacca cgcccagcta atttttgtat ttttagtaga gatgggattt caccatgttg 129060
gccaggatgg tctcaatctc ttgacctgca atctgcccac cttggcctcc caaagtgctg 129120
ggattacagg cataagccac catgccagcc tttttttttt tttttttttt ttttgagatg 129180
gagtttcgct cttgttgcct aggctggagt gcaatggccc tatctcagct cactgcaacc 129240
tctgcctccc gggttcaagc gattctcctg cctcagcctc ccgagtaact gggattacat 129300
gcatgcacca ccacgattgg cgaatttttt tttttttttt tttttgtag agacaaggtt 129360
tctccatgtt ggtcaggctg gtctcgaact ccgagcctca ggtgatccgc ctgcctcggc 129420
ttcccaaagt gctgggatta caggcatgag ccaccgcgcc cagccatttt tgtattttta 129480
atagagatgg ggcttcacca tgttggccag gctgctctgg aactcctgac ctcaaatgat 129540
ccgcccacct tggcctccca aagtgctggg attacaggca tgagccactg ggcccggcct 129600
aattatattt ttgtaaaacc taagtgcttc tcttatagca gtagttccca aaggaggtta 129660
actgctctgc cagggaacag ctgccaatca atgtctggag acatttttgg ttgttacagc 129720
tgtggagatg aaaccactgg catttcgtgg gcggaagcca gagaggctgt tccatgtcct 129780
gcaacacaca ggatgcaccc tccttcatga caaagaatta tccagtccta aaagccaata 129840
gtactaaggg tgagaaaccc cgtcctgtag gctcaaattc aagctttttt tttttttttt 129900
tttttttaa cggagtttca ctcttgtctc tcaggctgga gttcaatggc gcattctcag 129960
ctcactgcaa cctctgccca ggttcaagat tctcctgcct cagcctccca ggaagctgag 130020
attacaggcg cccaccacca tgtccagcta attttttttt tttttttttt tttttagtag 130080
agatagggtt tcaccatgtt ggccaggtgt agtctcgaac tcctgatctc aggtgattca 130140
gatgattcgc ccacctcggc cttctaaagt gctgggatta caggcatgag ccactgtgcc 130200
tggcctcgaa ttcaaacttt ataaatcaac cctatcttct tcagttaatc cccgctcatt 130260
catcctgtat cttttagtga caccaaaaga cttacagttt tcagaaactt ctagctccca 130320
ggtgtttgga ctccctcccc atccccagct ccctcggcca cctccgttac tttgggtttt 130380
ttgggttttg tttggttggt tggtggtggt tttttttttc ttttttgttt tgttttgttt 130440
tgagacggac tcttgctctg tcacccaggc tggagtgcag tggcgcaatc tcggctcact 130500
gcaagctccg cctcccaggt tcacgccatt ctcctgcctc agcctcccaa gtagctggga 130560
ctacaggcgc ccaccaccac acctggctaa tttttgtat ttttagtaga gacggggttt 130620
cactgtgtta accaggatgg tctcgatctc ctgacctcgt gatccgcctg ccttggccgc 130680
ccaaaatgct gggatgggtg ccctcatgat gtctttaact tgtgtgtccc ccgccatcct 130740
cccaccagct ttctttgcac actgtttctc atgatggacc catttccttt ctccctgaca 130800
acccctctgt gcccctggat ccaatctcag tgtctaactc atcatcccag attattctga 130860
agtggaaacc accctccgac cccaatggca acatcaccca ctacctggtt ttctgggaga 130920
ggcaggcgga agacagtgag ctgttcgagc tggattattg cctcaaaggt gagtgcaggc 130980
agctgtgcta ggatcggtgg ggtttgcaca cgtgtgtctg atgcactttg cttcacctct 131040
agggaagcag ctatctcttc ctgtgtctca gtgtcggaag gcacacacac acacactcca 131100
ttctatctca tatgaaaaca cacatacatg tttttatcta tttatttatt tattttattt 131160
tttatttatt tacttttttg agatggagtt tcactcttgt tgcccaggct ggagtgcaat 131220
gacgcgacct tggctcatcg caacctccac ctctcgggtt caagtgattc tcctgcatca 131280
gcctcccgag tagctgggat tacaggcacg cgccaccacg cccggctaat ttggtatttt 131340
tagtagggac ggggtttctc catgttggtc agcctggtct caaactcccg acctcaggtg 131400
acctcaggtg atccacccac cttggcctcc caaagtgctg ggattacagg catgagccac 131460
cacacccggc ctattttttt tttttttttg agacagggtc ttactctgtt gcccaggctg 131520
gagtgcagtg gcatgatctc tgctcactgc aacctccacc tcccaggctc aagcaatcct 131580
cttgcctcag cctcatgagt tgctggaaca ccacaattgt ctgcaggtgt gcaccagcat 131640
gcccaggtaa tttttttttt tttttttttt tttgagacag ggtctcactc tgtcacccag 131700
gctggagtgc agtggcatga tctcggctca ttgcaacttc tgcctcccag gcgcaagcga 131760
ttctcctgcc tcaggctcct gagtagctgg gactacaggc gcctgccacc acacccggct 131820
aatttttgta tttttagtag agatggggtt tcaccatgtt ggccaggctg gtcttgaact 131880
cctgacctca aatgatccac ccgcctcggc ctcccaaagt gctgtgatta caggcatgag 131940
ccaccacgcc tggccctggc taatttttaa acttcttttt gtagagatgg agtctcctta 132000
tattgcccag gctggtctca aactcctggc ttcaagcaat tcacccccct cagcctccca 132060
aagcgctggg attacaggcg tgagccacta tgaccggctc atacatacac atttttaaac 132120
atcgtaacac aagcacgcac tgaagacttg tgtcaaaacc agatttttcc catgtcttgg 132180
caccatttcc ctctgggatt ttctcctctt gtctctcctt ctttctccct ccctgccttc 132240
cttgttctct tcatccctcc tcacactgat ggggatgcag ctgtgttaac ccacgcaaga 132300
cttctgtgca aagctagaaa cacaactaat ggttattgac aaagtcaggg aaggattttg 132360
gccccactga gatcctttag ttgtaaggat cgaaggcagc aagaattggt tatctcatat 132420
cccccacccc atactttcaa ttaaaaatgt ctgccaggct tggcgctcat gcctgtaatc 132480
ccagcacatt gggaggccaa ggtgggagga tcactggagg ccgggagttt gagaccagcc 132540
tgggcaacat agcaagatcc catctctaaa aaaatttaaa aaaatggtgg tgtacacctg 132600
tagtcccagt tacttgggag gcccaggcgg gaggatctct tgagcccagg agttcaagtc 132660
tgcagtgagc tatgattatt ccagtgcact ccagcctggg tgacagagcg agaccctgtc 132720
tctatatata taaaaaaaat tatacaaaat taaaaaaaaa aggcattaag tgcattcaca 132780
atgttgtgca atcattttat tgtataaaaa ttataaataa aatttataaa taattatata 132840
aataatttta ttataaaact taatgacaaa tttttcttaa tcttgtttac ttaatagacc 132900
tccatccatc tgaaggaaaa tggaataata tttaaagtct caaactagtg tgtatacatt 132960
agtttaaaat tattattatt attattttct tttttttttt ttttgacacg gagtctcact 133020
ccgtcaccca ggctggagtg cagtggcttg atcttggctc actgcaacct ccgcctgctg 133080
ggttcaagcg attcttgtgc cttagcctcc tgaatagctg ggattacagg tgctgccact 133140
acaccggcta atttttgtat ttttagtaga gacggggttt caccatgttg gccagggtgg 133200
tcttgaattc ctgacctcaa atgatccacc cgtctcagcc tcccaaagtg ctgggattac 133260
aggcgtgagc caccgcgccc agcctaaaat tattttaaca ttgggttttt ttagaaccca 133320
ccaaactgga gaagcatctg tcactttttt ctttttcttt ttcttcttct tttttaagat 133380
ggggtctcac tctgttgtcc aggctggagt gcagtggcac aatcatagct cactgcaggc 133440
ttgaactcct gggctcaaac gatcttcccg cctcagcctc ctgagtagct ggactacaca 133500
ggactacagg cctgagacac tatacctggc taattattta aaataatttt ttaggccggg 133560
cacagtggct catgcctgta atcccagcac tttgggaggc cgaggcgggt ggatcaccag 133620
gggtcaggag tttgagacca ccctggccaa tatggcaaaa ccccgtctct actcaaaata 133680
caaaaattag ccaggcgtgg gcctgtaatc ccagctactc aggaggctga ggcagaagaa 133740
tcgcttgaac ccgggaggtg gaggttgcaa tgagccgagc ttgcaccatt gcactccagc 133800
ctgggtaaca aaagcaaaac tccatctaag aaaaataata ataataaaaa taataataat 133860
tttttagagg tggggatctt gatatgttgc ccagggtggt ctcgaactcc tgaccacaag 133920
cgatcctcct gcctcagcct cccaaagtgc tggtattaca gacctgagcc actgcgctgg 133980
gcccatttcc ttctttagtt ttggtttcct tgtgcatctt gatgtatttt tcttgagata 134040
ttttctgtta gtgatatcct cggtccatga ccctggagga gaaggccagg gggccactgg 134100
cgaggtgtgg ctgaggccag gagctcaaca tttgctcttg gctctggccc tgacctgctg 134160
aagggctttg gctaagttcc caagcaagtc accgtctgcc tcctttttgg gagaaggggc 134220
gggaggacag atgatctctg ggagctgtcc cagctctaag ctcatatgct atatgtatgt 134280
gtgtgacatc atccccgcct gagccgaggg ttgcaaacgt gatttatctg ctctgatgct 134340
ttatataact ccagggcgag tccagtcatc agctccgctg taagctgttg gccctgcatt 134400
caagtaacca gaaccacccg tgagagctgc caccagtaat gtcactcgaa gcttcctttt 134460
tttttttttt aattccgaaa gtctaaatct gtaattacca agggaccatt taaacatggt 134520
tttatttgta attgtcacaa agttaatatc attaaaagga aactcactaa ggacaaattc 134580
tgtgtgattt cactcctagg aggtccctag agtcctcaga ttcatagaga cagaaagtag 134640
aatggggagt gccagggact gcggagggga cgggttgagg acagagtttc agtttgggaa 134700
gatgagaaag ttccggagat gatggtggtg atgattgcac aacattgtga atgcacttaa 134760
taccacagaa ctgcacactt aaaatggttg agatttaccg ggcacagtgg ctcacgcctg 134820
taatcccagc acactgggag gccgaggtgg ggtggatcac tttgaggcca ggagttcgag 134880
accagcctgg gcaacatggt gaaaccccgt ctctactaaa aatacaaaaa ttagttgggt 134940
gtggtggtgg gtgcctgtaa tcccagctac tcaggaggct gaggcaggag aatcgcttga 135000
atctgggagg cagaggttgc agtgagccga gatcacgcca ttgcactcca gcctggcaac 135060
agagcaagac tccaccaaaa acaaaacaaa acaaaaattg agatggtaaa ttggtatatt 135120
ttatgtgatg cttattttc cacaatttca aacacacaca cacacaaata aataagctta 135180
caaacccttc ctgttaatat cactagtgta tatgttgtta ccacggtaaa atatacatca 135240
catacaattt attattataa ccatgtttaa gagcacagtt gagctgcatt aagtgcattg 135300
ccgtggttgt gcggccatta ccaccatcat ctccagaact ttctcatctt ctcaaactga 135360
aactctgtcc ccatgaaaca ctcactcccc ttctccttcc cccagcccca gcacccacca 135420
tcctcctttc tgtctctgtg aatctgattc tagagacttc attatgctca tttttctttt 135480
cttttctttt tattttttg agacggagtc tcgctctgtc acccaggctg gagttcagtg 135540
gcgtgatctc ggctcactgc aagctccgcc tcccgggttc acgccattct cctgcgtcag 135600
cctcccgagt agctgggact acaggcgccc gccaccacgc ccggctaatt ttttgtattt 135660
tttagtagag acggggtttc accatgttag ccaggatggt ctcgatctcc tgacctcgtg 135720
atctgcccac cttggcctcc caacgtgctg ggattacagg cgtgagtcac cgcgcctggc 135780
ccattatgct tcatttttct aatctcagga aaaccacagt gtaccatgtt tcatgcagtg 135840
gattctagga agaggtagca ggtatcagga atgatacctg tgcctgaaca aatatccctt 135900
cctctccaaa taataataat aataataata ataataataa taataataat aataccagga 135960
gcttccctta ttcaggcagt tctacatttt tttttccatc tgtaatgctg taactagctc 136020
ccatcagagt taacccaggc agggtattct atgtctattt ataaacttaa gaagtatttt 136080
ccagtctctc ataggctttt aaagctgtgt aaatacttgg gtttccgagt ggatactcac 136140
cattcacagg aaggtacttg atacacgatt tagagcttat tgtctatcct cgaggcatta 136200
aggggaggag agaaaatgga atttcctttg ctcagcagtc accaggcacc aagcagagtg 136260
gcagcagggg aggtggctct ccagggactg ttgcagattt tgcttgtaaa gagctgtgtc 136320
cgtccatctc agtggctgta ccagaggcat aactgtgctt gcaccgtggg tcacaagaac 136380
cctgggattt gacttcgggg cttaagacat gaccagctgc ggtacttaag tattgtaggc 136440
tgggtgcgat ggctcatgcc tgtaatccca gcactttggg aggccaaggc gggcagatcg 136500
ttcgagctca ggagtttgag atcagcctgg ccaacacagc aaaactctgt ctctaccaaa 136560
aaaaaaaaaa aaaaatacaa aaatcggctg ggcgcagtgg ctcacgcctg taatcccagc 136620
actttgggag gccaaggcgg gtggatcacc tgaggtcggg agatcaagac cagcctggcc 136680
aacatggcaa aaccccgtct ctaataaaaa tacaaaaaaa atgccaggcg cagtggctca 136740
agcctataat cccagcactt tgggaggctg aggcgggtgg accacctgag gtcaggagtt 136800
cagaccagcc tggccaacat ggccaaaccc cgtctctact aaaaatacaa aattagccgg 136860
gcatggtggt gcacgcctgt agtcccagct acttgggagg ctgaggcagg agaatggcgt 136920
gaacccggga ggcagagctt gcagtgagcc gagatagcgc cactgcagtc cggcctgggc 136980
aacaagagcg agactccatc ccaaaaaaac aaaaacaaaa aacaaacaaa caaacaaaaa 137040
attagccagg tgtgatggtg catgcctgta atcccagtta cggggagtgg agctgagaca 137100
ggagaatcgc ttgaacccag gaggcagagg ttgcagtgag ccaagattgc gccactgcac 137160
tgcagcctgg gcgacagagc aagaccccat ctcaaaaaaa aaaaaaaaaa aaaaaaagag 137220
agaaatagta ttgtattttg tatttttagg actgctacct ttataagcta ctggtgttct 137280
tcttcattta ttaattttta aattcccttt tctatgcatg tttgaaaagt tccttcctct 137340
atctcctctc atgcctttag gtcagggttt ctctgtcttg gtgtttttttc tgtctggcgt 137400
tggatcattc tctggggtgg gactgtcccg agcacttcag ggtgctcagc agcatctctg 137460
gtcttcaccc attccatgct ccaggaggac gccccagcca ggtcctgaca cctaaaaata 137520
tctccagatg ttgcccaatg tccctagtag gagacaaaat cacccccctgg gtgagaacca 137580
ttcactgatc aagtctgatt tctggactca tgaatggacc ccttagaatt ccatgtggag 137640
gcccagtgtg gtgacccagg cctgtaattc cagcactttg ggaggccgag gtgggcagat 137700
cacatgaggt caggagttcc agaccagcct ggccaacatg atgaaactct gtctctgcta 137760
aaaatacaaa acattagcca gggtggtggc aggcgcctgt aatcccagct acttgagagg 137820
ctgaggcagg agactcactt gaatccagga ggcggaggct gcagtgagcc aagatcacgc 137880
cactgcactc cagcctgggc gacagagcaa gactgtctca aaaaaaaaaa aaaaaaaaaa 137940

-continued aaaaaaagaa ttccatatgg cattctactc tgccctccca tcttatttgt gtggttgatt 138000
aattgattga ttgatatttt catgcagctg tgacctggct ccttctcctc ctccttcttc 138060
tccttcttct ttctttttct tcttcttcaa catgatttca ctctgttgcc caggctggag 138120
tgcagtggcc ccatctcagc tcactgcagc ctcgacttcc caggctcaag caatcctcct 138180
acctcagcct cctgagtagc tgggattaca ggcgcacacc accatgcctg gctaattttt 138240 gtatttttttg gtagagacgg agtttcatct tgttggccag gcttatcttg aactcctggg 138300
ctcaagtgat ccttccccct cagcctccca aagttctggt attacaggca agagccactg 138360
tacctggccc cctttatctt tttctaaccc cctcccacca ttctctctct caccccccttc 138420 cagctatatt ggtttccaga gatttttttt ttttttttg agagatggaa tgcttcctct 138480
gtcacccagg ctggagtgca gtggcgcaat cttggctcaa tgcaacctcc gccttccagg 138540
ttcaagtgat tctcctgcct cagcctccca agtagctggg actacaggca tgtgccacca 138600
cgtgcagctg atttttggat tttttagtag agacagcgtt tcactatatg ttggccaggc 138660
tggtctcgaa ctcctgacct caagtgatcc tcctgcctcg gcttcccaaa gtgctgggat 138720
tacaggagag ggccaccacg cctggccaga cgttttttaa tgtgccaaga aaattcctgt 138780
cctggggcct ttctgctggg tttctgctat gtctgaattg ctttacacca cgatatgtgg 138840
atggtgcttt cctttgctga attcaggatg tctcagtggt gactttcttt gagacccctt 138900
catgaaaatg gcacccgcag acacccactg ttcttttacc ccaacatctg acctgtgact 138960
gtgtatttat gagtttattg tagactgtaa gtccactgaa gacagaagca ttgtctggtt 139020
accttataat cttcagtcct gtgattatgg tgtcgggcag ttgttgcctt tttttgagac 139080
agagtctcgc tgttgtcgcc taggctggag tgcaatggct caatctcggc tcactgcaac 139140
ctctgcttcc cgggttcaaa caatcctcct gcctcagcct cctgagtagc tgggattaca 139200
ggcacccacc accacgcccg gctaactttt gtattttgag tagagacggg gtttcgccat 139260
gttggctagg atggtccgga cctcctgacc tcaggtgatc tgcccgcctc ggcctcccaa 139320
agtgctggga ttacaggagt gagccaccgc gcccagccac ctggcagttt ctattaggtt 139380
ggtgcaaaag taattgtggg ccgggtgcag tggctcacgc ctgtaatccc agcactttgg 139440
gaggccaagg cgggcagatc acgaggtcag gagatcgaga ccatcctggc taacacaatg 139500
aaaccccatc tctactaaaa atacaacaaa ttagccgggc gtggcagcgg ccgcctgtag 139560
tcccagctac tcaggaggct gaggcaggag aatgccatga acccaagcgg tggagcttgc 139620
agtgagccaa gatcgcgcca ctgcactcca gcctgggtaa cagaacgaga ctccatctca 139680
aaaaaaaaaa aaaaaaaaag taattgtggt tttttgccat tacttttaat agcaaaagct 139740
gcaattactt atgcactaaa ctaataaaac atgttgacat gcacttctca gatgacactc 139800
tagatacaga tattttattt atttatttat tatttttttg agacggagtc tcgctctgtc 139860
acccaggctg gagtgcagtg gtgccatctc agctcactgc aacctccacc tcccaggttc 139920
aagcgattct cctgcctcga cctcctgagt agctgggatt acaggcatgc gccactacac 139980
ctggctaatt tttgtatttt tagtaaagac ggggtttcac catgttggcc aggctggtct 140040
cgaactcctg acctcaggtg gtctgcctac ctcagcctcc caaagtgctg ggattacagg 140100
tgtgagctgc ctggcctatt tttattggtt attttacttt atttttagta gagacagggt 140160
ttcaccacat tgcccaggct ggtcttgaac tcctgggctc acgtgatcct cacacctcgg 140220
cctccgaaag tgccaggatt aagggtgtga gccactgtgc tcggctatat ttttaatctt 140280
ttgagacagg gttctactct gtcacccagg ctgaagtgta ggggtgcaat catagctcac 140340
tgcagcctcg aactcctggg ctcaagcgat cctctcacct gagcctccca agtagctggg 140400
accacaggcg tgaaccatag tgtctggctt ttttccaaag cggagctcaa atctaggctc 140460
tgtctcagct cagcctctct gagaaggccc ccttcactgt gtgtgtgtgt ggtgcgtgtg 140520
tggtgtgtgt gtggtgtgtg gcgtgggtgt ggtggtgtgt gtgatttgtg tggtgtgtgg 140580
tgtgtgtgaa gtgtgtatgt ggtgtgtgtg tggtgcgtgt atggtgtgtg tggggtgtgt 140640
ggtgtgtggt ctgtggtgtg tggcgtgggt gtgtgtggtg tgtgtgtgat ttgtgtggtg 140700
tgtgtgcggt gtgtggtgtg gtgtgtgagg tgtgcatgta gtgtgtgtgt ggtgcgtgta 140760
tggtgtgtgt gtggtgcgtg tgtgtggtgt gtggtgtgtg tggtgtgtgt gtggttgtgt 140820
gtttgtggtg tgtgtatgtg tggtgtgttg tgtggtgtgt gtggtgtgtg gtgtgtgtgt 140880
gtggttgtgt gtttgtggtg tgtgtatgtg tggtgtgttg tgtgatgtgt gtggtgtgtg 140940
tgtgtggggg ggtgtgtggt gtgtgtgtgt gtggtgtgtg tgtgtggtgt gtgtgtgtgt 141000
ggggtgtgtg tgtgtgtgta tgtgtgttca gccgcagaga cttgagcccc ccttttctgt 141060
ttctttctcc agggctgaag ctgccctcga ggacctggtc tccaccattc gagtctgaag 141120
attctcagaa gcacaaccag agtgagtatg aggattcggc cggcgaatgc tgctcctgtc 141180
caaagacaga ctctcagatc ctgaaggagc tggaggagtc ctcgtttagg aagacgtttg 141240
aggattacct gcacaacgtg gttttcgtcc ccaggtcagg acttggcgct gggctctctt 141300
agtgggtgcc aattggcttg gtgttggtgg aaggtcatta cttagggacc gagaggtagt 141360
gggacccaga gacggcagaa gggtgggtgg agtctgaatg gagccctttc ctgggtggag 141420
gaagagatct tgcagtttcg aaatttcgag gggaatttta tcaggaagag caaataatcg 141480
cacaaaaggg gaaaaatgga caaaactcag catttgcctt tcttacctct cctgagctgg 141540
tctccacgtg agttccaaaa caaactccgt tagacgatta acattttttt ttttctctct 141600
ctctcttttt tttttttttt tgacagagtc tcactctatc gtccaggctg gagtgcggtg 141660
gtgcgatttc agctcaccct ttccgggttc gagtgattct tgtgcctcag cctcccaagt 141720
agctgggact acaggtgcgc agcaccacgc ccagctaatt tttatatttt tagtagagac 141780
ggggttttgc catgttggct aggctggtct ctaacccctg acctcaggtg atctgcctgc 141840
ctcggcctcc cagagtgctg ggattatagg tgtgagccac cgtgcctggc cgtgattatt 141900
gaggctttag ctgagcgcag tggtgtaagc ctgtggtccc agctagttgg gaagccgagg 141960
tggtagggtt gcttgaggcc agcctgggca acataatgag accccatcgc taccaaaaaa 142020
aaaaaaaaac agtttaaaaa ttagtcaggc atggtaatgc atgtctgaac tcctagccca 142080
tggggaggct gagaaagaag gatcacaaga ggccaggaga tggaggctac gataagcgat 142140
gatggcgcca ctgcgctcca gcctgggtga cagagtgaga ccctgtctct aaaaaaaaat 142200
taaaagtatc tgttcagatg tttaccaatg ctattcatcc gagcagactt ttctcccaga 142260
accaccagtg tgtaagaatc ctcttttttt tttttctttt ctttttcttt ttttgttgca 142320
tgtttcccct atgaccctga gtccaaaaga atgttcaggg ggacagccaa ggcttcaaag 142380
tggttactgt ttcacctgtt acaaacaaaa tgttggctag gcacagtggc tcactcgtgt 142440
aatcccagca ctttgggagg ccgaagtggg agaatcagtt gaggccaaag gtggagacca 142500
gcctgagcaa cagagtgaga ccctatctct actaaaaaag gaaaaaaaaa aaaaaaatag 142560
ccagacatgt tggtgcatgc cttgtagtcc cagctactcc ggaggctgag gcgggagaat 142620
tgctggagca caggagttgg aggctgctgt gagctatgat ggcaccattg cactccagcc 142680

-continued tgggcaacag agcaagaccc tgtctcaaaa aggaaggaag ggaaaaaaag aaagaaagaa 142740
aggaatggag ggagggaggg aaagaggaag gaaggaagag agaaagaaaa agaaagaaag 142800
aaagaaagaa agaaagaaag aaagaaagaa agaaagagaa agaaagaaag gaaagagaga 142860
aagaaaggac agagaaagga agggggcaag ggagggagag aggagggaag gaaggaagga 142920
aaaaaggaaa agaaagaaaa gaaagagaaa gaaaatgaaa aaaagaagga aggaaagaga 142980
aagaaagcaa atgaaggaag gaaagaggga aaaagagaga aagaaagtaa aagaggaaag 143040
aaggaaggaa ggagagagag ggagagagaa aagagaaaga gaaaagaaaa ggagaaagag 143100
gaaagaaacc agaaagagag agagaaagaa gaaagaaggg aaagaaaaga aaaattctgc 143160
cagacttgga gaagtggctg agtcagttgt gatgtccaca tgtagtcacg tttgacatcc 143220
cagggccacc tcagcaggcc gtctctgggg agaattttct ctgatttctt ccccttccct 143280
tgctggaccc ctgcacctgc tggggaagat gtagctcact ccgtctagca agtgatggga 143340
gcgagtggtc cagggtcaaa gccagggtgc ccttactcgg acacatgtgg cctccaagtg 143400
tcagagccca gtggtctgtc taatgaagtt ccctctgtcc tcaaaggcgt tggttttgtt 143460
tccacagaaa aacctcttca ggcactggtg ccgaggaccc taggtatgac tcacctgtgc 143520
gacccctggt gcctgctccg cgcagggccg gcggcgtgcc aggcagatgc ctcggagaac 143580
ccaggggttt ctgtggcttt ttgcatgcgg cgggcagctg tgctggagag cagatgcttc 143640
accaattcag aaatccaatg ccttcactct gaaatgaaat ctgggcatga atgtggggag 143700
aaaccttcac taacacactc ttgctaaaac atagaatcat gggagtgctt cctgggtacc 143760
ccctccctgc cttctgtttg cagccactgt ttgctcacta aacatctctg cacctcccgc 143820
gtgcatttgc agaggtgggt gggggtcccc ggagtctgag ctccccgcgg ctgggtgccc 143880
cgacccagca gctcctacac catgaatgga ggttgatctg gaaacagaat attttcatga 143940
aagggcgaca gggtatgaac aaaagaacac cgtgtcgctc actgaattcc acggaggaga 144000
gtcagggatc tcttccttcc ttccttcctt ccttccttcc ttccttcctt ccttccttcc 144060
ttctttcttt ttttccttct ttctttcttt ccttctttct tttcttttct ttattccctc 144120
cctctctccc tccgtccgtc cctccctccc ttccttcttt ccttcttctt ttttttttgg 144180
atggaatttc actcttgttg cccaggctag agtgcagtgg tgcgatctcg gctctccaca 144240
acctccacct cccgggttca agcaattctc ctgcctcagc ctcctgagta gctgggatta 144300
caggcatgcg ccaccacgcc cggctaattt ttgtactttt agtagagaca gggtttctcc 144360
atgttggtca ggctggtctc gatctcccga cctcaggcga tccgcccgcc tcggcctccc 144420
aaagtgctgg aattacaggc gtgagccacc gcccctggcc agggacgttt cttttcaact 144480
tgagtcttaa gagaatgaag cagtatggtc ctgggagaga gaaaaagctt ggagaacttg 144540
ggagaaaggc aaggagatgt ttacctgtcg tggcttttgg gaggaacagg aggtgagact 144600
aaagaggcaa gttgggacca cttggagaga ttttcttcct ttagcagagt gtttatttat 144660
ttattttttc ccaggcacct gtgtggcctg atctgccctc tagtggccat ttgcaatact 144720
aactgtagcc aagaagggtc taaaaatgta cgggcttggt ccaaagcaga tctcaatctc 144780
agtcctgcta ttaataatat tcgggtggct cacgcctgta atcccagcac tttgggaggc 144840
cgaggcgggc ggatcatgag atcagaagat cgagaccatc ctggctaaca cggtgaaacc 144900
ccgtcactac taaaaataca agaaattagc tgggcgtggt gacgcagcta ccccaggcgg 144960
ggcaatcact tgaggccagg agttcgagac cagcctgacc aagatggtga aaccccgtta 145020
ctacaagaaa cataaaaatt agccgggcgt ggtgacacac gcctgtagtc ccagctactc 145080

```
gggaggctga ggcaggagaa tggcgtgaac ctgggacgcg gagcttgcag tgagccaaga 145140
tcgtgccact gcactccagc ctgggccaca gagcgagact ccgtctcaaa aaaaataaaa 145200
ataaaataat atttggggcc acagctggac ttggtagctc acgcctgtaa tcccaacact 145260
ttgagaggcc caggcggggc aatcacttga ggccaggagt tcgagaccag cctgaccaag 145320
atggtgaaac cccgttacta caagaaatat aaaaattagc cgggcatggt gacacacgcc 145380
tgtagtccca gctacttggg aggccgaggc aggagaatca cttgatttct ggaggcggag 145440
gttgcggtga gccgagatct cgccactgca ttccagcctg ggtgacagag cgagactctg 145500
tctcaaaaaa aaaaaaaaaa aagaataaat acataatact aataataata ataaataata 145560
tttggggtca gattattcta gggcactgtc caacaacact gagaagcatc cctggcttcc 145620
actcatctga tgccagtagt gtgtcttccc cctaaagtag taataaccaa aaatatcttc 145680
agacattgct aaatatcccc ctgggtgatg gggtcagaag gacccttggt tgagatgacc 145740
aggttagtgt gggattgctg gataataaaa tgctgcctag gccaggtgct gtggctcatg 145800
cctgatgcct gtaatcccag cactttggga ggcccaggca ggcagatcac ctgaggtcaa 145860
gagtttgaaa ccagcctggg caacatggcg aaaccccgtc tctactaaaa atacaaaaat 145920
tagccgggca tgatgatgca cgcctgtaat cccagctact tgggaggctg aggcaggaga 145980
atcgcttgaa cccagaaatt ggaagttaca gtgagccaag atcacaccac tgcactccag 146040
cctgggcaac agagcaagac tctgtctcaa aaaaaaaaat cagttgatgc tttgtctttt 146100
gccacttcat ggtctttttg gttataatct ttttggtata taaactcatt tggcctgttt 146160
gatgagccca ttttacatct ctggttgttg agataccaat ttctcagtag ttactcatga 146220
agcaccaacg tcttggttat tttcacgaga cccatttgtg cctgtataga aattatctga 146280
atcttgctaa tacggacata tctttggctt gataagtggt ggagctgttt tcttttccat 146340
tctacaatgt tgttagtctt ttaatacaaa aagaccataa agagaatctt aagaaatgcc 146400
cccaaagtag gatttgtttt ctgaccacac attttctgat gacgctgcaa tagaaactaa 146460
aagttaattt caaaagatta aacagaaaac ttcacttctt ggtggttaaa agttaaacac 146520
ttacaggctg ggcgcagtga ctcacacctg taatcgcagc actttgggag gcccaggcag 146580
gcggatcacc tgaggtcagg agtttgagac cagcctggcc aatatggtga aaccccttct 146640
ctactaaaaa tacaaaaatt agccagatgt ggtaacgtgc gcctgtagtc ccagctactc 146700
aggagactga ggcagaagaa tcacttgaac ctgggaggtg gaggttgcag tgagccgaga 146760
tcacgccact gccctccagc ctgggcaaca gagcgagact ctgtctaaaa aaaaaaaaag 146820
ttaaaaagtt aaacacttac atatctatcg ggccaaagca gaaatggaaa cttccattga 146880
agtccttttg gaaaataatg aaaatgtgaa tatcacatac cttaacttgt agaatattgt 146940
caaagcttgg ctttgatgtt acttagcaga cttaaatgga ttgataaatt aagaaataaa 147000
ctttaaacta taaaactata aatgtgttag gaagggaaaa gcaataacag ctaagcctat 147060
ggtaaacata atcaaaggga aaacacaaac cagaaggaaa gaagatgaca taaaactagc 147120
gtctgaagaa aattttaatg tgttaagttc tttggacaat ggtgcacttg ctaaatttga 147180
aagtttcagt aaggtgggaa aatttaactt gtctaaatgg attcaaaaag aagcagaaaa 147240
attaagtggt tatgaacctt ggaaaaagat atgtgtcaaa taatttcctc aaaaaagtcc 147300
cttggcccag agagttttat agacacgttc tttcaaattg tgagagagca actatttcct 147360
ataatagaaa aactatttta gggcacagaa atctataaaa gttatcccag ttcattttat 147420
```

-continued gaaatgaaca taacaccctt aaagaacttg acaaagaggt tgagcatggt ggctcatgcc 147480
tgtaatccca gtactttggg aggctgaggt ggggggcgga tcacaaggtc aagagattga 147540
gaacattctg gtcaacatgg tgaaacactg tctctactaa caatacaaaa attagccaga 147600
catggtggca cacgcctgta atcccagcta cttgggaggc tgagccagga gaatcgcttg 147660
aacctgggag gcagaggttg cagtgaaccg aggttgcgcc attgcacact ccagcctggc 147720
aacagagcaa aactctgtct caaaaaaaaa aaaaaaaaaa aaagaacttg acaaagatac 147780
tgcactgaac aaaagccaca ggccaagcta atatgtgatg ttagattcaa atgtcccaaa 147840
taaaacactg cactggcaat attgtttatc tccaaaatgc aaggatggtt taagatcaga 147900
agatttgata acatcatcta gttcatcaag aggtgcaata aggaagatca tatctgtttc 147960
aataacctta atttaaaatt cctaacttag agaaagggga ggaaaaaaag aggcttcata 148020
aaactcataa tagaatattt cttctacaag ataaatatta cctaggttaa accaacagcc 148080
aagctaacat cattcttaaa attattctta gcagagttag gaacaaaaca aggaagcccc 148140
atctcatcat tactaattaa catttctctg ggcatccagc caatgtaata agacaagaaa 148200
cagaaatcag agttgtaaag aatggaatgt gggaaataaa gtcattgcta tttgcagagc 148260
gtctagctca agggtaggca aactatggcc catgggctag ctgcctgttt ttgtaaatga 148320
actcttattg gaatgcaacc ccacccactt gtttacacat catgtagggc tgctttaagc 148380
tacaatgaca gagtagttgt gacagaggtc atttggcttg caaaacccaa aatatttatt 148440
atctagccct ttacgggaaa attttgttga cccctcttct agtgtgtcat tgaaaaccca 148500
ggaaagccaa ttatgaaact ttttaaatga gttagagttt gggaaagtag gtacatagaa 148560
ataagcaaaa agactgtaga tacacaagca ataattagaa tataaaataa gggaaaagat 148620
ccctttcaaa attgccgtaa aaccttagca caactcataa taaccccatc tagaatgact 148680
tataaaggaa cacgttttaa agtgttactg atatattaaa ttgtacaaat aaacatgaaa 148740
gcctgtttca aatcatttaa agaaagctta ctggcaaatg gaaaagagta agttgtatag 148800
cacgatacat aaaaggttaa tatccttaat gaataaacaa cacaggagta aggaaaacac 148860
aagaaattca tggaaaaaca gacaaaagac aaggaggggga caattctttg gagaatcaca 148920
gagaaccaat aaaggaaaaa tgaagtcaca ctcagtaata taaagatccg caaataacgt 148980
agtcgagtga tagcatattt ttaatctctt gggttaaaga tctagacaaa caaacataga 149040
aagaaaaaaa aaaactatta aggcttaggg gttgctgaga ttgtcctgga atgcagtctc 149100
atggcctgct ggtgcaacca caagtcaata tagagtttct ggacaaccat ttagctgtag 149160
gtattaagaa gcttaaagag tttcttatct ccctgaacct agtaatattt tcctctagga 149220
atctactttg gggaagtaat aagacaatca gacaatgatc aaaggaatat ttataacagc 149280
aaaaaaaaaa aaaaagagcc atgtgcggtg gctcatgcct gtaatcctgg cactttggga 149340
ggctgaggtg ggcagatcac ctgaggtcag gagtttgaga ccagcctggc caacatggcg 149400
aaactccgtc tctactaaaa atacaaaaat tagctgggca tggtggcgga ctcctgtaat 149460
cccagctact caggaggctg aggcaggaga atcgcatgaa ctcaggaggc ggaggttgca 149520
gtgagccaag atcacgccgt cgcactccag cctgggcgac aagagtgaaa ctctgtctca 149580
aaataaataa ataaataagg aggatggtta agtgagtgac gactcacgta gcaaatggaa 149640
tattttacag tcattcatcg ttttccaagt tttctgcagg gaacacatgc tacttttgta 149700
gatgatggag gaaaacccta atattaaaaa ggaaaagtcc caaaattctc tcctaaaatg 149760
ttatgttgaa aggaaaatat ttagtaaatg cttccaatat aataagtaga caaagtttac 149820

-continued ttataaaaca ggcttgatcc tcatcatgtt cacacataat atttacaggg aaaaaattgt 149880
ccaaaggaag cagtgggctg tggatttatg agtgatttat attttctttt cttttttttt 149940
tttttgagac agagtctcac tctgtcgccc aggctggagt gcagtgacac gatctcagct 150000
cactgcaacc tccgcctccc gggttcaagc aattctcttg cctcagcctc ctgagtagct 150060
gggattaaag ctgtgcacca tcaggctcgg ctaatttttg tatttttagt agagacgggg 150120
tttccccatg ttggccagac tggtcttgaa ctcctaacct caggttatct gcccgccttg 150180
gcctcccaaa gtactgggat tataggcatg agccacctcg cccagcctac attttcttct 150240
ttatcctttt ttctttgtat tttaaaattt gttagctatc aacctttgtt gtttaatatg 150300
tcttcttaag ggatggggag aagtgtgcca attgcataga tgtttcttgg agttaatctt 150360
cctgacctga gtgatgtgat tccttttcta agaattgcag cttaatcact caaattatac 150420
aggtgcccta agcagcaata agaaggaaaa gatgtatttt ttcctattta aactgatgat 150480
gtcgatcagt agcttgggcc aatgagcaaa tgccatttgg cagggcttcc tgaaaagcta 150540
gactcttacg tgcttttggt gtcttatttt tgtcactgac cctggctggc ctatttatct 150600
gcaaaatgaa aaacctgaaa tcgagcatgt cgaggggaat atcggtgtgt gtctaccatt 150660
gacggtctta gaagcactca tccctcacga ggtgggcctg ctctaatcct tcagatgctc 150720
acaagggtat attgaaagct gctctgagtg gtcattcctg gcagtctgta ttgtaatcca 150780
tgttccccat tgctgcaccc tcctgcgctc tgatctttct tcttaatcaa gccttttatt 150840
ctccagtgtc actttttaa aaaaaatgat ggtgatggtg tcatcataca tgtcctactg 150900
tcgttccagg ccatctcgga aacgcaggtc ccttggcgat gttgggaatg tgacggtggc 150960
cgtgcccacg gtggcagctt tccccaacac ttcctcgacc agcgtgccca cgagtccgga 151020
ggagcacagg ccttttgaga aggtggtgaa caaggagtcg ctggtcatct ccggcttgcg 151080
acacttcacg ggctatcgca tcgagctgca ggcttgcaac caggacaccc ctgaggaacg 151140
gtgcagtgtg gcagcctacg tcagtgcgag gaccatgcct gaaggtaggg ctgctgctcc 151200
ggggtccgag tgtcatgggt gggacatcaa ggctgaccaa ggacagattc tccaccctct 151260
aagcagtgca tatctgtatt ttaccttatt ggccttcatt tttgtttgag acggagcctt 151320
gctctgtcgc ccaggctgga gtacagtggt gcgacctcag ctcactccag cctctgccac 151380
ctatgtcaag tgattccctg cttcagcctc ccaagtagct gggactacag gtgtctgcca 151440
ccacgcccag ctaatttttg tatttttagt agagatgggg tttcaccata ttgcccaggc 151500
tggtcttgaa ctcctgggct caagtgatcc acccacatcg gcctctcaaa gtgctgggat 151560
tacaggcatg agcaccgaac ctggcctttt tttttttttt tttttttttt gagatgaagt 151620
cttgctctgt cgcccaggct ggagtacaat ggcgcaatct tggctcactg caatctccgc 151680
ctccctggtt caagcaattc tcctgcctca gcctcctgag tagctgggac tacatgcgtg 151740
tgccaccaca cctgtatttt cagtagagat ggttccacca tgttgcccag gctggtctcc 151800
aatgcctgag ctcaagtggt ccgccaacct tgagctccca aagtgctggg attacaggca 151860
tgagccacca tgccaggtca tattttaaaa ttatgagtca taggcaatca ttatgtaaac 151920
tttagaaaat acaccactgc actcccgcct gggtgacaga gcaagactct gtctcaaaaa 151980
aaaaaaaaag ttatacgcag aaagtaaccc atttaatctt cctaacaatc ttgtgggatg 152040
agttttagat gtccgttctc tgacgaggaa aatgggttgt gggaaaatga cgtcaccagc 152100
ccaaggttgc accatggaca ggtggcagaa gtgggatctc atccaagagt tacatccctg 152160

-continued cctctcactt cctctcctta cagccaaggc tgatgacatt gttggccctg tgacgcatga 152220
aatctttgag aacaacgtcg tccacttgat gtggcaggag ccgaaggagc ccaatggtct 152280
gatcgtgctg tatgaagtga gttatcggcg atatggtgat gaggtaaggc ccttgactct 152340
tgggcatgcc cctgcacact tcagcatgcc ccttcagagt tgcacttggt acctccttcc 152400
tctgctgaaa ttttgattcc agtgcttctc tcatcaggta ctgtgctatt agtacttaaa 152460
gccttgatac ctgacttcgc aggaagatgg gtcagaaatg ccaatctacc agcttgttac 152520
ttttcttagt ttctcacatt gctttccagc tgtgtcctct aagttgaatg atgtctgcct 152580
cccaccacaa caggagactc atttcacttt agaaggagtt atttgagtct taaaacctta 152640
taaattgctg ggtacagtgg ctcacacctg taatccaagc actttgggag gccgaggcag 152700
gcagatcact tgaggccagg agtttgagac cagcctggcc aacatggtga aaccccatct 152760
ctacaaaaat acaaaaatta gccaggcgtg gtggtgggtg cctgtaatcc cagctactca 152820
ggaggccaag gtgggaagct gaggcaggag aatcacttga agccaggagg tggaggttgc 152880
agtgagcaga gattgcacca ttgcgctcca gcctgggtga cagagtgaga ctctgtctca 152940
aaaacagcaa caacaaaaac cttataagtt actttcatta gatgcttcca ttgagccaga 153000
caccatgcaa ggtgctgggt gagtgcagag atgcacaaga catagaatcc aagacaaata 153060
acccaaaaga acccaaacag ttgctaagct cttcccaggg ctcactgtat gtcccaaaca 153120
cattcagcac gttacacaga gtatctcatt gatcacattt tattacctct aggaaatttt 153180
gagaggcccc attattttta tggacagcta ggcaaaaaaa aaaaaagggc cgttaattct 153240
aattttattt ttttcgtaga atatagatcc tgagtactgt taagtgtttg taaaatgcat 153300
tgcttgtaag atgcattcca atttcagaaa tgccaaaatg caaaaataat atacctcttg 153360
ggactgagga agtacaatac gtcctcacat tatcccagtg agctgggtac tgaggcttcc 153420
agagtttaag ttgctgcaca aaacctggaa gaatagaatc atgatccaaa tgcatgactg 153480
atatttcaat ccagaaactg ccaaattttt tttaccataa aggtctggat agtaaacatg 153540
tttgactccg tggccagatg atttctgtta caactactca attccaccat tctactgaga 153600
aagctgccat gggtgatatg taaatgaatg gatgtggttg tgtaccaata aaactttatt 153660
tacaaaaaca cgtggtggac caggtttagt tggtgggcca gagtttgcca acaactaaca 153720
gagattacag caaaatgtct gatttcctgg aactttgaga gggagtcctc ctataaccag 153780
gtggacctcc ctctacccct cctgggacca catctactct tggcaaccaa agattttggc 153840
tttgacaata atttacaatt gagatctaat tctaaattat tgtggcttgt gggccaaatc 153900
tggcttgcag agcattgtaa agaatgtgca acagggttga ggtcaggagt tcaagaccag 153960
cctggccaac atggcgaaac tccgtctctg ctaaaaatac agaaattagc tggacgtaat 154020
ggtgggcgcc tataatccca gctgctcctc gggatgctga agcagggaga attgcttgaa 154080
cccgggacgc aaaggttgca gtgagccaag atcgtgccac tgcactccag cctgggcgac 154140
agaacaagac tctgtctcaa aaaaaaaaaa aaaaaaaaga atacgcaaca gagactatat 154200
gtggcccttc acagcttcac agaaaaagta aactttcaaa aatagaaagt gtccttactg 154260
aacttgtcat tctgggccta ttttggggcc ctgtttgcta aatgaatggc ttgatttgcc 154320
ttttttaaca ttcattttta aaataaaatt gctaaatgaa tggcttgatt tgcctttttt 154380
aatattcatt tttaaaataa aattccttat catacagagc tcagctagtt tttaattggc 154440
agaaacgtgc atatgcctct aatccatatt catgagttac tttcctctgc cttttgatgt 154500
ctctgtccac aatagccttt ggaattatga tttgtagttg ctagatagaa tttaatctca 154560

-continued tgattggggt atcatttatt tttggggatt tggattgcct ctggttttta ccatgttagg 154620
taatactaat tttatctgga aaccatttta gctttttgga ttgacagctt tagttattgt 154680
ttcagtcagt tcttgctgcg taacaaactg cccccaaagg tactggttta aaacaaagga 154740
catttattct ttctctcaat tctgcaggtt cactgggtga ttcctttgtc ctgggccagt 154800
ttggctgggg ctggatggcc tcattcacat ggctggggcc tcagctgggg gcacttggag 154860
ctttgtcctc atgtgttctc tcactgccca gtgagctagc ccaggcaagg aaggacatgc 154920
cccatataca aacacttctt aggactctgt ttgcatcaca tttgctagtg tccctttggc 154980
aaagtgagcc catggctaag cccagaatga ggaagtacaa tacatcctct gagtatctca 155040
gtgagctgga tactgaggct tccagagtct catagacaca gaaagtcatg attccctggg 155100
ggccataatt gcaaagttta ttaatatatt atcctatatg tattaatcct gtaggtccta 155160
aggaaataat tcaaatttgg ggcagggaac aaagctctat gcataagatt ttcatcagta 155220
gcaaaatatg caaaccacta agatgtccat ccattggaga atggacacat ggaagacggt 155280
gcatccatag aattggtgga tgaagagcca ttgaaaatga tgtttggggg ccaagcatgg 155340
tggctcatgc ctgtaattcc agtgactcag gaagctgagg tgggaggatt gcttgaggcc 155400
aggagtttga gcctgggcaa cacagccaga ccccatctct gcaaaaaaaa aatttcaaaa 155460
ttagctaggt gtggtggtct atgcctgtag tcccatctac ttgggaggct gaggagagaa 155520
ttgcttgagc tcaggagctc caggttatag tgggctgtga ctcactcact acactgcaga 155580
ctgggtgaca gagcaagaag actctgtctc caaaaaaata agataaaatg tttgggatga 155640
cctttgttca gtgtaatgta gaagttaaaa ttacatgctc tggagtttag ttcgtttgtg 155700
ttgttatccc ccagcagtta agaatccccc tgtatctgct gggtgcagtg gctcacgcct 155760
gtaatcccag cactttggga ggctgaggcg ggtggatcat gaggtcagga gatcgagacc 155820
atcctggcta acacggtgaa accccgtctc tactaaaaat acaaaaaaat tagccgggca 155880
tggtggcggg cgcctgtagt cccaactact tgggaggctg aggcaggaga atggcgtgaa 155940
cccaggaggt ggagcttgca gtgagccgag atcacgccac tgcactccag cctgggcgac 156000
agagtgagac tccatctcaa aaaaaaaaaa aaagaaaaag aaaaaagaag aaaaaggaat 156060
ccccctgtat ccagactagc ttatgataga ggaaaagctt cttagctccc agagttgaac 156120
aactgaagag cttctcacat ggctggatcc aggattcctt tgggtcggtt gcatcttttt 156180
tttttttttt tttttttttt tgagatggag tctcactcac tctgtcatcc tgtcatccgg 156240
gctggagtgc agtggtgcag tctcagctca ctgcaacctc tgcctccctg tttaagcgat 156300
tctcctgcct cagcctcctg agtagctggg attacaggca cccacgacca cacccagcta 156360
atatttgtat ttttaatgga gacgaggttt caccatgttg gcctggctgg tctcgagctc 156420
ttaacctcag gtaatccacc caccttggca tcccaaagtg ctgggattac aggcgtgagc 156480
caccatgcct agcctgggtc agttgcatct taacggctcc tggcagtgag cccagtagcc 156540
cctggttgtc caccggtggt tgtagtggtt ccaaacctca tttctttgca gtgccaaacc 156600
cagaggaaga cagagtgcat cccagcattc ccagctagac tgaggtcatg tgacatccag 156660
tgcccaatca tgtgaccaga ggaatgctgt atgctgattg gcttgggcat gagggatttt 156720
tttttttttt ttaatttaga aacagcttta ttgagctgta acttacatac cataatattc 156780
actcccacca catgctagag agaattttgt aaatggagta aaattacact ccaacagtat 156840
aaattgtgca cataaaaata aagttttagg ccaggagcag tggctcacgc ctgtaatcct 156900

-continued agtaccttca gaggccatgg tgggtggatc acctgaggtc agggttcaag accagcctgg 156960
ccagcatggt gaaacttcgt atctactaaa aatacaaaaa ttagccgggc gtggtggtgc 157020
acgcctgtaa tcccaactac tcgggaggct aagacaagag aatcacttga acccgggagg 157080
cagaggttgc agtgattccg agatcacacc actgcactcc agcctgggtg acagagtgag 157140
acaccatctc aatatatata tatatatata tgtaaataaa taaataaagt tttacatcac 157200 ttttttttctt gatcaaagca atgctaggta attaaggaca ttgttggcaa taacagaaat 157260
gtgtctatga aaaggttctt aagaaggtga ctgtaacctc acattctcct ttcattttct 157320
cccccatctc tgcttctctc tagggtgaac acagttggtc tgggtgggat tggggttgtg 157380
ctgtgtgggg cagaggctgt tggggattcg tgatgggaat tcctaatagt gacccttggg 157440
tcccaggaac aggagacacg ggccagtcaa aggcatggga agaagctagg agaagttagg 157500
attcgagtta aatccagtgc caacagggtg accagttgtc taggtttagc caggactgag 157560
ggctccctgg gatgtgagat tttcaatgtc cacactcaga aagttctggg caaatgggga 157620
caagttggac acagaagcag aaaaaaaatc aaggagggtc tgcagtggaa acgggcattg 157680
ttcactctgc agaatctgta ttcttgctgt caacaatgcc ccgaacttcc tctggaatct 157740
gctcctcacc cttgagtggc tctcacctcc cactctcaac cccagcctgg taccagggca 157800
aaacacaaaa ctcagcccca aattagccat gacaaaaatg caaatcaaga ccacgatgca 157860
ataccacttc atgcccacga gcgtggcaaa aaacaaacag acggacaata acaagtgtcg 157920
gtgaggatga ggagaaatcg gaaccctcat acattgctgg tgggaacata aaatggcaca 157980
gctgctttag gaaagagttt ggcatttctt tcattctttc tttttttttt ttgagatgga 158040
gtctatctct gtagcccagg ctacggtgca ttggtacgat cttggctcac tgcaacctcc 158100
gcttcctggg ttcaagtgat tctcctccct cagcctcttg agtatctggg actacaggaa 158160
cccacgacct cgcccggcta atttttgtct tttagtagag acgaggtttc accatgttgg 158220
tcaggctggt ctcaaactcc tgacctcgtg atctgcccgc ctcggccttc caaagtgctg 158280
ggattatagg cgtgaaccac cgtgcccagc tggtggaagg tatttttttt ttcttttgct 158340
agtttcataa acaaagccac ctctagctat ttaattgcat tttcagtatc tcccgttaaa 158400
aaaatttttt ttttcagaga cagagtcatg gtgtgtcacc caggcccgcc atccgccacc 158460
atgcccagat aatttttttt tttttttcaa acagagtctt gctttgttgc ccaggctgga 158520
gtctcgcttt gtggcacacg cctataatcc cagttactca ggaggctgag gcaggagaat 158580
cgcttgaact cgggaggcgg aggtcgcagt gagccaagat catgccactg cactccagcc 158640
tgggtgacaa gagcgaaact ccgtctccaa aaaaaaaaaa aaaaaaaaaa aaaaagaaga 158700
tgcatttccc ctttgtcctg gatagcagct accttgggtt tctatatttg cttatttgtc 158760
cctctctact cggtgactca ttccacttgg aagaaacttt ggactggagt tccctgcccc 158820
cacccctgcc accagactga tttgttttct tgctgttatt gtcacacgat aagcatgggg 158880
ttgttggctt tttttttttt ttttttttta acatttcttt ctcttctcca ctctccaccc 158940
ccctcctaaa tgttccagcc cggttctctg catgcactat tagcttggaa ctgtgtcgaa 159000
aacttttcag agttttgggc tcgatgcttg caggtttcat ggtcttattc ccaagagcct 159060
cctgtctctt ctcataagtt ctggaattat ctctagttac gtgcttatca cagggtatgt 159120
ttcccacttt gcaaatctcc atttgggtgg atcccaactg ttttatttat ttatttatta 159180
ttttatttta tgtgtttatt tttgaggcaa agtataccac attttctttt tctttttgag 159240
acagtcttgc tctgttgccc aggctggagt gcagtgtcac gatctcgact cactacaaac 159300
tctgcctccc gggttcaagt gattctcctg cctcagcctc tcgagtagct gggattacag 159360
gcgcacacca ccacaactgg ctaatttttg tatttttagt ggagacgggg tttcaccatg 159420
ttggcaagga tggtctcaat ctcttgacct cgtgatctgc ccgccttggc ccctgaaagt 159480
gctggaatta caggcatgag ccaccgtgcc cgggcttcaa ctgtttttat aatgattaaa 159540
aaaaaaaaaa tcgaaaggca gcaccgtggc aaagaaagag ctttttttatt tgtccttaga 159600
cattaagcac atttatccat ttggttctga tgtgacagag gctgggagtt gcagggaaag 159660
gcaggaaatc tggcataggc cctgcagatc cttcatttcc actcttttct aattttgctg 159720
gatacatggc aaaaatattc tgcagtggtc ttaaggagaa gttctagagc cagacagttc 159780
tcttttttta gtttctttct ttttatttat ttattttttt tgagatggag tcttgctctg 159840
tcacccaggc tggacttaag tggcgcgatc tcggctcact acaagctccg cctcccgggt 159900
tcacgccatt ctcctgcctc agcctcccaa gtagctgtag agccagacag ttctgagttc 159960
aagagctggc cctgccactt tgcagctatg agatctcgga caaaccatat aatctcttaa 160020
accaggggtc agtcagtaag ctatatccca taggctaaat gtggcctgct gcctgatttc 160080
taatgatttg tgagctagga gtcacttttg cattttattt atttatgtat ttatttttga 160140
gatggagtct tgctctgtca cccaggctgg agtgcagtgg cacaatcttg gctcactgca 160200
acctccacct cctgggttca agtaattctc ctgtctcacc ctccaagtag ctgggattac 160260
aggcgtgtgc cgccatgccc agctaatttt tgtattttgg gtagaggtgg gggtttcacc 160320
atcttgacca ggctggtctc gaactcctga cctcaggtga tccgcccacc tcggcctccc 160380
aaagtattgg gattacaggc atgagccacc acgccctgcc cacttttgca ttttaaaatg 160440
attaaaggaa aaacaaggag agacgtgaac caaagggtgc aaagtttcag atgggaggaa 160500
tacgttctag gaatccactg ctctgtagat gaatggtgac tatagctaat aacacatatt 160560
gcaaaatggc tagaagaata gattttaaat gttctcacaa caaagaaata agtacatgaa 160620
gtgatgagga tttaattagc ttgttttaat cattccacaa tttatactgt aacataactt 160680
tacactgtac cccatacgtg tacacaacta ttatttttat ttttgtttat ttattttaga 160740
gacagggtct agctctgtca cccaggctgg agtacggtgg agccttcata gctcactgca 160800
cccttgacct cctgggctca agtgattctt ccgccttagc ctcctgagta gctgggacta 160860
caggtgcgaa ccatcgtgcc cggctaattg ttctattttc tgtggaaatg gggtctggct 160920
atgttgccca ggttggtctc taactcctgg gctccagcaa tcctcccttc acggcctccc 160980
atagggctgg gattacaggc acgagccact gtgcctgacc tataatactg ttgtcaatta 161040
aaaataaaac aaatgatttt tagaaagata atattatgga aattaatatt aatagaaaat 161100
agataatagg gctgggagct gtggctcacg cctgtaatct cagcactttg ggaggccgag 161160
gtgggcggat cacttgaggt caggagtttg agaccagcct ggccaacatg gtaaaaccct 161220
gtctttactg aaaatacaaa attaggcagg cgcggtggtg agcgcctgta atcccagcta 161280
ctcgggaggc tgaggcagga gaatcacttg aacccgggag gcagaggttg cagtgagccg 161340
agattaagcc attgcgctcc agcctgggca acaagagtga aactccgtct ggaaaaaaaa 161400
aaaaaaggaa aagaaaagaa accatcaggg tttaatgctc agcttctggc ttaggaagtc 161460
tggctcttac cgataatgat aacctctgca tatatcttta tccatagcac tatggttata 161520
aaattctgca attctcaaag tcgcttatgt gtcttagtct gtgctttgct gccttggcgt 161580
catttctgag caggatcctg gctgtgagct ccctgcgagg ggtggacact cccagatgtg 161640

-continued caaagctcag ccaccctcct tctcctcctc tcttcctccc aggagctgca tctctgcgtc 161700
tcccgcaagc acttcgctct ggaacggggc tgcaggctgc gtgggctgtc accggggaac 161760
tacagcgtgc gaatccgggc cacctccctt gcgggcaacg gctcttggac ggaacccacc 161820
tatttctacg tgacagacta ttgtaagtct ccatggcagc ctcagctgac tggggctgtg 161880
cttagcactg agcatggtgg gacattgcag gggatgactt ggagaggccg caggtgctgg 161940
ccctggcctt gactctcagg cctatcagct gctgcggtgc ttgccctctt tgatcctgca 162000
cttttttttt ttttgagatg gaggcttgct ttggagtgca ctggcacaat ctcagctcac 162060
tgtagcctcc gcctcccggg ttcaagtgat tctcccacct cagcctcaca gtagctggga 162120
ctacaggtgc ccaccaccac gcccggctaa ttcttgtatt tttagtagag atggcatttc 162180
accatgttgg ccaggctggt ctcaaactcc tgacctcaag tgatccaccc gcctcggcct 162240
cccaaagtgc tggaattaca ggcatgagcc accatgcctg gcctgatcct gcacttaaaa 162300
aaaaaaaaaa aagtttcaga ggtacctgtg cagttcatta tataagtaaa ttgtggctgg 162360
gcacggtggc tcacacctgt aatcccagca ctttgggagg ccgaggcggg cagatcacaa 162420
ggtcaggaga tcgagaccat cctggccaac atggtgaaac cccatctcta ctaaaaatac 162480
aaaaataaat tagccaggca tggtggcggg cgcctgtagt cccagctact caggaggctg 162540
aggcaggagc ctcaggaacc cgggaagcag agcttgcagt gaaccgagat cgtgccactg 162600
cactccagcc tgggcaacac agtgagactc tgtctcaaaa aataaaataa aataagtaaa 162660
ttgggtgttg ttgggggttt gctgtacaga taattttgtc acccatgtaa tcagcatagt 162720
acctgatagg tcgtttttttg atcctttccc tcttctcacc caccactctc aagtaggcac 162780
ctgtgttagt ctgtacttac actgcaataa agaaatacct ggccgggcac agtggctcac 162840
acctgtaatc ccagcacttt gggaggccga ggtgggcgga tcacttgagg tcaggagttc 162900
gagaccagcc tgaccaacat ggtgaaaccc catctctacc caaaaataca aaaattagct 162960
gggcatagtg gtgtgcaccc gcagtcccag ctactcagga ggctgaggca ggagaatcac 163020
ttgaacccgg gaggcggagg ttgcagtgag ccgacatcac gccactgcac tccagcctgg 163080
gtgacagagt gagactctgt ctcaaaaaat aaaaaagaaa gaaagagtga aagagagaga 163140
gaagaaaaag aaaaagaaag aaaaggaaag aaagagagaa aaagagagat aaaagaaaga 163200
aaaagaaaga agagaagaga gagaggaaga ggaagaggtc tgagactggg actcagtaat 163260
ttataaagaa aagaggttta attggctccc agttctgcag gcagtacagg aaccatgatg 163320
ctggcatctg ctcagcttct gaggaagcct caagaaactt tcaatcatgg tggaaggtga 163380
agtgggagca aggtgttaag acggggagat ggtgctacac acttcttaaa caaccagatc 163440
ccatgagaac ccacttatta tacagtaccc agtagggatg ttgctaaccc attagaaacc 163500
gcctccatga tccaatcacc tcccacccgg ccactcctcc aacattgggg attacatttc 163560
aacaagagct ttgggtgggg acacagatcc aaaccatagc agtcccggtg tctactgttc 163620
acttctttct gtccatgtgt ggtcagtgtc tcactctcac ttatgggtga gaacatgagg 163680
tagttggttt tctgtccctg tgttaattca gttaggataa tcacctccag ctccattcat 163740
gttgctgcaa agaacatgat ctcattcttt ttcatggctg tgtagtattc catggtgtgt 163800
atgtatcaca ttttctttat ctggcaatcc tgcacttcct catctgtaca tggagataat 163860
aacagaacca cttcaggagg tggagggaca ttttaatgac acaaatgtta agtgcctggc 163920
acctgttgct agtgtctcca tctttgttac tagagttttt tggctagatg aggtggctca 163980
cacctgtaat cccagaactt tgggaggctg aggcaacagg attgcttgag gacaggcatt 164040
agagaccagc ctgagcaaca tagcgagact ctgtctccac aaaaaaatac aaaaattagc 164100
cagctatggt ggtgcatgct tgtaatccca ggtacttggg aggctgagac agggggatca 164160
cttgggccca ggaatttgag gttgcggtga actgtgattg tgccactgta ctccagcctg 164220
ggtgacagag taagaccctg tctctaaaaa ataaaaatta aaagaagttt acatctgtca 164280
aaagtcatgc tgggatcggg actagctatg taatttgcaa gacccagtga acaatgaaaa 164340
tgcagaactc cttgctttaa aattattaag aatttggccg ggcacgttgg ctcacgcctg 164400
tcatcccagt actttcggag gctgaggcgg gaggatcacc tgaggtcagg agtttgaggc 164460
cagcctggcc agcaaggtga aaccctgtct ctattaaaaa tacaaaaatt agccgggtgt 164520
ggtggtgcat gcctgtagtc ccagctactt gggaggctga ggcaggagaa tcacttgaac 164580
ccgaaaggag gaggttccag tgagccgaga tcgtgccact gaactctagc ctgggtgtca 164640
gagcaagact ctgtcacaaa aataagtaaa taaataaaaa ttaaaataaa atgaataagc 164700
atttcagagg ggcaacagca gagcattaaa ctgacagaaa agggtcctgc atccactgcc 164760
tgagatgtgg gagggatgga aatgagcagt gatttggggc aggggtgggg aagagtgtgc 164820
ttccagaata ctgacctctg agcccactgc ctggtcccac tgcacctacg ggactgtttc 164880
gggactgctg gaaaatcagg atgtggaaga gcagcagaga ggtttatgga caagggaggg 164940
aaggaacagg gtggcccacc cattccagga gtggatgtga tttttgatgt gaactttgtt 165000
ggaaacacat tgatatgaaa catatatttt cttattctat ttcagtagac gtcccgtcaa 165060
atattgcaaa aattatcatc ggccccctca tctttgtctt tctcttcagt gttgtgattg 165120
gaagtattta tctattcctg agaaagaggt gagttcagtg agttcagtgg tgtgctggga 165180
acagttggtt ctctggggga aaacatgcct tgatataggt ataggcatat ttaagtttat 165240
tatgaatttt gctgatatag gatgtgtaac atgcaattta cagataattg tcataatatg 165300
atatacacaa ctctttattg taaattccct ctagacagtt gattctcaca gaatgttttt 165360
attgattttt tttttgccc aaacctttat atccgaagct aacctattat tgcaattgat 165420
aaacaagtaa agctccaatg tgaatgttga ttaatttttc aaaatttaca ttaaggagta 165480
ggacttgact gggcacagtg gctcacacct gtaatgctag cactttggga ggccaaggcg 165540
ggtgaatcac ctgaggtcag gagtttgaga ccagcctggc caacatggtg aaacctcgtc 165600
tctactaaaa atactaaaaa attaaccggg catggtggtg ggcgcctgta atcccagcta 165660
ctcaggaggc tgaggcagga gaattactga accctggtgg cggaggttgc agtgagctga 165720
aatcgcacca ttgcattcta gcctgggcga cagagggaga ctccgtctcg ggaaaaaaaa 165780
aaaaagtagg acaaaactga aataagacat atatgttcat cagtgatatg agtgacgtct 165840
ttgctgagtc agatggtaat ttttaaatat cagaagaaca ttttgtgcca catgcaacat 165900
cacagttgca gacatgacac gcttttaagt ttaatctaca tgattaaaca tttttctcag 165960
ctgggcacgg tggctcacac ctgtaatccc aacactttgg gaggccgagg cgggcggatc 166020
atgaggtcag gagttcgaga ccagcctgac caacatggtg aaaccccgtc tctactaaaa 166080
atacaaaaat tagcaaggtg tggtgatgtg cgcctgtaat cccagcttct caggaggctg 166140
aggcaggaga atcgcttgaa cccaggaggc agaggttgca gtgagccgag atcgcaccat 166200
tgcactccag cctgggcaac agagtgagac tttgtctcaa aaacaaaaca aaacaaaaaa 166260
atatttttct catcactttc tcaagcctgg acaaacaaca gaacaacaaa tccagtcctg 166320
agttatagca tttgccagtt tctgtaatgt aaatattccc aggatgtcta aattcaagct 166380
gtagacataa tattactgag tgcagtgtta gaaagagata cataatagct ccccattgaa 166440
tccaccctat ggatacaata tggtgtataa atgatataat gtaaataacc tcaactgcat 166500
tgatcatatt taaatgtagt atgagagtta ggaagtgatg agttttgaac atgtattgtc 166560
tttgctttta ggataattta tttaattgta agcctctata atttatattt tttgttctat 166620
ttggaaggca ttgtacaatt taatctttaa tgatgcttgt atttaacaac tggctcacta 166680
gtttcctgaa aatttaataa ttgtttctca tcagtcggga tgagctcgct ctagaacagt 166740
actgggtgag tggcttttaa gtgttacatg gatggccata aattatttaa aaagccagcc 166800
agagccctgc atggtcgtgc atatctgtag tcccagccgc tcgggaggat gaggcaggag 166860
gatcacttga gaccaagagt tcaagaccag cctgggcaac atagtgagac cctgtctata 166920
tgaaatttta caaattagcc aggtgtggtg gtgagcacct gtattcccag ctattcagaa 166980
agctgaagtg ggaggatctc tggagcccag aaggttaaga ctgcagtgag ctatgattat 167040
accactgccc tccagccaca acagagcaag actgcaactc tgaaatgtaa aaacaaaaac 167100
aaaaacaaaa caaaaaaaaa accacccagg gagggatgag tgctcccatg ttgatgcact 167160
tacatacctg tctgatgggc ttccattcaa aacataaagg tcccccatcc ctgccctaga 167220
ctgcatctag gattatgggg attctgctgg taagggctgc catttgcctt ggggagtctt 167280
gtatgaaaca cctttctgca gagtcccatg agaatctcaa gctaacgtgc ctcgttttcc 167340
tcctccaggc agccagatgg gccgctggga ccgctttacg cttcttcaaa ccctgagtat 167400
ctcagtgcca gtgatggtga gtaccatccc ttccctgtgg gtggccagaa ccctactcat 167460
cagcttcctt tgccttcacc attgagtgag agtgaaggat gggttcccca gggaggccaa 167520
gaaaagccct cttattcatt tgagcttgcc aaactgccct tgctgcagaa acctcattac 167580
tgtgtgcatc tggacacatg gtatttggca cctgcctgaa tgggctcatc tagccggtct 167640
gggacccttg ggcagggtcg accacttggg ctgggctcag ctgggcagtt cttctggtct 167700
tgcctggctt cacccatgta gctacatttt gctggtgtgt cagctagcac tcggtagtct 167760
tagatgattt cactcacatg tctggtggtc agtaggctgg gtggtcccaa ggtgggggcc 167820
ctaagctggg ggaggctgag cctcactctg tccatctagc ctcttaggct ccagcaggct 167880
ggctcaggct tcattccatg gtcctctgtt ggttcctagt agaaagctcc agggcaagct 167940
ccagggcaac agtccattcc aaatctctgc ttggacaatt cttgttgatt cccattgacc 168000
aaaataactc acaaggccat gcccagggcc aaggggtggt gagatagact ccaccttttc 168060
atgggaagag ctccaagtat cctggctttt tttttcccca acctattaca acctgtcttc 168120
catccccttg gcactttgca gaaacagtag tctcaggtgg gaagtagcat cattccatag 168180
caagggtctg aaatcagaca agaaggatgg ggatgcaggt ttgcctcagg acatattggc 168240
caggatcttg gaccagttgt ggctccttcc ttgagtctct gccatgccct ctccatgggt 168300
gcagatgcct gtcctgttct cggccatatg cccagtgccc ggcatgggtc ctggatcaca 168360
gaactcattt catgagtgtt ttcgaggggg tttgggtgag ggcttgggtg gaaggtggct 168420
gcagaccccc aagggatcct ccaaggatgc tgtgtagata agtaagaagt agtgtttcca 168480
tgctctgtgt acgtgccgga cgagtgggag gtgtctcgag agaagatcac cctccttcga 168540
gagctggggc agggctcctt cggcatggtg tatgagggca atgccaggga catcatcaag 168600
ggtgaggcag agacccgcgt ggcggtgaag acggtcaacg agtcagccag tctccgagag 168660
cggattgagt tcctcaatga ggcctcggtc atgaagggct tcacctgcca tcacgtggtg 168720
agtccagtgg gggtgggaca tgggctggct ttcctgaccc ttccctttct ctgcctcctc 168780
ctcctgcaca gagcgacaga ggacacaggg tgtaacctcc tacccacccc tcactccact 168840
aagcttccca tcctagaggt gtgaggaggg atcattccct tctcaaatcc catcctctcc 168900
cacttcgcct ggaaccagac tctatcactg tctcatcact ttctggaatg tttcattgct 168960
ttccagaatc tttcatcact ttctggaatc ttccatcatt ttctggaatc ttccaccact 169020
ttccggaatc ttccatcatt ttccacaatc ttccattgct ttttagactc ttccatttct 169080
tgctttttcc tggcaccttt gtaacccagg accacataga ggtccacctg ataccacctg 169140
ccctcgttcc tactctcctt tgaaggcagc accaactctt cctgcctttc tgctcctttg 169200
ttcctctttg agtcctatgt gctttcatcc ttgccacaca tatttatggg gcatttaaag 169260
ccctgctctt gtccctgtga tacagtggat acctgcccct gtagagcttc caaaacagca 169320
ggcggagaca gactccaaaa cctttatttt tattttattt catatatata tatatatata 169380
tatatatata tatatatata tatatatata tttttttttt tttttttttt tttttttttt 169440
tttttttttt ttttttttcc tgaaacggag tctcgctttg ttgtgcaggc tggagtgcag 169500
tggcacaatc tcagctcact gcaagctcca cctcctggat tcacactatt ctcctgcctc 169560
agcctcccga gtagctggga ctacaggcgc ctgctaccac gcctggctga ttgttttttt 169620
tttttttttt tgagatggag tctcactctg tcacccaggc tggagtgcag tggcatgatc 169680
tcagctcact gcaacctctg cctgctggat tcaagcaatt atcctgcctc agcctcccga 169740
gtagctggga ctgcaggtgc ctgccaccac gcccagctaa tgctttttat actttttttt 169800
attagagacg gggtttcacc atgctggcca ggctggtctt gaactcctga cctcgtgatc 169860
cacccgcctt ggcctcccaa agtgctggga ttacaggcgt gagccaccac gcccagtgcc 169920
tggctaattt ttttgtattt tcagtagaga cggggtttca ctgtgttagc caggatggtc 169980
tcgatctcct gacctcatga tccgcctgcc ttggcctccc aaagtgctgg gattacaggc 170040
gtgagccacc acgcccagcc tatttttata tatttttaag acagagtctc tctctgtcgc 170100
ccagagtgga gtgcagtggc acaatctcgg ctcactgcaa cctctgcctc ccaggttcaa 170160
gcaattctcc tgccgcggcc tcctgagtag ctgggataac aggagcccac caccacaccc 170220
agctaatttt tgtattttta gtagagatgg ggtttcgcca tgttggccag gctggtctcg 170280
aactcctgaa ttcaggtgat ccaccggcct cagcctccca aagtgctggg attacaggca 170340
taagccacca cccccagctg actccaaacc ctttatacat taggagcaaa tgctatggaa 170400
acatgaagaa agggaggaaa ggagggttgg acaggggtgt atttgagcaa agacttagag 170460
gacatgagga gctgggccct gtggatgtgg cagggaacag agagccaggc agagggaatg 170520
attaaaatac aaaggcctgg ctgggtgcag tggctataat cccagcactt tgggaggctg 170580
aggcaggcgg atcaccagag gtcaggagtt caagaccagc ctgaccaaca tggagaaatc 170640
ctgtctctac taaaaataca aaaattagcc gggtgtggag gcgggcacct gtaaccccag 170700
ctactcggga gactgaggca ggagaattgc ttgaacccgg gaggcaaagg ttgcagtgag 170760
ccgagatcac gccactgcac tctagcctgg gtaacagcaa gattccgtct cgaaaattaa 170820
aaaaaaaaaa atacaaaggc ctatctgtct gctgtccggg caggtatgtc tgctctccta 170880
gaccagggct gagcacgctg catccaggcc acagggtgct gtgtgtgaca tagacaccag 170940
ggagggagga gaaccctggt gagtcgaatc acggaccctc ctccaagaac cctggttgct 171000
tgctctgcag gtgcgcctcc tgggagtggt gtccaagggc cagcccacgc tggtggtgat 171060
ggagctgatg gctcacggag acctgaagag ctacctccgt tctctgcggc cagaggctga 171120

```
ggtaagctgc ttcgggggac ccagcggggt actcggtgga gcacccgctc ctggcctcct 171180
cggatcccag tgctgctgaa acaccaaccc cgtgtttctg ttttagaata atcctggccg 171240
ccctccccct acccttcaag agatgattca gatggcggca gagattgctg acgggatggc 171300
ctacctgaac gccaagaagt ttgtgcatcg ggacctggca gcgagaaact gcatggtcgc 171360
ccatgatttt actgtcaaaa ttggaggttc gtctggcttt ctgctttgaa aacataacga 171420
cccaggccag gtttgatttc agaaggaagt tgtctataat gagccgttaa gtcttttctg 171480
ataatataaa ggggcaagat acttcttttt tttttgtggg gtttttttg ttttgttttg 171540
tctttttgtt tttgagacgg agtcttactc tgtctgttgc ccaggctgga gtgcagtggt 171600
gtgatctcag ctcactgcaa cctccacctc ccaggttcaa gtgattcacc tgcctcagcc 171660
ttccaagtag ctgggactac aggtgtgcgc caccatgcct ggctaatttt tgtattttta 171720
gtggagatgg ggtttcatcc atgttggcca ggatagtctt gatctcctga cctcgtgatc 171780
ctcctgcctc ggcctcccaa agtgctggga ttacaggcgt gagccactgc accggctttt 171840
ttttttttc tttttctga catggagtct tgctctgtcg cccaggctgg agtgcagtga 171900
caggatctcg gctcactgaa cctccacctc ttgggttcaa gcgattctcc tgcctcagcc 171960
tcctgagtag ctaggattac aggcgtgcgc caccacaccc agctactttt tgtattttta 172020
gtagagacgg agtttcactg tgttggccaa gatggtctca aactcctgac ctcatatgat 172080
ccacctgtgt tggcctccca aagcactggg attacaggca tgagccactg tgcctggctg 172140
ggcaagattt tggatgggga ccccccacca gctgtcattt aattgcatgt attgataaac 172200
tcacttaccc attcacttct ttaaaagata tgtttgtagg accgggggtc ccgcctgtaa 172260
tctcagtgct ttggaagtcc aatgtgtaaa gactgcttga gtccaggagt ttgagaccag 172320
cctgggcaac atagtgagac tccatctcct tgaaaagatt ttttaaaaag tggggtgtgg 172380
tggtgcacac ctgtggtccc agctactcag gaggctgggg tgggaggatt gcttgagccc 172440
aggaggtgga ggctgcagtg agctgtgaca gcatcactgc actccagcct gggtgacagt 172500
gagacgctat ttcaaaaaac aaataaaaaa ggaatataga ggggaccaga gcagcgtgag 172560
atgtgaggat gaggagagag gcagaaacca gacccagaag gaccttgcgt gtcacagcaa 172620
gtcatctcga cattatctta cattagcaag gggcagcagg aagtgatatg attctattta 172680
tgactcaaaa agacatctcc tggccaggtg cggtggctca cccctgtaat cccagcactt 172740
tgggaggctg aggtgggtag attacctgag atcaggagtt cgagaccagc ctggtcaaca 172800
cggtgaaacc ctgtctctac tcaaaataca aaacattagc tagacatggt ggcagacagc 172860
tgtaatccta gctactcagg aggctgaggc aagagaattg cttgaatcag ggaggtagag 172920
gttgcagtga gccaagattg caccactgca ctccagcctg gaggacagag tgaggctcca 172980
tatcaaagaa aaaaaaaaag aaaaatgtag cttctttgtg atttggtacc ttcttttccc 173040
tccctttaaa cagtagccca tcttcccccct tcacttcccc atgcgtaccc tcagaatcca 173100
ttcttactgg atttggccac cacccaggtg agcgcagacg tgggccaggt gaacccctct 173160
tagggctctg tgagaggtgg ggcagtcaag gtggcagatg ctaggaccaa ggctgaaggt 173220
taagagcgtg tgaacctttt gtgttgtcag actttggaat gaccagagac atctatgaaa 173280
cggattacta ccggaaaggg ggcaagggtc tgctccctgt acggtggatg gcaccggagt 173340
ccctgaagga tggggtcttc accacttctt ctgacatgtg gtgagttgtg tgtggatggg 173400
tggatggacg ctgggcttga attccaggtg ctagtgagag ccaagagcgg gggaaggaag 173460
cctgccatcc tcctggacgc cccatcaagg aaaggaaggc agcgtcctgt cttaggatct 173520
```

tcccacggct actcttatgt cctgactaat cctgtaggca ttgtgaaccc cgaaaatctg 173580
agacaggtct cagttaattt aggaagttta ttttgccaag gttgaggacg tgtgcccgtg 173640
gcacagcctc aggtggtcct gaggacaggt gcccaaggtg gtcagagcac agtttggttt 173700
tatacatttt agggagacat gagacatcag tcaacatata taagatgaac attggttcgg 173760
tctggaaaga cgagacaact cgaagtgggg agggagcttc caggttgtag gtagataaga 173820
gacaaatggt tgcattcttt tgagtttctg atgcgcctct ccaaaggagc caatcagata 173880
tgcaggtatc tcagtgagca gagtggggac tctgaataga atgggaagca ggtttgtcca 173940
agcagttcct agctggactt tttccttgag tttagtgatt tgggagcccc aaattgattt 174000
tcctttcaca gcatttatga actgcagcat gaattgtttt attaagtggc taaccatgtt 174060
ctagaaacca agagatgtgt ttgtgtgtgt gtttgtgtgt gtatgtgtgt gcatatgtgt 174120
gtttgtgtgt gtttgcatgt gtgtgcgtgt gtgtgtttgg gtgtgtgtgt ttgtgtgtgt 174180
atatgtgttt gtgtgtttgc atatttgtgt gtgcatgtgt gcgcatgcgt gtttgtgtgt 174240
atttgcatgt gtgtgcacgt gtatgtgcgt gtgtgtttgc atgtgtgtgt ttgcatgtat 174300
gtgttggcat gtgtgtttgc gtgtgtgtgt gcgtttgcgt gtgtgtgttt gcgcgcgcgc 174360
gtgtgtgtgt gtgtctaaat ggcttctttg ttactactat caactgtcat cggcaggtcc 174420
tttggcgtgg tcctttggga aatcaccagc ttggcagaac agccttacca aggcctgtct 174480
aatgaacagg tgttgaaatt tgtcatggat ggagggtatc tggatcaacc cgacaactgt 174540
ccagagagag tgtaagtgta gaaagggttt aaggtgtgtg aggtgttcgt tgaaagggta 174600
ttgcccttta cacgtgtgct tggttttgcc tttcctatgt ctacacgctc accgtgtttg 174660
catgctgtat gttacaggtg tgtttgtgtt tgcatagctt gtctttacat gcatgcttgc 174720
atttgcatat tgcattgtgg tacacacact tgagttccca tatgtgctac atgtacgctt 174780
acgtttgcat attatatatt tacataggta tttatgtttg catattatat gtttctgtgt 174840
gcatcagcat atcatggcac atgtacacct catttacata ttataagcac acatgtttac 174900
atattatgtc tttacctgcc tgcttgtgtt cacaaatcat atgattttct tgcatattgt 174960
atctttggaa ggttgcacaa aacacctata gcggtagtta tcttgggaga agggaactgg 175020
agacctgggg ttgggggaga gagacctgtt tgcctgttaa tttttttttt tttttttttt 175080
tttttgagac ggaatcttgc tctgtcaccc aggctggagt gcagtggtgc gagctcggct 175140
gacttcaagc tccgcctccc gggttcacac cattctcttg cctcagcctc ccgagtagct 175200
aggactacag gcacccacca ccgcgcctgg ctaatttttt tttttttttg tatttttagt 175260
agaaatgggg tttcaccgtg gtctcgatct cctgacctcg tgatccaccc accttggctt 175320
cccaaagtgc tgggattaca gccgcctgtt aattctttat acacttaaaa ttttgtcagg 175380
tagctgggca tgggtggctc acgcctgtaa tcccaagcaa tttgggagac cgaggtgaac 175440
gatcacctaa ggtcaggagt tcaagaccag cctggccaac atggtgaaac cccgcctcta 175500
ttaaaaatat aaaaattacc caggcgcggt cgtgggcgcc tgtaatccca gctactcagg 175560
aggctgaggc aggagaattg cttgaatcgg ggaggcagag gttgcagtga gcagagactg 175620
caccattgca ctgcagcatg ggtgacagag tgagattctg tctcaaaaac aaacacagac 175680
acacaaaaat tttgtcaggc atacatatta tatattcccc cctccaaata tatatgcata 175740
tgtacatata tatatattta gatgaagtct cgctgtgtca cccaggctgg tagagcgcag 175800
tggcacaatc acagctcact gcaaccttga actcctggac tcagcctcct ggctcaacct 175860
cccaaagtgc tgggattact cttgagccag ttttgaaatg aggaatccct tttcaaaacc 175920
atctttcagg ctggacagga tggctcatgc ctggaacctc agcactttgg gaggttgagg 175980
caggaggatg gcttgagccc aggagttcaa ggctgcaatg agctatgatt gcgccactgc 176040
actccatcct gggtgacaaa gtgagaaacc ctgtctcaaa aaaaaaaaaa agcggccagg 176100
catggtggct aacacctgta atcccagcac cttgggaggc caaggtgggt ggatcatttg 176160
agcctaggag tttgaggcca gcctgggcaa catagcaaaa ccctgtctct gcaaaaaata 176220
caaaaattag ctaggcatgg tggtgcacac ctgtggtccc agctacttgg gaggccaagg 176280
tgagaggatt gctcgagcct aggaggcaga ggctgcagtg agctatgatc atgccactgc 176340
actccagcct gggtgacaga atgagacgct gtgtccaaaa taagaagaag aaaagcaaaa 176400
agaaaacacc atctctcagc acctctagca atgctatttc tgccttgaca attgtccaca 176460
cacacagcca gcatctgatg tgagcacatg tggtccgtgg gtgtcggctg cagggacaag 176520
agtgggggtt tgggaggatg cgtggcaggg cccccagact cacccaggac gtgtccttct 176580
gccccgcagc actgacctca tgcgcatgtg ctggcaattc aaccccaaga tgaggccaac 176640
cttcctggag attgtcaacc tgctcaagga cgacctgcac cccagctttc cagaggtgtc 176700
gttcttccac agcgaggaga acaaggctcc cgagagtgag gagctggaga tggagtttga 176760
ggacatggag aatgtgcccc tggaccgttc ctcgcactgt cagagggagg aggcgggggg 176820
ccgggatgga gggtcctcgc tgggtttcaa gcggagctac gaggaacaca tcccttacac 176880
acacatgaac ggaggcaaga aaaacgggcg gattctgacc ttgcctcggt ccaatccttc 176940
ctaacagtgc ctaccgtggc gggggcgggc aggggttccc attttcgctt tcctctggtt 177000
tgaaagcctc tggaaaactc aggattctca cgactctacc atgtccaatg gagttcagag 177060
atcgttccta tacatttctg ttcatcttaa ggtggactcg tttggttacc aatttaacta 177120
gtcctgcaga ggatttaact gtgaacctgg agggcaaggg gtttccacag ttgctgctcc 177180
tttggggcaa cgacggtttc aaaccaggat tttgtgtttt ttcgttcccc ccacccgccc 177240
ccagcagatg gaaagaaagc acctgttttt acaaattctt tttttttttt tttttttttg 177300
ctggtgtctg agcttcagta taaaagacaa aacttcctgt ttgtggaaca aaagttcgaa 177360
agaaaaaaca aaacaaaaac acccagccct gttccaggag aatttcaagt tttacaggtt 177420
gagcttcaag atggtttttt tggttttttt tttttctctc atccaggctg aaggattttt 177480
tttttcttta caaaatgagt tcctcaaatt gaccaatagc tgctgctttc atattttgga 177540
taagggtctg tggtcccggc gtgtgctcac gtgtgtatgc acgtgtgtgt gtccattaga 177600
cacggctgat gtgtgtgcaa agtatccatg cggagttgat gctttgggaa ttggctcatg 177660
aaggttcttc tcaagggtgc gagctcatcc ccctctctcc ttccttctta ttgactggga 177720
gactgtgctc tcgacagatt cttcttgtgt cagaagtcta gcctcaggtt tctaccctcc 177780
cttcacattg gtggccaagg gaggagcatt tcatttggag tgattatgaa tcttttcaag 177840
accaaaccaa gctaggacat taaaaaaaaa aaaagaaaaa gaaagaaaaa acaaaatgga 177900
aaaaggaaaa aaaaaaagaa ctgagatgac agagttttga gaatatattt gtaccatatt 177960
taatttttaa agtctctggt attagcctca taagttattg actattcccc ggggttggcg 178020
gggagtgggg acatgagttg gtctgcctgt tgtggggccg ggaaggggag ggagtcaggc 178080
acaagtggcc tctttgtttg gtcttaaagg catccatttc tgggaatgaa gccatgttcg 178140
ctgctaacac ttttggatgt tgtgaggcca cgtggagtgt gtgagagact aggttttatg 178200
gatggtctgg ttcaggtacc aggtctgctg gaaggttcct gttcggataa gctggtagct 178260

-continued acctagctct gagcctgcct tcaagaacac ctgtgttcat cctctgattc tctgtgtgta 178320
cctcttgtgg cgtttcctct cccgggtgtg aacatcctaa ccgttattgt gcaaacccaa 178380
gaacgtcaga tcccaaagca caacaacctg gatggacttt gggaacatct aagcaatgta 178440
agagagaggt gcactgagag tacgtcttgg tcccctccac cctgagagca tctgacggtc 178500
ctcagtactg aactcccgga agctgctctg agcccggtga cctcatctgg gccaggtgtg 178560
gtgcctgagc tgaatgctca ggtgcttaca gtgttgcaat ccctaagaga gtagagtctg 178620
gaggagaaac cgtgaaaaag accttacaca ccaccaagaa cttccgaatg ggcgtgaatc 178680
caccgtttct tctctttgca aaaagaacca ccacagctgc tcaaagaaca cagtgaactc 178740
atcactttgg ttcatcaaaa aatcatcgcc catgcgttat tcctgagtgc attttcttac 178800
aactttttga ctgcttcctt ttcttcttct cttaagagtt gtgggcttaa gaatgggata 178860
gagtcataat ggcaacctcc aagccctctc aattcttgat taagaacaca ggtagacatg 178920
aatcccaatt gtctattgct atcttattta tatgattcgg gaaaatacag catgtaaaaa 178980
tattgctgag gagcctcagt gattgggtac aagaagcaag agtacagaaa ttatttttgc 179040
caaatttatt ttgtaaatat gagggtctgt acctaaattt aaaaaaaaaa cacgtagaac 179100
taggtatttt gttctcttct tagtaaattt gtagtggttg tatactacac tagctgcaat 179160
tttcacattt ttctaattca gaaaggtttt tcttatatta ggggaaaaag tatttatttt 179220
aatatataaa atcactctga aaatcactct cataaaaaat ggagcgcatg taaattttta 179280
tcaaagaaaa ataaacaggt gaatggggga tagtgatttt ctttttcag cacagtctac 179340
ctcagtgtat tgttaagatg tgattcaatc atggacatct ttgagatttc agaattctac 179400
ctggaaccgg tctgaatcag ggaacgtgtg tatcagctga ttcgaatgcc agggaccagt 179460
aagaattttg agggagggag ttgggatgga gaaggtatgg cctttatgcg agcatagatc 179520
cttttcttcc tggctggtaa tattcttctc tgaatttaat cttcctttaa aaaaaaatcc 179580
tccatctatt gtcactatgt tccccaaaca taaactaagt tccaggctgt catgatgtat 179640
ctgatatatg gggtaaccca gcaaggtgta ccttcctttg gtgagagatg gctgccgggg 179700
caaagacggg ctttgattca gagcaagcat tcccacctgt tccatggaat ccccctgaag 179760
tgagcacaaa ggtgccctgg gctccctgat ggtttatgcc cactcctttc aggctggtga 179820
tgcaccttac acacaaacac ctaatgcaat gtctttttaa attctccaag tgggatggga 179880
gcatgtgagg gaaattccaa tccaaaaccc attaatgtgc tgaacgcttt tttttttttt 179940
tttttttttt ttgcaacaac accttggacc tctgtgttgg ggtttgactg acctcaagct 180000
gatattattg gaccttgtgc agctttgata acccatgtga gagtctaggc aggaccagtg 180060
gggcccaaat cttgctgctc ttgtactttt aggcactgcc cttgcagact cacctttctc 180120
cacctgccct ggagaaaggt agggtgtgct gggcctgccc cttgcaaatg ggattcacca 180180
gtttcattta tttgactcta ctgccacagt gaaaagagca aacagctatt gggttgcaaa 180240
cctcctttga cattaggaaa tgttgacttt gtaacaataa aactttggtc ctagaaagac 180300
acggttgtcc tgggagtttg tagtgttaag ttgcaacaac aacaacaaaa agcaacaaaa 180360
ccagcttagg ataacacttt ttgttgcttg ttcttaaaga tgtctcacta tgattaaaac 180420
ccttttcatt aatgtagtga aagccacaca ggagttcctt cttccaggag gagaatacca 180480
agcacatcac tttctctctg catcagtgat gtcaaatacg catcagaaaa tgttcaggtt 180540
ttaggagctg tcctaggtgc tgtttcatca ttggaagcag tgagaaagag aagcactgct 180600

-continued

```
gcttgtctgg atataggctg aggatgattg agagaagctg tgggaactga cacaagggtc 180660
tgcataggtc atcctgtgac cctggggact atgttaccaa ctgacagaca gatctttcac 180720
tgtatcctag cagggcaggt agtccaccaa gaaatgtgct tattggattg ggaggtgttt 180780
atttgtagtc tgctgtaaca cgtgtgaaag agcaggagcg tcatcagcat atgacttgcg 180840
ctggtcatcc ggtaaatgga tgtgctgtag tcccagtgct aatcatttct ctccttcaca 180900
gtgggtggaa gtttagggtt aaatgtcctt tgaatgtcac ctggtgagtc cttgacacct 180960
taggctcttc agaaacaatg gttttgttga ggatggggaa cagggaatgc cgattttata 181020
tacatggtac acagagaggg gtgtcacttc agaaaatctt ccagcatgtt cttcagaata 181080
ttaatttata tgcgaggtga ggttgggaat gaaaagaaca ggtcagcact tttttttttc 181140
ctagaacata caaaagaaca tggtggactt tcagggagtg caatggaagg tgaatatttc 181200
cttaagggtc cccgagaaat gggagtgagg ggaggggaca caatggcttt ttgagcttac 181260
ttttaccttc tgatactagt caaggtccag aaccagccac cagccaaatt tctatctggg 181320
tgcgggccac tgaaaatcct tgttaaaaac cagatcacaa atctggggct cttggtccca 181380
ttggagaagg aaggaagagc ctcaaaataa gtgtgcaccc atgcacatat tcaggaacag 181440
cttgtttagt ctttacactt tgcctgaaag ttgcttctcc tcgtcccttt gtgtgcctgg 181500
gtggcctcgg ccctgtgcgt tggcaacgca ggatcaaatg tgctgcagct tttgcagaaa 181560
acaactcaga aacacaaaac cccccaacag ctcaattatt attttttcaa tgttttccta 181620
caagagccaa gtagcaccat gtacagaaga cgccttttttt tttggaatat tgaaatcgtt 181680
ctgcatgtaa aatatgggat aatgacctgt ttatattaaa attctgatta aattatctga 181740
gaata                                                              181745
```

SYSTEM AND METHOD FOR ANALYZING SPLICING CODES OF SPLICEOSOMAL INTRONS

RELATED APPLICATIONS

This application is a continuation-in-part of U.S. patent application Ser. No. 12/006,898, filed on Jan. 6, 2008 and titled METHOD OF IDENTIFYING EXONS AND INTRONS AND DIAGNOSTIC USES THEREOF, the contents of which are herein incorporated by reference in its entirety.

REFERENCE TO SEQUENCE LISTING SUBMITTED ELECTRONICALLY

The content of the electronically submitted sequence listing, file name Patent2_seq_patent_in35_v2_ST25.txt, size 427,239 bytes; and date of creation Nov. 7, 2015, filed herewith, is incorporated herein by reference in its entirety.

FIELD OF THE INVENTION

This application relates generally to a system and method for analyzing splicing codes of spliceosomal introns. One embodiment of the invention comprises methods of identifying introns and exons in genomic DNA or pre-mRNA sequences by locating characteristic markers in splicing junctions by computation. Exon sequences predicted by computation can be verified and characterized by employing standard amplification methods, such as comparative genomic, RNA-seq, next-generation sequencing, RT-PCR, DNA/RNA/oligo, electrophoretic or protein chip technologies. If a given sample is found to contain a characterized splicing junction, the sample is analyzed for the presence of introns or exons. When a putative intron or exon is found, it will be verified and characterized by the methods described above. The isoform associated with this splice site can be deduced and can be translated into protein sequence. It is compared to a database which correlates the known intron or exon to known diseases or genetic mutations. If a given sample is found to contain a characterized splicing junction, but not characterized introns or exons, the presence of novel introns or exons is likely and can be determined.

Our computational and experimental data have shown that a mammalian gene can generate hundreds or thousands of alternatively-spliced isoforms, and these alternatively-spliced isoforms may have different or even opposed functions. For example, under normal conditions, an insulin receptor (insr) gene encodes isoforms that promote normal metabolism and growth. However, other truncated isoforms of the insulin receptor (insr) gene can have opposite functions to suppress the normal functions which cause insulin insistence and leading to metabolic syndromes or even cancer. By detecting varieties of isoforms of genes at RNA levels including RNA (characterized or uncharacterized) and/or protein levels in conjunction with individual genetic backgrounds, devices can be developed to detect the balances of these isoforms to predict health conditions. A variety of methods (traditional or nontraditional; chemical or physical) can be developed to restore these balances to achieve the diagnosis and/or treatments of aging and complex diseases, such as diabetes, cardiovascular disease, Parkinson's disease, Alzheimer's disease and/or cancer. Thus, the methods herein are applicable for predicting disease or genetic mutations, or for searching for novel introns and exons.

BACKGROUND OF THE INVENTION

Prokaryotic genes differ from eukaryotic genes in that every base pair in a prokaryotic gene is reflected in the mRNA base sequence. In eukaryotic genes there are often intervening sequences which do not appear in the mRNA base sequence for the gene product. The DNA sequences which are expressed and retained in the final product of mRNAs are "exons". The intervening sequences which are not expressed are called "introns".

Genomic DNA sequence, including exons and introns, are transcribed to produce a precursor of the mature mRNA or pre-mRNA. Genes from eukaryotic organisms contain a variable number of introns of varying sizes, which range from more than 20 bp to 800 kp. For example, the gene for mouse Tbc1d2 gene encoding TBC1 domain family, member 2 contains 12 introns, the mouse Col1a1 gene coding for procollagen, type I, alpha 1, contains 50 introns.

During the processing of pre-mRNA, the introns are excised out and the exons are spliced and joined together to generate a mature mRNA, which is exported into cytoplasm for translation into protein. Aberrations in pre-mRNA splicing have played an essential role in almost every known disease with genetic aetiology, disease susceptibility and severity and maybe in all aspects of life including development, differentiation, aging and cancer. See Baralle, D., Lucassen, A., Buratti, E., *Missed threads. The impact of pre-mRNA splicing defects on clinical practice*. EMBO Rep. 2009:10(8):810-6 ("Baralle"); Cooper T A, Wan L, Dreyfuss G., *RNA and disease*. Cell 2009:136(4):777-93 ("Cooper"); Belfiore, A., Frasca, F., Pandini, G., et al., *Insulin receptor isoforms and insulin receptor/insulin-like growth factor receptor hybrids in physiology and disease*. Endocr. Rev. 2009:30(6):586-623 ("Belfiore").

Introns are removed from pre-mRNAs via two consecutive trans-esterification reactions before mature mRNAs are exported from the nucleus into cytoplasm for translation into proteins. See Black, D. L., *Mechanisms of alternative pre-messenger RNA splicing*. Annu. Rev. Biochem. 2003:72:291-336 ("Black"). Intron removal from pre-mRNAs is mediated by spliceosomes, which are known to be comprised of several hundred proteins and five small snRNAs packaged as ribonucleoprotein particles (RNPs). See Black; Sanford J. R., Gray N. K., Beckmann K., et al., *A novel role for shuttling SR proteins in mRNA translation*. Genes Dev. 2004:18(7):755-68 ("Sanford"); Moore, M. J., *From birth to death: the complex lives of eukaryotic mRNAs*. Science 2005:309(5740):1514-8 ("Moore"). In brief, the 5' intronic conserved sequence, GURAGU, of pre-mRNAs is base-paired with the 5' end of U1 snRNP and the conserved branch-point and 3' splice site of pre-mRNAs are recognized by U2 snRNP1. See Black. The pre-assembled U4/U6, U5 tri-snRNPs associates with pre-mRNA and snRNPs already bound to pre-mRNA. This dynamic rearrangement leads to 2'-hydroxyl of adenosine of the branch-point to attack the last nucleotide of 5' exon, producing the "free" 5' exon and lariat intron-3' intron intermediates. In the second step the 3' hydroxyl of the 5' exon attacks 3' splice site to generate a spliced mRNA and lariat intronic product.

Many approaches have been developed to predict pre-mRNA splicing and alternative splicing with only a limited success. Introns were first identified by highly conserved sequences, which begin with highly conserved sequence among different eukaryotic organism, GTRAGT, and end with (C/T)AG ("Black"). Traditionally, alternative spliceo-variants were identified by aligning different cDNAs/ESTs to the different regions of the same genomic sequences. See Zhuo, D., Zhao, W. D., Wright, F A, Yang, H. Y., and Wang, J. P. et al., *Assembly, annotation, and integration of UNIGENE clusters into the human genome draft*. Genome Res. 11(5): 904-918 (2001) ("Zhuo I"); Brent, M. R., *Steady progress and recent breakthroughs in the accuracy of automated genome annotation*. Nat Rev Genet 9(1): 62-73(2008) ("Brent"); Kim, N. and Lee, C., *Bioinformatics detection of alternative splicing*. Methods Mol Biol 452: 179-197 (2008) ("Kim"); Bonizzoni, P., Mauri, G., Pesole, G., Picardi, E., Pirola, Y. et al. *Detecting alternative gene structures from spliced ESTs: a computational approach*. J Comput Biol 16(1): 43-66 (2009) ("Bonizzoni").

Comparative analyses exploit homology searches to identify highly conserved exon-intron boundaries. See Lee, C., Wang, Q., *Bioinformatics analysis of alternative splicing*. Brief Bioinform 6(1): 23-33 (2005) ("Lee and Wang"). Two approaches have been used: inter-genomic or cross species comparisons. See Clark, A. G., Eisen, M. B., Smith, D. R., Bergman, C. M., Oliver, B. et al. *Evolution of genes and genomes on the Drosophila phylogeny*. Nature 450(7167): 203-218 (2007) ("Clark"). Effectiveness of both approaches is limited by constraints of phylogenetic distance and homologies within databases. Neural networks, Fourier transforms and Markov models have been developed to predict the gene structures. See Lu, D. V., Brown, R. H., Arumugam, M., Brent, M. R., *Pairagon: a highly accurate, HMM-based cDNA-to-genome aligner*. Bioinformatics 25(13): 1587-1593 (2009) ("Lu"). The statistics programs require a set of parameters, which are often estimated, based on training datasets of well-characterized sequences. See Brent.

Deep sequencing of the human transcriptome makes it possible to identify novel splice sites. See Hartmann, L., Theiss, S., Niederacher, D., et al, *Diagnostics of pathogenic splicing mutations: does bioinformatics cover all bases*? Front. Biosci. 2008:13:3252-72 ("Hartmann"); Sultan, M., Schulz, M. H., Richard, H., et al., *A global view of gene activity and alternative splicing by deep sequencing of the human transcriptome*. Science 2008:321(5891):956-60 ("Sultan"). Using polyA capture, RNA-seq. and other methods, Mangone et al. identified large numbers of cis- and trans-alternative splicing isoforms originated from *C. elegans* 3' UTR. See Mangone, M., Manoharan, A. P., Thierry-Mieg, D., et al., *The landscape of C. elegans 3' UTRs. Science:*329 (5990):432-5 ("Mangone"). Using paired-end RNA sequencing and RNA-seq, surprisingly >23,000 introns have been identified in *D. melanogaster*. See Soller, M., *Pre-messenger RNA processing and its regulation: a genomic perspective*. Cell. Mol. Life Sci. 2006:63(7-8):796-819 ("Soller"); Chen, M., Manley, J. L., *Mechanisms of alternative splicing regulation: insights from molecular and genomics approaches*. Nat. Rev. Mol. Cell. Biol. 2009:10(11):741-54 ("Chen").

To solve diversity and specificity of pre-mRNA splicing and alternative splicing, exonic and intronic splicing enhancers and silencers have been suggested to be potential candidates of splicing codes. See Fu, X. D., *Towards a splicing code*. Cell 2004:119(6):736-8 ("Fu"); Matlin, A. J., Clark, F., Smith, C. W., *Understanding alternative splicing: towards a cellular code*. Nat. Rev. Mol. Cell. Biol. 2005:6 (5):386-98 ("Matlin"); Wang, G. S., Cooper, T. A., *Splicing in disease: disruption of the splicing code and the decoding machinery*. Nat. Rev. Genet. 2007:8(10):749-61 ("Wang"). More recently, Barash et al. used computation methods to assemble several hundreds of RNA features (the "splicing code") to predict tissue-dependent changes in alternative splicing for thousands of exons. See Barash, Y., Calarco, J. A., Gao, W., et al., *Deciphering the splicing code*. Nature: 465(7294):53-9 ("Barash"). Although this splicing code model may explain some tissue-dependent alternative splicing, unlike genetic codes, it fails to explain the conundrums of university, diversity, specificity and fidelity of pre-mRNA splicing as does the nature of splice site choice in alternative splicing. See Soller; Chen.

Ever since their discovery about 30 years ago, introns have intrigued the scientific community and stimulated debate about the nature and timing of their origin. See Black; Roy, S. W., Gilbert, W., *The evolution of spliceosomal introns: patterns, puzzles and progress*. Nat. Rev. Genet. 2006:7(3):211-21 ("Roy I"); Rodriguez-Trelles, F., Tarrio, R., Ayala, F. J., *Origins and evolution of spliceosomal introns*. Annu. Rev. Genet. 2006:40:47-76 ("Rodriguez-Trelles"). There has also been curiosity about the apparent recent explosion in intron number in mammals and its contribution to expanded protein diversity and regulation through alternative splicing pathways. See Pan, Q., Shai, O., Lee, L. J., et al., *Deep surveying of alternative splicing complexity in the human transcriptome by high-throughput sequencing*. Nat. Genet. 2008:40(12):1413-5 ("Pan"); Nilsen, T. W., Graveley, B. R., *Expansion of the eukaryotic proteome by alternative splicing*. Nature:463(7280):457-63 ("Nilsen"). Correct removal of introns from genes has become a central issue in the medical research and biological sciences. However there currently are no known methods to accurately identify the introns, that is, to accurately define exon/intron boundaries.

SUMMARY OF THE INVENTION

Many newly-acquired introns in the human genome have been found to share a signature of similar 5' and 3' splicing junctions consistent with an origin via DNA duplication or gene duplication. See See Zhuo, D., Madden, R., Elela, S. A., et al., *Modern origin of numerous alternatively spliced human introns from tandem arrays*. Proc. Nat'l. Acad. Sci. U.S.A. 2007:104(3):882-6 ("Zhuo II"). According to one aspect of the invention, previously-identified introns from a eukaryotic species, which are supported by cDNA/EST data and/or comparative genomics, can be used to identify novel control trans- or cis-elements and to predict novel alternatively spliced mRNA isoforms. Markers are located 150 bp upstream (E5) and 150 bp downstream (I5) nucleotides of 5' splicing sites, and 150 bp upstream (I3) and 150 bp downstream (E3) nucleotides of 3' splicing sites. The invention provides for computational and/or experimental and/or diagnostic methods employing the characteristic markers of associated introns and exons.

Specifically, the invention comprises a method for indirectly detecting introns and exons by detecting whether a DNA pre-mRNA sequence contains characteristic markers or splicing codes. Splicing junction databases from a eukaryotic organism are constructed by introns determined by EST/cDNAs and/or comparative genomics from a species. DNA or pre-mRNA samples are compared and searched to have identical or similar sequences in these pre-determined splicing junction databases. If putative splicing junctions are found to be present in these splicing junction databases by pre-determined factors, the presence of these splicing junctions can be verified and characterized by RT-PCR amplifications, RNA-seq, next-generation sequencing, comparative genomics, gel electrophoresis or protein chip technologies. When a putative intron or exon is determined, it is compared to a database which correlates the characterized intron or exon to characterized diseases or genetic mutations. If a given sample is found to comprise introns or exons that are associated with diseases, the novel isoforms of the associated gene can be determined. The polypeptides of the novel isoforms can be deduced based on existing databases and common knowledge. The functions of these polypeptides can be roughly determined by database and computation methods. The isoforms can be further tested to determine the detailed functions. Thus, the methods herein are applicable for predicting disease or genetic mutations, or for searching for novel introns and exons.

In one embodiment, the invention comprises a computerized method of predicting alternative splice sites, comprising:

determining the 5' splice sites and 3' splice sites of a sample from a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host;

searching the splicing code table for positive matches with the generated E5-first intronic dinucleotide-I3 sequences;

constructing a list of positive matches which constitute predicted putative alternative splice sites;

generating protein or polypeptide sequences based on predicted isoforms DNA/RNA sequences related to the predicted putative alternative splice sites;

determining and analyzing the functions and characteristics of the predicted isoforms; and determining the predicted putative alternative splice sites and isoforms that correlate to a complex disease in the host, wherein the sample comprises at least one pre-mRNA sample or DNA sequence, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences.

In another embodiment, the invention comprises a computerized method of constructing an expression vector to enable insertion of mRNA sequences for use in gene therapy to treat a complex disease, comprising:

determining the 5' splice sites and 3' splice sites of a sample from a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-first intronic dinucleotide-I3 sequences starting from the first nucleotide of a gene of interest of the host;

searching the splicing code table for positive matches with the generated E5-first intronic dinucleotide-I3 sequences;

constructing a list of positive matches which constitute predicted putative alternative splice sites;

generating protein or polypeptide sequences based on predicted isoforms DNA/RNA sequences related to the predicted putative alternative splice sites;

determining and analyzing the functions and characteristics of the predicted isoforms;

determining the predicted putative alternative splice sites or isoforms that correlate to a complex disease in the host; and constructing an expression vector that enables the insertion of one or more mRNA sequences for use in gene therapy to treat the complex disease, wherein the sample comprises at least one pre-mRNA sample or DNA sequence, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences, wherein further determining the predicted putative alternative splice sites or isoforms that correlate to a complex disease in the host comprises:

generating messenger RNAs by removing putative introns from DNA of the host;

designing primers based on the messenger RNAs for PCR amplification and DNA/RNA sequencing;

designing oligomers based on the messenger RNAs for DNA/RNA capturing to increase concentrations of minor isoforms of the gene of interest of the host;

translating the messenger RNA into proteins;

identifying antigens for generating antibodies specific to the proteins; and determining if the proteins are over-expressed or under-expressed compared to a predetermined level of expression, wherein the predetermined level of expression correlates to the presence of a complex disease in the host.

In another embodiment, the invention comprises a computerized method of identifying splice sites to enable removal of mRNA sequences for use in gene therapy to treat a complex disease, comprising:

determining the 5' splice sites and 3' splice sites of a sample from a host;
dividing the 5' splice sites into 5' exonic (E5) and 5' intronic (I5) splicing sequences;
dividing the 3' splice sites into 3' intronic (I3) and 3' exonic (E3) splicing sequences;
aligning the E5 sequences with the I3 sequences from positions −1 to −150;
aligning the I5 sequences with the E3 sequences from positions 1 to 150;
scoring the number of uninterrupted identical nucleotides (LIN) outwards from the splice sites;
scoring the number of interrupted identical nucleotides (LIN) outwards from the splice sites;
constructing a splicing code table by parsing out high quality E5 sequences plus the first intronic dinucleotide and I3 sequences from the host genome sequences and storing the splicing code table in a programmable, searchable computer database;
generating by a computer processor putative introns comprising E5-first intronic dinucleotide-I3 sequences starting from the first nucleotide of a gene of interest of the host;
searching the splicing code table for positive matches with the generated E5-first intronic dinucleotide-I3 sequences;
constructing a list of positive matches which constitute predicted putative alternative splice sites;
generating protein or polypeptide sequences based on predicted isoforms DNA/RNA sequences related to the predicted putative alternative splice sites;
determining and analyzing the functions and characteristics of the predicted isoforms;
determining the predicted putative alternative splice sites or isoforms that correlate to a complex disease in the host; and
identifying the splice sites to enable removal of mRNA sequences for use in gene therapy to treat the complex disease,
wherein the sample comprises at least one pre-mRNA sample or DNA sequence,
wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences,
wherein further determining the predicted putative alternative splice sites and isoforms that correlate to a complex disease in the host comprises:
generating messenger RNAs by removing putative introns from DNA of the host;
designing primers based on the messenger RNAs for PCR amplification and DNA/RNA sequencing;
designing oligomers based on the messenger RNAs for DNA/RNA capturing to increase concentrations of minor isoforms of the gene of interest of the host;
translating the messenger RNA into proteins;
identifying antigens for generating antibodies specific to the proteins; and
determining if the proteins are over-expressed or under-expressed compared to a predetermined level of expression, wherein the predetermined level of expression correlates to the presence of a complex disease in the host.

In another embodiment, the invention comprises a computerized method of constructing expression vector mRNA constructs without splice sites, comprising:
determining the 5' splice sites and 3' splice sites of a sample from a host;
dividing the 5' splice sites into 5' exonic (E5) and 5' intronic (I5) splicing sequences;
dividing the 3' splice sites into 3' intronic (I3) and 3' exonic (E3) splicing sequences;
aligning the E5 sequences with the I3 sequences from positions −1 to −150;
aligning the I5 sequences with the E3 sequences from positions 1 to 150;
scoring the number of uninterrupted identical nucleotides (LIN) outwards from the splice sites;
scoring the number of interrupted identical nucleotides (LIN) outwards from the splice sites;
constructing a splicing code table by parsing out high quality E5 sequences plus the first intronic dinucleotide and I3 sequences from the host genome sequences and storing the splicing code table in a programmable, searchable computer database;
generating by a computer processor putative introns comprising E5-the first intronic dinucleotide-I3 sequences starting from the first nucleotide of a gene of interest of the host;
searching the splicing code table for positive matches with the generated E5-the first intronic dinucleotide-I3 sequences;
constructing a list of positive matches which constitute predicted putative alternative splice sites;
generating protein or polypeptide sequences based on predicted isoforms DNA/RNA sequences related to the predicted putative alternative splice sites;
determining and analyzing the functions and characteristics of the predicted isoforms; and
constructing an expression vector mRNA construct wherein the putative alternative splice sites and isoforms are changed into non-splice sites in the expression vector mRNA constructs,
wherein the functions of the expression vector mRNA constructs are the same as the functions of expression vector mRNA constructs with the putative alternative splice sites or the predicted isoforms,
wherein the resultant expression vector mRNA constructs and resultant mRNA sequences do not generate unintended isoforms.

In another embodiment, the invention comprises a computerized method of treating diabetes by reducing soluble insulin receptors and/or truncated insulin receptors on the cell membrane, comprising:
detecting a plurality of isoforms of a insulin receptor (insr) gene of host;
comparing the levels of the isoforms to predetermined levels of the isoforms;
determining whether the presence of certain of the isoforms correlate to the presence of Type 2 diabetes in the host; and
reducing the levels of the isoforms that are found to correlate to the presence of Type 2 diabetes in the host,
wherein the plurality of isoforms are detected by:
determining the 5' splice sites and 3' splice sites of a RNA sample of the host;
dividing the 5' splice sites into 5' exonic (E5) and 5' intronic (I5) splicing sequences;
dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host;

searching the splicing code table for positive matches with the generated E5-first intronic dinucleotide-I3 sequences;

constructing a list of positive matches which constitute predicted putative alternative splice sites;

generating protein or polypeptide sequences based on predicted isoforms DNA/RNA sequences related to the predicted putative alternative splice sites;

determining and analyzing the functions and characteristics of the predicted isoforms; and determining the predicted putative alternative splice sites or isoforms that correlate to isoforms of the insulin receptor (insr) gene of the host, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences.

In another embodiment, the invention comprises a computerized method of detecting cancer by detecting isoforms, comprising:

determining the 5' splice sites and 3' splice sites of a RNA sample of a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host;

searching the splicing code table for positive matches with the generated E5-the first intronic dinucleotide-I3 sequences;

constructing a list of positive matches which constitute predicted putative alternative splice sites;

generating protein or polypeptide sequences based on predicted isoforms DNA/RNA sequences related to the predicted putative alternative splice sites;

determining and analyzing the functions and characteristics of the predicted isoforms; and determining the predicted putative alternative splice sites or isoforms that correlate to the presence of cancer in the host.

In another embodiment, the invention comprises a computerized method of predicting novel putative alternative splice sites in a RNA sample from a host, comprising:

determining the 5' splice sites and 3' splice sites in a RNA sample of a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host;

searching the splicing code table for positive matches with the generated E5-the first intronic dinucleotide-I3 sequences; and constructing a list of positive matches which constitute predicted putative alternative splice sites, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences.

In another embodiment, the invention comprises a computerized method of generating primers based on exon sequences, comprising:

determining putative introns;\ identifying specific isoforms based on the putative introns; and amplifying the specific isoforms using isoforms-specific primers, wherein amplification comprises PCR amplification, and wherein further determining putative introns comprises:

determining the 5' splice sites and 3' splice sites in a RNA sample of a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host; and searching the splicing code table for positive matches with the generated E5-the first intronic dinucleotide-I3 sequences, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences.

In another embodiment, the invention comprises a computerized method of detecting Alzheimer's disease (AD) by detecting isoforms, comprising:

determining the 5' splice sites and 3' splice sites of a RNA sample of a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host;

searching the splicing code table for positive matches with the generated E5-the first intronic dinucleotide-I3 sequences;

constructing a list of positive matches which constitute predicted putative alternative splice sites;

generating protein or polypeptide sequences based on predicted isoforms DNA/RNA sequences related to the predicted putative alternative splice sites;

determining and analyzing the functions and characteristics of the predicted isoforms; and determining the predicted putative alternative splice sites or isoforms that correlate to the presence of AD in the host.

In another embodiment, the invention comprises a computerized method of detecting Parkinson's disease (PD) by detecting isoforms, comprising:

determining the 5' splice sites and 3' splice sites of a RNA sample of a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host;

searching the splicing code table for positive matches with the generated E5-first intronic dinucleotide-I3 sequences;

constructing a list of positive matches which constitute predicted putative alternative splice sites;

generating protein or polypeptide sequences based on predicted isoforms DNA/RNA sequences related to the predicted putative alternative splice sites;

determining and analyzing the functions and characteristics of the predicted isoforms; and determining the predicted putative alternative splice sites or isoforms that correlate to the presence of PD in the host.

In another embodiment, the invention comprises a computerized method of cloning full-length cDNA, comprising:

amplifying 5' and 3' regions using isoform-specific primers to produce DNA;

recovering expectant DNA fragments;

mixing and amplifying the expectant DNA fragments; and cloning the produced mixed and amplified expectant DNA fragments in TA vectors, wherein the 5' and 3' regions are produced by the process of:

determining the 5' splice sites and 3' splice sites in a RNA sample of a host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host; and searching the splicing code table for positive matches with the generated E5-the first intronic dinucleotide-I3 sequences, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences.

In another embodiment, the invention comprises a computerized method of diagnosing and treating Cardiovascular Disease (CD) by detecting and balancing full-length/soluble/truncated receptors, ion channels, transporters and other proteins on the cell membrane, in blood and in cellular and extracellular tissues, comprising:

detecting a plurality of isoforms of the genes of a host;

comparing the levels of the isoforms to predetermined levels of the isoforms for the host;

determining whether the presence of certain of the isoforms correlate to the presence of CD in the host; and reducing the levels of the isoforms that are found to correlate to the presence of CD in the host, wherein the plurality of isoforms are detected by:

determining the 5' splice sites and 3' splice sites of a RNA sample of the host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-the first intronic dinucleotide-I3 sequences starting from the first nucleotide of a gene of interest of the host;

searching the splicing code table for positive matches with the generated E5-the first intronic dinucleotide-I3 sequences;

constructing a list of positive matches which constitute predicted putative alternative splice sites;

generating protein or polypeptide sequences based on predicted isoform DNA/RNA sequences;

determine and analyzing the functions and characteristics of the predicted isoforms; and determining if any of the predicted putative alternative splice sites and isoforms correlate to CD of the host, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences.

In another embodiment, the invention comprises a computerized method of diagnosing and treating aging by detecting and balancing full-length/soluble/truncated receptors, ion channels, transporters and other proteins on the cell membrane, in blood and in cellular and extracellular tissues, comprising:

detecting a plurality of isoforms of the genes of a host;

comparing the levels of the isoforms to predetermined levels of the isoforms for the host;

determining whether the presence of certain of the isoforms correlate to aging in the host; and reducing the levels of the isoforms that are found to correlate to aging in the host, wherein the plurality of isoforms are detected by:

determining the 5' splice sites and 3' splice sites of a RNA sample of the host;

dividing the 5' splice sites into 5' exonic (E5) and 5' intronic (I5) splicing sequences;

dividing the 3' splice sites into 3' intronic (I3) and 3' exonic (E3) splicing sequences;

aligning the E5 sequences with the I3 sequences from positions −1 to −150;

aligning the I5 sequences with the E3 sequences from positions 1 to 150;

scoring the number of uninterrupted identical nucleotides (LIN) outwards from the splice sites;

scoring the number of interrupted identical nucleotides (LIN) outwards from the splice sites;

constructing a splicing code table by parsing out high quality E5 sequences plus the first intronic dinucleotide and I3 sequences from the host genome sequences and storing the splicing code table in a programmable, searchable computer database;

generating by a computer processor putative introns comprising E5-first intronic dinucleotide-I3 sequences starting from the first nucleotide of a gene of interest of the host;

searching the splicing code table for positive matches with the generated E5-the first intronic dinucleotide-I3 sequences;

constructing a list of positive matches which constitute predicted putative alternative splice sites;

generating protein or polypeptide sequences based on predicted isoform DNA/RNA sequences;

determine and analyzing the functions and characteristics of the isoforms; and determining if any of the predicted putative alternative splice sites and isoforms correlate to aging of host, wherein the splicing code table comprises information from relevant existing databases, wherein the relevant existing databases comprise single nucleotide polymorphism (SNP) databases, Online Mendelian Inheritance in Man® database (OMIM) (compendium of human genes and genetic phenotypes) and nucleotide sequence and protein databases comprising the host genome sequences.

DESCRIPTION OF THE DRAWINGS

The invention will be described with reference to the accompanying drawings, in which like elements are referenced with like numerals.

FIG. 2*a* provides signatures of typical splice site consensus sequences and human spliceosomal introns (top panel), for intron with E5-I3 LIN≥6 (middle panel) and introns with I5-E3 LIN≥6 (bottom panel).

FIG. 2*b* provides a schematic drawing of alignment of sequences flanking intron 8 of the human ciz1 gene, specifically human genomic CIZl premessenger nucleotide sequences (SEQ ID NO.: 3); genomic region: 24968-25675 of NM 001131015.1.

FIG. 2*c* summarizes data of comparison analysis results of human, mouse, chicken, zebrafish and *D. melangaster.*

FIG. 9*a* is a schematic diagram of the mouse insulin receptor (insr) gene. The arrows represent epitopes of the antibodies 4B8 and sc-711, respectively.

FIG. 9*b* depicts a Western blot analysis of protein lysates from brain, heart, liver, lung, gastrocnemius muscle, seleus muscle and white fat using antibody 4b8. The minor bands are consistent with proteins predicted by the mouse splicing code table.

FIG. 9*c* depicts a Western blot analysis of protein lysates from brain, heart, liver, lung, gastrocnemius muscle, seleus muscle and white fat using antibody sc-711. The differences between two Western blot (FIG. 9*b* vs. FIG. 9*c*) analysis show reflection of shorter isoforms predicted by the mouse splicing code table.

FIG. 10A and B depict the sequence results of the cloned PCR products in FIG. 7*c*, which are amplified on pooled cDNAs from various mouse tissues using primers described in Tables 12a & 12b. specifically. seven sequences: (1) 8-175, 176-285, 286-448, 449-458 of sf1 F1R3 that correspond to 115778-115945, 117391-117500, 117683-117845 and 119118-119207 of NM_010568 genomic sequences; (2) 1-15 and 16-953 of isf2F1R12 that correspond to 119320-119335 and 119342-118399 of NM_010568 genomic sequences; (3) 565-699. 698-908, 909-919 and 920-930 of isf3FR2 that correspond to 1 17709-117843, 117843, 119598-119808, 125748-125758 and 119790-119800 of NM_010568 genomic sequences: L4)367-501 and 500-710 of isf4F3 that correspond to 117709-117843 and 119598-119808 of NM_010568 genomic sequences: (5) 8-110, 109-242, 240-316, 311-332 and 333-343 of ist9FR2 that correspond to 117741-117843, 1195898-119731, 120351-120351-120427, 125274-125295 and 125577-125588 of NM_010568 genomic sequences: (6) 21-149 and 186-294 of isfl0FR3 that correspond to 124467-124595 and 124642-124750 of NM_010568 genomic sequences; and (7) 1-7 and 8-1-8 of isfl 1FR1 that correspond to 12054-120551 and 125214-126201 of NM_010568 genomic sequences.

DETAILED DESCRIPTION OF THE INVENTION

The inventor previously found many newly-acquired introns in the human genome have been found to share a signature of identical 5' and 3' splicing junctions consistent with an origin via DNA duplication. See Zhuo II. Therein, he proposed that 5' exonic sequence and 3' intronic sequence constitute spliceosomal splicing codes, which are deciphered by yet uncharacterized splicer-RNAs or splicer proteins as described in FIGS. 1a and 1b.

Figure 1B:
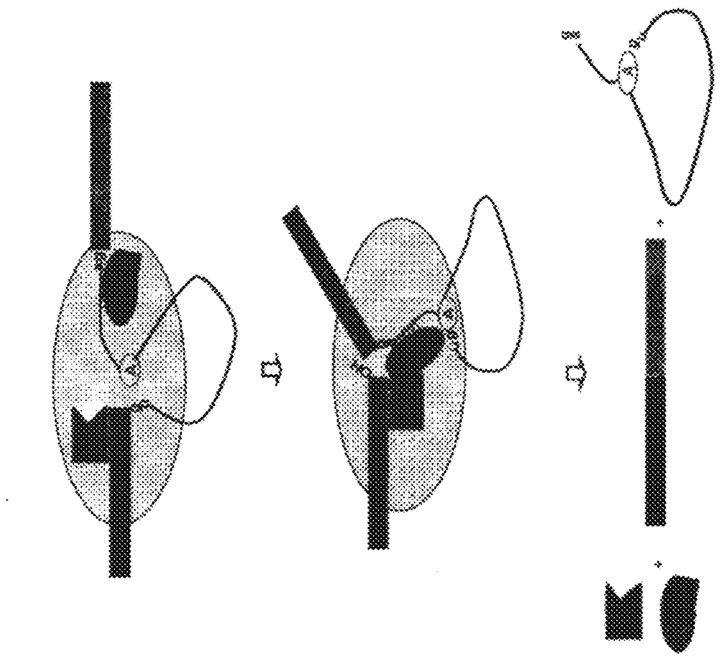
FIGS. 1*a* and 1*b* depict a schematic model of a nuclear pre-mRNA splicing pathway involving a splicer RNA and proteins.
Figure 1A:
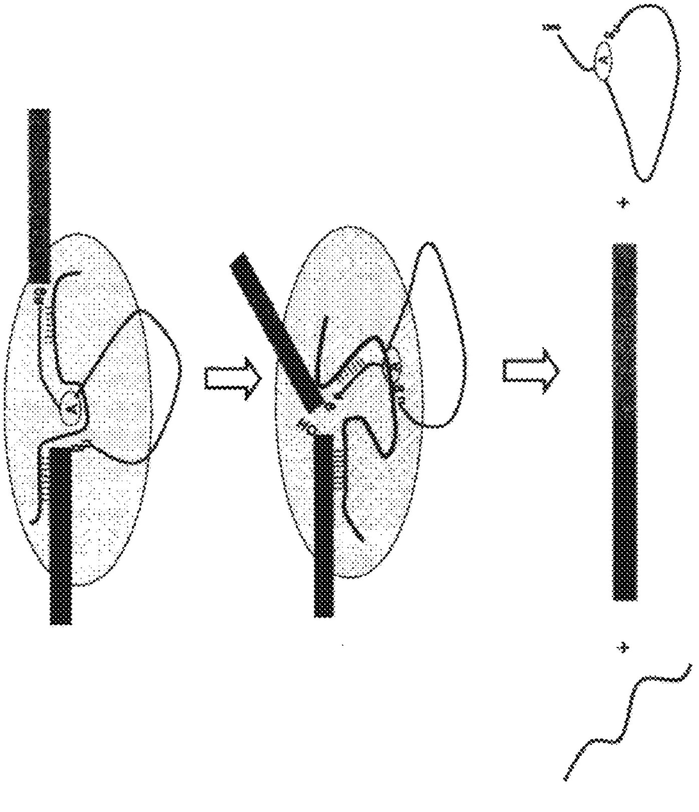

FIG. 1a depicts 5' and 3' exon sequences and a core spliceosome, including the intron and putative splicer RNA sequences. The circled A represents the branchpoint adenosine, and gu and ag represent the nucleotides typically present at the 5' and 3' ends of introns, respectively. The vertical lines represent base-pairing between the putative splicer RNA and pre-mRNA (although these two cis-elements in a splicer RNA are not expected to be identical). The last nucleotide of the 5' exon and the last two nucleotides of the intron may lack perfect complementarity. See Wu, S., Romfo, C. M., Nilsen, T. W., et al., *Functional recognition of the 3' splice site AG by the splicing factor U2AF35.* Nature 1999:402(6763):832-5 ("Wu"). For simplicity, a single splicer RNA has been shown, although the model is compatible with two RNAs (recognizing the 5' exon and 3' intron, respectively) in conjunction with other spliceosomal components. This model is conceptually similar to that first proposed by Holliday and Murray. See Holliday, R., Murray, V., *Specificity in splicing.* Bioessays 1994:16(10):771-4 ("Holliday"); Murray, V., Holliday, R., *Mechanism for RNA splicing of gene transcripts.* FEBS Lett. 1979:106(1):5-7 ("Murray").

FIG. 1b depicts a schematic model of E5 and I3 sequences recognized by as yet uncharacterized proteins, including 5' and 3' exon sequences and a core spliceosome. The black line represents the intron. The circled A is the branchpoint adenosine, and gu and ag represent the nucleotides typically present at the 5' and 3' ends of introns, respectively. The E5 interacts in a sequence-specific manner with an as yet uncharacterized protein and I3 is recognized by a different unknown protein. These two proteins interact with each other to assist in bringing together the 5' and 3' splice sites.

Based on this concept, a method of identifying putative alternative splice sites has been developed. According to one aspect of the invention, mammalian genes to identify novel control trans- or cis-elements and to predict novel alternatively spliced mRNA isoforms are accurately predicted and annotated. Markers are located 150 bp upstream (E5) and 150 bp downstream (I5) nucleotides of 5' splicing sites, and 150 bp upstream (I3) and 150 bp downstream (E3) nucleotides of 3' splicing sites. The invention provides for diagnostic methods employing the characteristic markers of associated introns and exons.

The invention comprises a method for indirectly detecting introns and exons through analysis of correlating splice junctions. Samples are analyzed for the presence of characterized splicing junctions via bioinformatics, genomics, comparative genomics, RT-PCR, gel electrophoresis, DNA/RNA chips, RNA-seq next generation sequencing or protein chip technologies. If a given sample is found to contain a known splicing junction, the sample is analyzed for the presence of known introns or exons. Novel isoforms mRNAs can be generated and can be translated into proteins. When a characterized intron or exon is verified and characterized, it is compared to a database which correlates the characterized intron or exon to characterized diseases or genetic mutations. If these proteins are over-expressed or expressed at extremely low levels relatively to dominant forms, they will disrupt the balances of these isoforms which results in disease. For example, over-expressed soluble insulin receptor proteins, which are secreted into the blood or tissues or outside the cell membranes, can directly bind to incoming insulin and therefore result in reduced level of insulin entering into cells. This is the best way to explain the insulin resistance or insulin insensitivity. Therefore, the cells cannot metabolize the intake of sugar and cause the human body to display insulin resistance. On other hand, if the soluble isoforms proteins are expressed at very low level and proteins with dominate tyrosine kinase are expressed at higher level, the cells will eventually overgrow and cause cancers. If a given sample is found to contain a known splicing junction, but not known introns or exons, the presence of novel introns or exons is likely and can be determined. Thus, the methods herein are applicable for predicting disease or genetic mutations, or for searching for novel introns and exons.

FIGS. 2a-2c provide signatures of typical splice site consensus sequences and human spliceosomal introns (top panel), for intron with E5-I3 LIN≥6 (middle panel) and introns with I5-E3 LIN≥6 (bottom panel). The graphics were generated by Pictogram (genes.mit.edu/pictogram.html). The splice junctions are located between the nucleotide positions −1 and +1.

Recently-acquired human spliceosomal introns have been shown to have signatures of similar 5' and 3' splice sites. See Zhuo II. FIG. 2a provides a plot of consensus sequences of 5' and 3' splice sites from the total human intron dataset (top panel), for E5-I3 with LIN≥6 (middle panel) and I5-E3 with LIN≥6 (bottom panel). The sequence below E5-I5 shows the 5' splice site recognition motif of U1 snRNA. The signatures of such introns are 5' and 3' intron boundaries that are very similar to each other (FIG. 2a, middle and bottom panels) and that do not conform well to the typical splice site consensus sequences (FIG. 2a, top panel). Each splice junction is divided into its exonic and intronic portions (designated as E5 and I5 for the 5' splice site and I3 and E3 for the 3' splice site, respectively). The lengths of identical nucleotides (LIN) have been scored in an uninterrupted stretch independently for the E5-I3 and I5-E3 alignments, respectively.

FIG. 2b provides an example of E5-I3 and I5-E3 alignments for intron 8 (168 bp) of the human ciz1 gene. The italic uppercase letters represent the 5' and 3' exonic sequences at splice sites, respectively, and the italic lowercase letters indicate the 5' and 3' intronic sequences. The vertical lines indicate uninterrupted identical nucleotides extending from the splice junctions for the E5-I3 and I5-E3 alignments, and are designated as LIN (length of identical nucleotides). Asterisks represent identical nucleotides outside of this region.

Figure 3B:
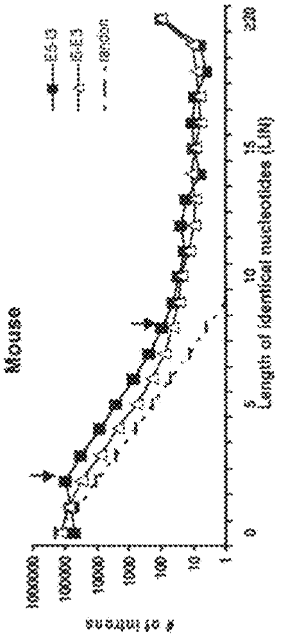
FIG. 3*b* provides a comparison analysis of LIN (length of identical nucleotides) distributions for E5-I3 and I5-E3 alignments of the total mouse intron dataset. Random sequences are used as a control represented by dashed line.
Figure 3A:
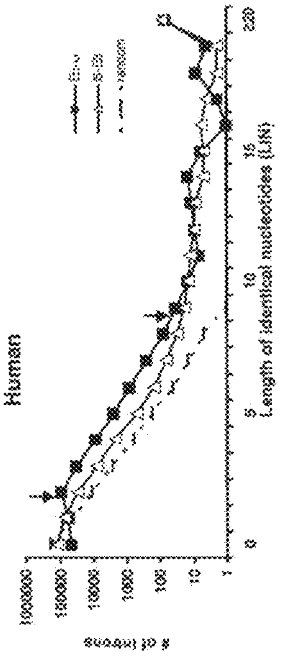
FIG. 3*a* provides a comparison analysis of LIN (length of identical nucleotides) distributions for E5-I3 and I5-E3 alignments analysis of the total human intron dataset. Random sequences are used as a control represented by dashed line.
Figure 3D:
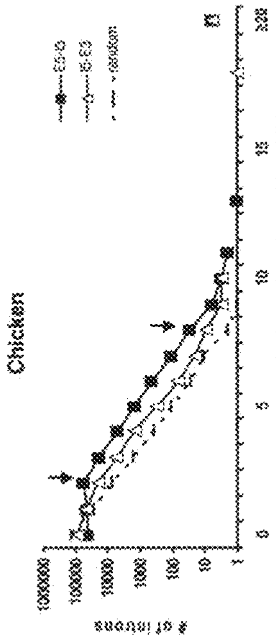
FIG. 3*d* provides a comparison analysis of LIN (length of identical nucleotides) distributions for E5-I3 and I5-E3 alignments of the total chicken intron dataset. Random sequences are used as a control represented by dashed line.
Figure 3C:
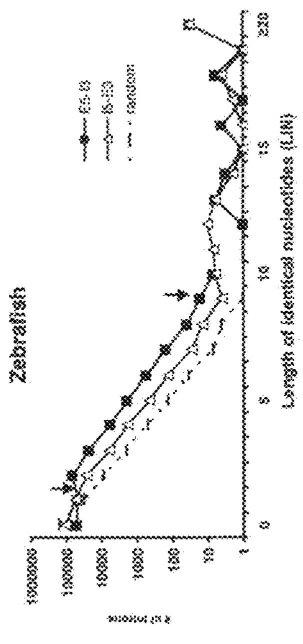
FIG. 3*c* provides a comparison analysis of LIN (length of identical nucleotides) distributions for E5-I3 and I5-E3 alignments of the total zebrafish intron dataset. Random sequences are used as a control represented by dashed line.
Figure 3F:
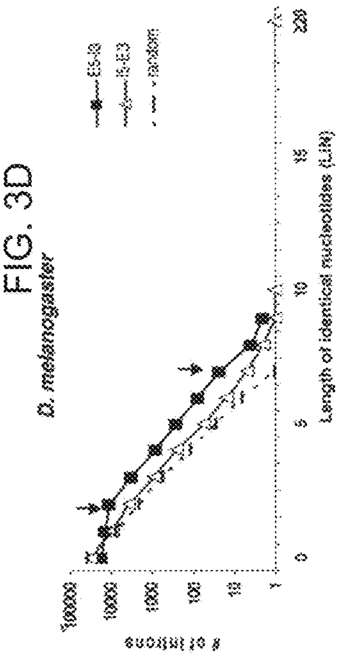
FIG. 3*f* provides a comparison analysis of LIN (length of identical nucleotides) distributions for E5-I3 and I5-E3 alignments of the total *D. melanogaster* intron dataset. Random sequences are used as a control represented by dashed line.
Figure 3E:
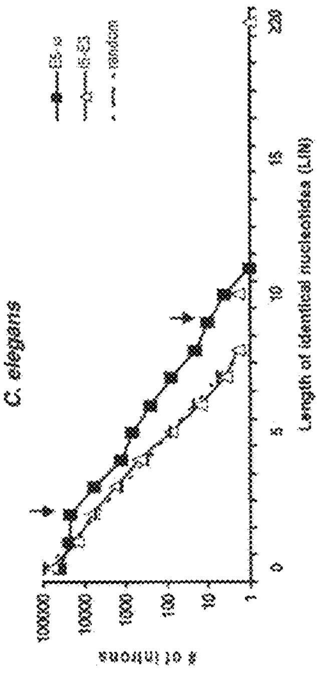
FIG. 3*e* provides a comparison analysis of LIN (length of identical nucleotides) distributions for E5-I3 and I5-E3 alignments of the total *C. elegans* intron dataset. Random sequences are used as a control represented by dashed line.

FIG. 2*b* provides a specific example showing the sequences flanking intron 8 of the human ciz1 gene, which encodes Cip1-interacting zinc finger protein 1. This was done for human introns as well as those for other vertebrates (mouse, zebrafish and chicken) (FIG. 2*c*) and the invertebrates *C. elegans* and *D. melanogaster* (FIG. 3*e*). As seen in FIG. 2*c*, the percentage of E5-I3 alignments with LIN≥6 is significantly higher ($p<0.001$) than for I5-E3 in humans (by 3-fold), in other vertebrates (by 2.4 to 5.3 fold) and in the invertebrate *D. melanogaster* (by 4.5 fold). In *C. elegans*, whose genome is believed to contain relatively few recently-gained introns, there is a 14-fold excess of E5-I3, driven in part by a low frequency of I5-E3 with LIN≥6 (compared to vertebrates). See Coghlan, A., Wolfe, K. H., *Origins of recently gained introns in Caenorhabditis*. Proc. Nat'l. Acad. Sci. U.S.A. 2004:101(31):11362-7 ("Coghlan II").

FIG. 2*c* provides sizes of animal intron datasets, and proportion with LIN≥6, also expressed as the ratio between E5-I3 and I5-E3. All observed differences between E5-I3 and I5-E3 were statistically significant ($p<0.001$).

FIGS. 3*a*-3*f* provide plots of the frequencies of distributions of E5-I3 and I5-E3 alignments for the full range of LIN from 0 to ≥20 for human, mouse, zebrafish, chicken, *C. elegans* and *D. melanogaster*. The data are set forth below in Tables 1-6. Table 1 presents comparative analysis of human E5-I3 and I5-E3 alignments. Probabilities reflect the random chance of differences between E5-I3 and I5-E3 proportions as judged by U-tests. One and two asterisks represent statistical significances at 0.05 and 0.001 levels, respectively.

TABLE 1

| Human | | | | |
|---|---|---|---|---|
| LIN | E5-I3 | I5-E3 | E5-I3/I5-E3 | Probabilities (p) |
| 0 | 44654 | 121410 | 0.37 | <0.001** |
| 1 | 59395 | 72673 | 0.82 | <0.001** |
| 2 | 87690 | 29250 | 3.00 | <0.001** |
| 3 | 31020 | 8102 | 3.83 | <0.001** |
| 4 | 8170 | 2290 | 3.57 | <0.001** |
| 5 | 2438 | 504 | 4.84 | <0.001** |
| 6 | 780 | 150 | 5.20 | <0.001** |
| 7 | 243 | 64 | 3.80 | <0.001** |
| 8 | 75 | 30 | 2.50 | <0.001** |
| 9 | 33 | 18 | 1.83 | <0.05 & >0.02 |
| 10 | 15 | 14 | 1.07 | >0.5 |
| 11 | 7 | 12 | 0.58 | <0.5 & >0.2 |
| 12 | 9 | 10 | 0.90 | >0.5 |
| 13 | 11 | 9 | 1.22 | >0.5 |
| 14 | 15 | 5 | 3.00 | <0.05 & >0.02 |
| 15 | 6 | 5 | 1.20 | >0.5 |
| 16 | 1 | 6 | 0.17 | <0.1 & >0.05 |
| 17 | 2 | 4 | 0.50 | <0.5 & >0.2 |
| 18 | 8 | 2 | 4.00 | <0.1 & >0.05 |
| 19 | 4 | 2 | 2.00 | <0.5 & >0.2 |
| ≥20 | 67 | 83 | 0.81 | <0.2 & >0.1 |

Table 2 presents comparative analysis of mouse E5-I3 and I5-E3 alignments. Probabilities reflect the chances of differences between E5-I3 and I5-E3 proportions by U-tests. One and two asterisks represent statistical significances at 0.05 and 0.001 levels, respectively.

TABLE 2

| Mouse | | | | |
|---|---|---|---|---|
| LIN | E5-I3 | I5-E3 | E5-I3/ I5-E3 | Probabilities (p) |
| 0 | 50374 | 130138 | 0.4 | <0.001** |
| 1 | 62590 | 76584 | 0.8 | <0.001** |
| 2 | 92948 | 31844 | 2.9 | <0.001** |
| 3 | 32172 | 8164 | 3.9 | <0.001** |
| 4 | 8214 | 2259 | 3.6 | <0.001** |
| 5 | 2478 | 555 | 4.5 | <0.001** |
| 6 | 726 | 189 | 3.8 | <0.001** |
| 7 | 231 | 79 | 2.9 | <0.001** |
| 8 | 92 | 45 | 2.0 | <0.001** |
| 9 | 43 | 29 | 1.5 | <0.1 & >0.05 |
| 10 | 28 | 24 | 1.2 | >0.5 |
| 11 | 19 | 14 | 1.4 | <0.5 & >0.2 |
| 12 | 24 | 10 | 2.4 | <0.02 & 0.01* |
| 13 | 16 | 9 | 1.8 | <0.2 & >0.1 |
| 14 | 6 | 12 | 0.5 | <0.2 & >0.1 |
| 15 | 10 | 9 | 1.1 | >0.5 |
| 16 | 11 | 6 | 1.8 | <0.5 & >0.2 |
| 17 | 9 | 7 | 1.3 | >0.5 |
| 18 | 4 | 8 | 0.5 | <0.5 & >0.2 |
| 19 | 6 | 11 | 0.5 | <0.5 & >0.2 |
| ≥20 | 94 | 99 | 0.9 | >0.5 |

Table 3 presents comparative analysis of zebrafish E5-I3 and I5-E3 alignments. Probabilities reflect the chances of differences between E5-I3 and I5-E3 proportions by U-tests. One and two asterisks represent statistical significances at 0.05 and 0.001 levels, respectively.

TABLE 3

| Zebrafish | | | | |
|---|---|---|---|---|
| LIN | E5-I3 | I5-E3 | E5-I3/ I5-E3 | Propabilties (p) |
| 0 | 56829 | 120429 | 0.5 | <0.001** |
| 1 | 53399 | 60571 | 0.9 | <0.001** |
| 2 | 74414 | 28975 | 2.6 | <0.001** |
| 3 | 25713 | 6933 | 3.7 | <0.001** |
| 4 | 6296 | 2028 | 3.1 | <0.001** |
| 5 | 2120 | 498 | 4.3 | <0.001** |
| 6 | 646 | 152 | 4.3 | <0.001** |
| 7 | 175 | 28 | 6.3 | <0.001** |
| 8 | 44 | 15 | 2.9 | <0.001** |
| 9 | 20 | 5 | 4.0 | <0.005 & >0.002** |
| 10 | 7 | 6 | 1.2 | >0.5 |
| 11 | | 7 | 0.0 | <0.5 & >0.2 |
| 12 | 1 | 21 | 0.0 | <0.001** |
| 13 | 6 | 7 | 0.9 | >0.5 |
| 14 | 4 | 2 | 2.0 | <0.5 & >0.2 |
| 15 | 1 | 1 | 1.0 | >0.5 |
| 16 | 5 | 1 | 5.0 | <0.1 & >0.05 |
| 17 | 1 | 3 | 0.3 | <0.5 & >0.2 |
| 18 | 6 | 5 | 1.2 | >0.5 |
| 19 | 1 | 1 | 1.0 | >0.5 |
| ≥20 | 32 | 32 | 1.0 | >0.5 |

Table 4 presents comparative analysis of chicken E5-I3 and I5-E3 alignments. Probabilities reflect the chances of differences between E5-I3 and I5-E3 proportions by U-tests. One and two asterisks represent statistical significances at 0.05 and 0.001 levels, respectively.

TABLE 4

| Chicken | | | | |
|---|---|---|---|---|
| LIN | E5-I3 | I5-E3 | E5-I3/ I5-E3 | Probabilities (p) |
| 0 | 42496 | 90642 | 0.5 | <0.001** |
| 1 | 41048 | 47333 | 0.9 | <0.001** |
| 2 | 56186 | 20243 | 2.8 | <0.001** |
| 3 | 18761 | 5287 | 3.5 | <0.001** |
| 4 | 4814 | 1430 | 3.4 | <0.001** |
| 5 | 1471 | 305 | 4.8 | <0.001** |
| 6 | 421 | 65 | 6.5 | <0.001** |
| 7 | 102 | 20 | 5.1 | <0.001** |
| 8 | 30 | 9 | 3.3 | <0.001** |
| 9 | 6 | 3 | 2.0 | <0.5 & >0.2 |
| 10 | 3 | 3 | 1.0 | >0.5 |
| 11 | 2 | | | <0.2 & >0.1 |
| 12 | | | | |
| 13 | 1 | | | <0.5 & >0.2 |
| 14 | | | | |
| 15 | | | | |
| 16 | | | | |
| 17 | | | | |
| 18 | | 1 | 0.0 | <0.5 & >0.2 |
| 19 | | | | |
| ≥20 | 6 | 6 | 1.0 | >0.5 |

Table 5 presents comparative analysis of *C. elegans* E5-I3 and I5-E3 alignments. Probabilities reflect the chances of differences between E5-I3 and I5-E3 proportions by U-tests. One and two asterisks represent statistical significances at 0.05 and 0.001 levels, respectively.

TABLE 5

| *C. elegans* | | | | |
|---|---|---|---|---|
| LIN | E5-I3 | I5-E3 | E5-I3/ I5-E3 | Probabilties (p) |
| 0 | 38200 | 64331 | 0.6 | <0.001** |
| 1 | 22059 | 15756 | 1.4 | <0.001** |
| 2 | 20604 | 6486 | 3.2 | <0.001** |
| 3 | 5609 | 1696 | 3.3 | <0.001** |
| 4 | 1303 | 450 | 2.9 | <0.001** |
| 5 | 701 | 87 | 8.1 | <0.001** |
| 6 | 241 | 17 | 14.2 | <0.001** |
| 7 | 80 | 4 | 20.0 | <0.001** |
| 8 | 20 | 2 | 10.0 | <0.001** |
| 9 | 10 | | | <0.002 & >0.001** |
| 10 | 4 | 2 | 2.0 | <0.5 & >0.2 |
| 11 | 1 | | | <0.5 & >0.2 |
| 12 | | | | |
| 13 | | | | |
| 14 | | | | |
| 15 | | | | |
| 16 | | | | |
| 17 | | | | |
| 18 | | | | |
| 19 | | | | |
| ≥20 | | 1 | 0.0 | <0.5 & >0.2 |

Table 6 presents comparative analysis of *D. melanogaster* E5-I3 and I5-E3 alignments. Probabilities reflect the chances of differences between E5-I3 and I5-E3 proportions by U-tests. One and two asterisks represent statistical significances at 0.05 and 0.001 levels, respectively.

TABLE 6

| *D. melanogaster* | | | | |
|---|---|---|---|---|
| LIN | E5-I3 | I5-E3 | E5-I3/ I5-E3 | Probabilties (p) |
| 0 | 17183 | 32954 | 0.5 | <0.001** |
| 1 | 14137 | 9204 | 1.5 | <0.001** |
| 2 | 11321 | 3781 | 3.0 | <0.001** |
| 3 | 3347 | 890 | 3.8 | <0.001** |
| 4 | 807 | 265 | 3.0 | <0.001** |
| 5 | 270 | 55 | 4.9 | <0.001** |
| 6 | 80 | 15 | 5.3 | <0.001** |
| 7 | 23 | 5 | 4.6 | <0.001** |
| 8 | 4 | 2 | 2.0 | <0.5 & >0.2 |
| 9 | 2 | 1 | 2.0 | >0.5 |
| 10 | | 1 | 0.0 | <0.5 & >0.2 |
| 11 | | | | |
| 12 | | | | |
| 13 | | | | |
| 14 | | | | |
| 15 | | | | |
| 16 | | | | |
| 17 | | | | |
| 18 | | | | |
| 19 | | | | |
| ≥20 | | 1 | 0.0 | <0.5 & >0.2 |

The arrows of FIGS. 3*a*-3*f* delimit the windows for which there are a significantly higher value observed for E5-I3 than for I5-E3, as judged by U-test with $p<0.001$. The values for all vertebrates were significantly higher than for random sequences (FIGS. 3*a*-*d*). For large LIN (≥10 for human and *C. elegans,* ≥8 for *D. melanogaster* and ≥9 for the others), no significant difference was seen between E5-I3 and I5-E3 at distances that are more than 10 nt away from the splice junctions. For LIN between 2 and 9 in *C. elegans*, there is a very marked excess of E5-I3 relative to I5-E3 (FIG. 3*e*), whereas *D. melanogaster* shows a more vertebrate-like profile (FIG. 3*e*). For the invertebrates, the virtually complete absence of introns with long LINs is consistent with few recent intron gains. See Coghlan; Banyai, L., Patthy, L., *Evidence that human genes of modular proteins have retained significantly more ancestral introns than their fly or worm orthologues*. FEBS Lett. 2004:565(1-3):127-32 ("Coghlan I").

The E5-I3 and I5-E3 alignments were also compared to scramble (mix-and-match) data produced by randomly aligning E5 with I3, and I5 with E3, from a non-redundant intron dataset. A statistically significant difference was seen in all cases as set forth below in Tables 7 and 8 for human and *C. elegans.*

Tables 7a and 7b present comparative analysis of human E5-I3 and their scrambles (SC5) with I3 and E5 randomly selected from non-redundant human introns and I5-E3 and their scrambles (SC3) with randomly selected E3 and I5. One and two asterisks represent statistical significances at 0.05 and 0.001 levels, respectively.

TABLE 7a

| Human | | | | |
|---|---|---|---|---|
| LINs | E5-I3 | SC5 | E5-I3/ SC5 | Probabilities (p) |
| 0 | 44655 | 68328 | −34.65 | <0.001** |
| 1 | 59396 | 69024 | −13.95 | <0.001** |
| 2 | 87690 | 69549 | 26.08 | <0.001** |
| 3 | 31022 | 20672 | 50.07 | <0.001** |
| 4 | 8170 | 5196 | 57.24 | <0.001** |
| 5 | 2438 | 1384 | 76.16 | <0.001** |

TABLE 7a-continued

| Human | | | | |
|---|---|---|---|---|
| LINs | E5-I3 | SC5 | E5-I3/ SC5 | Probabilities (p) |
| 6 | 780 | 356 | 119 | <0.001** |
| 7 | 243 | 95 | 156 | <0.001** |
| 8 | 75 | 27 | 178 | <0.001** |
| 9 | 33 | 10 | 230 | <0.001** |
| 10 | 15 | 6 | 150 | >0.05 & <0.02* |
| 11 | 7 | | | <0.01 & >0.005** |
| 12 | 9 | | | <0.005 & >0.002** |
| 13 | 11 | | | <0.001** |
| 14 | 15 | | | <0.001** |
| 15 | 6 | | | <0.02 & >0.01* |
| 16 | 1 | | | <0.5 & >0.2 |
| 17 | 2 | | | <0.2 & >0.1 |
| 18 | 8 | | | <0.005 & >0.001** |
| 19 | 4 | | | >0.05 & <0.2 |
| ≥20 | 67 | | | <0.001** |

TABLE 7b

| Human | | | | |
|---|---|---|---|---|
| LINs | I5-E3 | SC3 | E5-I3/ SC3 | Probabilties (p) |
| 0 | 121411 | 120692 | 0.6 | >0.05 & <0.02* |
| 1 | 72674 | 73436 | −1.04 | >0.01 & <0.02* |
| 2 | 29251 | 30344 | −3.6 | <0.001** |
| 3 | 8103 | 7645 | 5.99 | <0.001** |
| 4 | 2290 | 1990 | 15.08 | <0.001** |
| 5 | 504 | 415 | 21.45 | >0.005 & <0.002** |
| 6 | 150 | 88 | 70.45 | <0.001** |
| 7 | 64 | 26 | 146.15 | <0.001** |
| 8 | 30 | 6 | 400 | <0.001** |
| 9 | 18 | 5 | 260 | <0.01 & >0.005** |
| 10 | 14 | | | <0.001** |
| 11 | 12 | | | <0.001** |
| 12 | 10 | | | <0.002 & >0.001** |
| 13 | 9 | | | <0.002 & >0.001** |
| 14 | 5 | | | <0.05 & >0.02* |
| 15 | 5 | | | <0.05 & >0.02* |
| 16 | 6 | | | <0.02 & >0.01* |
| 17 | 4 | | | <0.05 & >0.02* |
| 18 | 2 | | | <0.2 & >0.1 |
| 19 | 2 | | | <0.2 & >0.1 |
| ≥20 | 83 | | | <0.001** |

Tables 8a and 8b present comparative analyses of *C. elegans* E5-I3 and their scrambles (SC5) with I3 and E5 randomly selected from non-redundant *C. elegans* introns and I5-E3 and their scrambles (SC3) with randomly selected E3 and I5. One and two asterisks represent statistical significances at 0.05 and 0.001 levels, respectively.

TABLE 8a

| *C. elegans* | | | | |
|---|---|---|---|---|
| LINs | E5-I3 | SC5 | E5-I3/ SC5 | Probabilities (p) |
| 0 | 38200 | 44445 | −14.1 | <0.001** |
| 1 | 22059 | 22461 | −1.8 | <0.05 & >0.02* |
| 2 | 20604 | 16231 | 27 | <0.001** |
| 3 | 5609 | 4128 | 36 | <0.001** |
| 4 | 1303 | 959 | 36 | <0.001** |
| 5 | 701 | 402 | 74 | <0.001** |

TABLE 8a-continued

| *C. elegans* | | | | |
|---|---|---|---|---|
| LINs | E5-I3 | SC5 | E5-I3/ SC5 | Probabilities (p) |
| 6 | 241 | 128 | 88 | <0.001** |
| 7 | 80 | 56 | 43 | <0.05 & >0.02* |
| 8 | 20 | 14 | 43 | <0.2 & >0.1 |
| 9 | 10 | 6 | 67 | <0.2 & >0.1 |
| 10 | 4 | 2 | 100 | <0.2 & >0.1 |
| 11 | 1 | | | <0.2 & >0.1 |
| 12 | | | | |
| 13 | | | | |
| 14 | | | | |
| 15 | | | | |
| 16 | | | | |
| 17 | | | | |
| 18 | | | | |
| 19 | | | | |
| ≥20 | | | | |

TABLE 8b

| *C. elegans* | | | | |
|---|---|---|---|---|
| LINs | I5-E3 | SC3 | E5-I3/ SC3 | Probabilities (p) |
| 0 | 64331 | 62969 | 2.2 | <0.001** |
| 1 | 15756 | 16332 | −3.5 | <0.001** |
| 2 | 6486 | 7155 | −9.4 | <0.001** |
| 3 | 1696 | 1759 | −3.6 | <0.2 & >0.1 |
| 4 | 450 | 526 | −14 | <0.02 & >0.01* |
| 5 | 87 | 64 | 36 | <0.1 & >0.05 |
| 6 | 17 | 21 | −19 | >0.5 |
| 7 | 4 | 5 | −20 | >0.5 |
| 8 | 2 | 1 | 100 | >0.5 |
| 9 | | | | |
| 10 | 2 | | | <0.2 & >0.1 |
| 11 | | | | |
| 12 | | | | |
| 13 | | | | |
| 14 | | | | |
| 15 | | | | |
| 16 | | | | |
| 17 | | | | |
| 18 | | | | |
| 19 | | | | |
| ≥20 | 1 | | | >0.5 |

Because it is known that U1 snRNA, in addition to base-pairing with sequences at the 5' end of the intron, also imposes a strong constraint on the terminal AG of the upstream exon (within E5), as does the binding of U2AF35 to the cAG region at the 3' end of the intron (within I3), this analysis was repeated omitting the sequences located at positions −3 to +3 of both the 5' and 3' splice sites. See Carmel, I., Tal, S., Vig, I., et al., *Comparative analysis detects dependencies among the 5' splice-site positions*. RNA 2004:10(5):828-40 ("Carmel"); Wu. As shown in Table 9 below, the frequencies of LINs with values ≥1 and ≥5 for human E5-I3 and I5-E3 were significantly higher ($p<0.05$) than those of the corresponding scrambles.

Tables 9a and 9b present comparative analyses of human E5-I3 and their scrambles (SC5) with I3 and E5 randomly selected from non-redundant human introns and I5-E3 and their scrambles (SC3) with randomly selected E3 and I5 after removing the last and first three nucleotides adjacent the 5' and 3' splice sites (namely, from positions −1 to −6 and from +1 to +6) of E5, E3, I3 and I5. One and two asterisks represent statistical significances at 0.05 and 0.001 levels, respectively.

TABLE 9a

| Human | | | | |
|---|---|---|---|---|
| | E5-I3 | | | |
| LINs | E5-I3 | SC5 | E5-13/SC5 | Probabilities (p) |
| 0 | 172558 | 175984 | −0.02 | <0.001** |
| 1 | 44258 | 42841 | 0.03 | <0.001** |
| 2 | 12700 | 11672 | 0.09 | <0.001** |
| 3 | 3586 | 3040 | 0.18 | <0.001** |
| 4 | 999 | 790 | 0.26 | <0.001** |
| 5 | 282 | 238 | 0.18 | >0.05 & <0.02* |
| 6 | 84 | 66 | 0.27 | <0.2 & <0.1 |
| 7 | 35 | 11 | 2.18 | <0.001** |
| 8 | 13 | 4 | 2.25 | <0.05 & >0.02* |
| 9 | 11 | 3 | 2.67 | <0.05 & >0.02* |
| 10 | 15 | 1 | 14.00 | <0.001** |
| 11 | 16 | | | <0.001** |
| 12 | 6 | | | <0.02 & >0.01* |
| 13 | 1 | | | <0.5 & >0.2 |
| 14 | 3 | | | >0.1 & >0.05 |
| ≥15 | 83 | | | <0.001** |

TABLE 9b

| Human | | | | |
|---|---|---|---|---|
| | I5-E3 | | | |
| LINs | I5-E3 | SC3 | E5-I3/SC3 | Probabilities (p) |
| 0 | 175253 | 176744 | −0.84 | <0.001** |
| 1 | 44840 | 44150 | 1.56 | <0.02 & >0.01* |
| 2 | 10675 | 10508 | 1.59 | >0.2 & <0.5 |
| 3 | 2648 | 2381 | 11.21 | <0.001** |
| 4 | 761 | 649 | 17.26 | <0.005 & >0.002** |
| 5 | 215 | 156 | 37.82 | <0.005 & >0.001** |
| 6 | 67 | 46 | 45.65 | <0.02 & >0.01* |
| 7 | 30 | 12 | 150.00 | <0.01 & >0.005** |
| 8 | 23 | 3 | 666.67 | <0.001** |
| 9 | 14 | 1 | 1300.00 | <0.001** |
| 10 | 11 | | | <0.001** |
| 11 | 5 | | | <0.02 & >0.01* |
| 12 | 6 | | | <0.02 & >0.01* |
| 13 | 6 | | | <0.02 & >0.01* |
| 14 | 4 | | | <0.02 & >0.01* |
| ≥15 | 93 | | | <0.001** |

No statistical differences were observed for I5-E3 as seen in Table 10, consistent with the profiles shown in FIG. 3*e*.

Tables 10a and 10b present comparative analyses of *C. elegans* E5-I3 and their scrambles (SC5) with I3 and E5 randomly selected from non-redundant *C. elegans* introns and I5-E3 and their scrambles (SC3) with randomly selected E3 and I5 after removing the last and first three nucleotides adjacent the 5' and 3' splice sites (namely, from positions −1 to −6 and from +1 to +6) of E5, E3, I3 and I5. One and two asterisks represent statistical significances at 0.05 and 0.001 levels, respectively.

TABLE 10a

| *C. elegans* | | | | |
|---|---|---|---|---|
| | I5-E3 | | | |
| LINs | I5-E3 | SC3 | E5-I3/SC3 | Probabilities (p) |
| 0 | 64795 | 65057 | −0.40 | >0.05 & <0.1 |
| 1 | 19528 | 19489 | 0.20 | >0.5 |
| 2 | 3321 | 3211 | 3.43 | >0.05 & <0.1 |
| 3 | 849 | 800 | 6.13 | >0.5 & >0.2 |
| 4 | 248 | 212 | 16.98 | >0.05 & <0.1 |
| 5 | 61 | 43 | 41.86 | >0.05 & <0.1 |

TABLE 10a-continued

| *C. elegans* | | | | |
|---|---|---|---|---|
| | I5-E3 | | | |
| LINs | I5-E3 | SC3 | E5-I3/SC3 | Probabilities (p) |
| 6 | 19 | 17 | 11.76 | >0.5 |
| 7 | 8 | 2 | 300.00 | >0.05 & <0.1 |
| 8 | 2 | 1 | 100.00 | >0.5 |
| 9 | | | | |
| 10 | | | | |
| 11 | | | | |
| 12 | | | | |
| 13 | | | | |
| 14 | | | | |
| ≥15 | 1 | | | >0.2 & <0.5 |

TABLE 10b

| *C. elegans* | | | | |
|---|---|---|---|---|
| | I5-E3 | | | |
| LINs | I5-E3 | SC3 | E5-I3/SC3 | Probabilities (p) |
| 0 | 64795 | 65057 | −0.40 | >0.05 & <0.1 |
| 1 | 19528 | 19489 | 0.20 | >0.5 |
| 2 | 3321 | 3211 | 3.43 | >0.05 & <0.1 |
| 3 | 849 | 800 | 6.13 | >0.5 & >0.2 |
| 4 | 248 | 212 | 16.98 | >0.05 & <0.1 |
| 5 | 61 | 43 | 41.86 | >0.05 & <0.1 |
| 6 | 19 | 17 | 11.76 | >0.5 |
| 7 | 8 | 2 | 300.00 | >0.05 & <0.1 |
| 8 | 2 | 1 | 100.00 | >0.5 |
| 9 | | | | |
| 10 | | | | |
| 11 | | | | |
| 12 | | | | |
| 13 | | | | |
| 14 | | | | |
| ≥15 | 1 | | | >0.2 & <0.5 |

The E5-I3 values for the LIN≥3 (and therefore comparable to LIN≥6 in FIG. 1*c*) are still significantly higher ($p<0.001$) than those for I5-E3 by about 0.3-fold for human introns and about 2.7-fold higher in the case of *C. elegans*.

Figure 4A:
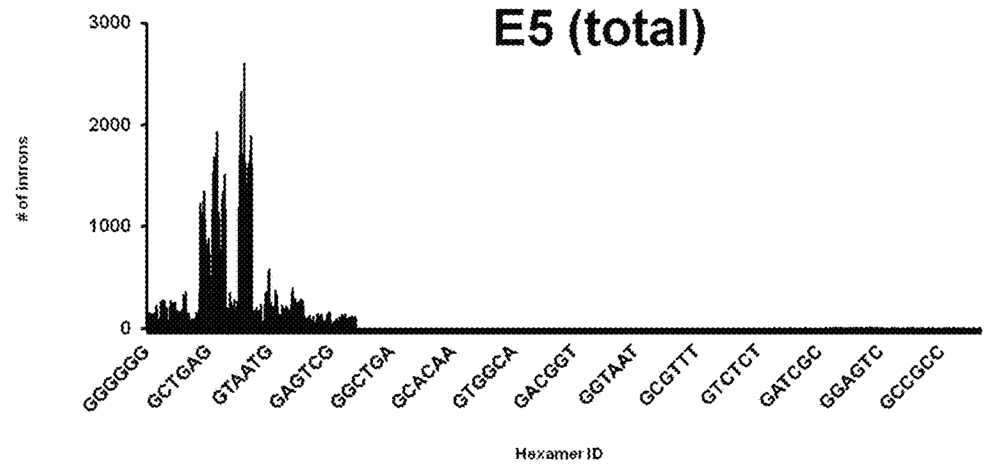
FIG. 4*a* provides a plot of the distributions of the E5 hexamers (from positions −1 to −6) for the total human intron.
Figure 4B:
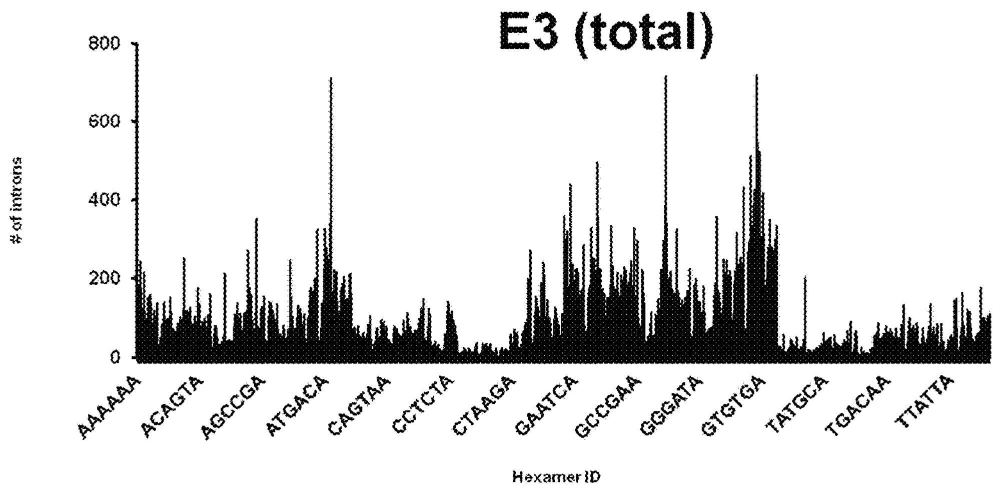
FIG. 4*b* provides a plot of the distributions of the I5 hexamers (from positions −1 to −6) for the total human intron.
Figure 4C:
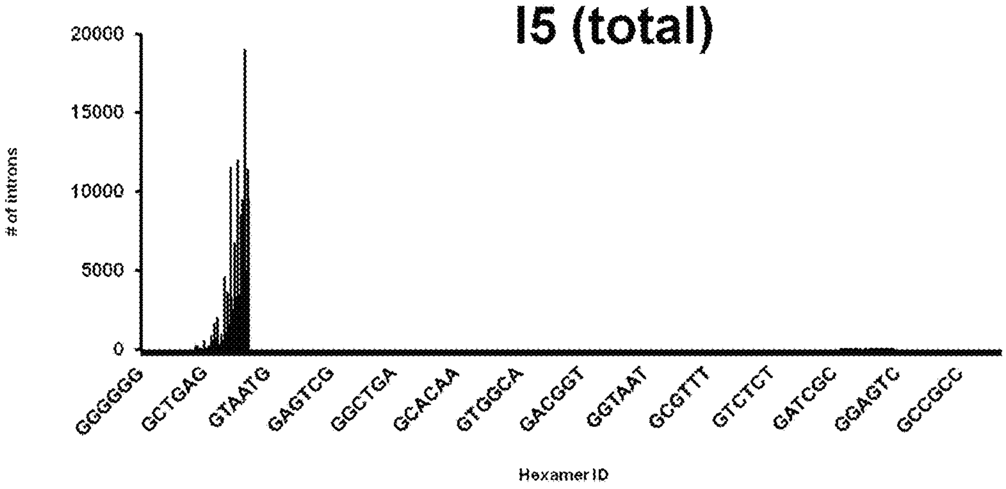
FIG. 4*c* provides a plot of the distributions of the I3 hexamers (from positions −1 to −6) for the total human intron.
Figure 4D:
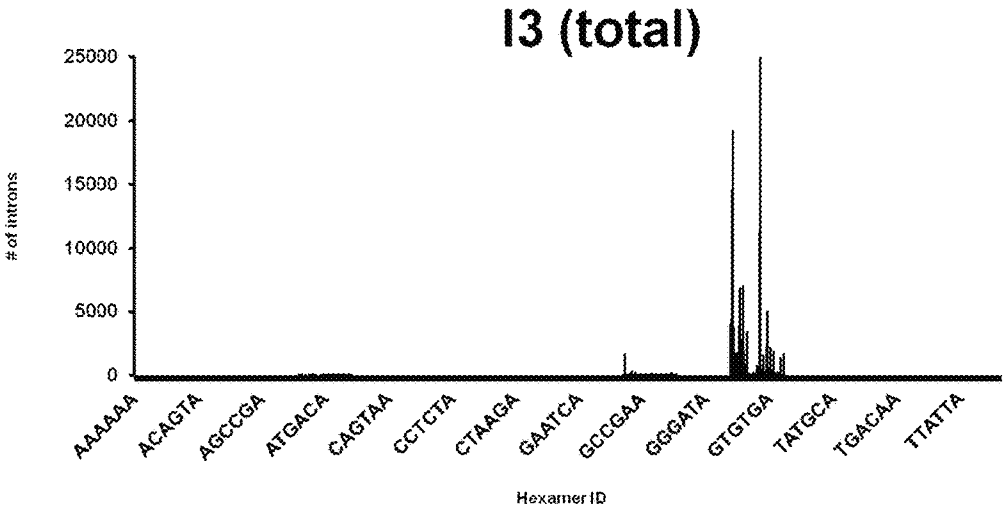
FIG. 4*d* provides a plot of the distributions of the E3 hexamers (from positions −1 to −6) for the total human intron.
Figure 4E:
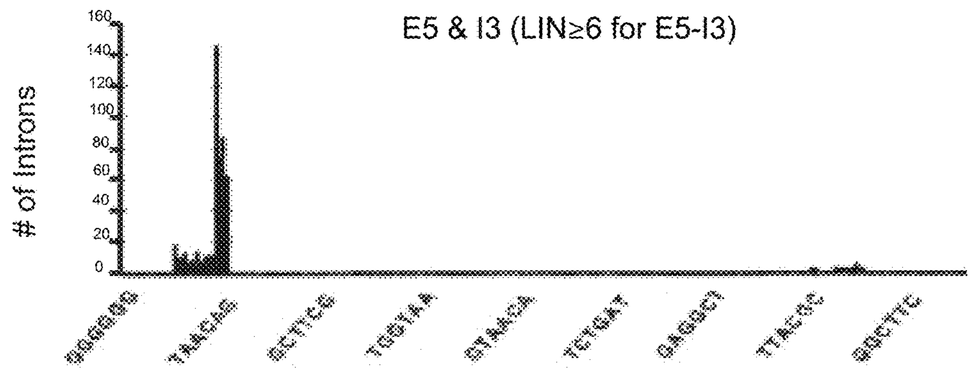
FIG. 4*e* provides plots of the distributions of hexamers overlayed for E5 and I3 which are adjacent to the 5' and 3' splice sites for the LIN≥6 datasets.
Figure 4F:
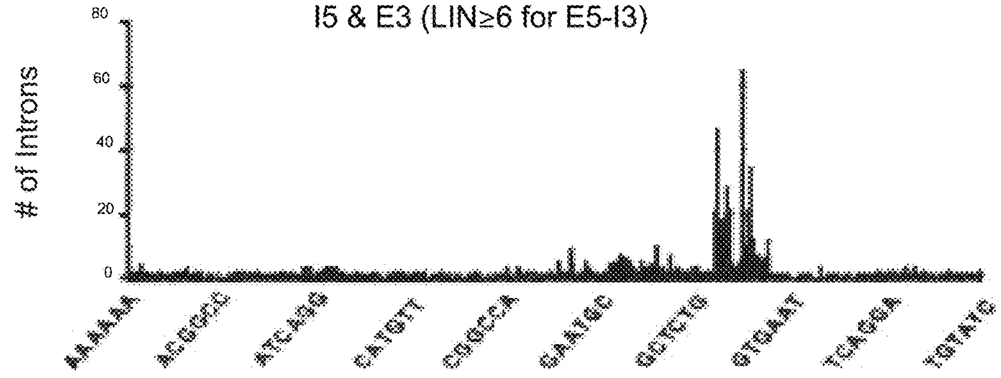
FIG. 4*f* provides plots of the distributions of hexamers overlayed for I5 and E3 which are adjacent to the 5' and 3' splice sites for the LIN≥6 datasets.
Figure 4G:
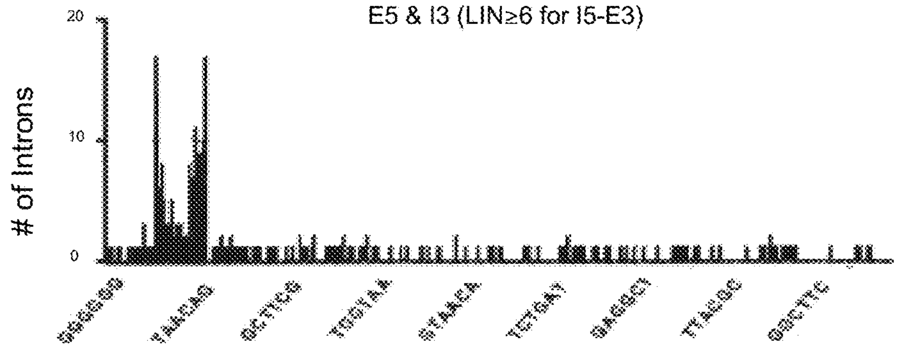
FIG. 4*g* provides plots of the distributions of hexamers overlayed for E5 and I3 which are adjacent to the 5' and 3' splice sites for the LIN≥6 dataset.

The distributions of hexamers which are adjacent to the 5' and 3' splice sites (from positions −1 to −6 and from +1 to +6) for each of E5, I5, I3 and E3 for the total human intron set are plotted in FIGS. 4*a*-4*d*. The distributions for the LIN≥6 subset for E5 are plotted in FIGS. 4*e*-4*f* and for E3 in FIGS. 4*g*-4*h*. For the total set (FIGS. 3*a*-*d*), the distribution of exon hexamers (E3) located immediately downstream of introns is much broader than for those upstream (E5) (FIG. 4*b* vs. FIG. 4*a*). This uneven distribution of E5 for the I5-E3 with LIN≥6 dataset is supported by an E5 variance ($\sigma 2$) which is 50% larger than E3 variance for the E5-I3 LIN≥6 set (F-test, $p<0.00001$) (FIG. 4*g* vs. FIG. 4*f*).

Figure 4H:
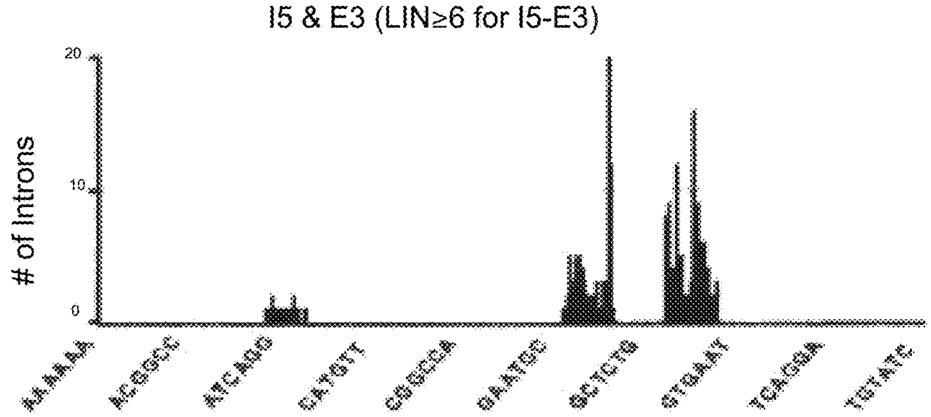
FIG. 4*h* provides plots of the distributions of hexamers overlayed for I5 and E3 which are adjacent to the 5' and 3' splice sites for the LIN≥6 dataset.
Figure 5A:
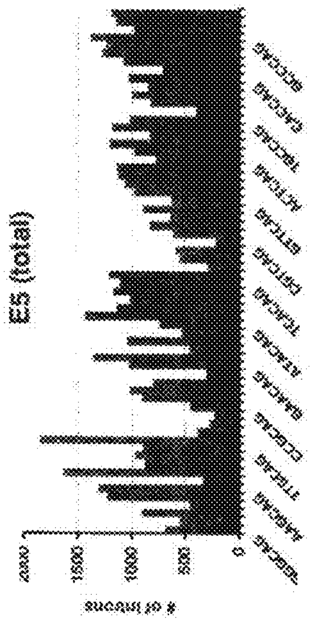
FIG. 5*a* provides the distribution of total E5 hexamers ending with CAG in FIG. 4*a*.
Figure 5B:
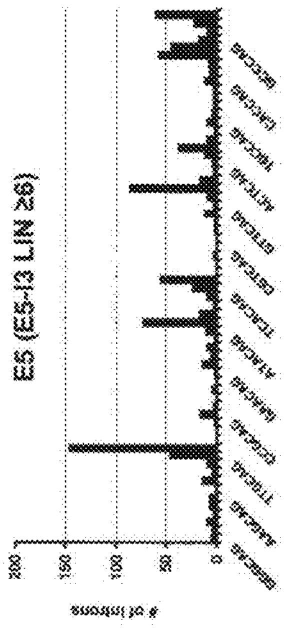
FIG. 5*b* provides a plot of the distribution of E5 hexamers of E5-I3 LIN≥6 ending with CAG in FIG. 4*a*.
Figure 5C:
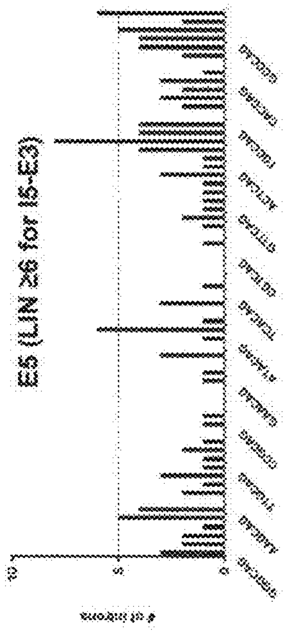
FIG. 5*c* provides a plot of the distribution of E5 hexamers of LIN≥6 for I5-E3 ending with CAG in FIG. 4*f.*
Figure 6A:
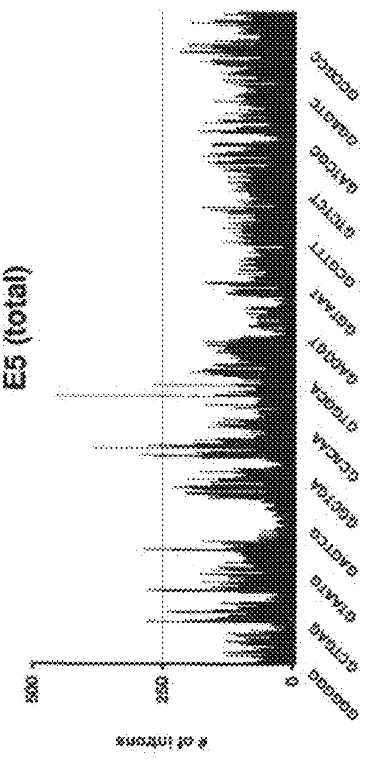
FIGS. 6*a*-6*l* provide plots of the distribution of the hexamers from the human introns after removing the last and first three nucleotides adjacent the 5' and 3' splice sites (namely, from positions −1 to −3 of E5 and I3, and from +1 to +3 of I5 and E3). Hexamers for the total intron dataset are shown for E5 in FIG. 6*a*; for E3 in FIG. 6*b*; for I3 in FIG. 6*c*; and for I5 in FIG. 6*d*. Hexamers for the E5-I3 LIN≥3 dataset are shown for E5 in FIG. 6*e*; for E3 in FIG. 6*f*; for I3 in FIG. 6*g*; and for I5 in FIG. 6*h*. Hexamers for the I5-E3 LIN≥3 dataset are shown for E5 in FIG. 6*i*; for E3 in FIG. 6*j*; for I3 in FIG. 6*k*; and for I5 in FIG. 6*l*.
Figure 6B:
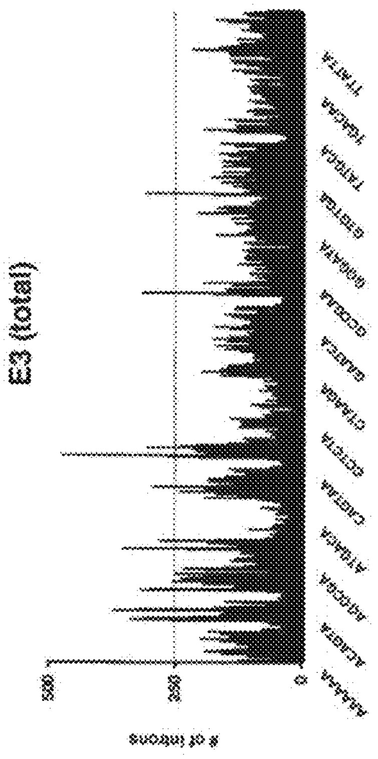
Figure 6C:
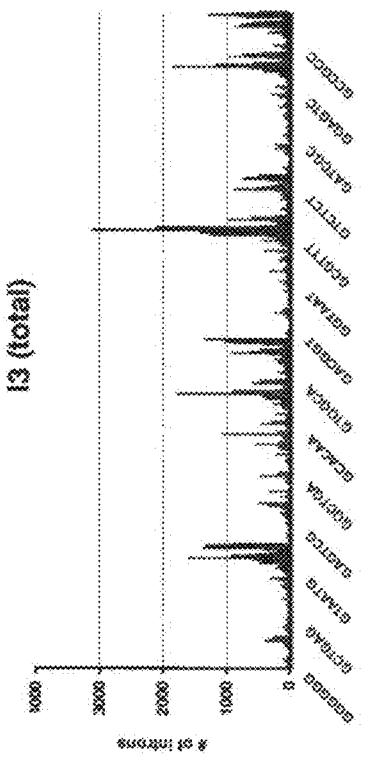
Figure 6D:
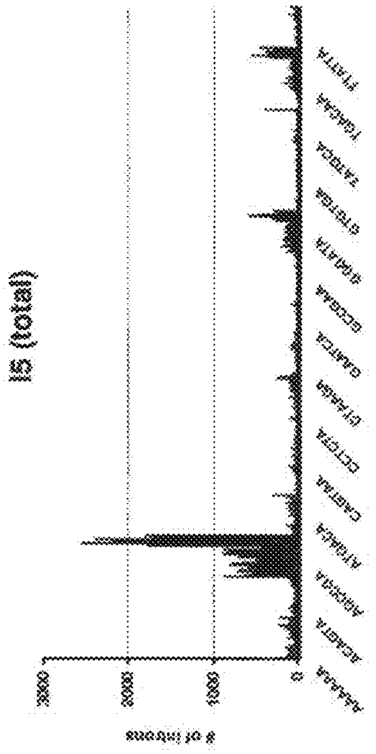
Figure 6E:
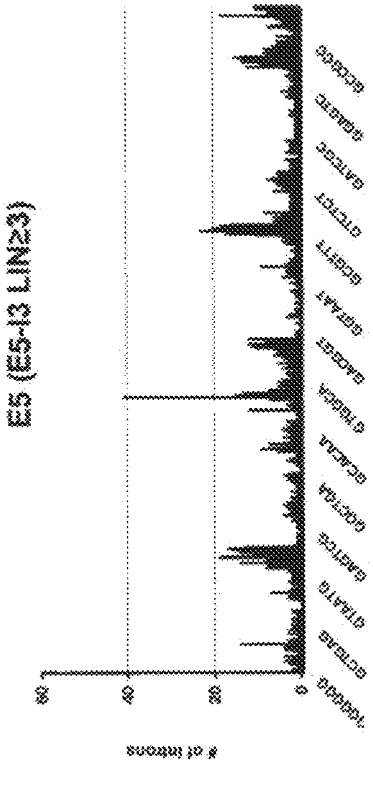
Figure 6F:
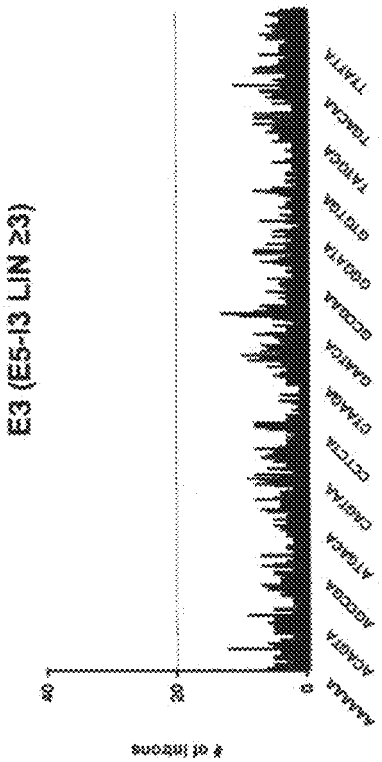
Figure 6G:
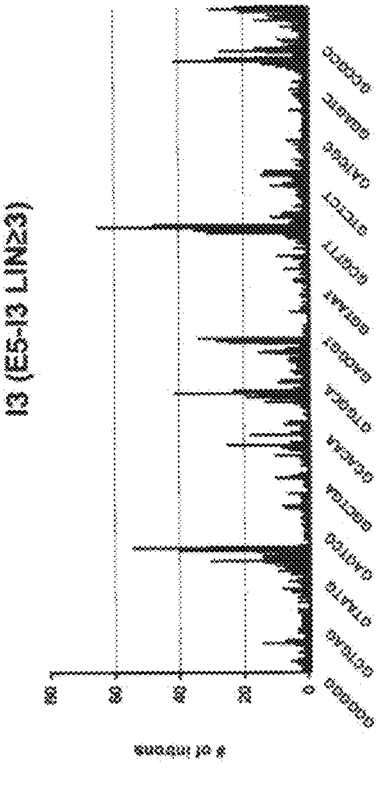
Figure 6H:
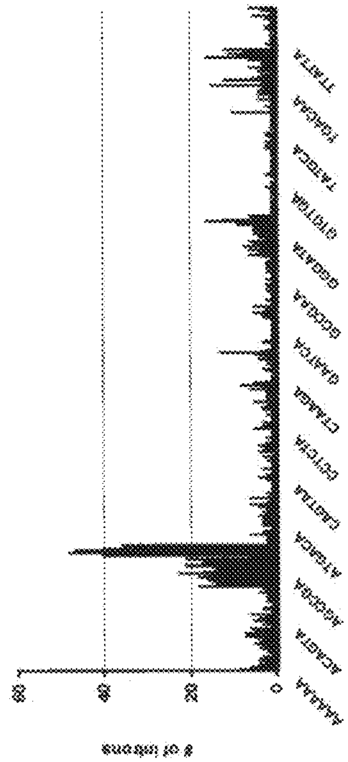
Figure 6I:
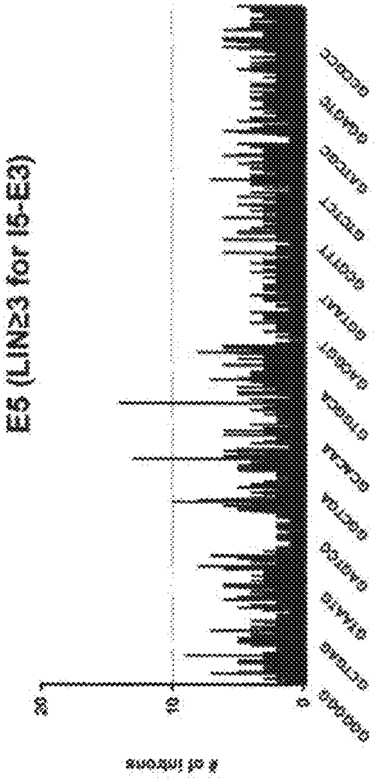
Figure 6J:
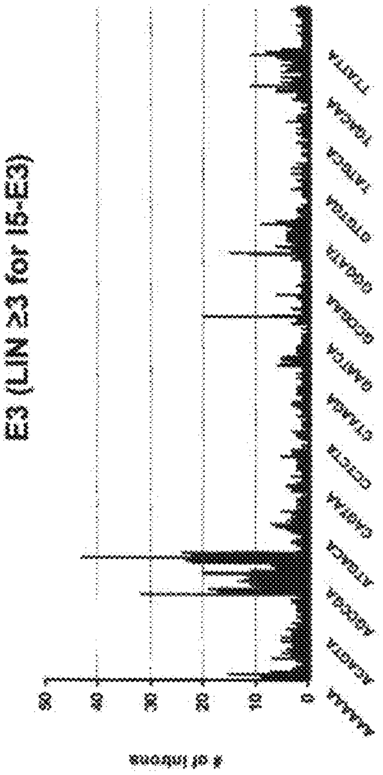
Figure 6K:
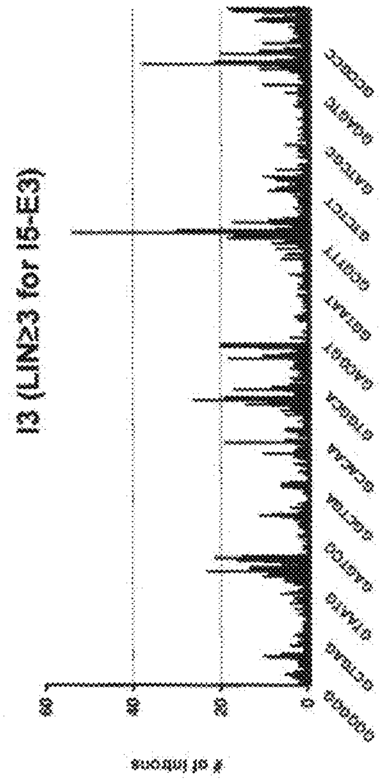
Figure 6L:
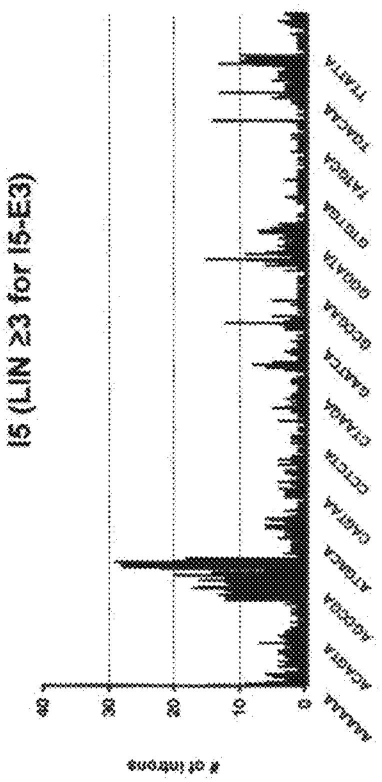

These non-random distributions are also seen for the subset of E5 hexamers which end with CAG as seen in FIGS. 5*a*-5*c*. In the case of the I5 hexamer plots, the two sharp peaks (FIG. 4*d*), namely GTGAGT and GTAAGT, are consistent with a role in U1 snRNA base-pairing (FIG. 2*a*), as are those seen LIN≥6 dataset, namely GTAAGA and GTAAGT (FIG. 4*h*). For the profiles in FIGS. 4*e* and 4*h* (which overlay substantially perfectly in keeping with their LIN≥6 values), the highest peaks in FIGS. 4*a*, 4*e* and 4*g* represent the hexamer CTGCAG, which incidentally is present in Alu repeats. Furthermore, the E5 hexamers from positions −4 and −9 are as divergent as the E3 hexamers from positions+4 and +9 as seen in FIG. 2*a* and FIGS. 6*a*-6*b* and 6*f* vs. 6i, while the corresponding I3 pyrimidine-rich hexamers are more restricted as seen in FIG. 6*k*].

5' exonic (E5) and intronic (I3) sequences constitute splicing codes of spliceosomal introns, which determine splicing sites in conjunction with the conserved intronic GTRAGT (R: purine) recognized by U1 snRNA. Like the genetic codes whose genetic codons specify amino acids, the splicing codes also form splicing code tables to determine which sequences are potential splicing sites. Since up to 9 bp between E5 and I3 sequences are conserved as seen in FIGS. 3 and 4, after removing the last intronic dinucleotide, AG, such a splicing code table will contain $4.29\times10^{9}$ unique splicing codes. Nature selection, genetic drifts and evolution result in much different and much smaller numbers of splicing codes, which are supported by FIGS. 2*c*, 3 and 4. Accordingly, each species has its own splicing code table, which confers specificity and fidelity of splicing and alternative splicing as suggested by FIGS. 3 and 4. Splicing code tables can be constructed using databases known to those skilled in the art, including but not limited to single nucleotide polymorphism (SNP) databases, and nucleotide sequence and protein databases.

The conservation between E5 and I3 sequences and independent evolution between E5 and I5 sequences, as seen in FIGS. 3 and 4, suggest that E5 sequences are dynamically conserved (without a conserved nucleotide sequence pattern like the first six nucleotides) and that E5 and I5 evolved differently. These data suggested that the conserved E5 sequences are similar to those of their ancestor, self-spliced group II introns. Since the 5' exonic sequences provide specificity of the group II introns, E5 and I3 sequences are potential splice codes. Based on characteristics of self-splicing group II introns, we can bold speculate that these splicing codes of the spliceosomal introns are believed to be deciphered by splicer RNAs or equivalent splicer-RNA protein (or proteins) as seen in FIGS. 1*a* and 1*b* This model is a derivative of the proposal of Holliday and Murray, who suggested that splicer RNAs hybridize to sequences near the splice junctions to guide intron removal. This splicing code model is similar to the genetic codons, which are deciphered by tRNAs and ribosome. In addition, the splicing code model is further supported by its similarities with the splicing of ribozymic group II introns in which 5' intronic-binding sites sequences (IBSs) are complementary to specific exonic-binding sites (EBSs) within domain 1D3 in addition to long-range single base-pair interaction at the 3' splice-site.

Characterized introns from a species must be deciphered by their splicer RNAs (or proteins), so characterized E5-I3 sequences from a species can be used to predict alternative splicing from this species. If the splicing codes of spliceosomal introns are deciphered by splicer RNA (RNAs) or equivalent splicer-RNA proteins (FIGS. 1 and 1*b*), they are believed to be alternatively-spliced if they exist in the splicing code table. To consider contribution of the conserved intronic GTRAGT, the splicing code table, which contains the E5-I3 sequences plus the first dinucleotide from the spliceosomal introns from a species, can therefore be used accurately to predict novel alternative splice sites of pre-mRNAs.

Verification of the Splicing Code Model to Predict Alternative Splice Sites of the Mouse Insulin Receptor (Insr) Gene.

To verify splicing code model, a mouse gene of insulin receptor (insr) encoding insulin receptor (IR), which is 128,255 bp in length and interrupted by 20 introns, was chosen as a model. In addition, this gene has been well studied in vivo and in vitro, and has only two isoforms that have been identified in human so far since 1985. A mouse splicing code table was constructed from the mouse introns supported by cDNA and EST sequences and containing 290000 sequences, which consists of 9 bp E5 sequence plus the first dinucleotide of I5 (GT/GC/AT) and 9 bp of I3 sequence for total of 20 bp in length. A probability to find one 20 bp identical sequences in the mouse genome is $1.1\times10^{-12}$ or 0.28% if the mouse genome is randomly distributed. A possibility to find one of the random sequences in this splicing code table is $5.8\times10^{-5}$ after excluding the first and last invariable dinucleotides. When 128,255 bp of the mouse insulin receptor (insr) gene scan the mouse splicing code table using intron sizes of 500 bp to 50,000 bp, the mouse insulin receptor (insr) gene is predicted to encode surprisingly large numbers of 4,631 putative novel splice sites (PPASSs), which is three time larger than the expected number of 1358 ($p<0.001$). It suggests that the mouse insulin receptor (insr) gene encodes 36 PPASSs per kb and is $1.2\times10^{5}$ times larger than the expected numbers of PPASSs.

Figure 7A:
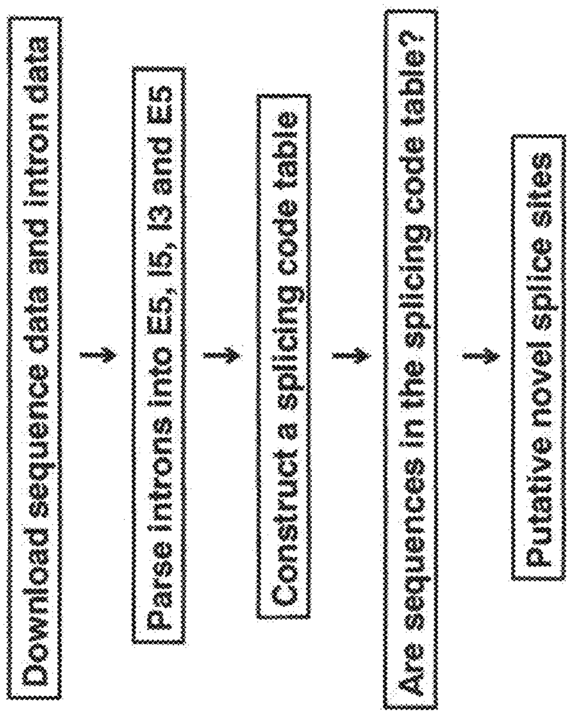
FIG. 7*a* depicts a schema of predicating potential alternative splicing sites.
Figure 7B:
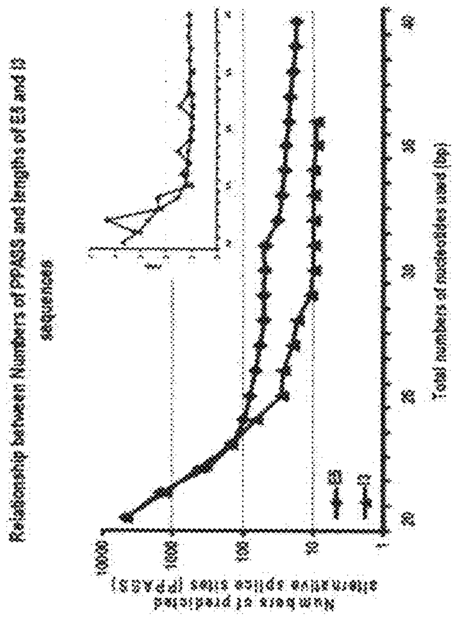
FIG. 7*b* depicts the relationship between predicted putative alternative splice sites and lengths of E5 and I3 sequences. The number of PPASSs predicted when the numbers of I3 sequences are fixed at 9 bp are shown, along with the number of PPASSs using a fixed 9 bp of E5 sequences plus the first intronic dinucleotide-the last 9 bp intronic sequences. The insert of FIG. 7*b* depicts ratios between the number of PPASSs at n+1 and those at n of E5 and I3 sequences, respectively.

Various lengths of E5 plus the first dinucleotide of I5 sequences and fixed 9 bp of I3 sequences were used to predict putative alternative splice sites. FIG. 7*b* shows that the numbers of predicted putative alternative splice sites (PPASSs) displays two different phases as the total numbers of nucleotides used to predict PPASSs are increased. From 20 to 24 bp (9 bp to 13 bp of E5), the numbers of PPASSs are dramatically decreased and range from 4.3 to 1.5 folds per decreasing nucleotide (see Insert in FIG. 7*b*). From 25 bp on, the numbers of PPASS are slowly declined and almost flat. At 40 bp (or 29 bp of E5), the mouse insulin receptor (insr) gene is still predicted to encode 17 PPASSs, among which 7 are alternative splice sites of the existing exons (1, 9, 13, 14, 15, 16, and 17) and the remaining 10 of them are novel putative splice sites. Only three of 17 PPASSs have ≥6 bp of identical sequences between 5' and 3' splice sites. Based on intron-types, 12 of them are GT-AG and five are GC-AG introns without AT-AC introns.

Fixed numbers of nine bp E5 sequences plus the first dinucleotides of I5 and various lengths of I3 sequences can be used to characterize the use of I3 nucleotide sequences affect the prediction of alternative splice sites. The mouse insulin receptor (insr) I3 sequences have shown a trend similar to that of E5 sequences (FIG. 7B). The difference is that the numbers of PPASSs are decreased much faster from 20 bp to 26 bp (9 bp to 15 bp of I3) and range from 2.4 to 3.7 folds. From 26 bp on, the numbers of PPASSs are extremely stable and in fact from 30 bp to 36 bp (19 bp to 25 bp of I3), the numbers of PPASSs is decreased only by one as seen in FIG. 7*a*. From 25 bp to 36 bp, the numbers of PPASSs predicted by increasing I3 sequences are 2.4 to 4.8 folds smaller than those observed by corresponding E5. A total of 36 bp (or 25 bp of I3), the mouse insulin receptor (insr) gene were predicted to encode the nine PPASSs. Only one out of nine is alternative splicing of a known exon, which is expected to result in deletion of one amino acid from the normal insulin receptor. None of nine PPASSs are simple sequences with long stretch of polypyrimidine tracts. Only two out of nine are GT-AG intron types and seven out of nine are GC-AG intron types, which are much higher than those predicted by E5. Two of nine PPASSs have more than ≥6 bp of identical sequences between 5' and 3' splices. Low proportions of introns with ≥6 bp of identical sequences between 5' and 3' splice sites predicted by long E5 and I3 sequences have ruled out that long-stretch of DNA conservation between 5' and 3' splice sites is caused by template switching or misplicing. See Roy, S. W., Irimia, M., *Intron mis-splicing: no alternative*? Genome Biol. 2008:9(2):208 ("Roy II").

Experimental Verification of PPASSs.

Figure 8:
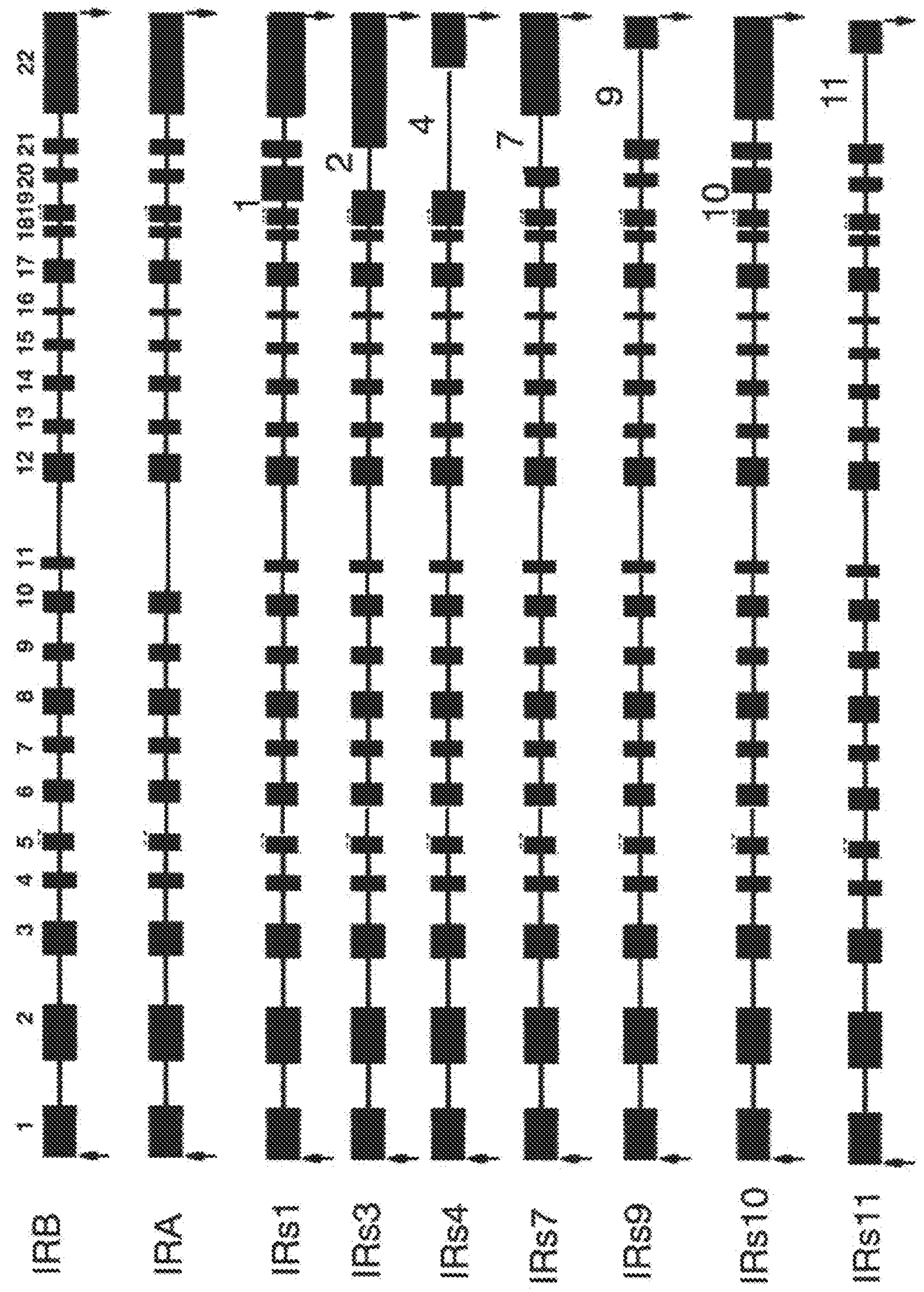
FIG. 8 depicts schematic diagrams of experimentally verified alternatively expressed isoforms shown in FIG. 7*c*. Protein-coding and none-coding exon sequences are represented. The lines depict intronic sequences.

4,631 putative splicing sites predicted by the splicing code model using total 20 bp are expressed in the normal mouse cells and tissues. 12 out of 4,631 PPASSs are exclusively selected from the IR β region, which regulates IR signal transduction including tyrosine kinase, regulation and other functional domains. See Belfiored. 58.3% of the pseudo-randomly selected predicted splice sites (7 out of 12) were verified by RT-PCR and sequencing of cloned RT-PCR products as seen in FIG. 7*b*. FIG. 8 shows that these alternatively-spliced isoforms result in much shorter β subunits that lack tyrosine kinase domains and/or their regulation domains, which have functions different from full-length wild-type IR proteins. Out of seven IR isoforms, three of these alternatively-spliced spliceovariants will produce almost identical truncated IR proteins and therefore have similar functions.

Since the splicing code table generated by all known mouse introns cannot predict all novel splicing sites, novel methods, such as "splice-site walking," has been used to identify more than 20 novel alternatively-spliced IR isoforms, including previously-uncharacterized mice IR-A isoforms. These data are consistent with notion that the mammalian insulin receptor (insr) genes encode large numbers of extremely complex alternatively-spliced isoforms which are tissue-specific and are regulated developmentally.

Performance of "Splice-Site Walking" PCR

To overcome non-specific PCR amplifications and artifacts, "splice-site walking" technology was developed to amplify different cDNAs from the different tissues under the identical conditions. Using the "splice-site walking" method, novel soforms including isoforms expressed at very low levels can be amplified disproportionately. "Splice-site" walking includes changing PCR amplification conditions including temperatures, extension time, ion conditions and primers to preferably amplify novel isoforms expressed at very low levels. RNAs were isolated from various mouse tissues as described above. Mouse cDNAs were made by TaqMan Reverse Transcription Reagents (Applied Biosystems Inc., Foster City, Calif., USA) as the manufacturer suggests except that equal amounts of pooled reverse-transcription reaction mixes were added to 3 μg RNA. To perform PCR on different cDNAs, all reagents were pooled together except cDNAs and then were equally divided into different samples. PCR reactions were carried out by HiFi Taq polymerase (Invitrogen, Carlsbad, Calif., USA). The extension time was about 20% shorter than 1 kb/min which the manufacturer suggests. For example, 2.0-2.4 minutes were used for 3 kb fragments. Under this condition, the minor products, which are expressed at very low levels, were preferred to be amplified. The PCR products were separated on 2.0% agarose gels in 1×TBE buffer (Tris-HCl (pH8.0) 89 mM, boric acid, 89 mM and 2 mM EDTA).

Differential Western Blot Analysis.

Western blot analysis was performed against mouse tissue lysates by a monoclonal rabbit antibody, insulin receptor 4b8 (Cell Signaling, MA), whose epitope is residues surrounding Tyr960 of human insulin receptor β and rabbit polyclonal antibody, sc-711 (Santa Cruz Biotech, CA), whose epitopes are mapped to the last 20 residues of the C-terminus of the β chain of the human insulin receptor to determine that these minor alternatively-spliced isoforms were translated. The polypeptides detected by antibody 4b8, but not by sc-711, should be insulin receptor which have epitope surrounding Tyr960 and without the last 20 residues of the C-terminus.

Figure 9A:
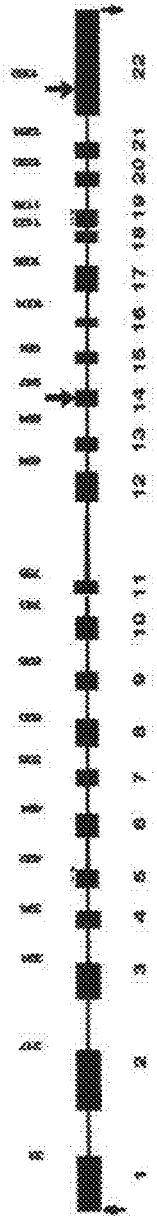
FIGS. 9*a*-9*c* depicts Western blot analysis of various mouse tissues.
Figure 9B:
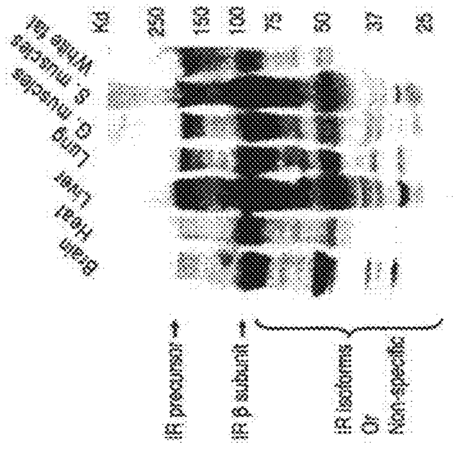
Figure 9C:
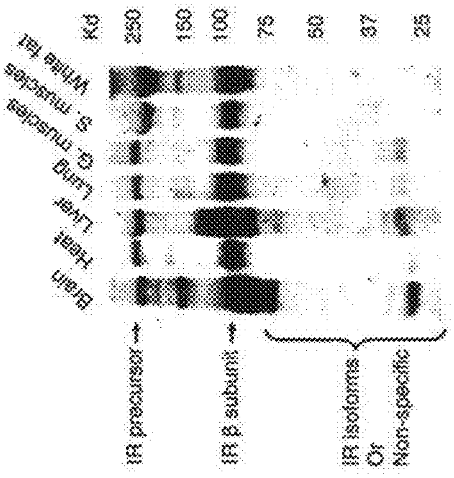

FIGS. 9*a*-9*c* depicts Western blot analysis of various mouse tissues. FIG. 9*a* is a schematic diagram of the mouse insulin receptor (insr) gene. The arrows represent epitopes of the antibodies 4B8 and sc-711, respectively. FIG. 9*b* depicts Western blot analysis of protein lysates from brain, heart, liver, lung, g. muscle, seleus muscle and white fat by antibody 4b8. The minor bands are consistent with proteins predicted by the mouse splicing code table. FIG. 9*c* depicts Western blot analysis of protein lysates from brain, heart, liver, lung, g. muscle, seleus muscle and white fat by antibody sc-711. The differences between these two Western blot analyses show reflection of shorter isoforms predicted by the mouse splicing code table. FIG. 9*a* showed that Western blot analysis against the 4b8 antibody detected not only the main isoforms, but also complex minor bands, many of which are different in sizes, in abundances and in numbers among different tissues and approximated to the IR β subunit isoforms predicted by the mRNA isoforms above. On the other hand, the Western blot analysis against the sc-711 antibody showed the main informs and much less minor bands as seen in FIG. 8. The differences of minor bands detected by the two Western blots against the antibodies, 4b8 and sc-711, reflect the differences of the IR proteins translated from alternatively-spliced isoforms predicted by the splicing code model discussed above. The differences of the minor bands among the different tissues reflect that alternatively-spliced spliceoforms encoded by the different tissues are different in numbers of polypeptides, their sizes and their abundances, which are believed to contribute the tissue functional specificities, diversities and plasticity. These extra minor polypeptides support that predicted alternatively-spliced isoforms are translated into proteins, which attenuate insulin signaling pathway among tissues. These differences may only reflect one individual at the time when it was harvested.

In vertebrates there are 2.5-5 fold more cases of ≥6 nt identical length between 5' exonic (E5) and 3' intronic (I3) sequences than between 5' intronic (I5) and 3' exonic (E3) ones. It is believed that 5' exonic and 3' intronic sequences of the splice junctions constitute splicing codes of the spliceosomal introns, which are sequence-specifically decoded by as yet uncharacterized RNAs or proteins as suggested in FIGS. 1*a* and 1*b*. The mechanisms of deciphering splicing codes by splicer RNAs (or proteins) are similar to that of genetic codons decoded by tRNAs except that splicer RNAs/proteins hybridize to both E5 and I3 sequences, bring two exons together and guide spliceosome's removal of intronic sequences.

Evidence supports that conservation between E5 and I3 sequences and E5 and I5 independent evolution can be explained by the splicer RNA model rather than protein models of pre-mRNA splicing. For example, *S. pombe* and *S. cerevisiae* have similar genome sizes (13.8 Mb vs 12.2 Mb) and encode similar protein-coding genes (4730 vs 5796). See Wood, V., Gwilliam, R., Rajandream, M. A., et al., *The genome sequence of Schizosaccharomyces pombe*. Nature 2002:415(6874):871-80 ("Wood"). Nonetheless, *S. pombe* encodes more than 4,730 spliceosomal introns while *S. cerevisiae* codes for less than 260 introns. See Wood; Davis, C. A., Grate, L., Spingola, M., et al., *Test of intron predictions reveals novel splice sites, alternatively spliced mRNAs and new introns in meiotically regulated genes of yeast*. Nucleic Acids Res. 2000:28(8):1700-6 ("Davis"). Unlike those found in mammalian systems, no complex alternative splicing has been identified so far in both *S.*

*pombe* and *S. cerevisiae*. See Wood; Davis. If each gene encoding RNA-binding protein can be alternatively expressed to generate 100 isoforms, each of whom recognize one specific intron, the expectation would be that the *S. pombe* genome would encode 47 members of such gene family and the *S. cerevisiae* genome would encode 3 ones, such that *S. pombe* would encode 44 more genes coding for such RNA-recognizing protein superfamilies than would *S. cerevisiae*. The fact that no large RNA-binding protein superfamilies have been identified in *S. pombe* strongly suggests that the splicing codes are decoded by splicer RNAs instead of splicer proteins.

Secondly, since domains of self-splicing group II introns and small spliceosomal U snRNAs are structurally conserved, these domains were thought to be ancestors of the spliceosomal snRNAs. See Pyle, A. M., *The tertiary structure of group II introns: implications for biological function and evolution*. Crit. Rev. Biochem. Mol. Biol.; 45(3):215-32 ("Pyle"). Like small U snRNAs, exonic-binding sites (EBSs) within domain I of self-splicing group II introns might have been expected to be more ready to co-evolve into splicer RNAs, rather than development by their ancestors of a revolutionary splicer protein system de novo. This model of splicing codes deciphered by splicer RNAs also shares similarities with the splicing of ribozymic group II introns in which 5' intronic-binding sites (IBSs) are complementary to specific exonic-binding sites (EBSs) within domain 1D3 in addition to long-range single base-pair interaction at the 3' splice-site, and these interactions are important for the accuracy of pre-mRNA splicing. Moreover, the eukaryotic genomes easily have these capacities and the number of identified non-coding RNAs keeps increasing, as does an appreciation for the extent of transcriptionally-active regions which lie outside of known coding regions in eukaryotes. See Mattick, J. S., Makunin IV. *Non-coding RNA*. Hum. Mol. Genet. 2006:15 Spec. No. 1:R17-29 ("Mattick"); Kapranov, P., Cheng, J., Dike, S., et al., *RNA maps reveal new RNA classes and a possible function for pervasive transcription*. Science 2007:316(5830):1484-8 ("Kapranov"); Birney, E., Stamatoyannopoulos, J. A., Dutta, A., et al., *Identification and analysis of functional elements in* 1% *of the human genome by the ENCODE pilot project*. Nature 2007:447(7146):799-816 ("Birney").

Splicing codes of spliceosomal introns require yet-to-be characterized splicer RNAs to be decoded via a manner similar to genetic codons decoded by tRNAs within ribosome. The splicer RNA has sequences complementary to 5' exonic and 3' intronic sequences and maybe to U RNAs. Any diseases can be treated by injecting the splicer RNA into target cells or tissues, which could form the basis of future medicines.

Similar to tRNAs, which are required to translate the genetic codons into amino acids, splicer RNAs are required to hybridize E5 and I3 sequences of splicing codes and guide spliceosomes to remove intron sequences from pre-mRNAs, whose mechanisms are little understood. The up to 9 bp of conserved regions between E5 and I3 sequences and no significant differences beyond that as seen in FIG. 3 suggest that at least 9 bp of the conserved E5-I3 regions under functional constraints are coevolved. Like I5 sequences as seen in FIG. 4 that are constrained by U1 snRNA, I3 sequences have become more clustered together as seen in FIG. 4 and I3 sequences between branch and the last conserved intronic dinucleotide, AG, have become the polypyrimidine tracts during evolution, as seen in FIG. 2*a* from the bottom panel to the top panel, whose locations are quite variable among different introns. This may reflect that two distinct essential functions—university and individuality (diversity)—are driving forces of evolution of I3 sequences. The most reasonable explanation is that a domain of a splicer RNA that interacts with a common components of spliceosomes (the most likely candidate is U5 snRNA, whose conserved loop functions as a carrier, and/or those interacting with branch points) are adjacent to a domain of a splicer RNA that recognizes I3 sequence. Because of these structures of I3 sequences, E5 sequences may play more important role in determining specificity and fidelity of removing spliceosomal introns by splicer RNAs like those of self-splicing group II introns. See Toor, N., Robart, A. R., Christianson, J., et al., *Self-splicing of a group IIC intron: 5' exon recognition and alternative 5' splicing events implicate the stem-loop motif of a transcriptional terminator*. Nucleic Acids Res. 2006:34(22):6461-71 ("Toor"). Both E5 and I3 sequences may form stem-loop structures with splicer RNAs to avoid accidental havocs of RNA-induced silencing complex (RISC).

Using a mouse splicing code table, constructed from the characterized sequences of 9 bp of E5 plus the first dinucleotide of I5 and the last 9 bp of I3 sequences, the mouse insulin receptor (insr) gene are predicted to have surprisingly large numbers of 4,631 predicted putative splice sites (PPASSs), which is 3.3 times larger than the expected number, 1358, of PPASS. To verify this prediction, 12 out of the PPASSs of 4631 PPASSs that resulted in alternative splicing in the IR β region were pseudo-randomly selected, which regulated IR signal transduction including tyrosine kinase regulation and other functional domains. See Belfiore. To perform isoform-specific PCR, a primer was designed to cross the 5' and 3' exonic sequences of a PPASS while the other primer was located upstream or downstream of the mouse insulin receptor (insr) exonic sequences (12 pairs of forward and reverse primers are shown below in Tables 12a and 12b). The 12 pairs of forward primers are identified as follows: (1) primer regions 1-25 of mIRs2F sequence GCAAGAAATGATTCAGATGACAGCA (SEQ ID NO.:4) correspond to 117712-117737 of NM_010568 genomic sequences; (2) primer regions 1-25 of mIRs2F sequence CCTTGCAAGAAATGATTCAGATGAC (SEQ ID NO.: 5) correspond to 117709-117733 of NM_010568 genomic sequences; (3) primer regions 1-25 of mIRs1F sequence GCAAGAAATGATTCAGATGACAGCA (SEQ ID NO.:4) correspond to 117713-117737 of NM_010568 genomic sequences; (4) primer regions 1-25 of mIRs1F sequence GCAAGAAATGATTCAGATGACAGCA (SEQ ID NO.:4) correspond to 117713-117737 of NM_010568 genomic sequences; (5) primer regions 1-25 of mIRs1F sequence GCAAGAAATGATTCAGATGACAGCA (SEQ ID NO.:4) correspond to 117713-117737 of NM_010568 genomic sequences; (6) primer regions 1-21 of mIRs3F sequence TTGGTATGGTGTATGAAGGCA (SEQ ID NO.: 7) correspond to 115788-115808 of NM_010568 genomic sequences; (7) primer regions 1-21 of mIRs4F sequence TCCCCCTACCTTGCAAGAAAT (SEQ ID NO.:8) correspond to 117701-117721 of NM_010568 genomic sequences; (8) primer regions 1-21 of mIRs4F sequence TCCCCCTACCTTGCAAGAAAT (SEQ ID NO.:8) correspond to 117701-117721 of NM_010568 genomic sequences; (9) primer regions 1-22 of mIRs5F sequence ATTGCTGATGGCATGGCATACT (SEQ ID NO.:9) correspond to 117741-117762 of NM_010568 genomic sequences; (10) primer regions 1-15 and 15-27 of mIRs6F sequence GTCTGTATATTTTAGTCACATCAGAAG (SEQ ID NO.:10) correspond to 120543-120557 and 124468-124480 of NM_010568 genomic sequences; (11) primer regions 1-7 and 8-20 of mIRs7F sequence ATTTTAGCTGCTCTTGGCGT (SEQ ID NO.:11) correspond to 120544-120551 and 125214-125227 of NM_010568 genomic sequences; and (12) primer regions 1-11 and 12-20 of mIRs8F sequence TTTGCTTCCTTCTGCTCTTG (SEQ ID NO.: 12) correspond to 122469-122479 and 125208-125217 of NM_010568 genomic sequences. The 12 pairs of forward and reverse primers are identified as follows: primer regions 1-11 and 12-24 of mIRs2F/mIRs1R sequence TCCTCCAACCTCCAATTTTGACAG (SEQ ID NO.:13) correspond to 119214-119204 and 117848-117829 of NM_010568 genomic sequences; primer regions 1-8 and 9-23 of mIRs2F/mIRs2R sequence AAGAGCAGCTTGCTTCTTGCTGA (SEQ ID NO.:14) correspond to 125223-125215 and 119342-119328 of NM_010568 genomic sequences; primer regions 1-8 and 9-25 of mIRs1F/mIRs3R sequence CAAATTTACTCCTGATGAGCACATT (SEQ ID NO.:15) correspond to 128272-128264 and 119808-119792 of NM_010568 genomic sequences; primer regions 1-8 and 9-25 of mIRs1F/mIRs4R sequence ACACACATCTCCTGATGAGCACATT (SEQ ID NO.:16) correspond to 119800-119792 and 119808-119792 of NM_010568 genomic sequences; primer regions 1-14 and 15-30 of mIRs1F/mIRs5R sequence GGACGACCCAGTTCTTCATTTCTA (SEQ ID NO.:17) correspond to 122565-122548 and 119848-119838 of NM_010568 genomic sequences; primer regions 1-13 and 14-20 of mIRs3F/mIRs6R sequence ACGACCCAGTTCTCCTGATGA (SEQ ID NO.:18) correspond to 119812-119799 and 122551-122557 of NM_010568 genomic sequences; primer regions 1-8 and 9-22 of mIRs4F/mIRs7R sequence TGATGTGAAGTCTCTCTGGACA (SEQ ID NO.: 19) correspond to 124478-124470 and 120486-120473 of NM_010568 genomic sequences; primer regions 1-14 and 15-30 of mIRs4F/mIRs8R sequence TGAGGTAGACTGTACTAAAATATACAGACA (SEQ ID NO.:20) correspond to 125984-125967 and 120557-120542 of NM_010568 genomic sequences; primer regions 1-22 of mIRs5F/mIRs9R sequence GAGACTCAAACATAAGCACCTGTTC (SEQ ID NO.:21) correspond to 125925-125274 of NM_010568 genomic sequences; primer regions 1-20 of mIRs6F/mIRs10R sequence CACCACTGCTCCCAAAGAAA (SEQ ID NO.:22) correspond to 124750-124731 of NM_010568 genomic sequences; primer regions 1-21 of mIRs7F/mIRs11R sequence CAGGGAAACATTTAGAAAGGC (SEQ ID NO.:23) correspond to 127110-127090 of NM_010568 genomic sequences; and primer regions 1-21 of mIRs8F/mIFs12R sequence TGAGCAGCTGTGGTTTTATGC (SEQ ID NO.:24) correspond to 125406-125386 of NM_010568 genomic sequences.

TABLE 12a

Forward and Reverse Primers for PPASS
Forward Primers

| Names | Sequences |
|---|---|
| mIRs2F | GCAAGAAATGATTCAGATGACAGCA |
| mIRs2F | CCTTGCAAGAAATGATTCAGATGAC |
| mIRs1F | GCAAGAAATGATTCAGATGACAGCA |
| mIRs1F | GCAAGAAATGATTCAGATGACAGCA |
| mIRs1F | GCAAGAAATGATTCAGATGACAGCA |
| mIRs3F | TTGGTATGGTGTATGAAGGCA |

TABLE 12a-continued

Forward and Reverse Primers for PPASS
Forward Primers

| Names | Sequences |
|---|---|
| mIRs4F | TCCCCCTACCTTGCAAGAAAT |
| mIRs4F | TCCCCCTACCTTGCAAGAAAT |
| mIRs5F | ATTGCTGATGGCATGGCATACT |
| mIRs6F | GTCTGTATATTTTAGTCACATCAGAAG |
| mIRs7F | ATTTTAGCTGCTCTTGGCGT |
| mIRs8F | TTTGCTTCCTTCTGCTCTTG |

TABLE 12b

Reverse Primers for PPASS
Reverse Primers

| Names | Names | Sequences |
|---|---|---|
| mIRs2F | mIRs1R | TCCTCCAACCTCCAATTTTGACAG |
| mIRs2F | mIRs2R | AAGAGCAGCTTGCTTCTTGCTGA |
| mIRs1F | mIRs3R | CAAATTTACTCCTGATGAGCACATT |
| mIRs1F | mIRs4R | ACACACATCTCCTGATGAGCACATT |
| mIRs1F | mIRs5R | GGACGACCCAGTTCTTCATTTCTA |
| mIRs3F | mIRs6R | ACGACCCAGTTCTCCTGATGA |
| mIRs4F | mIRs7R | TGATGTGAAGTCTCTCTGGACA |
| mIRs4F | mIRs8R | TGAGGTAGACTGTACTAAAATATACAGACA |
| mIRs5F | mIRs9R | GAGACTCAAACATAAGCACCTGTTC |
| mIRs6F | mIRs10R | CACCACTGCTCCCAAAGAAA |
| mIRs7F | mIRs11R | CAGGGAAACATTTAGAAAGGC |
| mIRs8F | mIRs12R | TGAGCAGCTGTGGTTTTATGC |

Figure 7C:
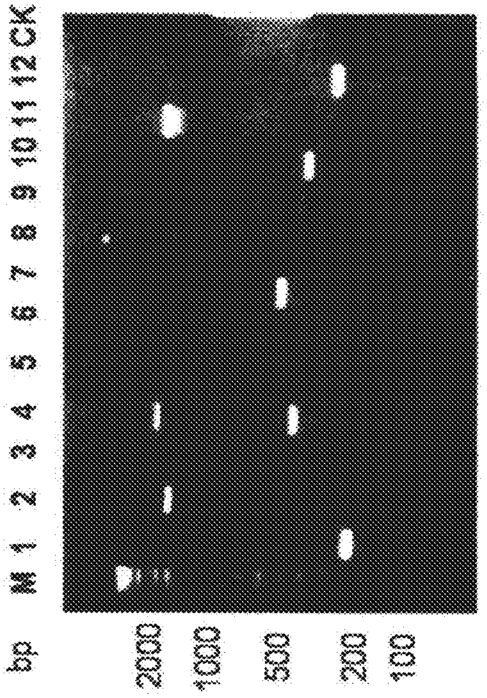
FIG. 7*c* depicts RT-PCR verification of PPASSs identified using a fixed 9 bp of E5 sequences plus the first intronic dinucleotide-the last 9 bp intronic sequences in FIG. 7*b*. M is DNA markers. CK is negative control.

PCR was performed on the pooled cDNAs from various mouse tissues as indicated in FIGS. 10A and 10B and PCR products were separated on a 2.0% agarose gel. Nine out of 12 PCR reactions had products and were cloned into pCR2.1 TA vectors. Eight of them were shown to have inserts by agarose gel separation of EcoRI-digested plasmids. As shown in FIG. 8, seven of the clones (7 out of 12) had been verified by RT-PCR and sequencing of cloned RT-PCR products in FIG. 7*c*). FIGS. 10A and 10B showed the seven sequence data (58.3%) of these alternatively-spliced isoforms, which would result in much shorter β subunits that lacked tyrosine kinase domains and/or their regulation domains and which had functions different from full-length wild-type IR proteins. Out of seven IR isoforms, three of these alternatively-spliced spliceovariants would produce almost identical truncated IR proteins and therefore had similar functions. These data indicated that the mouse insulin receptor gene encoded a far more complex system of alternatively-spliced isoforms than what had been discovered so far.

Figure 11:
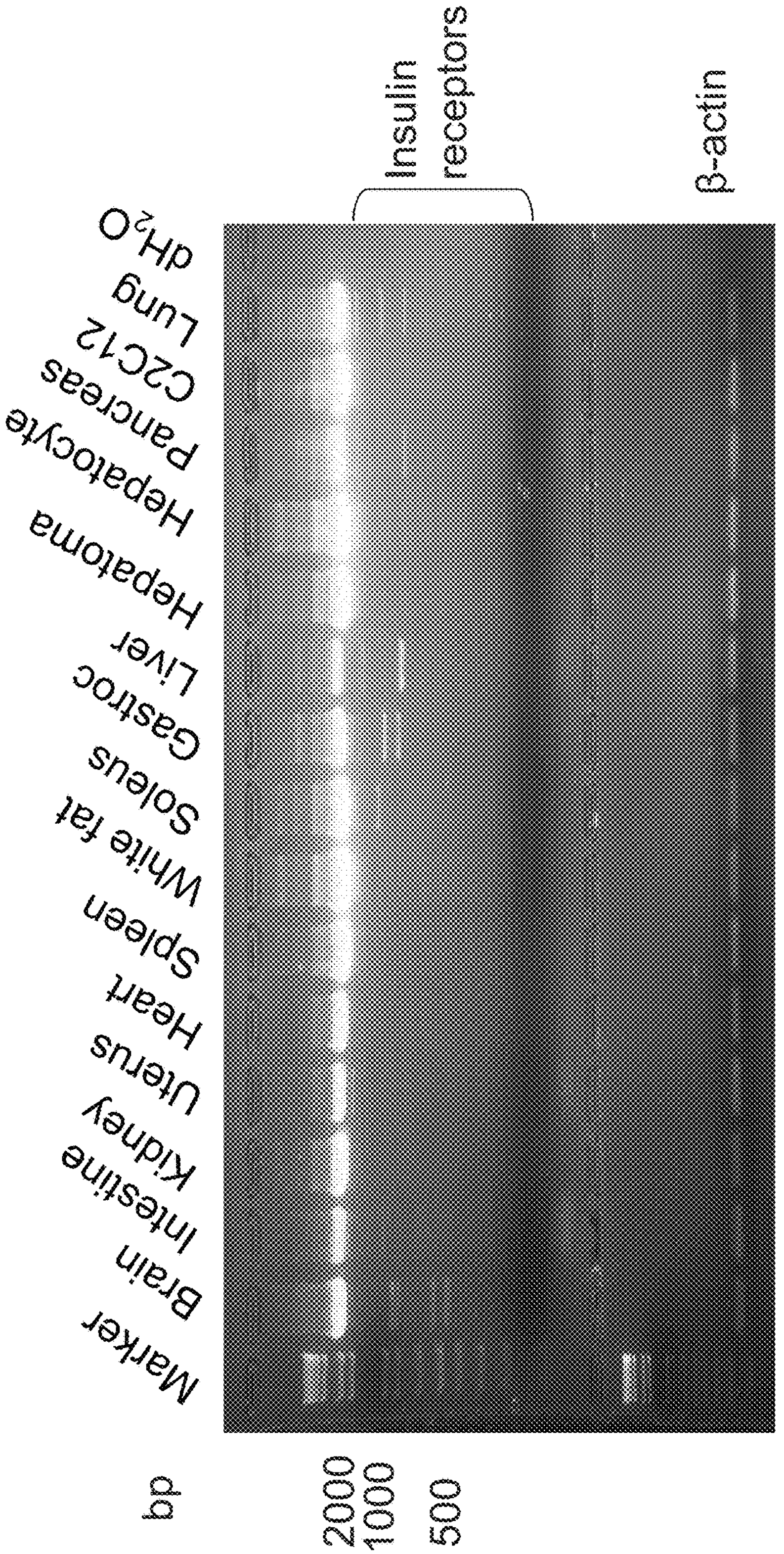
FIG. 11 depicts results of "splice site walking" on total RNAs isolated from brain, intestine, kidney, uterus, heart, spleen, white fat, soleus muscle, gastrocnemius muscle, liver, hepatoma, hepatocyte, pancreas islet, c2c12 and lung, and specifically shows the presence of minor PCR products in some mouse tissues in addition to the major isoforms.
Figure 12:
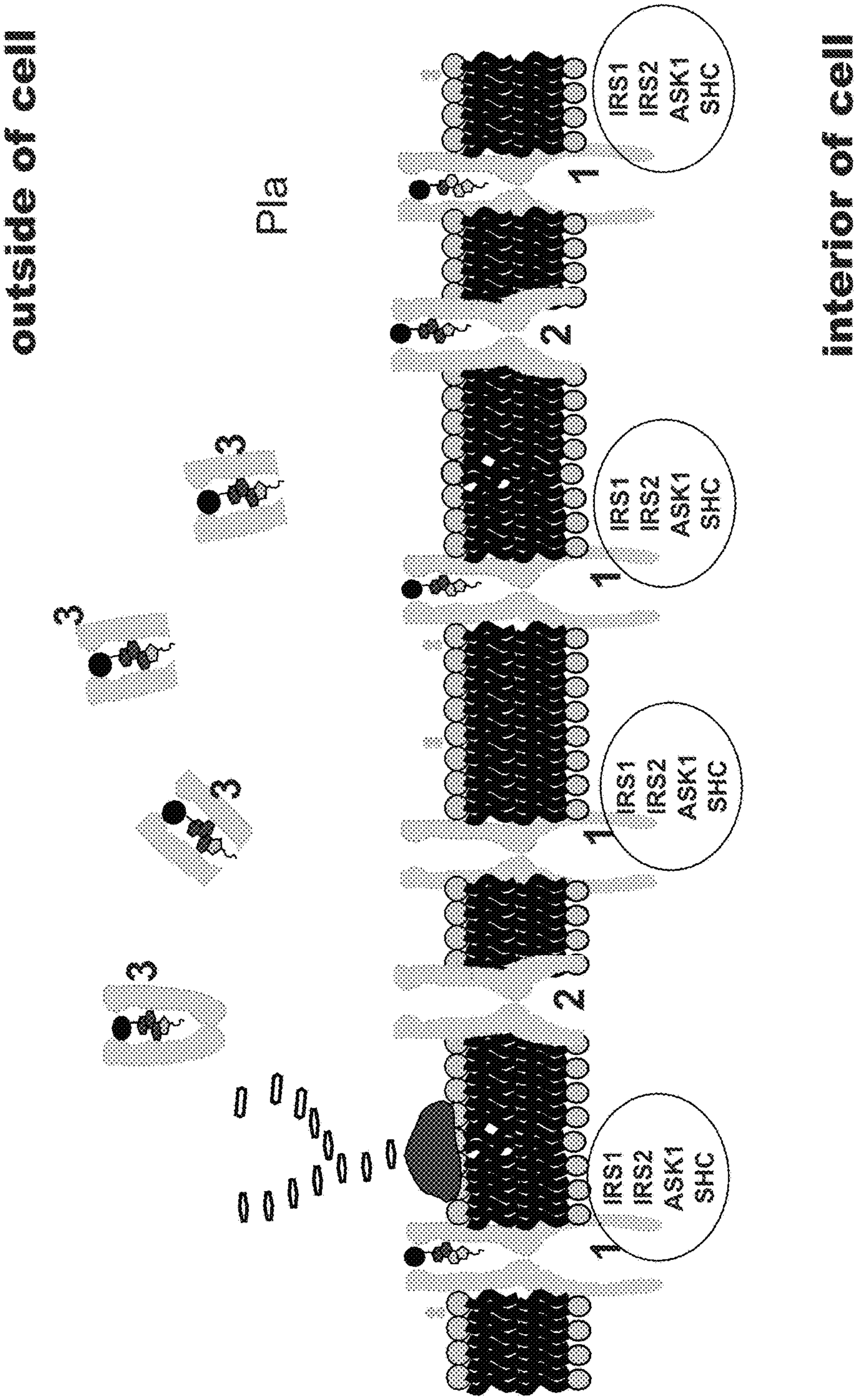
FIG. 12 depicts how different insulin receptor isoforms outside cell membranes and on the plasma membranes regulate insulin concentrations.

To show that the mouse insulin receptor (insr) gene encoded large numbers of alternatively spliced isoforms, "splice-site walking" PCR was developed to detect alternatively-spliced isoforms. A pair of primers (5'-GAGATG-GTCCACCTGAAGGA-3', SEQ ID NO.: 25, and 5'-TGT-GCTCCTCCTGACTTGTG-3', SEQ ID NO.: 26) were designed, which were located at the exon 2 and exon 12, to perform PCR with cDNAs constructed from various tissues of 8-week C57BL/6 male mice under the identical conditions. Primer regions 1-20 sequence GAGATGGTCCACCTGAAGGA (SEQ ID NO.: 25) correspond to 20518-20537 of NM_010568 genomic sequences. Primer regions 1-20 sequence TGTGCTCCTCCTGACTTGTG (SEQ ID NO.: 26) correspond to 104412-104393 of NM_010568 genomic sequences. FIG. 11 had shown that there were numbers of clear minor PCR products in some tissues in addition to the major isoforms. Some PCR products were much weaker and were observed only under careful scrutiny. Most of these minor isoforms encoded ectodomains of insulin receptors, which were predicted to be soluble and to secret into blood and/or extracellular matrixes and which previously had been thought to be generated by an undefined "protein shedding" process. Different tissues have almost completely different profiles of minor PCR products, which indicated these isoforms were tissues-specific and the same insulin receptor (insr) pre-mRNA from different mouse tissues had different secondary structures that resulted in template switching and/or missplicing. That different tissues had different PCR products ruled out that these products were not artifacts generated by template switching or mis-plicing. Using this and other methods, more than 20 low-level and tissue-specific alternatively-spliced IR isoforms were identified and verified, including previously-uncharacterized mouse IR-A isoform (data not shown). These data were consistent with the notion that the mammalian insulin receptor (insr) gene encoded large numbers of extremely complex alternatively-spliced isoform system, which enable mice to support their diverse functions. However, that some of these large numbers of alternative spliceovariants are caused by partial loss of specificity of splicer-RNAs as observed in self-splicing group II introns cannot be ruled out. See Toor. FIG. 12 shows relationships between different insulin receptor isoforms. Isoforms of normal functional insulin receptors are marked by 1. The truncated insulin receptor isoforms on cell membrane are indicated by 2 in FIG. 12 and can bind the insulin competitively. These isoforms may have some functions which are different from the normal functions. The soluble insulin receptor receptors were released into the outsides of cell including extracellular matrix and blood. The soluble and truncated plasma membrane insulin receptors had been shown that they can bind to insulin in vitro.

When the soluble insulin receptors can bind to insulin in blood and extracellular matrix, the numbers of insulin molecules reached to target cells will be reduced. When the reduced numbers of insulin reaches the plasma membranes of the target cells, they can be bound to both normal and truncated insulin receptors. The normal insulin receptors and activate the normal tyrosine kinase function, which result in reducing the glucose concentration in blood. The truncated insulin receptors will have opposite effects and can bind to insulin without activating the normal tyrosine kinase. That is, when concentrations of normal insulin receptors marked by 1 are reduced or the concentrations of truncated plasma membrane insulin receptors and soluble insulin receptors indicated by 2 and 3 are increased, it will result in insulin resistances.

When concentrations of normal insulin receptors marked by 1 are increased or the concentrations of truncated plasma membrane insulin receptors and soluble insulin receptors indicated by 2 and 3 are decreased, it will result in increased sensitiveness to insulin and cancer.

These results suggest that disrupting equilibrium of environmentally and developmentally regulated isoform system may be directly responsible for majority of complex diseases. The natural and/or medically-assistant restoration of these equilibriums may be the best method to cure complex diseases from diabetes to cancer.

These equilibriums are true for other receptors, ion-channels and neurotransmitters. They may be used to diagnose and treat the complex disease. These are listed in the receptor list seen in Table 13.

TABLE 13

| | | | | |
|---|---|---|---|---|
| G protein-coupled receptors | 5-Hydroxytryptamine receptors | Acetylcholine receptors (muscarinic) | Adenosine receptors | Adrenoceptors |
| Anaphylatoxin receptors | Angiotensin receptors | Apelin receptor | Bile acid receptor | Bombesin receptors |
| Bradykinin receptors | Calcitonin receptors | Calcium-sensing receptors | Cannabinoid receptors | Chemokine receptors |
| Cholecystokinin receptors | Corticotropin-releasing factor receptors | Dopamine receptors | Endothelin receptors | Estrogen (G protein coupled) receptor |
| Formylpeptide receptors | Free fatty acid receptors | Frizzled receptors | GABAB receptors | Galanin receptors |
| Ghrelin receptor | Glucagon receptor family | Glycoprotein hormone receptors | Gonadotrophin-releasing hormone receptors | Histamine receptors |
| Hydroxycarboxylic acid receptors | Kisspeptin receptor | Leukotriene receptors | Lysophospholipid receptors | Melanin-concentrating hormone receptors |
| Melanocortin receptors | Melatonin receptors | Metabotropic glutamate receptors | Motilin receptor | Neuromedin U receptors |
| Neuropeptide FF/neuropeptide AF receptors | Neuropeptide S receptor | Neuropeptide W/neuropeptide B receptors | Neuropeptide Y receptors | Neurotensin receptors |
| Opioid receptors | Orexin receptors | P2Y receptors | Parathyroid hormone receptors | Peptide P518 receptor |

TABLE 13-continued

| | | | | |
|---|---|---|---|---|
| Platelet-activating factor receptor | Prokineticin receptors | Prolactin-releasing peptide receptor | Prostanoid receptors | Protease-activated receptors |
| Relaxin family peptide receptors | Somatostatin receptors | Tachykinin receptors | Thyrotropin-releasing hormone receptor | Trace amine receptor |
| Urotensin receptor | VIP and PACAP receptors | Vasopressin and oxytocin receptors | Class A Orphans | Class B Orphans |
| Class C Orphans | Non-signalling 7TM chemokine-binding proteins | BLT1 | BLT2 | CysLT1 |
| CysLT2 | OXE | CCRL2 | CMKLR1 | GPR1 |
| GPR3 | GPR4 | GPR6 | GPR12 | GPR15 |
| GPR17 | GPR18 | GPR19 | GPR20 | GPR21 |
| GPR22 | GPR25 | GPR26 | GPR27 | GPR31 |
| GPR32 | GPR33 | GPR34 | GPR35 | GPR37 |
| GPR37L1 | GPR39 | GPR42 | GPR45 | GPR50 |
| GPR52 | GPR55 | GPR61 | GPR62 | GPR63 |
| GPR65 | GPR68 | GPR75 | GPR78 | GPR79 |
| GPR82 | GPR83 | GPR84 | GPR85 | GPR87 |
| GPR88 | GPR101 | GPR119 | GPR120 | GPR132 |
| GPR135 | GPR139 | GPR141 | GPR142 | GPR146 |
| GPR148 | GPR149 | GPR150 | GPR151 | GPR152 |
| GPR153 | GPR160 | GPR161 | GPR162 | GPR171 |
| GPR173 | GPR174 | GPR176 | GPR182 | GPR183 |
| LGR4 | LGR5 | LGR6 | LPAR6 | MASI |
| MAS1L | MRGPRD | MRGPRE | MRGPRF | MRGPRG |
| MRGPRX1 | MRGPRX2 | MRGPRX3 | MRGPRX4 | OPN3 |
| OPN5 | OXGR1 | P2RY8 | P2RY10 | SUCNR1 |
| TAAR2 | TAAR3 | TAAR4 | TAAR5 | TAAR6 |
| TAAR8 | TAAR9 | | Calcium-Activated Potassium Channels | CatSper and Two-Pore Channels |
| Cyclic Nucleotide-Regulated Channels | Inwardly Rectifying Potassium Channels | Transient Receptor Potential Channels | Two-P Potassium Channels | Voltage-Gated Calcium Channels |
| Voltage-Gated Potassium Channels | Voltage-Gated Sodium Channels | 5-HT3 receptors | GABAA receptors | Glycine receptors |
| Ionotropic glutamate receptors | Nicotinic acetylcholine receptors | P2X receptors | ZAC | Thyroid Hormone Receptors |
| Retinoic acid receptors | Peroxisome proliferator-activated receptors | Rev-Erb receptors | RAR-related orphan receptors | Liver X receptor-like receptors |
| Vitamin D receptor-like receptors | Hepatocyte nuclear factor-4 receptors | Retinoid X receptors | Testicular receptors | Tailess-like receptors |
| COUP-TF-like receptors | Estrogen receptors | Estrogen-related receptors | 3-Ketosteroid receptors | Nerve growth factor IB-like receptors |
| Fushi taruzu F1-like receptors | Germ cell nuclear factor receptors | DAX-like receptors | Human Epidermal growth factor Receptor 1 | Human Epidermal growth factor Receptor 2 |

These equilibriums are true for steroid hormone receptors. They may be used to diagnose and treat the complex disease. These are listed in the receptor list seen in Table 14.

TABLE 14

| Steroid hormone receptor |
|---|
| Estrogen receptor-α (ERα; NR3A1, ESR1) |
| Estrogen receptor-β (ERβ; NR3A2, ESR2) |
| Estrogen-related receptor-α (ERRα; NR3B1, ESRRA) |
| Estrogen-related receptor-β (ERRβ; NR3B2, ESRRB) |
| Estrogen-related receptor-γ (ERRγ; NR3B3, ESRRG) |
| Glucocorticoid receptor (GR; NR3C1) (Cortisol) |
| Mineralocorticoid receptor (MR; NR3C2) (Aldosterone) |
| Progesterone receptor (PR; NR3C3, PGR) (Sex hormones Progesterone) |

TABLE 14-continued

| Steroid hormone receptor |
|---|
| Androgen receptor (AR; NR3C4, AR) (Sex hormones Testosterone) |

These equilibriums are true for RXR heterodimer receptors. They may be used to diagnose and treat the complex disease. These include the thyroid receptor (TR), vitamin D receptor (VDR), the retinoic acid receptor (RAR), the ecdysone receptor (ECR), the bile acid receptor (BAR), the androstane receptor (CAR), the liver X receptor (LXR), the steroid and xenobiotic sensing nuclear receptor (SXR) and the peroxisome proliferator-activated receptor (PPAR).

These equilibriums are true for dimeric orphan receptors. They may be used to diagnose and treat the complex disease. These include the farnesoid X receptor (FXR), the NMDA receptor, the retinoid X receptor (RXR), COUP orphan receptors, the tumor necrosis factor receptor (TNFR), the hepatocyte nuclear factor 4 receptor α (HNF4-α), the TR2 and TR4 orphan nuclear receptors, the TLX orphan nuclear receptor, GCNF orphan nuclear receptor (GCNF) and the retinoic acid receptor (RAR).

These equilibriums are true for monomeric/tethered orphan receptors. They may be used to diagnose and treat the complex disease. These include the orphan nuclear receptor NGFI-B, the SF-1 orphan nuclear receptor (SF-1), the Rev-Erb orphan receptors, RAR-related orphan receptors (RORs) and Estrogen receptor-related receptors (err).

These equilibriums are true for any receptors and ion channels to be characterized. They may be used to diagnose and treat the complex disease.

Many predicted and observed spliceovariants are generated via 4.7 kb of the mouse insulin receptor (insr) 3' UTR region and suggest that 3' UTR sequences are essential to generate complex alternative spliceovariants, which are consistent with recent finding that the *C. elegans* 3' UTRs are used to generate trans- and cis-alternative spliceoforms. Even though their mRNA sequences resulted from many PPASSs may be dramatically different among themselves, splice variants may have almost identical proteins as seen in FIG. 7, which render their ecological plastics and adoptability. These predicted PPASSs result in heterogeneous spliceovariants, ranging from deletion of one amino acid to very large truncation of IR proteins and may be responsible for wide-range diverse functions of the insulin receptor (insr) gene. However, long-term aberration expression of some of these spliceovariants may have very significant pathological consequences and may be directly responsible for the insulin resistance and diabetes.

Increasing lengths of E5 sequences demonstrated that the numbers of PPASSs have the two distinct phases as do the I3 sequences as seen in FIG. 7: in Phase I, the numbers of PPASSs are dramatically decreased and range from 1.5 to 4.3 folds as seen in the insert of FIG. 7*b* and in Phase II, there are long tails of gradual decreases as the E5 and I3 sequences are increased, respectively. In Phase II, the numbers of PPASSs predicted by increasing I3 sequences are 2.4 to 4.8 folds smaller than those by E5 sequences, are consistent with the notion that E5 and I3 sequences in these long tails may have somewhat different functions discussed above as seen in FIG. 12. Since E5 and I3 sequences used to predict PPASSs can be 29 and 25 bp long, respectively, PPASSs predicted by both E5 and I3 sequences are shown to have few simple sequences and relatively low ratio of introns with ≥6 bp of identical sequences between 5' and 3' splice sites.

There are several possibilities to explain this long tail of gradual decreases. First, removal of introns from pre-mRNAs requires additional cis-acting regulatory sequences. One of the cis-acting regulatory sequences can tightly regulate the expression of groups of spliceoforms from the different genes, which are consistent with the notion of splicing codes. Alternatively, splicing codes of many introns are decoded by the same conserved splicer RNAs, which may control expression of a group of spliceovariants to regulate gene expression. Further, splicing codes are much longer than what have been expected. Each of E5 and I3 sequences may have much longer than 12 to 14 base-pairing than those found in self-splicing group II introns. These data not only support that many mammalian introns have originated by DNA duplications, but also have ruled out that long-stretch of DNA conservation between 5' and 3' splice sites of recently-acquired introns is caused by template switching or misplicing. See Roy, S. W., Irimia, M., *When good transcripts go bad: artifactual RT-PCR 'splicing' and genome analysis*. Bioessays 2008:30(6):601-5 ("Roy III"); Roy II.

By using the mouse splicing code table, the mouse insulin receptor (insr) gene is predicted to encode more than 4,631 novel alternative splice sites and express extreme and complex heterogeneous alternative spliceovariants, which make a single gene function as multiple traits. One other hand, many of these alternative spliceovariants encode almost identical proteins, which confer redundancy. Both heterogeneity and redundancy within a gene may explain why many genome-wide studies fail to identify the insulin receptor (insr) gene as one of candidate genes for type 2 diabetes and metabolic syndrome. See McClellan, J., King, M. C., *Genetic heterogeneity in human disease*. Cell:141(2):210-7 ("McClellan"). Many widely-used technologies, such as microarray, siRNA, real-time PCRs and Western blot analysis as well as gene knockout and knock-in, can only detect partial events and therefore cannot use them as an entire gene function. For example, the main band in FIG. 9*b* has been previously thought to be the two alternatively-spliced IR isoforms (IR-A and IR-B). In fact, it may represent at least four alternatively-spliced and differentially-expressed IR isoforms. See Mosthaf, L., Grakom K., Dullm T. J., et al., *Functionally distinct insulin receptors generated by tissue-specific alternative splicing*. Embo. J. 1990; 9(8):2409-13 ("Mosthaf"). In the insulin receptor (insr) knockout gene for mice, the exons were knocked out which resulted in loss of IR function. See Rodriguez-Trelles. However, the identification of the mouse insulin receptor (insr) spliceovariant without the exon suggests that the insulin receptor (insr) knockout gene for mice may only reflect parts of insulin receptor functions. See id.

Increase of these soluble and truncated insulin receptors may lead to insulin resistance, a dominate phenotype of type II diabetes without any change in the main IR isoforms. Development of insulin insistence can be simply interpreted by the Michaelis-Menten equation for multiple competitive inhibitions and IR alternative splicing resulted in complexities of IR isoforms confers characteristics of complex traits. This is consistent with previous findings from the genetic and physiological studies, which have shown that Leprechaunism (OMIM 246200), the most extreme form of the insulin resistance syndromes, Rabson-Mendenhall syndrome (OMIM 262190), severe forms of insulin resistance syndrome, and type A insulin resistance (OMIM 147670), milder forms of insulin resistance, are related to mutations in the insulin receptor. The discovery that complex expression of IR spliceovariants may be responsible for diabetes II not only demonstrates more simple and effective methods to diagnose this complex disease, but also enables the development of novel and personalized methods to treat and even cure this complex disease, some of which may not involve any medication.

According to the invention, E5-I3 sequences that constitute the splicing code or a part of the splicing code can be systematically predicted by splicing code tables. One can also envision that these results not only lead to much simpler ways to diagnose complex diseases from type II diabetes to cancer, but also establish scientific foundations to personalized methods to treat and even cure these complex diseases, some of which may or may not require any "traditional" medication.

Materials and Methods.

The following describes the materials and methods used in the following description of the invention.

Materials.

Mice: (C57BL/6) were housed and treated according to the protocols approved by Institutional Animal Care and Use Committee (IACUC). Nitrocellulose immunoblotting filters were obtained from Bio-Rad (Hercules, Calif.). Monoclonal rabbit antibody, 4B8, against residues surrounding Tyr960 of human insulin receptor β was purchased from Cell Signaling Technology (Boston, Mass.). Polyclonal antibody, sc-711, against human insulin receptor epitopes was purchased from Santa Cruz biotechnology (Santa Cruz, Calif., USA) Epitopes of the antibodies sc-711 are mapped to the last 20 residues of the C-terminus of the β chain of the human insulin receptor.

Intron datasets: The AceView annotated human gene data (AceView NCBI Build35) were downloaded from www.ncbi.nlm.nih.gov/IEB/Research/Acembly/, the mouse NIA gene index (Version 5) from lgsun.grc.nia.nih.gov/geneindex5/, the *C. elegans* gene annotation and sequence data (WS 170) from ftp.wormbase.org/pub/wormbase/ and the *D. melanogaster* annotation and sequence from flybase.net/annot/. The exon-intron datasets from zebrafish (*Danio rerio*) (release Zv4) and chicken (*Gallus gallus*) (GenBank 1.1) were downloaded from The Exon-Intron Database (hsc.utoledo.edu/bioinfo/eid/).

Prior to analysis, steps were taken to remove misalignments, computation errors and dubious cDNA and genomic alignments as described previously. The human intron dataset from AceView (NCBI Build35) was selected from the transcripts supported by at least one cDNA and/or more than four ESTs with >99% identities to the genomic sequences. The mouse intron data were selected from the NIA-5 U-clusters with support of cDNA and/or at least five ESTs. The intron data from zebrafish and chicken were parsed from the Exon-Intron Databases, which have significant proportions of gene annotations by computational prediction. The *C. elegans* and *D. melanogaster* intron datasets were selected from the gene annotations with support of cDNAs and ESTs. Only GT-AG, GC-AG and AT-AC types of introns were included in the datasets.

Methods.

Splice Junction Analysis.

5' splice sites were divided into 5' exonic (E5) and 5' intronic (I5) splicing sequences and 3' splice sites into 3' intronic (I3) and 3' exonic (E3) splicing sequences, as shown in FIG. 2*b*. The E5 sequence (uppercase) was aligned with I3 sequence (lowercase) from positions −1 to −150 and the I5 sequence (italicized lowercase) was aligned with E3 sequence (italicized uppercase) from positions 1 to 150. The number of uninterrupted identical nucleotides (LIN) was scored outwards from the splice sites, independently for the E5-I3 and I5-E3 alignments. This differs from the method the inventor previously used to identify young introns in which similarity was scored on both sides of the splice junction as a single block. The largest LIN category included those ≥20. As a control, comparisons were made with randomized forms of these intron sequences.

To check whether the observed results might be due to random chances, the E5 and I3 sequences were scrambled with I3 and E5 sequences randomly selected from the non-redundant intron dataset, and similarly I5 and E3 sequences were mix-and-matched with E3 and I5 sequences.

To further assess how much of the E5-I3 sequence identity is due to constraints imposed on the last three nucleotides of 5' exons and introns (by U1 snRNA and U2AF35, for example), those nucleotides (as well as the first three nucleotides of 3' exons and introns) were removed and the analysis as described above was repeated. To construct a non-redundant scramble dataset, both the last six nucleotides of 5' exons and introns (compare to FIG. 2*b*) were combined as an ID. This collection of unique IDs from the entire intron dataset contained up to 1,000,000 introns. The programs, as well as all the other ones used, were written in Perl and computations were done on desktop computers.

Hexamer Distribution Analysis.

The six nucleotides immediately upstream and downstream of splice junctions were sorted in the order G, A, T and C with the first nucleotides being weighted least and the last nucleotides weighted most. Subsequently, the I5 and E3 hexamer sets were re-sorted by Excel in order of A, C, G and T for presentation purposes (so that the most biologically important nucleotides were weighted most, i.e. the first nucleotides of the 5'end of an intron vs. the last nucleotides of the 3' end of an intron).

Calculation of the Expected Numbers of Predicted Putative Alternative Splice Sites (PPASSs).

To estimate the random chance a sequence may be located when searching a database, the following formula can be used to approximate the expected numbers (E) of predicted putative alternative splicing sites (PPASSs):

$$E=N^*(S-I_{max}/2)^*(I_{max}-I_{min})/4^L$$

where N is the size of the splicing code table, S is the length of a sequence used to predict PPASSs, $I_{max}$ is the maximum length of a putative intron used, $I_{min}$ is the minimum length of a putative intron used and L is the length of E5-(GC/GT/AT)-I3 sequences used in the search.

Computational Prediction of Novel Putative Alternative Splice Sites Using a Mouse Splicing Code Table.

The mouse was selected as a model to predict novel putative alternative splice sites by splicing code table. To reduce potential noise in the dataset generated during data collection, the first intronic dinucleotide (GT/GC/AT) was treated as a part of E5 sequences in this study. To construct a mouse splicing code table, all mouse highly-quality E5 sequences plus the first intronic dinucleotide and I3 sequences from the mouse genome sequences (MM9) were parsed out based on the AceView annotated mouse gene data (AceView *Mus musculus* NCBI genome 37/mm9) downloaded from www.ncbi.nlm.nih.gov/IEB/Research/Acembly/. 290,000 numbers of unique combinations of E5 and I3 nucleotide sequences are present in the splicing code table. Mouse insulin receptor (insr) gene encoding insulin receptor protein was selected as a model, which is 128,255 bp. Intron sizes from 150 bp to 50,000 bp were used. Starting from the first nucleotide of the mouse insulin receptor (insr) gene, different putative introns were generated to search their E5-(GT/GC/AT)-I3 sequences in the mouse splicing code table. If a positive match was found, the E5-(GT/GC/AT)-I3 sequences were treated as a predicted putative alternative splice site (PPASS). Using a 20 bp of E5-(GT/GC/AT)-I3 sequence, the probability to find an identical sequence is 1.1×10-12 in a randomly-distributed genome of the mouse genome size.

Isolation of Mouse RNAs.

Mice were harvested according to the protocols approved by Institutional Animal Care and Use Committee (IACUC). Total RNAs were isolated from mouse tissues by Qiagen RNeasy Mini Kit as suggested by the manufacturer. 20 mg of mouse tissues were disrupted for 30 seconds in 350 μl of Buffer RLT by Cyclone Virtishere. The homogenates were centrifuged for 3 minutes at the maximum speed and supernatants were transferred into new tubes. One volume of 70% ethanol was added to the cleared lysate, and mix well by pipetting. 700 μl of the sample were transferred to RNeasy mini spin columns sitting in a 2-ml collection tube and the columns were centrifuged for 30 seconds at maximum speed and flow-through was discarded. 700 μl Buffer RW1 were added onto the RNeasy column, the RNeasy columns were centrifuged for 30 seconds at maximum speed and flow-through was discarded. 350 μl Buffer RWT were added into the RNeasy Mini spin column and centrifuge for 15 at 8000×g. To remove potential DNA contamination, after 10 μl DNase I stock solution was mixed with 70 μl Buffer RDD by gently inverting tubes, the DNase solution was added into the RNeasy columns and incubated at room temperature for 30 minutes. The columns were washed again by adding 350 μl Buffer RWT. After RNeasy columns were transferred to new 2-ml collection tubes, the columns were washed twice using 500 μl Buffer RPE by centrifuging for 30 seconds at maximum speed. RNAs were eluted from the columns by adding 30 μl of RNase-free water.

Verification of Alternatively-Spliced Insulin Receptor (IR) Isoforms.

To identify novel mouse IR isoforms, computation predication of putative splicing sites was performed using the mouse splicing code table. Isoform-specific primers were designed to cover the putative 5' and 3' splice sites. Normal primers were selected from upstream or downstream exonic sequences. The primers were designed using the software (www.yeastgenome.org). To minimize potential, no specific amplification and/or special care was taken when primers were designed, especially in the intronic sequences. 3-10 ug of total RNAs were first treated with RNase-free DNase at 37° C. for 30 min. To remove any potential genomic contamination, the first-strand cDNA synthesis was carried out using oligo(T)15 and/or random hexamers by TaqMan Reverse Transcription Reagents (Applied Biosystems Inc., Foster City, Calif., USA) as suggested by the manufacturer. 10-50 ng of the cDNAs were used to amplify for specific IR isoforms using isoform-specific primers by PCR. PCR amplifications were carried out by HiFi Taq polymerase (Invitrogen, Carlsbad, Calif., USA). To further reduce potential no specific amplification, higher annealing temperatures than optimized temperatures were used. PCR reactions were carried out by HiFi Taq polymerase (Invitrogen, Carlsbad, Calif., USA) using cycles of 94° C., 15", 60-68° C., 15" and 68° C., 2-5 min. The PCR products were separated on 1-2% agarose gels. The expected products were excised from gels and cloned into pCR2.1 TA vector (Invitrogen, Carlsbad, Calif., USA). The novel isoforms were then verified by sequence analysis.

Western Immunoblotting Analysis.

To perform immunoblotting analysis, a 20 μl sample was heated to 75° C. for 5 minutes, cool on ice and microcentrifuge for 5 minutes. For denaturing gels, DTT were added into samples at final concentration of 50 mM. A 20 μl sample was loaded onto SDS-PAGE gel and prestained molecular weight ladder (Bio-Rad) were used as markers to verify electrotransfer and to determine molecular weights. The samples were electrotransfered to nitrocellulose membrane for 2-3.5 hour in transfer buffer (25 mM Tris, 192 mM glycine). After transfer, wash nitrocellulose membrane was washed three time with 20 ml of TBS/T (20 mM Tris-HCl, pH 7.5, 150 mM NaCl, 0.05% Tween 20) for 5 minutes at room temperature. The membranes were blocked in 10 ml of 5% no-fat milk in TBS/T for 1 hour at room temperature. After being washed three times in TBS/T, the membranes were incubated with primary antibody (at the appropriate dilution) in 3 ml of 4% BSA in TBS/T with gentle agitation overnight at 4° C. After the membranes were washed three times for 5 minutes each with 15 ml of TBS/T buffer, the membranes were incubated with appropriate HRP-conjugated secondary antibody (1:1000 to 1:2000) in 10 ml of 5% fat-free milk in TBS/T buffer with gentle agitation for 1 hour at room temperature. After being washed three times for 5 minutes each with 15 ml of TBS/T, the membranes were incubated for 5 minutes with ECF Western blotting reagent (GE HealthCare BioScience, Piscataway, N.J., USA) and were scanned using a 570 nm filter by Typhoon 9410 (GE HealthCare BioScience, Piscataway, N.J., USA).

Clone Full-Length cDNAs into Expression Plasmids.

To get full-length cDNAs of the specific novel IR isoforms, the 5' and 3' regions were amplified independently from mouse cDNAs using the isoform-specific primers by pfu Taq polymerase, only expectant DNA fragments were recovered from agarose gels. The two fragments were mixed and amplified again using the 5' and 3' by pfu Taq polymerase. After incubating at 72° C. for 10 min, the resulted DNAs were then cloned into TA vectors and the positive clones were verified first by restriction enzyme analysis and then by sequence analysis. The cDNA inserts were then cloned into pcDNA3.1 (Invitrogen, Carlsbad, Calif., USA).

Statistical Analysis.

The means and variances for binomial data were calculated using u=Np and $\sigma_x^2$=Npq, where p is the probability that a given event has occurred, q is the probability that the event has not occurred and N is the population of the event. For the continuous data, the equations of $$u = \frac{\sum Xi}{N},\ \sigma^2 = \frac{\sum x_i^2 - \frac{(\sum x_i)^2}{N}}{N} \text{ and } s^2 = \frac{\sum x_i^2 - \frac{(\sum x_i)^2}{N}}{n-1}$$

were used to estimated the means, variance and sample variance, respectively. Comparisons of two proportions were performed by $$U = \frac{p_1 - p_2}{\sqrt{\frac{p_1 q_1}{n} + \frac{p_2 q_2}{m}}}.$$

The foregoing embodiments have been presented for the purpose of illustration and description only and are not to be construed as limiting the scope of the invention in any way.

What is claimed is:

1. A method of identifying at least one potentially alternatively spliced transcript in at least one pre-mRNA sequence obtained from biochemical analysis of a biological sample from a species, the method comprising:

(a) generating a splicing code table of the species, comprising the substeps of:

determining substantially all of the 5' splice sites and 3' splice sites from relevant existing databases, wherein the relevant existing databases comprise genome sequences of the species, and wherein the genome sequences comprise at least an intron dataset;

dividing the 5' splice sites into 5' exonic (E5) and 5' intronic (I5) splicing sequences;

dividing the 3' splice sites into 3' intronic (I3) and 3' exonic (E3) splicing sequences;

constructing the splicing code table by parsing out E5 sequences, I5 sequences, I3 sequences, and E3 sequences from the intron dataset, each splicing code comprising E5 junction sequence-the first intronic dinucleotide-I3 junction sequence, wherein an E5 junction sequence comprises eight twelve nucleotides of an E5 sequence upstream of the 5' splice site and an I3 junction sequence comprises six to ten nucleotides of an I3 sequence upstream of the 3' splice site, and storing the splicing code table in a programmable, searchable computer database;

generating by a computer processor putative markers, wherein each of the putative markers comprises an E5-the first intronic dinucleotide-I3 sequence of all genes of interest of the species;

(b) aligning the at least one pre-mRNA sequence with each of the putative markers in the splicing code table;

(c) determining that the at least one RNA sequence is an alternatively spliced transcript candidate if the at least one pre-mRNA sequence is found to have a substantially identical match with at least one of the putative markers in the splicing code table and it is not identical to putative markers; or determining that the at least one pre-mRNA sequence is not an alternatively spliced transcript candidate if no substantially identical matches are found between the at least one pre-mRNA sequence and any of the putative markers in the splicing code table;

(d) verifying, if the at least one RNA sequence is determined to be an alternatively spliced transcript candidate in step (c), that the at least one RNA sequence is a real alternatively spliced transcript by a biochemical assay, wherein the biochemical assay in step (d) comprises at least one of the RT-PCR, RNA sequencing, DNA sequencing, RNA-seq sequencing and array hybridization, and the biochemical assay comprises use of at least one primer and/or probe, wherein the at least one primer and/or probe is designed based on the E5 sequences and the E3 sequences of the at least one of the putative markers with which the at least one pre-mRNA sequence is found to be substantially identical and wherein the at least one primer and/or probe is designed to assay an alternatively spliced transcript.

2. The method according to claim 1, wherein the biochemical assay comprises RT-PCR, and the biochemical assay comprises use of a first primer and a second primer, wherein the first primer is designed based on the E5 sequence and the second primer is designed based on the E3 sequence.

3. The method according to claim 1, wherein the biochemical assay comprises array hybridization and the biochemical assay comprises use of a probe, and wherein the probe is designed based on a splice junction sequence connecting the E5 sequence and the E3 sequence.

4. The method according to claim 1, wherein the biochemical assay comprises RNA-seq and the biochemical assay comprises use of a probe, and wherein the probe is designed based on a junction sequence connecting the E5 sequence and the E3 sequence.

5. The method according to claim 1, wherein size of the putative markers has a range of 150 bp to 50,000 bp.

6. The method according to claim 1, wherein the species is a eukaryotic organism.

7. The method according to claim 6, wherein the species is a mammal.

8. The method according to claim 7, wherein the species is a mouse.

9. The method according to claim 7, wherein the species is a human.

10. The method according to claim 6, wherein the species is a vertebrate, selected from the group consisting of chicken and zebrafish, or an invertebrate, selected from a fungus, a protest, *C. elegans* and *D. melanogaster*, or a eukaryotic virus.

11. The method according to claim 1, wherein in step (c) the E5 sequence plus the first intronic dinucleotide and the I3 sequence of each of the putative markers in the splicing code table with which the at least one RNA sequence is aligned are mapped to a gene encoding a receptor, an ion-channel or a neurotransmitter, selected from a group consisting of insulin receptor, G protein-coupled receptors, 5-Hydroxytryptamine receptors, Acetylcholine receptors (muscarinic), Adenosine receptors, Adrenoceptors, Anaphylatoxin receptors, Angiotensin receptors, Apelin receptor, Bile acid receptor, Bombesin receptors, Bradykinin receptors, Calcitonin receptors, Calcium-sensing receptors, Cannabinoid receptors, Chemokine receptors, Cholecystokinin receptors, Corticotropin-releasing factor receptors, Dopamine receptors, Endothelin receptors, Estrogen (G protein coupled) receptor, Formylpeptide receptors, Free fatty acid receptors, Frizzled receptors, GABAB receptors, Galanin receptors, Ghrelin receptor, Glucagon receptor family, Glycoprotein hormone receptors, Gonadotrophin-releasing hormone receptors, Histamine receptors, Hydroxycarboxylic acid receptors, Kisspeptin receptor, Leukotriene receptors, Lysophospholipid receptors, Melanin-concentrating hormone receptors, Melanocortin receptors, Melatonin receptors, Metabotropic glutamate receptors, Motilin receptor, Neuromedin U receptors, Neuropeptide FF/neuropeptide AF receptors, Neuropeptide S receptor, Neuropeptide W/neuropeptide B receptors, Neuropeptide Y receptors, Neurotensin receptors, Opioid receptors, Orexin receptors, P2Y receptors, Parathyroid hormone receptors, Peptide P518 receptor, Platelet-activating factor receptor, Prokineticin receptors, Prolactin-releasing peptide receptor, Prostanoid receptor, Protease-activated receptors, Relaxin family peptide receptors, Somatostatin receptors, Tachykinin receptors, Thyrotropin-releasing hormone receptor, Trace amine receptor, Urotensin receptor, VIP and PACAP receptors, Vasopressin and oxytocin receptors, Class A Orphans, Class B Orphans, Class C Orphans Non-signaling 7TM chemokine-binding proteins, BLT1, BLT2, CysLT1, CysLT2, OXE, CCRL2, CMKLR1, GPR1, GPR3, GPR4, GPR6, GPR12, GPR15, GPR17, GPR18, GPR19, GPR20, GPR21, GPR22, GPR25, GPR26, GPR27, GPR31, GPR32, GPR33, GPR34, GPR35, GPR37, GPR37L1, GPR39, GPR42, GPR45, GPR50, GPR52, GPR55, GPR61, GPR62, GPR63, GPR65, GPR68, GPR75, GPR78, GPR79, GPR82, GPR83, GPR84, GPR85, GPR87, GPR88, GPR101, GPR119, GPR120, GPR132, GPR135, GPR139, GPR141, GPR142, GPR146, GPR148, GPR 149, GPR150, GPR151, GPR152, GPR153, GPR160, GPR161, GPR162, GPR171, GPR173, GPR174, GPR176, GPR182, GPR183, LGR4, LGR5, LGR6, LPAR6, MAS1, MAS1L, MRGPR, MRGPRE, MRGPRF, MRGPRG, MRGPRX1, MRGPRX2, MRGPRX3, MRGPRX4, OPN3, OPN5, OXGR1, P2RY8, P2RY10, SUCNR1, TAAR2, TAAR3, TAAR4, TAAR5, TAAR6, TAAR8, TAAR9, Calcium-Activated Potassium Channels, CatSper and Two-Pore Channels, Cyclic Nucleotide-Regulated Channels, Inwardly Rectifying Potassium Channels, Transient Receptor Potential Channels, Two-P Potassium Channels, Voltage-Gated Calcium Channels, Voltage-Gated Potassium Channels, Voltage-Gated Sodium Channels, 5-HT3 receptors, GABAA receptors, Glycine receptors, Ionotropic glutamate receptors, Nicotinic acetylcholine receptors, P2X receptors, ZAC, Thyroid Hormone Receptors, Retinoic acid receptors, Peroxisome proliferator-activated receptors, Rev-Erb receptors, RAR-related orphan receptors, Liver X receptor-like receptors, Vitamin D receptor-like receptors, Hepatocyte nuclear factor-4 receptors, Retinoid X receptors, Testicular receptors, Tailess-like receptors, COUP-TF-like receptors, Estrogen receptors, Estrogen-related receptors, 3-Ketosteroid receptors, Nerve growth factor IB-like receptors, Fushi taruzu F1-like receptors, Germ cell nuclear factor receptors, DAX-like receptors, Human Epidermal growth factor Receptor 1, Human Epidermal growth factor Receptor 2, Estrogen receptor-α (ERα; NR3A1, ESR1), Estrogen receptor-β (ERβ; NR3A2, ESR2), Estrogen-related receptor-α (ERRα; NR3B1, ESRRA), Estrogen-related receptor-β (ERRβ; NR3B2, ESRRB), Estrogen-related receptor-γ (ERRγ; NR3B3, ESRRG), Glucocorticoid receptor (GR; NR3C1), Mineralocorticoid receptor (MR; NR3C2), Progesterone receptor (PR; NR3C3, PGR), and Androgen receptor (AR; NR3C4).

12. The method according to claim 11, wherein the gene encodes an insulin receptor.

13. The method of claim 1, wherein each splicing code comprises an E5 junction sequence comprising nine nucleotides of an E5 sequence upstream of the 5' splice site and an I3 junction sequence comprising nine nucleotides of an I3 sequence upstream of the 3' splice site.

14. A method of identifying at least one potentially alternatively spliced transcript of a gene from a biological tissue from a species, the method comprising:

(a) obtaining at least one pre-mRNA sequence from the biological tissue;

(b) generating a splicing code table of the species, comprising the substeps of:

(i) determining substantially all of the 5' splice sites and 3' splice sites from relevant existing databases, wherein the relevant existing databases comprise genome sequences of the species, and wherein the genome sequences comprise at least an intron dataset;

(ii) dividing the 5' splice sites into 5' exonic (E5) and 5' intronic (I5) splicing sequences;

(iii) dividing the 3' splice sites into 3' intronic (I3) and 3' exonic (E3) splicing sequences;

(iv) constructing the splicing code table by parsing out E5 sequences, I5 sequences, I3 sequences, and E3 sequences from the intron dataset, each splicing code comprising E5 junction sequence-the first intronic dinucleotide-I3 junction sequence, wherein an E5 junction sequence comprises eight to twelve nucleotides of an E5 sequence upstream of the 5' splice site and an I3 junction sequence comprises six to ten nucleotides of an I3 sequence upstream of the 3' splice site, and storing the splicing code table in a programmable, searchable computer database; and (v) based on the splicing code table, generating by a computer processor a set of putative markers, wherein each of the set of putative markers comprises an E5-the first intronic dinucleotide-I3 sequence of the gene;

(d) identifying the at least one potentially alternatively spliced transcript in the at least one pre-mRNA sequence by a biochemical assay, wherein:

the biochemical assay comprises at least one of RT-PCR, RNA sequencing, DNA sequencing, DNA-seq sequencing and array hybridization; and the biochemical assay comprises use of at least one primer and/or probe, and wherein the at least one primer and/or probe is designed based on the E5 sequences and the E3 sequences of the at least one of the putative markers and wherein the at least one primer and/or probe is designed to assay an alternatively spliced transcript.

15. The method according to claim 14, wherein the at least one potentially alternatively spliced transcript is a truncated isoform of the gene; and step (b) further comprising, after substep (iv), a substep of removing putative markers to which the E5 sequences and the E3 sequences correspond are mapped to be a membrane-binding domain.

16. The method according to claim 15, wherein the species is a mammal.

17. The method according to claim 16, wherein the gene encodes a receptor, an ion-channel or a neurotransmitter, selected from a group consisting of insulin receptor, G protein-coupled receptors, 5-Hydroxytryptamine receptors, Acetylcholine receptors (muscarinic), Adenosine receptors, Adrenoceptors, Anaphylatoxin receptors, Angiotensin receptors, Apelin receptor, Bile acid receptor, Bombesin receptors, Bradykinin receptors, Calcitonin receptors, Calcium-sensing receptors, Cannabinoid receptors, Chemokine receptors Cholecystokinin receptors, Corticotropin-releasing factor receptors, Dopamine receptors, Endothelin receptors, Estrogen (G protein coupled) receptor, Formylpeptide receptors, Free fatty acid receptors, Frizzled receptors, GABAB receptors, Galanin receptors, Ghrelin receptor, Glucagon receptor family, Glycoprotein hormone receptors, Gonadotrophin-releasing hormone receptors, Histamine receptors, Hydroxycarboxylic acid receptors, Kisspeptin receptor, Leukotriene receptors, Lysophospholipid receptors, Melanin-concentrating hormone receptors, Melanocortin receptors, Melatonin receptors, Metabotropic glutamate receptors, Motilin receptor, Neuromedin U receptors, Neuropeptide FF/neuropeptide AF receptors, Neuropeptide S receptor, Neuropeptide W/neuropeptide B receptors, Neuropeptide Y receptors, Neurotensin receptors, Opioid receptors, Orexin receptors, P2Y receptors, Parathyroid hormone receptors, Peptide P518 receptor, Platelet-activating factor receptor, Prokineticin receptors, Prolactin-releasing peptide receptor, Prostanoid receptor, Protease-activated receptors, Relaxin family peptide receptors, Somatostatin receptors, Tachykinin receptors, Thyrotropin-releasing hormone receptor, Trace amine receptor, Urotensin receptor, VIP and PACAP receptors, Vasopressin and oxytocin receptors, Class A Orphans, Class B Orphans, Class C Orphans Non-signaling 7TM chemokine-binding proteins, BLT1, BLT2, CysLT1, CysLT2, OXE, CCRL2, CMKLR1, GPR1, GPR3, GPR4, GPR6, GPR12, GPR15, GPR17, GPR18, GPR19, GPR20, GPR21, GPR22, GPR25, GPR26, GPR27, GPR31, GPR32, GPR33, GPR34, GPR35, GPR37, GPR37L1, GPR39, GPR42, GPR45, GPR50, GPR52, GPR55, GPR61, GPR62, GPR63, GPR65, GPR68, GPR75, GPR78, GPR79, GPR82, GPR83, GPR84, GPR85, GPR87, GPR88, GPR101, GPR119, GPR120, GPR132, GPR135, GPR139, GPR141, GPR142, GPR146, GPR148, GPR149, GPR150, GPR151, GPR152, GPR153, GPR160, GPR161, GPR162, GPR171, GPR173, GPR174, GPR176, GPR182, GPR183, LGR4, LGR5, LGR6, LPAR6, MAS1, MAS1L, MRGPR, MRGPRE, MRGPRF, MRGPRG, MRGPRX1, MRGPRX2, MRGPRX3, MRGPRX4, OPN3, OPN5, OXGR1, P2RY8, P2RY10, SUCNR1, TAAR2, TAAR3, TAAR4, TAAR5, TAAR6, TAAR8, TAAR9, Calcium-Activated Potassium Channels, CatSper and Two-Pore Channels, Cyclic Nucleotide-Regulated Channels, Inwardly Rectifying Potassium Channels, Transient Receptor Potential Channels, Two-P Potassium Channels, Voltage-Gated Calcium Channels, Voltage-Gated Potassium Channels, Voltage-Gated Sodium Channels, 5-HT3 receptors, GABAA receptors, Glycine receptors, Ionotropic glutamate receptors, Nicotinic acetylcholine receptors, P2X receptors, ZAC, Thyroid Hormone Receptors, Retinoic acid receptors, Peroxisome proliferator-activated receptors, Rev-Erb receptors, RAR-related orphan receptors, Liver X receptor-like receptors, Vitamin D receptor-like receptors, Hepatocyte nuclear factor-4 receptors, Retinoid X receptors, Testicular receptors, Tailess-like receptors, COUP-TF-like receptors, Estrogen receptors, Estrogen-related receptors, 3-Ketosteroid receptors, Nerve growth factor IB-like receptors, Fushi taruzu F1-like receptors, Germ cell nuclear factor receptors, DAX-like receptors, Human Epidermal growth factor Receptor 1, Human Epidermal growth factor Receptor 2, Estrogen receptor-α (ERα; NR3A1, ESR1), Estrogen receptor-β (ERβ; NR3A2, ESR2), Estrogen-related receptor-α (ERRα; NR3B1, ESRRA), Estrogen-related receptor-β (ERRβ; NR3B2, ESRRB), Estrogen-related receptor-γ (ERRγ; NR3B3, ESRRG), Glucocorticoid receptor (GR; NR3C1), Mineralocorticoid receptor (MR; NR3C2), Progesterone receptor (PR; NR3C3, PGR), and Androgen receptor (AR; NR3C4).

18. The method according to claim 17, wherein the gene encodes an insulin receptor.

19. The method of claim 14, wherein each splicing code comprises an E5 junction sequence comprising nine nucleotides of an E5 sequence upstream of the 5' splice site and an I3 junction sequence comprising nine nucleotides of an I3 sequence upstream of the 3' splice site.

20. A method for identifying at least one potentially alternatively spliced transcript in at least one pre-mRNA sequence obtained from biochemical analysis of a biological sample from a species, the method comprising:

(a) generating a splicing code table of the species, comprising the substeps of:

determining substantially all of the 5' splice sites and 3' splice sites from relevant existing databases, wherein the relevant existing databases comprise genome sequences of the species, and wherein the genome sequences comprises at least an intron dataset;

dividing the 5' splice sites into 5' exonic (E5) and 5' intronic (I5) splicing sequences;

dividing the 3' splice sites into 3' intronic (I3) and 3' exonic (E3) splicing sequences;

constructing the splicing code table by parsing E5 sequences, I5 sequences, I3 sequences, and E3 sequences from the intron dataset, each splicing code comprising E5 junction sequence-the first intronic dinucleotide-I3 junction sequence, wherein an E5 junction sequence comprises eight to twelve nucleotides of an E5 sequence upstream of the 5' splice site and an I3 junction sequence comprises six to ten nucleotides of an I3 sequence upstream of the 3' splice site, and storing the splicing code table in a programmable, searchable computer database;

generating by a computer processor putative markers, wherein each of the putative markers comprises an E5-the first intronic dinucleotide-I3 sequence of all genes of interest of the species;

(b) aligning the at least one pre-mRNA sequence with each of the putative markers in the splicing code table;

(c) determining that the at least one RNA sequence is an alternatively spliced transcript candidate if the at least one pre-mRNA sequence is found to have a substantially identical match with at least one of the putative markers in the splicing code table and it is not identical to putative markers; or determining that the at least one pre-mRNA sequence is not an alternatively spliced transcript candidate if no substantially identical matches are found between the at least one pre-mRNA sequence and any of the putative markers in the splicing code table; and (d) verifying, if the at least one RNA sequence is determined to be an alternatively spliced transcript candidate in step (c), that the at least one RNA sequence is a real alternatively spliced transcript by a biochemical assay, wherein the biochemical assay in step (d) comprises contacting RNA isolated from the biological sample with at least one of primer and/or probe, wherein the at least one primer and/or probe is designed based on the E5 sequences and the E3 sequences of the at least one of the putative markers with which the at least one pre-mRNA sequence is found to be substantially identical and wherein the at least one primer and/or probe is designed to bind the alternatively spliced transcript, and detecting resultant binding between the RNA isolated from the biological sample and the at least one primer and/or probe.

21. The method of claim 20, wherein each splicing code comprises an E5 junction sequence comprising nine nucleotides of an E5 sequence upstream of the 5' splice site and an I3 junction sequence comprising nine nucleotides of an I3 sequence upstream of the 3' splice site.

* * * * *